(12) United States Patent
Lee et al.

(10) Patent No.: US 11,367,839 B2
(45) Date of Patent: Jun. 21, 2022

(54) COMPOUND FOR ORGANIC ELECTRIC ELEMENT, ORGANIC ELECTRIC ELEMENT USING THE SAME, AND AN ELECTRONIC DEVICE THEREOF

(71) Applicant: DUK SAN NEOLUX CO., LTD., Cheonan-si (KR)

(72) Inventors: Yun Suk Lee, Cheonan-si (KR); Min Ji Jo, Cheonan-si (KR); Jung Hwan Park, Cheonan-si (KR); Bum Sung Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 17/455,764

(22) Filed: Nov. 19, 2021

(65) Prior Publication Data

US 2022/0085296 A1    Mar. 17, 2022

Related U.S. Application Data

(62) Division of application No. 17/309,771, filed as application No. PCT/KR2019/016359 on Nov. 26, 2019.

(30) Foreign Application Priority Data

Dec. 17, 2018 (KR) .................. 10-2018-0163432

(51) Int. Cl.
  *C07D 405/04* (2006.01)
  *C07D 405/14* (2006.01)
  (Continued)

(52) U.S. Cl.
  CPC ........ *H01L 51/0073* (2013.01); *C07D 405/04* (2013.01); *C07D 405/10* (2013.01); *C07D 405/14* (2013.01); *C07D 409/10* (2013.01);

*C07D 409/14* (2013.01); *C07D 487/04* (2013.01); *C07D 487/14* (2013.01); *C07D 495/04* (2013.01); *H01L 51/0067* (2013.01);
(Continued)

(58) Field of Classification Search
  CPC .. C07D 405/04; C07D 405/14; C07D 409/10; C07D 409/14; C07D 487/04; C07D 487/14; C07D 495/04; H01L 51/0067; H01L 51/0071; H01L 51/0072; H01L 51/0073; H01L 51/0074; H01L 51/5016
  See application file for complete search history.

(56) References Cited

FOREIGN PATENT DOCUMENTS

| CN | 109265450 A | * | 1/2019 |
|---|---|---|---|
| KR | 10-2016-0110078 A | | 9/2016 |

(Continued)

OTHER PUBLICATIONS

Computer-generated English-language translation of CN-109265450-A.*

*Primary Examiner* — Vu A Nguyen
(74) *Attorney, Agent, or Firm* — Vorys, Sater, Seymour & Pease LLP; Mih Suhn Koh

(57) ABSTRACT

Provided are a compound of Formula 2-K, an organic electric element including a first electrode, a second electrode, and an organic material layer formed between the first electrode and the second electrode, and an electronic device thereof, including the compound of Formula 2-K in the organic material layer, and thereby achieving lowered driving voltage, improved luminous efficiency, and extended life time.

14 Claims, 1 Drawing Sheet

(51) Int. Cl.
*C07D 409/14* (2006.01)
*C07D 487/04* (2006.01)
*C07D 487/14* (2006.01)
*C07D 495/04* (2006.01)
*H01L 51/00* (2006.01)
*H01L 51/50* (2006.01)
*C07D 405/10* (2006.01)
*C07D 409/10* (2006.01)

(52) U.S. Cl.
CPC ...... *H01L 51/0071* (2013.01); *H01L 51/0072* (2013.01); *H01L 51/0074* (2013.01); *H01L 51/5016* (2013.01)

(56) References Cited

FOREIGN PATENT DOCUMENTS

| KR | 10-2017-0093061 A | | 8/2017 |
|----|-------------------|---|--------|
| KR | 10-2017-0102000 A | | 9/2017 |
| KR | 10-2018-0024306 A | | 3/2018 |
| KR | 20180024306 A | * | 3/2018 |

* cited by examiner

COMPOUND FOR ORGANIC ELECTRIC ELEMENT, ORGANIC ELECTRIC ELEMENT USING THE SAME, AND AN ELECTRONIC DEVICE THEREOF

CROSS-REFERENCE TO RELATED APPLICATION

This application is a Divisional application of U.S. patent application Ser. No. 17/309,771 filed on Jun. 17, 2021, which was a 371 of PCT/KR2019/016359 filed on Nov. 26, 2019, which claims priority from and the benefit under 35 U.S.C. § 119(a) of Korean Patent Application No. 10-2018-0163432 filed on Dec. 17, 2018, the contents of which are hereby incorporated by reference for all purposes as if fully set forth herein.

BACKGROUND

Technical Field

The present invention relates to compounds for organic electric element, organic electric element comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may comprise a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is very important factor in the portable display with a limited power source of the battery, and efficiency and life span issues must also be solved.

Efficiency, life span, driving voltage, and the like are correlated with each other. If efficiency is increased, then driving voltage is relatively lowered, and the crystallization of an organic material due to Joule heating generated during operation is reduced as driving voltage is lowered. As a result, life span tends to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, there is a need to develop a light emitting material that has high thermal stability and can efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electric element has not been fully developed yet, in particular, it is strongly required to develop host material of the light emitting layer.

Object, Technical Solution and Effects of the Invention

An object of the present invention is to provide compound lowering a driving voltage, improving luminous efficiency and lifetime of the element, an organic electric element comprising the same, and an electronic device thereof.

In an aspect of the present invention, the present invention provides an organic electric element comprising the compound represented by Formula 1 and the compound represented by Formula 2 and electronic devices thereof.

<Formula 1>

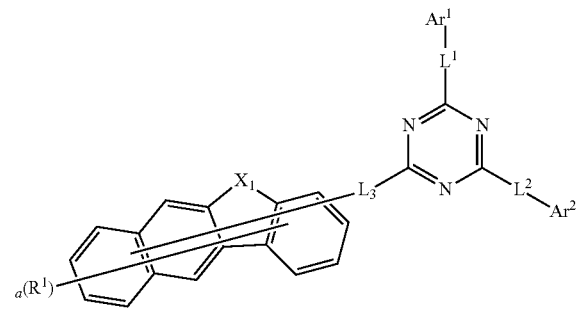

-continued

<Formula 2>

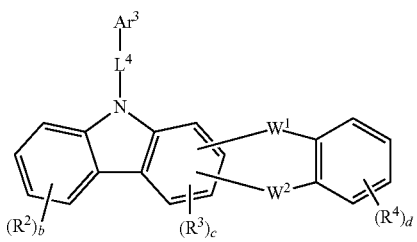

In another aspect of the present invention, the present invention provides compound represented by the following Formula, an organic electric element comprising the compound in a light emitting layer, and an electronic device thereof.

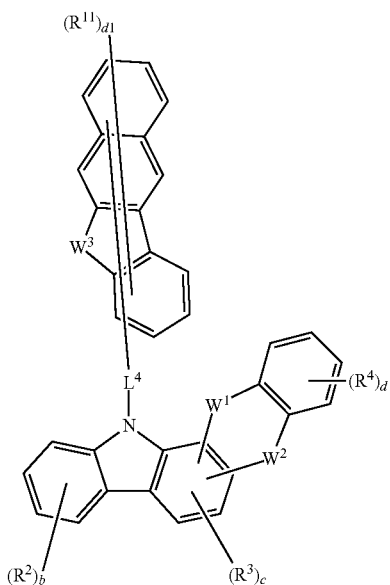

By using the compound according to embodiment of the present invention, a driving voltage of element can be lowered and the luminous efficiency and lifetime of the element can be also remarkably improved.

DETAILED DESCRIPTION

Figure 1:
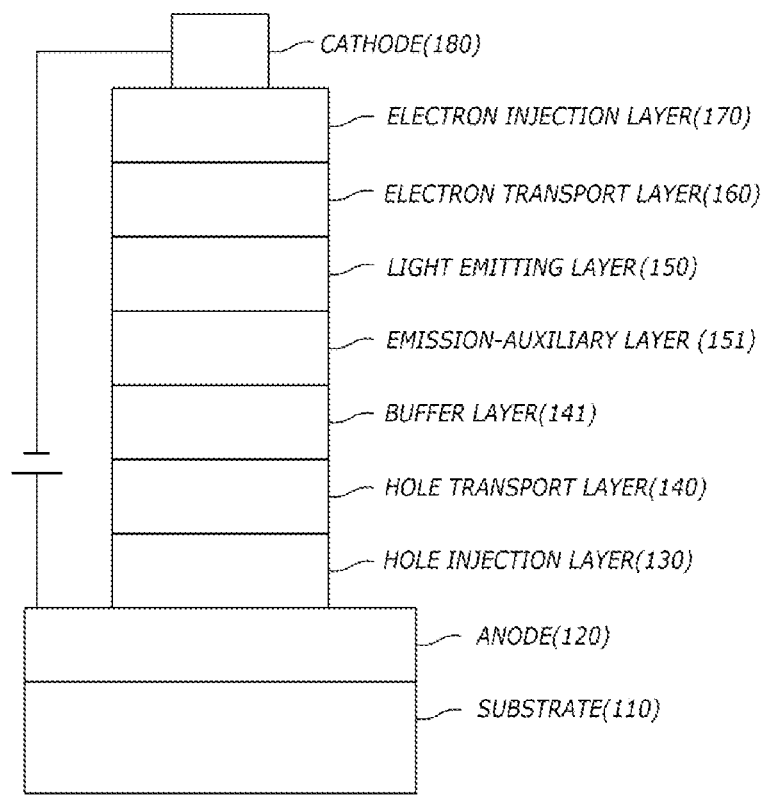
FIG. 1 illustrates an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.
Figure 2:
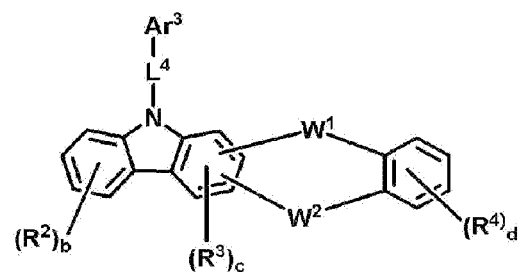
FIG. 2 illustrates Formula according to an aspect of the present invention.

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro-compounds and the like. In addition, unless otherwise stated, a fluorenyl group may be comprised in an aryl group and a fluorenylene group may be comprised in an arylene group.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and the case where R and R' are bonded to each other to form the spiro compound together with the carbon bonded to them is comprised.

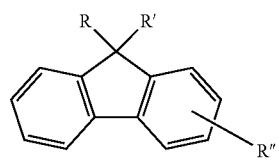

The term "spiro-compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein refers to N, O, S, P or Si and heterocyclic group means a monocyclic, ring assemblies, a fused polycyclic system or spiro compound containing a heteroatom.

The term "heterocyclic group" used in the specification may comprise compound comprising a heteroatom group such as $SO_2$, $P=O$, etc., as the following compounds, instead of carbon forming a ring.

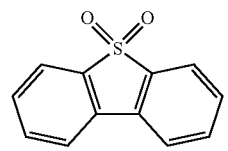 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and 'phenanthrylene (group)' when it is 'divalent group', and regardless of its valence, it may also be described as 'phenanthrene' which is a parent compound name. Similarly, in the case of pyrimidine, it may be described as 'pyrimidine' regardless of its valence, and it may also be described as the name of corresponding functional group such as pyrimidinyl (group) when it is 'monovalent group', and 'pyrimidinylene (group)' when it is 'divalent group'.

In addition, in the present specification, the numbers and alphabets indicating a position may be omitted when describing a compound name or a substituent name, For example, pyrido[4,3-d]pyrimidine, benzopuro[2,3-d]pyrimidine and 9,9-dimethyl-9H-fluorene can be described as pyridopyrimidine, benzofurropyrimidine and dimethylfluorene, respectively. Therefore, both benzo[g]quinoxaline and benzo[f] quinoxaline can be described as benzoquinoxaline.

In addition, unless otherwise expressed, where any formula of the present invention is represented by the following formula, the substituent according to the index may be defined as follows.

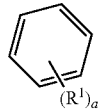

In the above formula, where a is an integer of zero, the substituent $R^1$ is absent, that is, hydrogen atoms are bonded to all the carbon constituting the benzene ring. Here, chemical formulas or compounds may be written described by omitting the indication of hydrogen bonded to carbon. In addition, one substituent $R^1$ is bonded to any carbon of the carbons forming the benzene ring when "a" is an integer of 1. Similarly, where "a" is an integer of 2 or 3, for example, as in the following formulas, substituents $R^1$s may be bonded to the carbon of the benzene ring. Also, where "a" is an integer of 4 to 6, substituents $R^1$s are bonded to the carbon of the benzene ring in a similar manner. Further, where "a" is an integer of 2 or more, $R^1$s may be the same or different from each other.

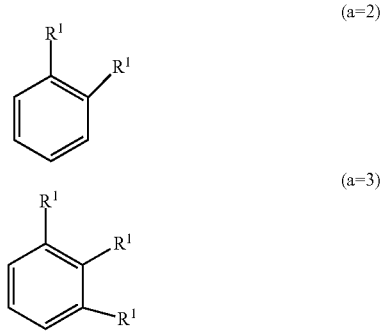

In addition, unless otherwise specified in the present specification, the ring formed by bonding between adjacent groups may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring of a $C_3$-$C_{60}$ aliphatic ring with a $C_6$-$C_{60}$ aromatic ring group and a combination thereof.

Hereinafter, a laminated structure of the organic electric element comprising the compound of the present invention will be described with reference to FIG. 1.

In the following description of the present invention, a detailed description of known configurations and functions incorporated herein will be omitted when it may make the subject matter of the present invention rather unclear.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

FIG. 1 illustrates an example of an organic electric element according to an embodiment of the present invention.

Referring to the FIG. 1, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 stacked in sequence on the first electrode 120. Here, at least one layer of the organic material layer may be omitted, or a hole blocking layer, an electron blocking layer, an emission-auxiliary layer 151, an electron transport-auxiliary layer, a buffer layer 141, etc. may be further included in the organic material layer, and the electron transport layer 160 or the like may serve as a hole blocking layer.

In addition, although not shown, the organic electric element according to an embodiment of the present invention may further include a protective layer or a layer for improving luminous efficiency. The layer for improving luminous efficiency may be formed on one side of sides of the first electrode or one side of sides of the second electrode, wherein the one side is not facing the organic material layer.

The inventive compound employed in the organic material layer may be used as a material of a hole injection layer 130, a hole transport layer 140, an emission-auxiliary layer 151, an electron transport-auxiliary layer, an electron transport layer 160 or an electron injection layer 170, as host or dopant of a light emitting layer 150, or as a material of a layer for improving luminous efficiency. Preferably, a mixture of compound of Formula 1 of the present invention and compound of Formula 2 of the present invention can be used as host of a light emitting layer. Also, preferably, compound of Formula 2-K of the present invention can be used as host of a light emitting layer.

On the other hand, even if the core is same or similar, the band gap, the electrical characteristics, the interface characteristics and the like may be different depending on which substituent is bonded at which position. Therefore, there is a need to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.) and the like among the respective layers of an organic material layer is achieved.

Therefore, the energy level and $T_1$ value between the respective layers of the organic material layer, inherent material properties (mobility, interfacial properties, etc.) and the like can be optimized by using a mixture of compound of Formula 1 and compound of Formula 2 or compound of Formula 2-K as host of a light emitting layer in the present invention.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or alloy on the substrate to form the anode 120, forming the organic material layer including the hole injection layer 130, the hole transport layer 140, the light emitting layer 150, the electron transport layer 160, and the electron injection layer 170 thereon, and then depositing a material which can be used as the cathode 180, thereon. In addition, an emitting auxiliary layer 151 may be formed between a hole transport layer 140 and a light emitting layer 150, and an electron transport-auxiliary layer may be formed between a light emitting layer 150 and an electron transport layer 160.

In addition, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to the present invention may be selected from group consisting of an organic electroluminescent element, an organic solar cell, an organic photo conductor, an organic transistor, an element for monochromatic illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, various kinds of computers and so on.

Hereinafter, compound and an organic electric element according to an aspect of the present invention and will be described.

In one aspect of the present invention, the present invention provides an organic electric element comprising a first electrode, a second electrode, and an organic material layer formed between the first electrode and the second electrode, wherein the organic material layer comprises a phosphorescent light emitting layer, and host of the phosphorescent light emitting layer comprises a first compound represented by Formula 1 and a second compound represented by Formula 2.

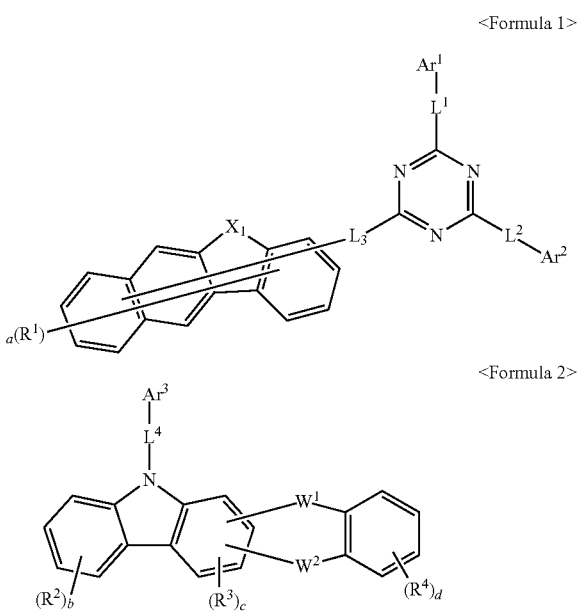

<Formula 1>

<Formula 2>

First, Formula 1 is described in detail.
In Formula 1, each of symbols is defined as follows:
$X_1$ is O or S.

$Ar^1$ and $Ar^2$ are each independently selected from the group consisting of a $C_6$-$C_{18}$ aryl group, a fluorenyl group, a $C_2$-$C_{18}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

Preferably, $Ar^1$ and $Ar^2$ are each independently selected from the group consisting of a $C_6$-$C_{18}$ aryl group, a fluorenyl group, a $C_2$-$C_{16}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

Where $Ar^1$ and $Ar^2$ are each an aryl group, the aryl group may be phenyl, biphenyl, naphthyl, terphenyl, phenanthrene, pyrene, triphenylene, anthracene and the like. Where $Ar^1$ and $Ar^2$ are each a heterocyclic group, the heterocyclic group may be dibenzothiophene, dibenzofuran, carbazole, phenylcarbazole, benzonaphthofuran, benzonaphthothiophene and the like. Where $Ar^1$ and $Ar^2$ are each a fluorenyl group, the fluorenyl group may be 9,9-diphenylfluorene, 9,9-dimethylfluorene and the like. Where $Ar^1$ and $Ar^2$ are each aliphatic ring, the aliphatic ring may be preferably a $C_3$-$C_{30}$ aliphatic ring, more preferably, a $C_3$-$C_{12}$ aliphatic ring, for example, cyclohexane, cyclohexylcyclohexane, or the like. Where $Ar^1$ and $Ar^2$ are each an alkyl group, the alkyl group may be preferably a $C_2$-$C_{10}$ alkyl group, for example, methyl, t-butyl and the like. Where $Ar^1$ and $Ar^2$ are each an alkenyl group, the alkenyl group may be preferably a $C_2$-$C_{10}$ alkenyl group, for example, ethene, propene and the like.

$L^1$ to $L^3$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Where $L^1$ to $L^3$ are each an arylene group, the arylene group may be preferably a $C_6$-$C_{30}$ arylene group, more preferably a $C_6$-$C_{18}$ arylene group, for example, phenyl, biphenyl, naphthyl, terphenyl and the like. Where $L^1$ to $L^3$ are each a heterocyclic group, the heterocyclic group may be preferably a $C_2$-$C_{30}$ heterocyclic group, more preferably a $C_2$-$C_{18}$ heterocyclic group, for example, carbazole, phenylcarbazole, dibenzofuran, dibenzothiophene and the like.

$R^1$ is selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be bonded to each other to form a ring.

a is an integer of 0-9, and where a is an integer of 2 or more, each of a plurality of $R^1$s is the same as or different from each other.

The ring formed by bonding between neighboring $R^1$s may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring $R^1$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

Where $R^1$ is an aryl group, the aryl group may be preferably a $C_6$-$C_{30}$ aryl group, more preferably a $C_6$-$C_{18}$ aryl group, for example, phenyl, naphthyl, biphenyl, terphenyl, phenanthrene, and the like.

L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

$R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Formula 1 may be represented by one of the following Formulas:

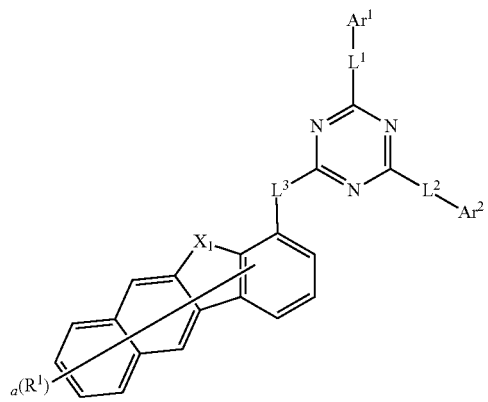

<Formula 1-A>

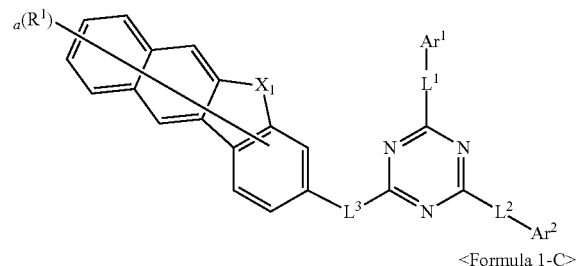

<Formula 1-B>

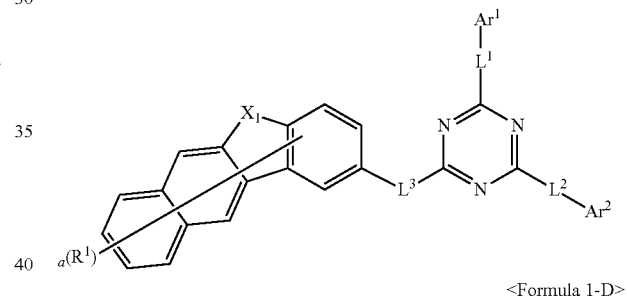

<Formula 1-C>

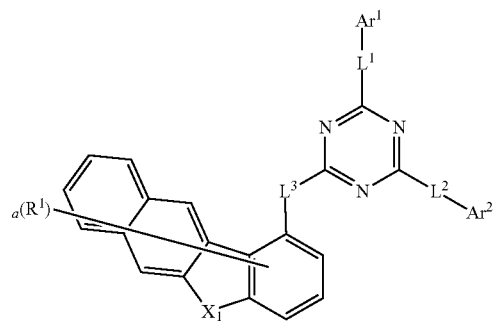

<Formula 1-D>

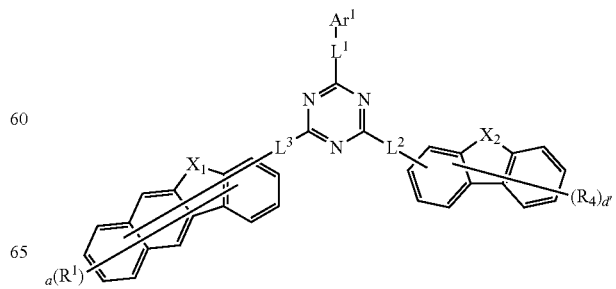

<Formula 1-E>

<Formula 1-F>

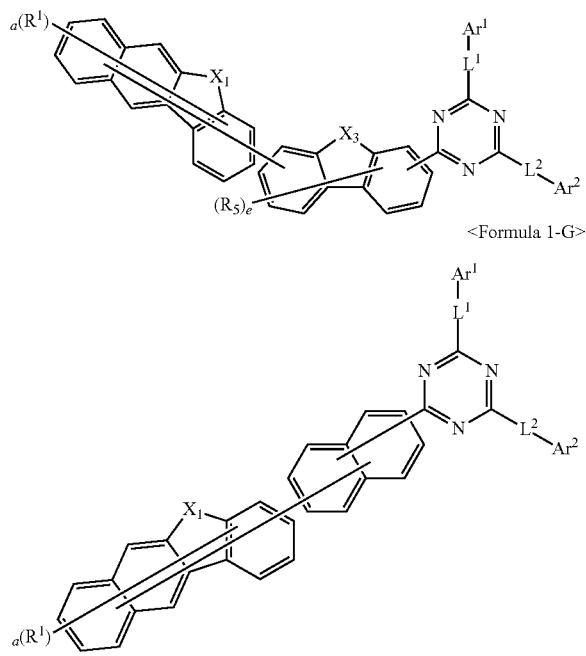

<Formula 1-G>

In Formulas 1-A to 1-G, each symbol can be defined as follows.

$Ar^1$, $Ar^2$, $L^1$-$L^3$, $X_1$, $R^1$ and a are the same as defined for Formula 1. Preferably, in Formulas 1-F and 1-G, $Ar^1$ and $Ar^2$ are different from each other, and preferably, $Ar^1$ and $Ar^2$ are each independently an aryl group, more preferably naphthyl.

$X_2$ and $X_3$ are each independently O or S.

$R_4$ and $R_5$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group and -$L^a$-N($R^a$)($R^b$), and adjacent groups may be linked to each other to form a ring.

'The ring formed by bonding between neighboring groups' may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring $R_4$s or between neighboring $R_5$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

d' is an integer of 0-7, e' is an integer of 0-6, and where each of these is an integer of 2 or more, each of a plurality of $R_4$s, each of a plurality of $R_5$s are the same as or different from each other.

$L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R^b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

Preferably, each symbol in the above Formulas may be further substituted. For example, in Formula 1, Formulas 1-A to 1-G, $Ar^1$, $Ar^2$, $L^1$-$L^3$, $L'$, $L^a$, $R^1$, $R_4$, $R_5$, $R_a$, $R_b$, $R^a$, $R^b$, and the ring formed by bonding between adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Specifically, the compound represented by Formula 1 may be one of the following compounds, but it is not limited only thereto:

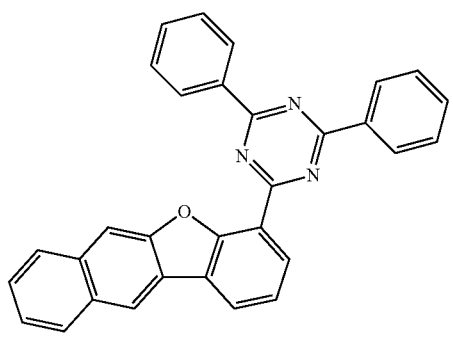

1-1

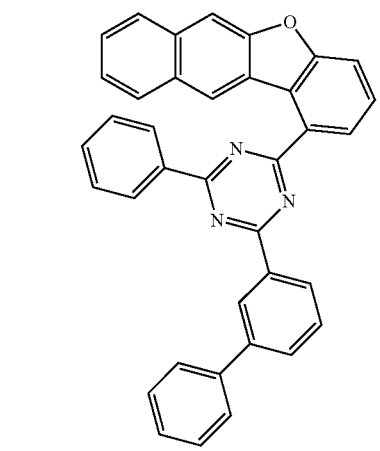

1-2

-continued
1-3
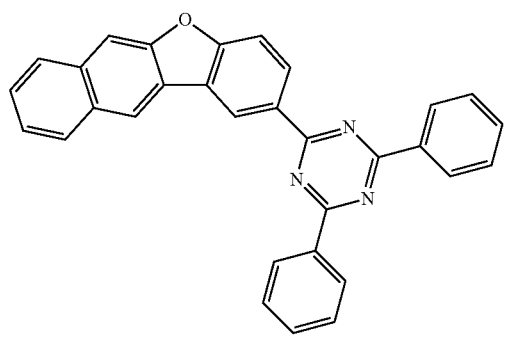
1-4
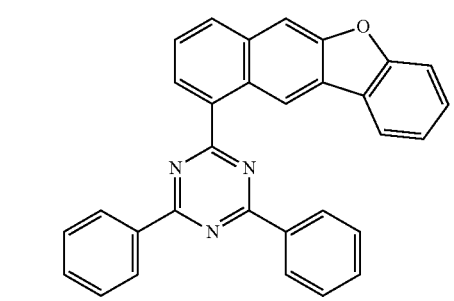
1-5
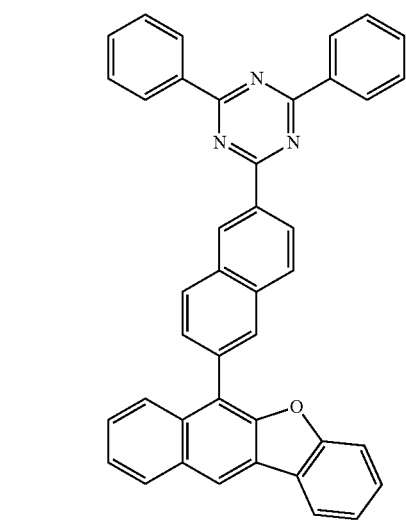
1-6
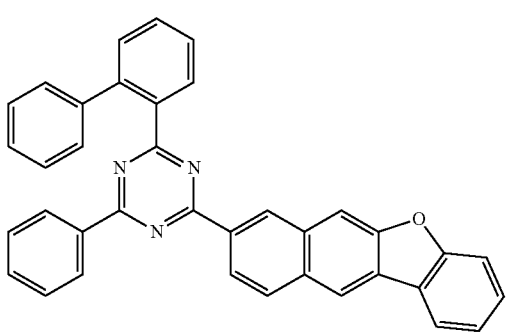
-continued
1-7
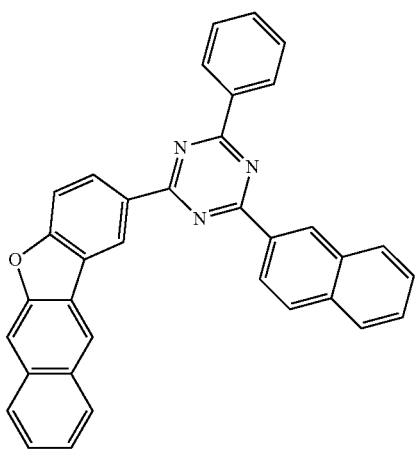
1-8
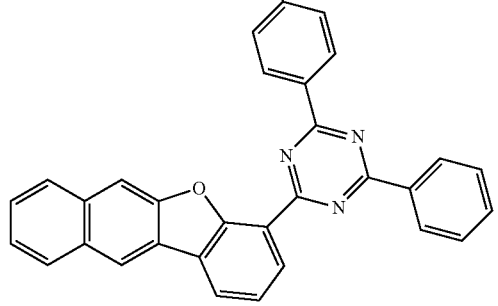
1-9
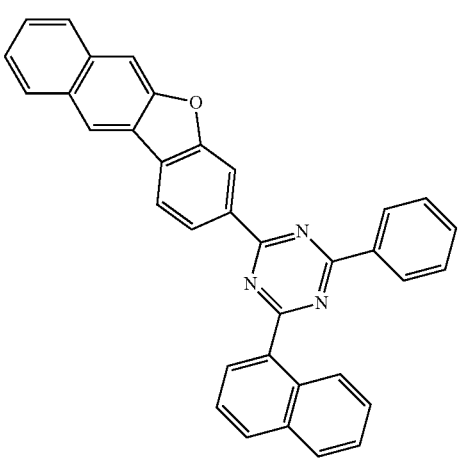

1-10 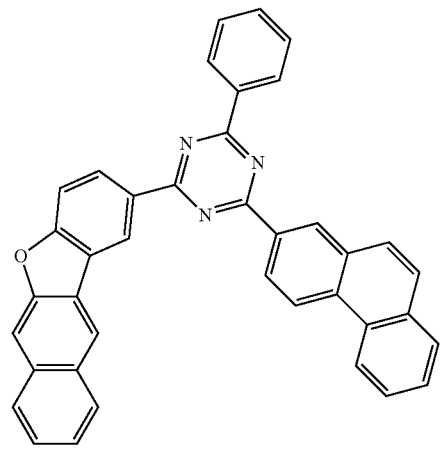
1-13 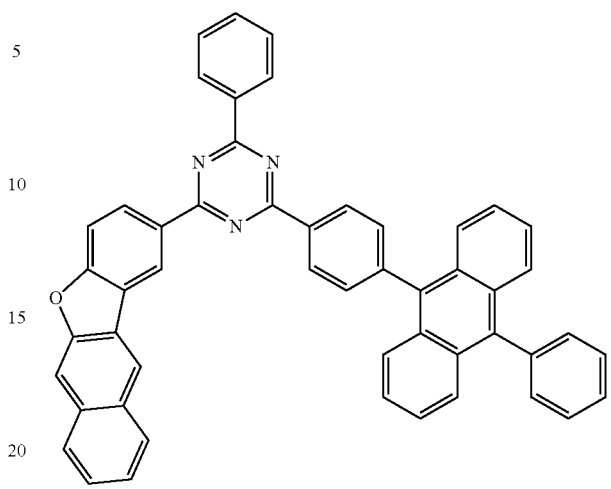
1-11 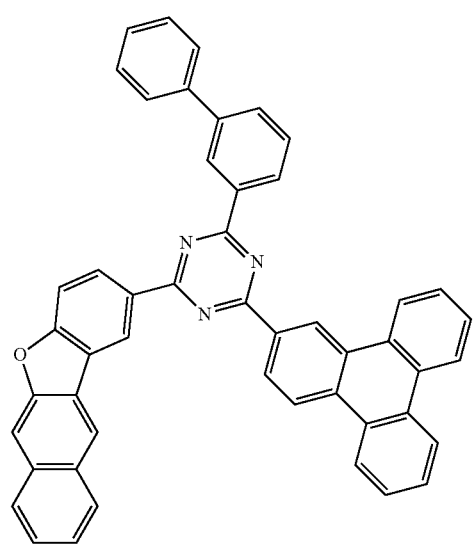
1-14 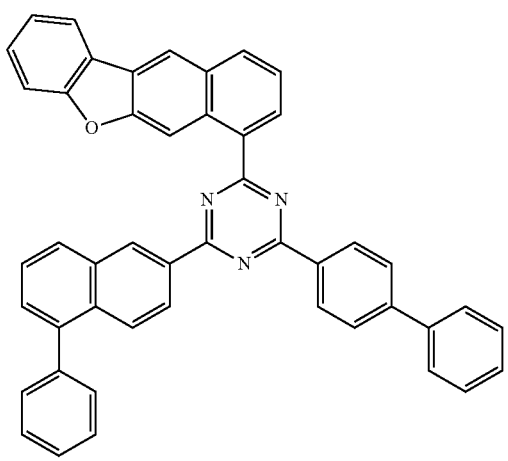
1-12 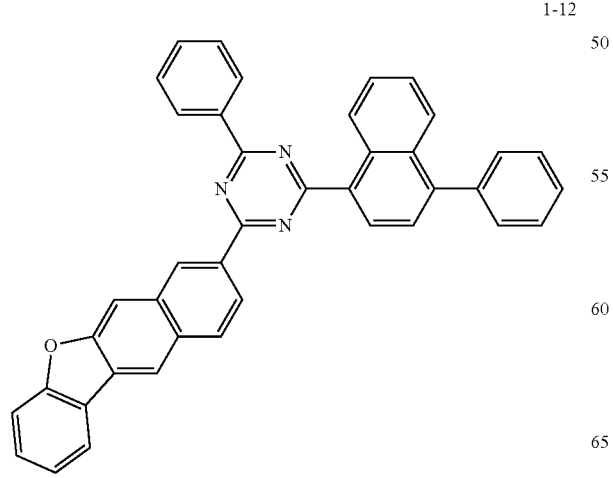
1-15 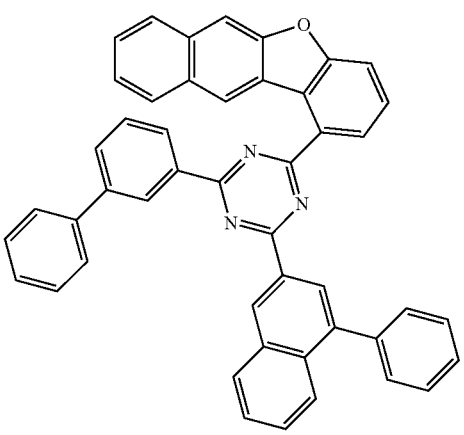

-continued
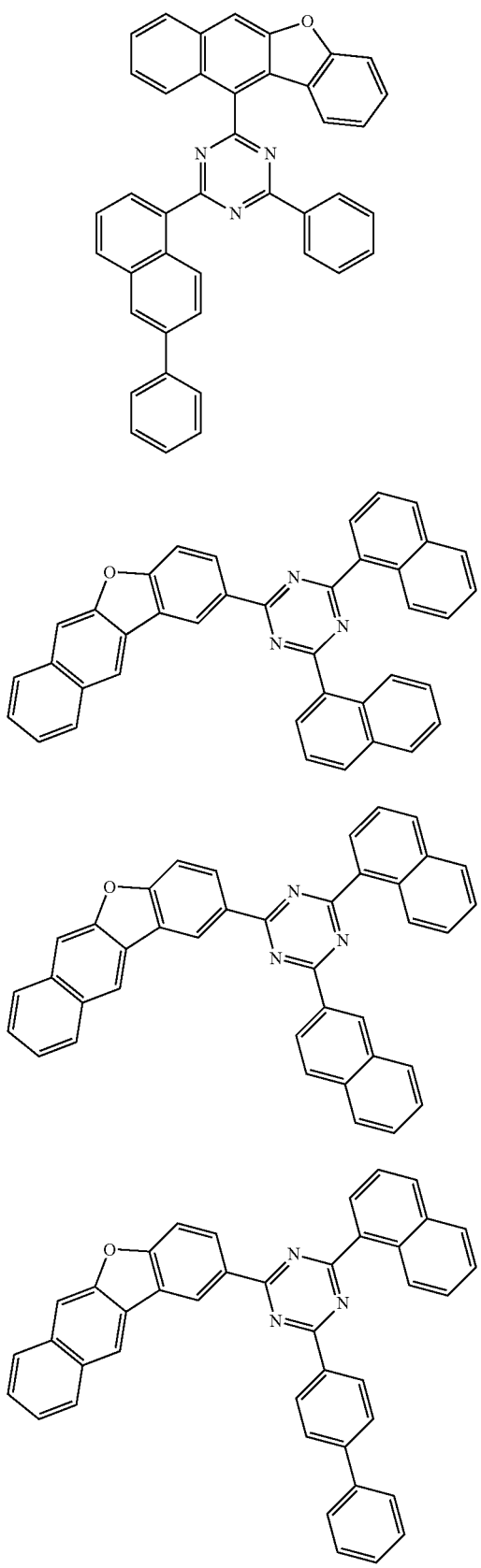
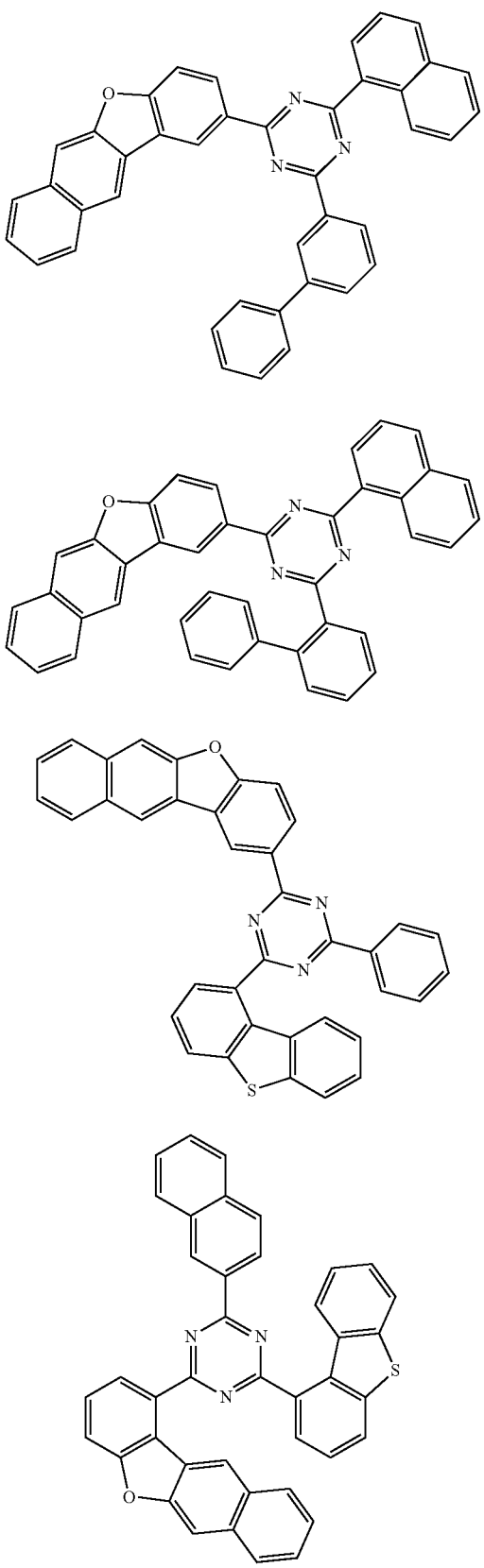

1-24
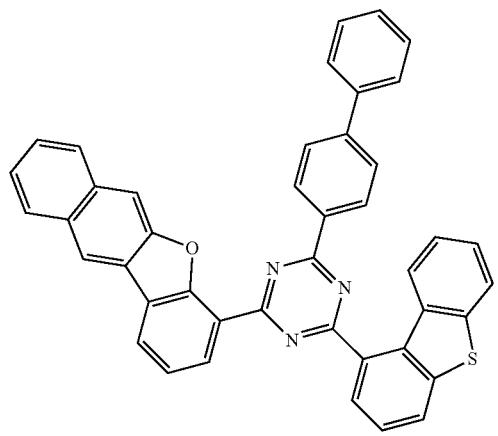
1-25
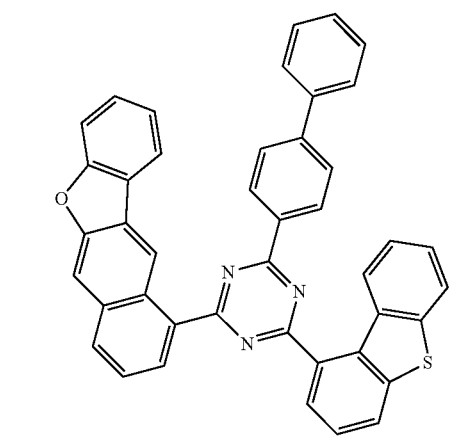
1-26
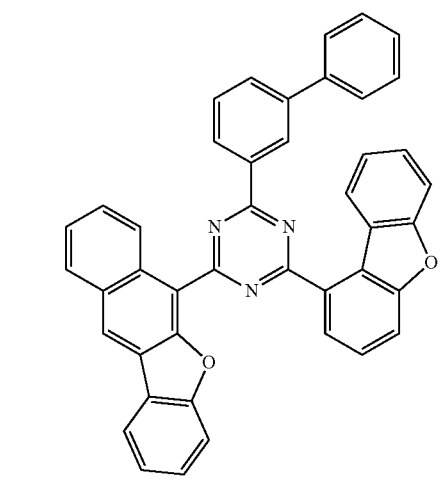
1-27
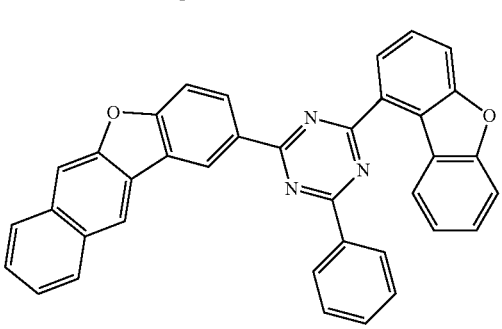
1-28
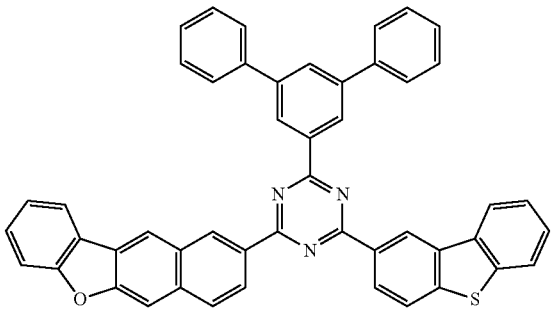
1-29
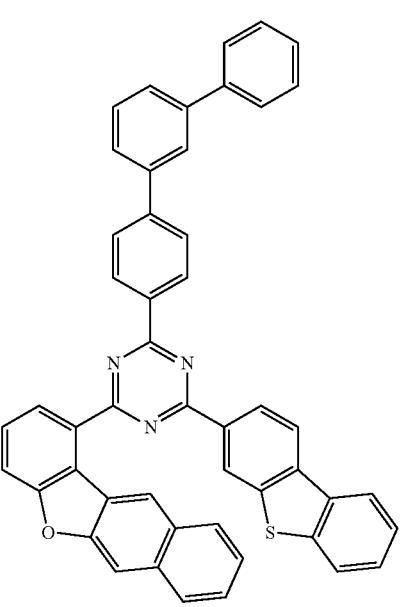
1-30
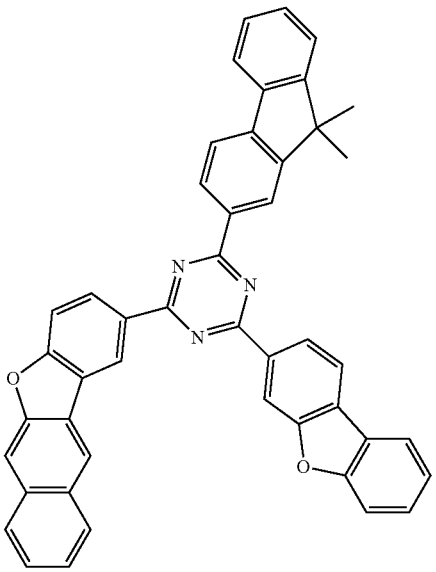

1-31
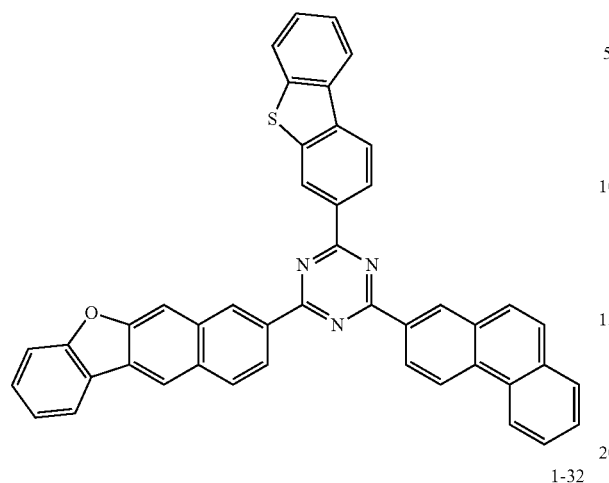
1-32
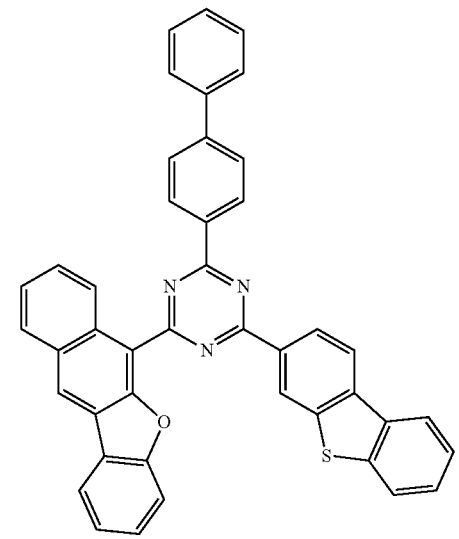
1-34
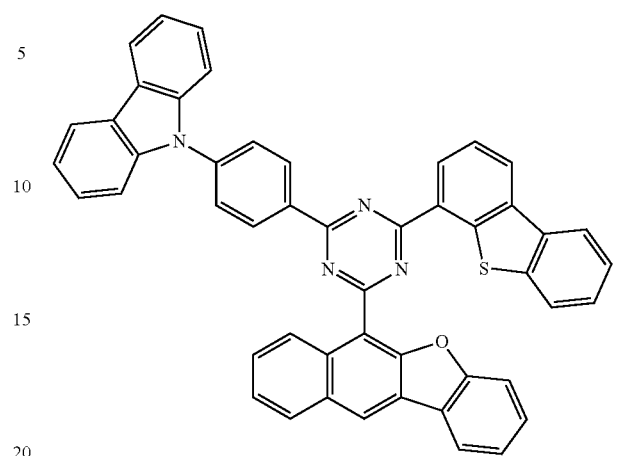
1-35
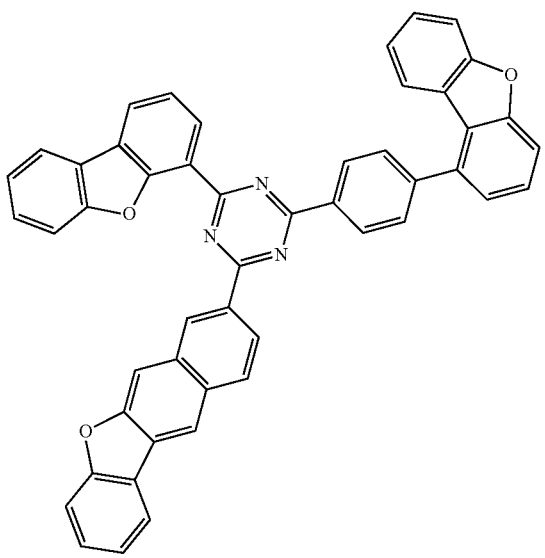
1-33
1-36
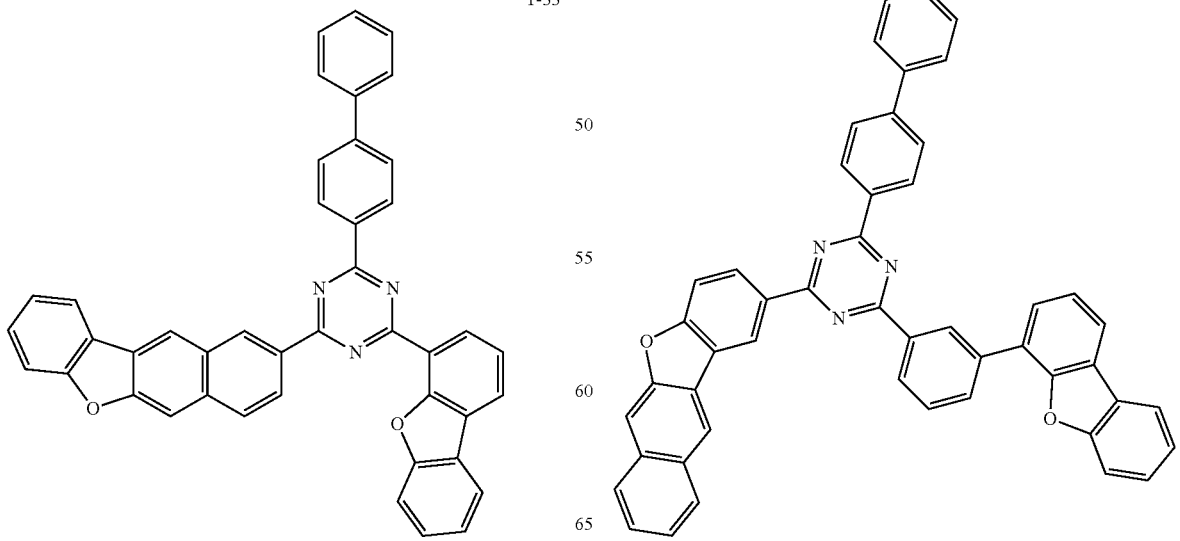

1-37
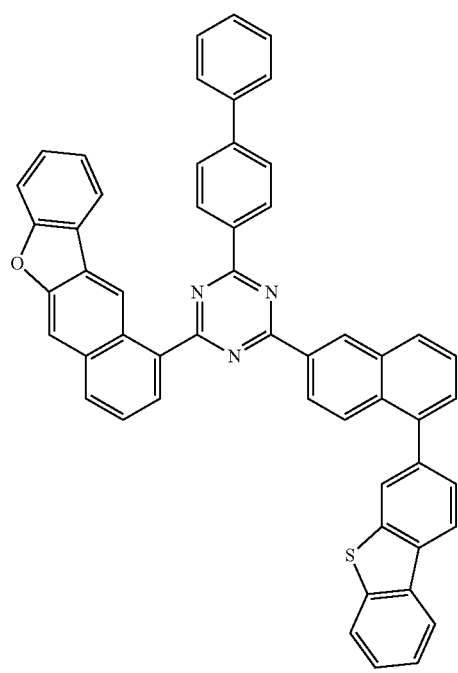
1-38
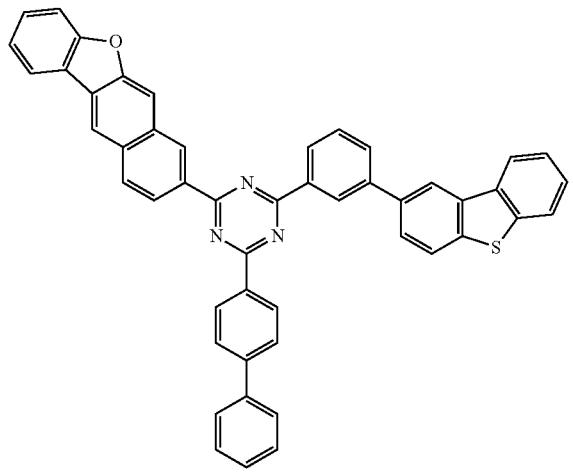
1-39
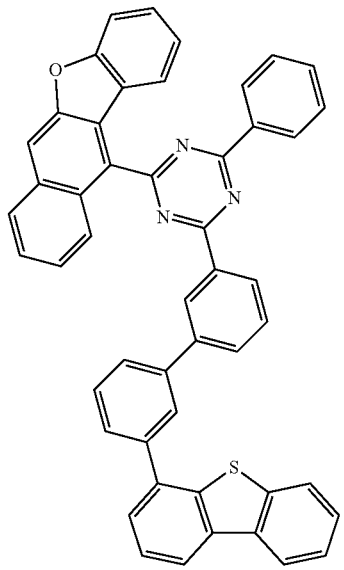
1-40
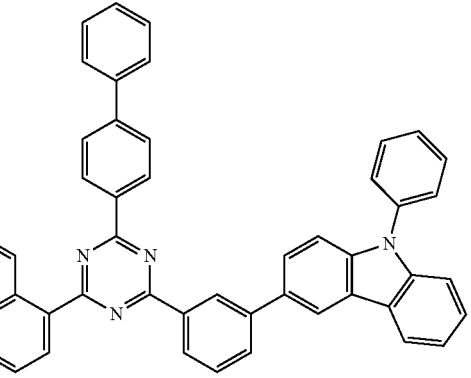
1-41
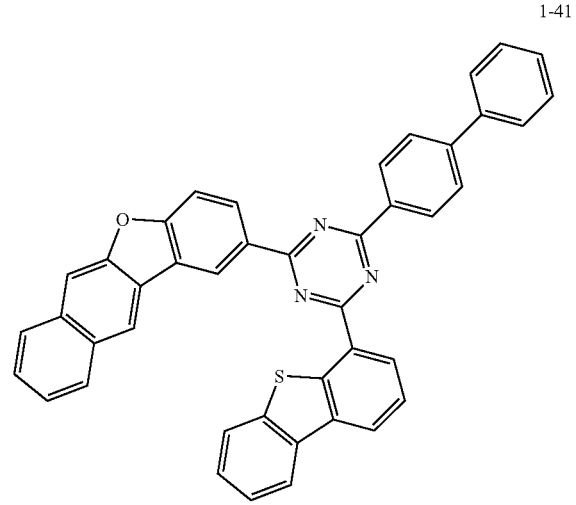

-continued
1-42
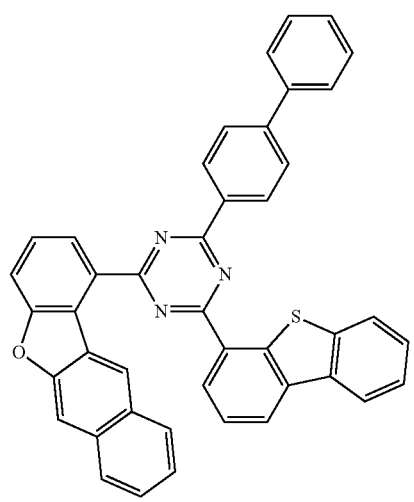
1-43
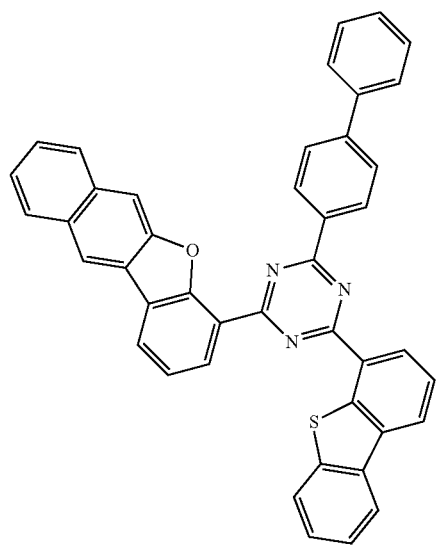
1-44
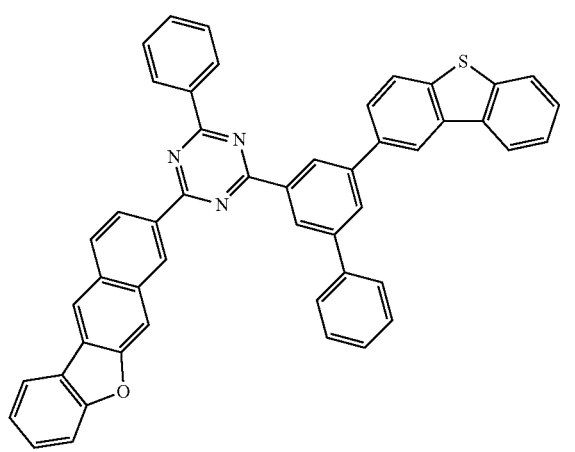
1-45
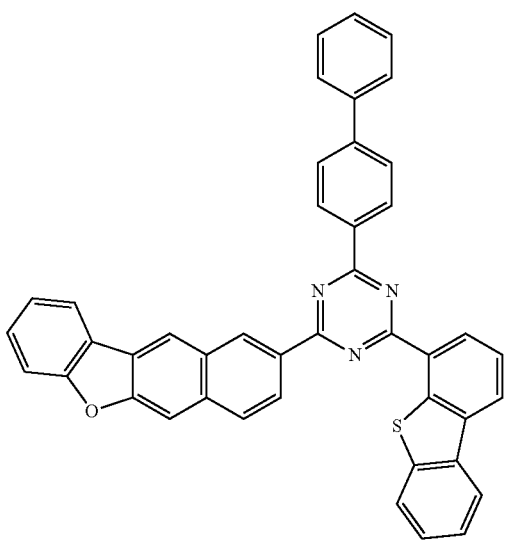
1-46
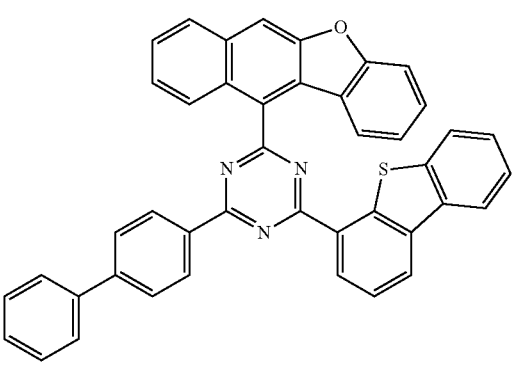
1-47
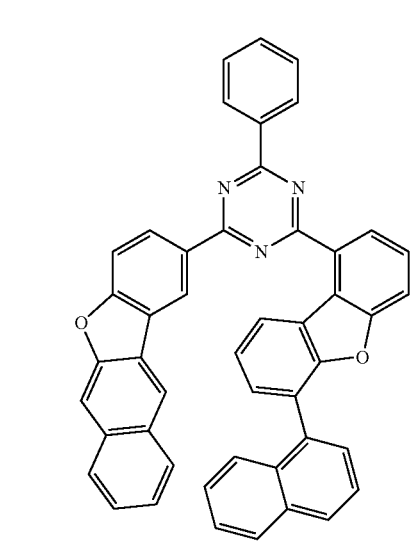

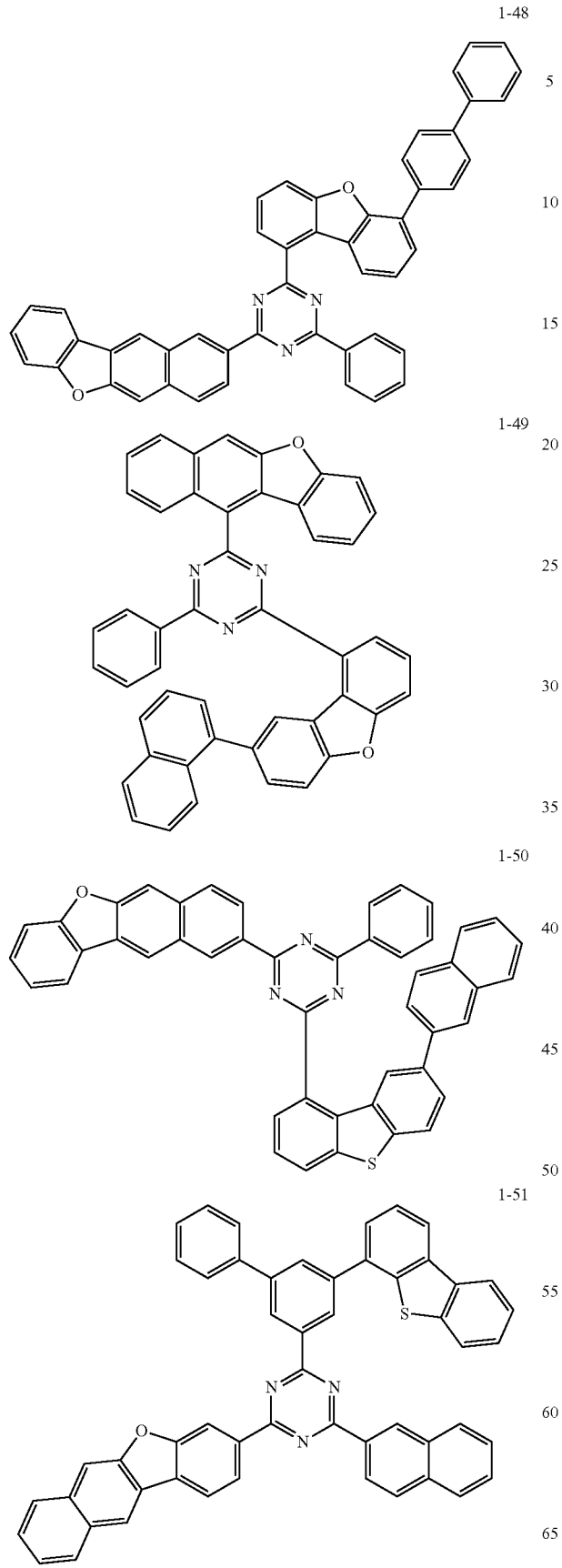

1-55
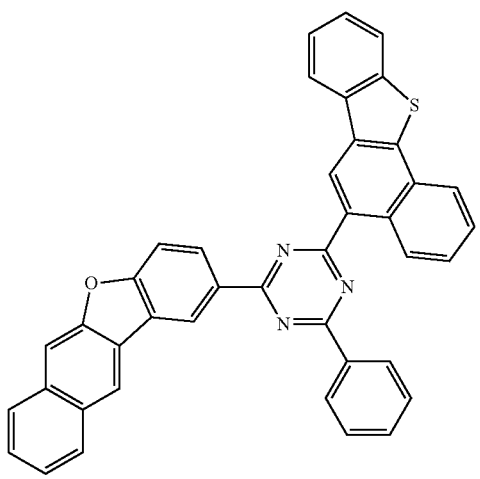
1-56
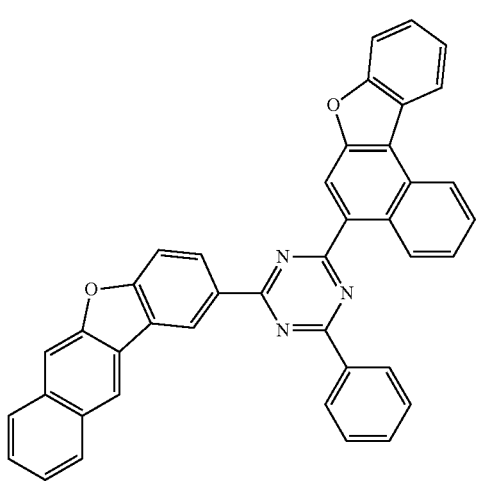
1-57
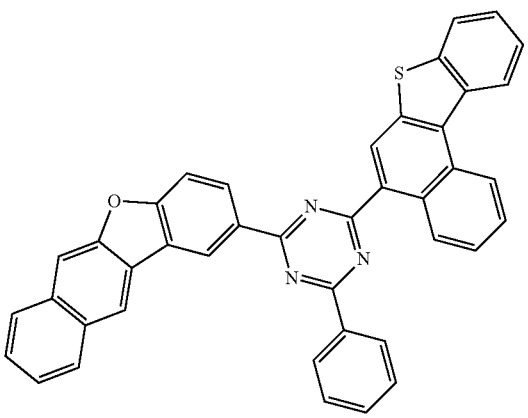
1-58
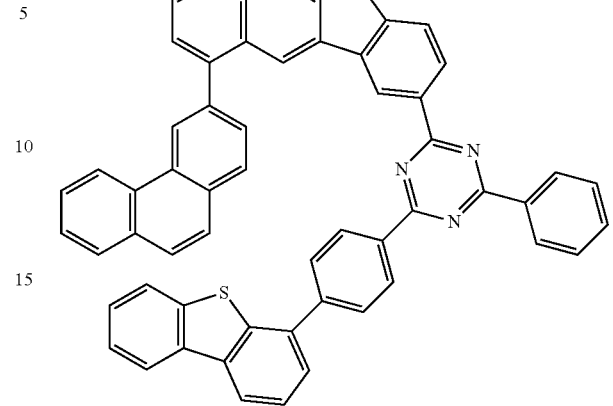
1-59
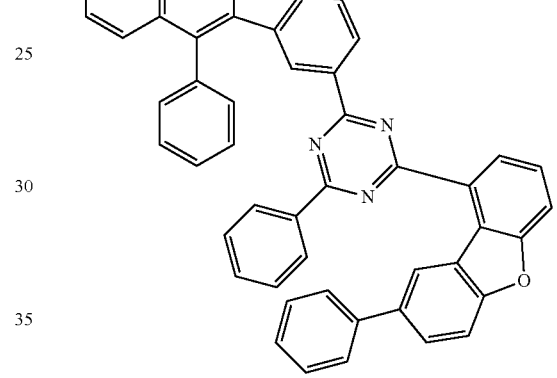
1-60
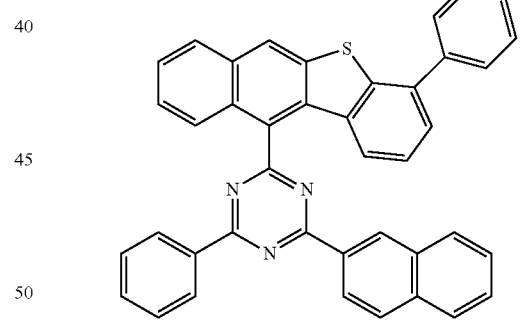
1-61
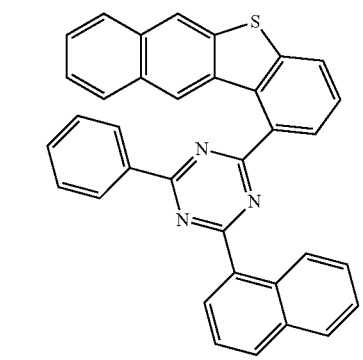

-continued
1-62
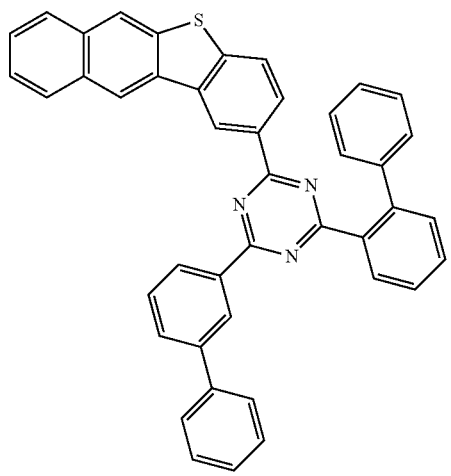
1-63
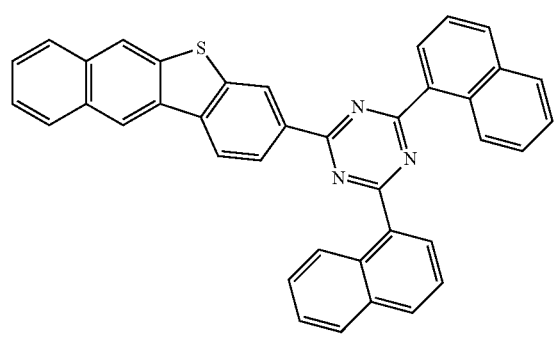
1-64
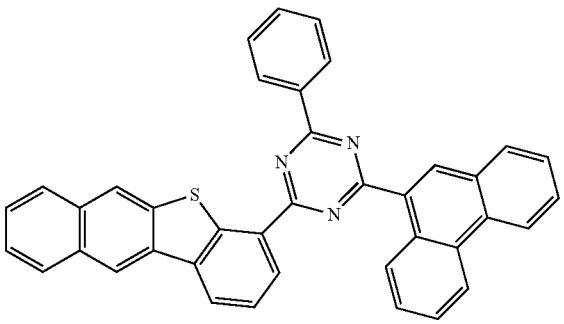
1-65
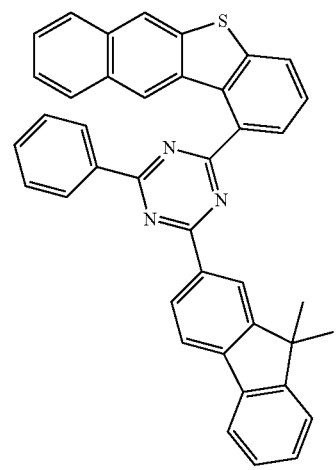
-continued
1-66
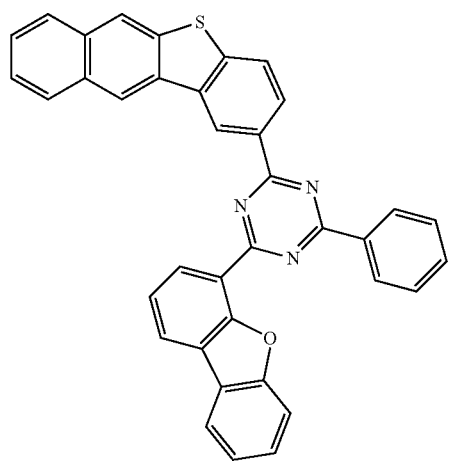
1-67
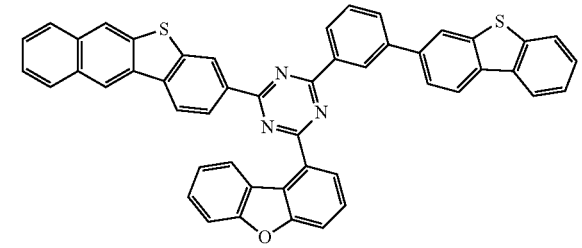
1-68
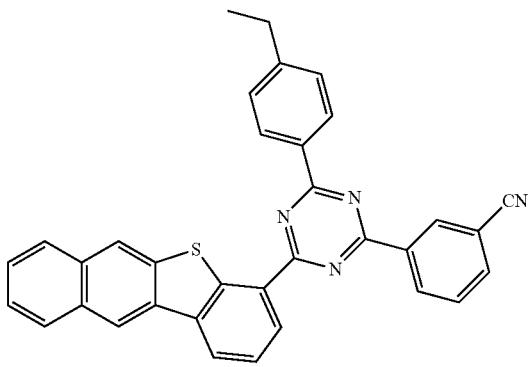
1-69
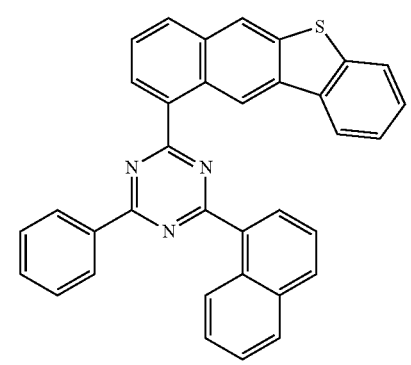

1-70
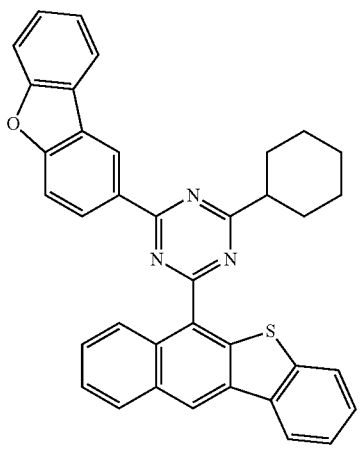
1-71
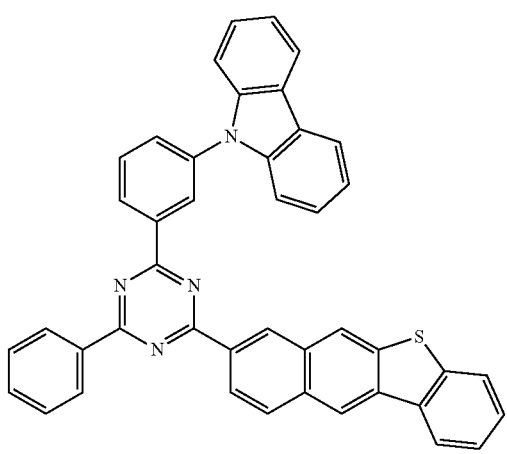
1-72
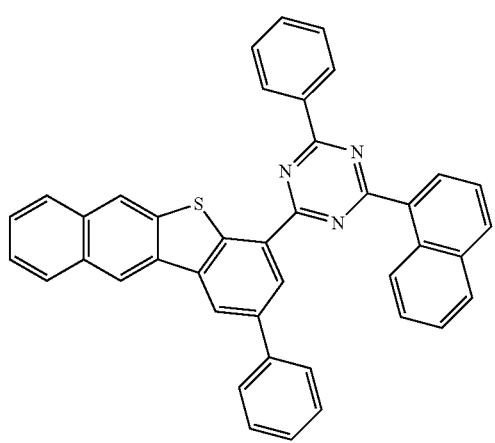
1-73
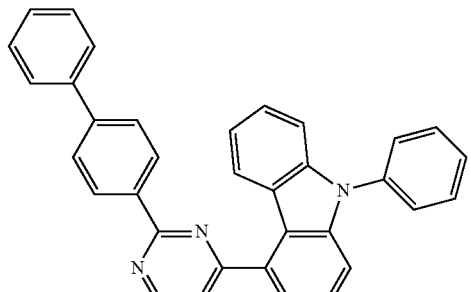
1-74
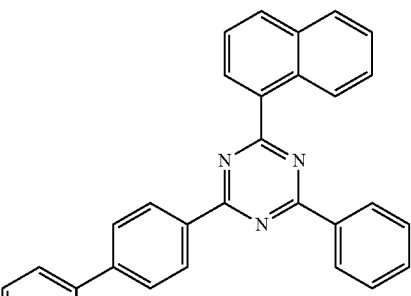
1-75
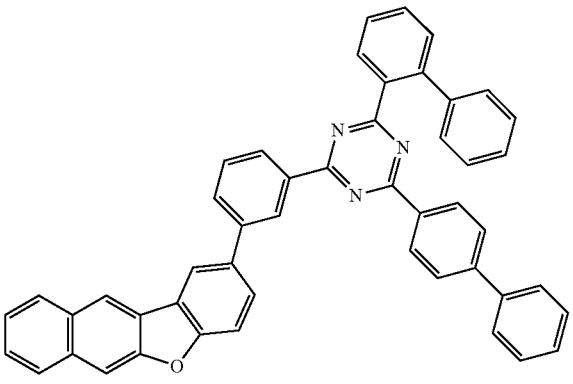

-continued
1-76
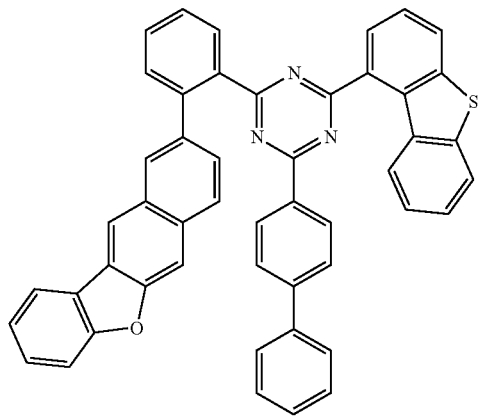
1-77
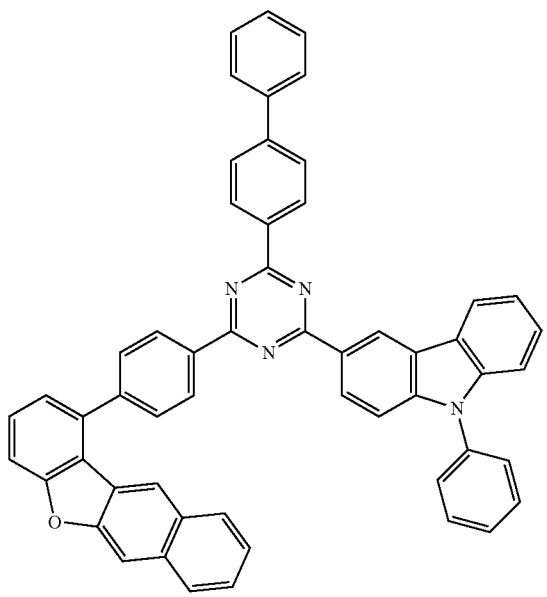
1-78
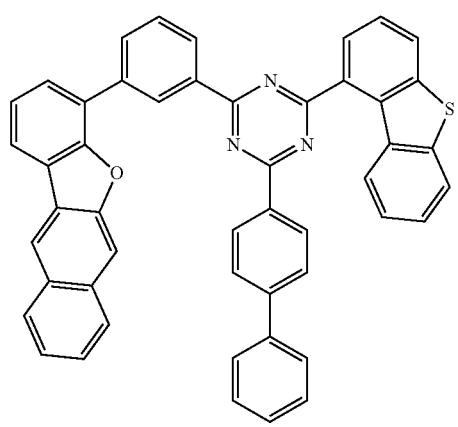
-continued
1-79
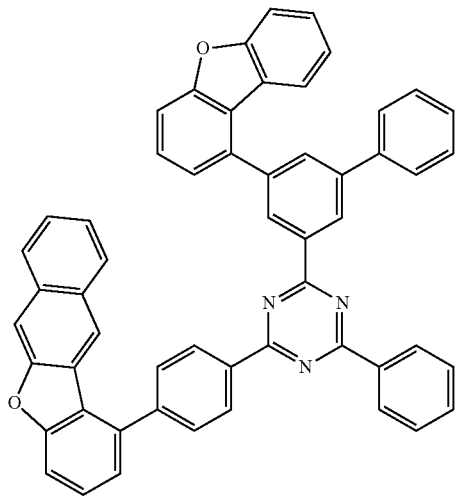
1-80
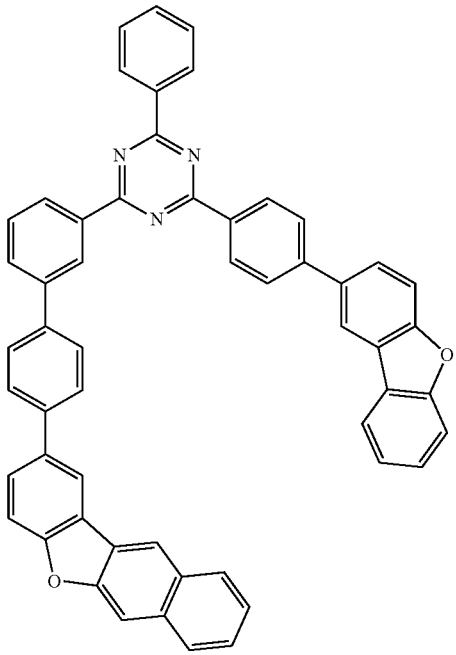
1-81
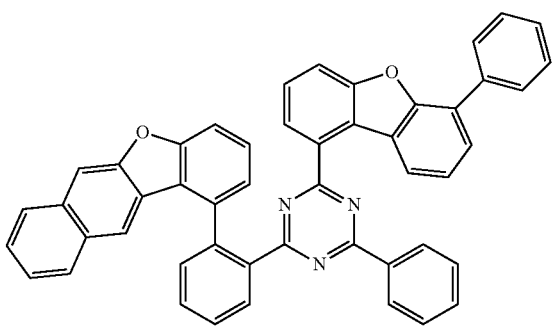

1-82
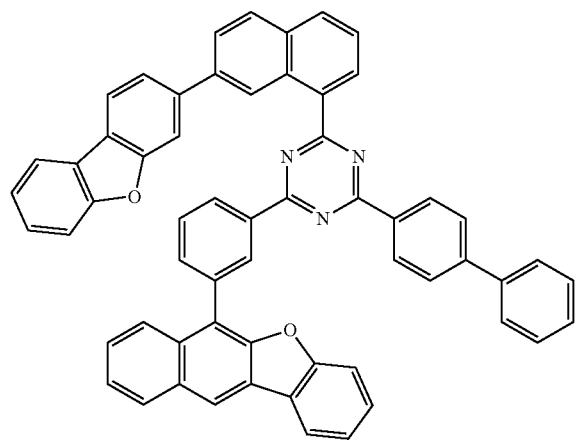
1-83
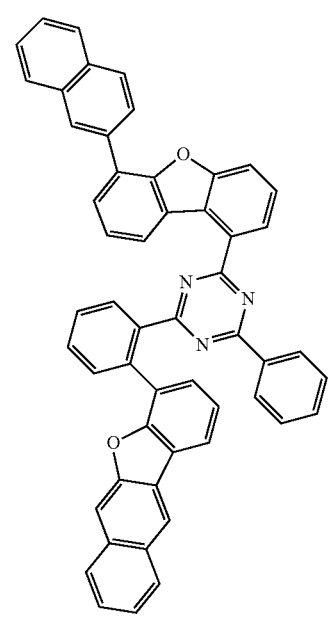
1-84
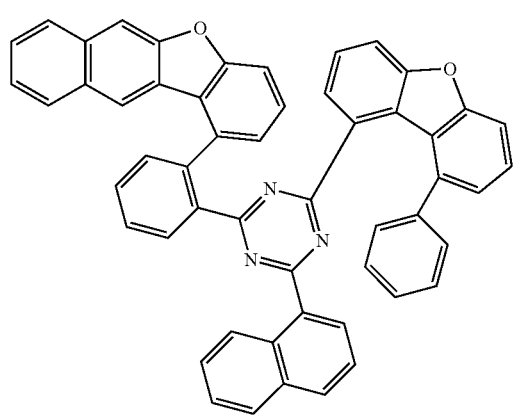
1-85
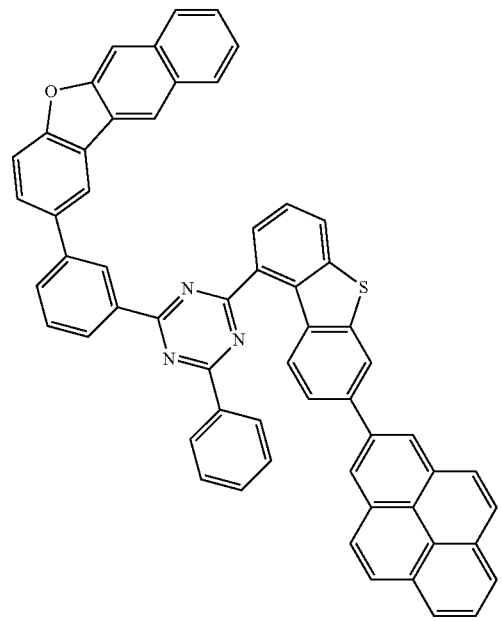
1-86
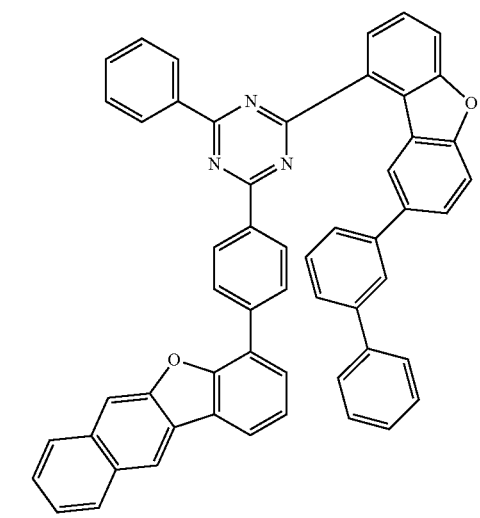
1-87
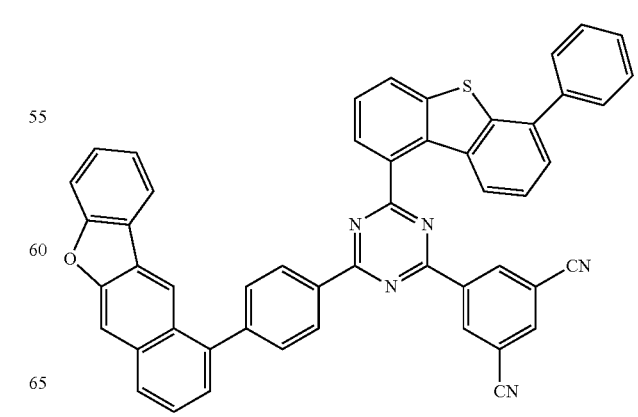

1-88
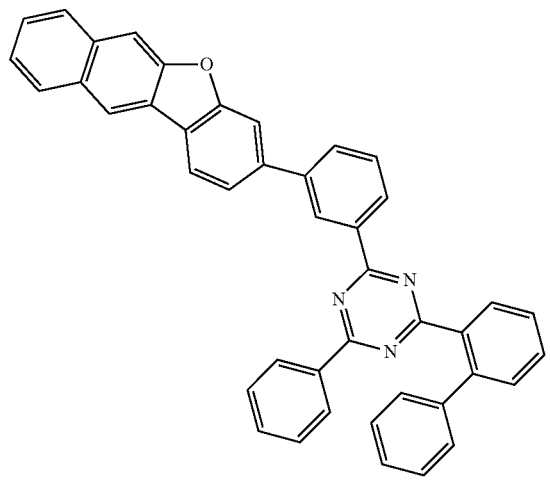
1-89
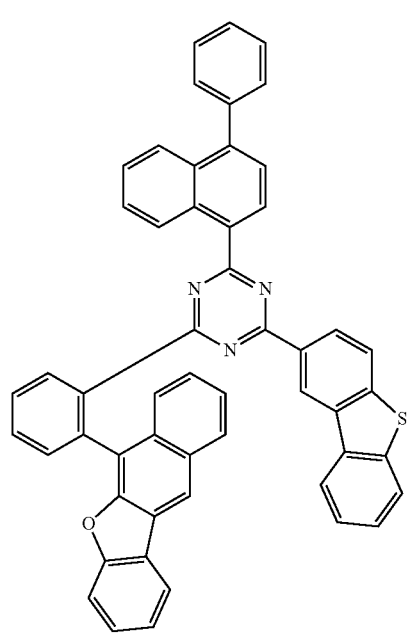
1-90
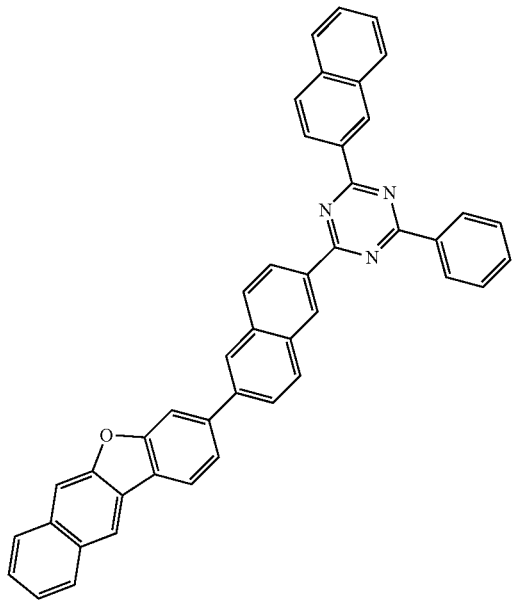
1-91
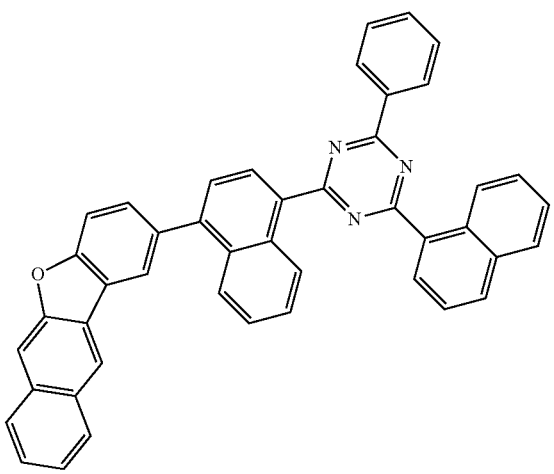
1-92

1-93
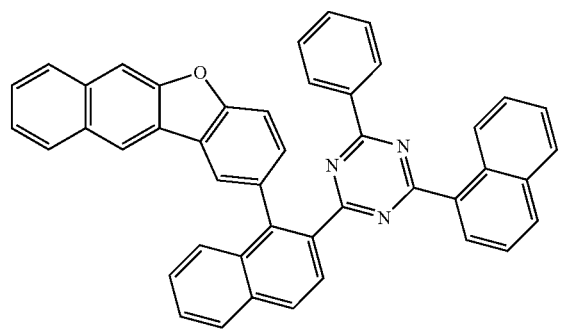
1-94
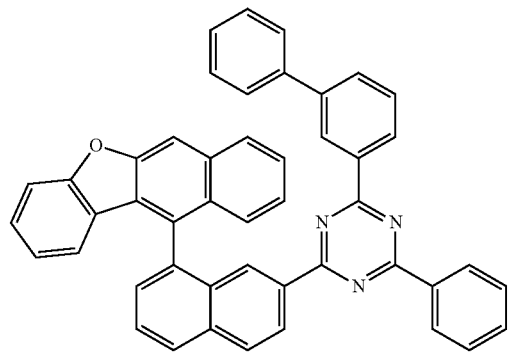
1-95
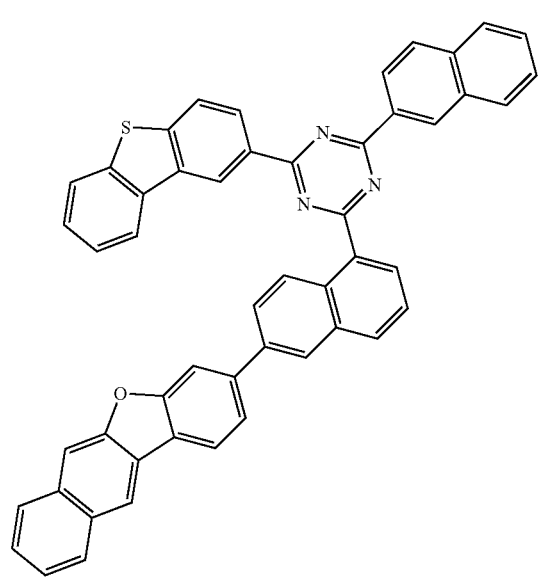
1-96
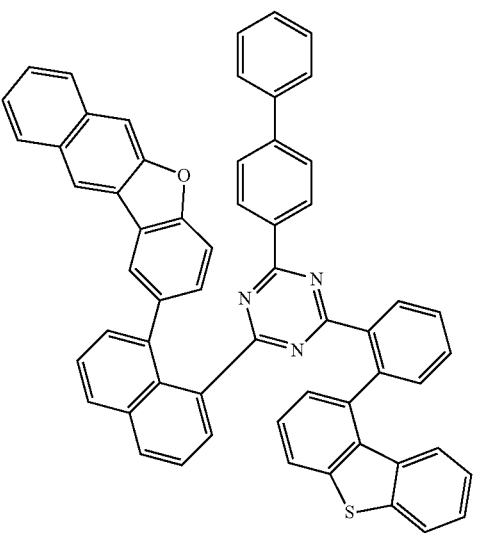
1-97
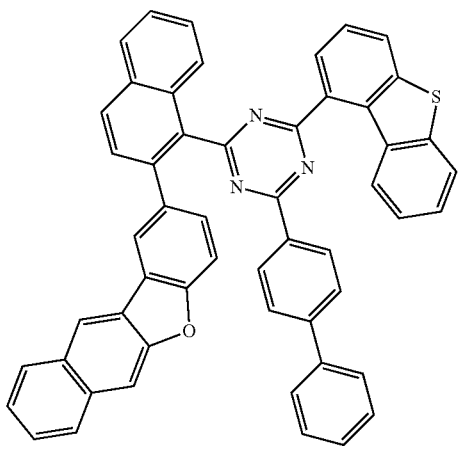
1-98
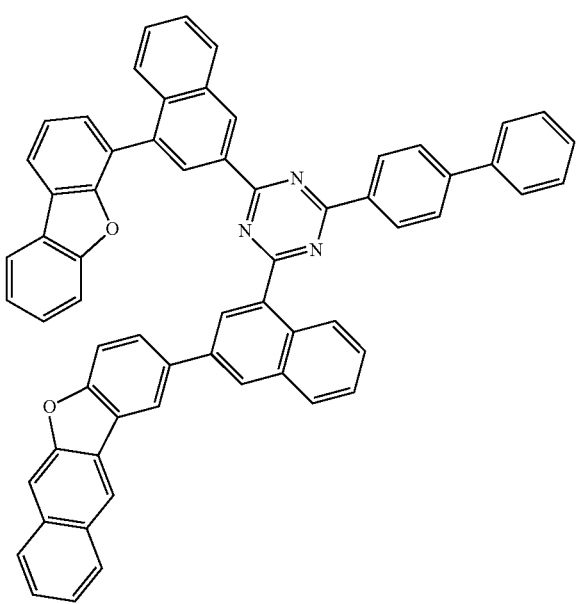

1-99
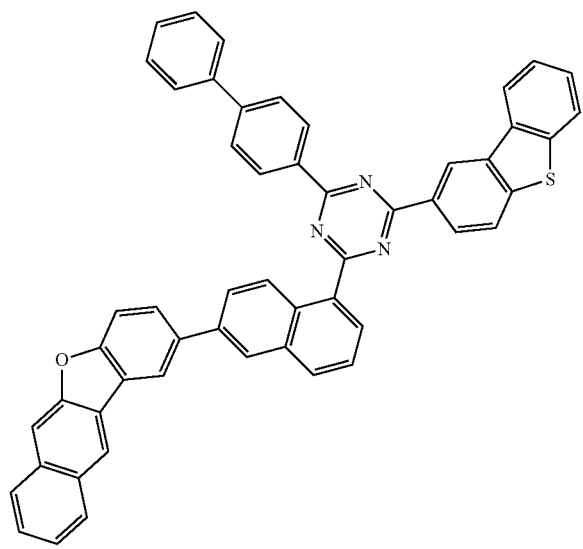
1-100
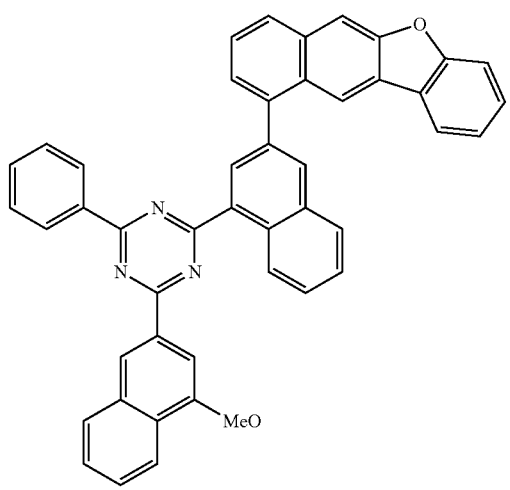
1-101
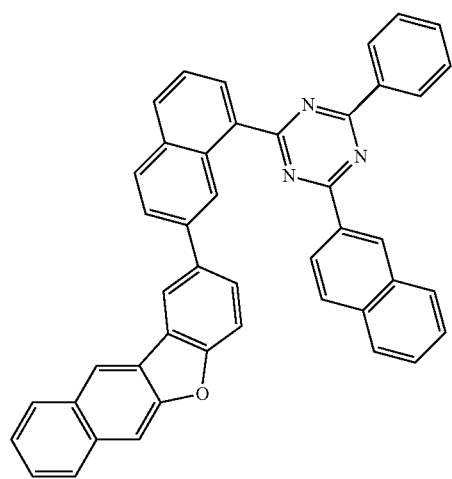
1-102
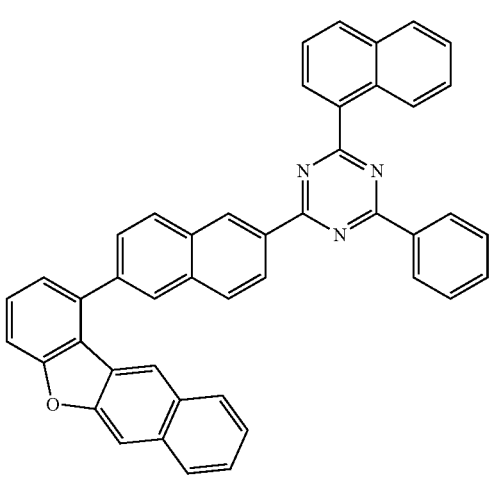
1-103
1-104
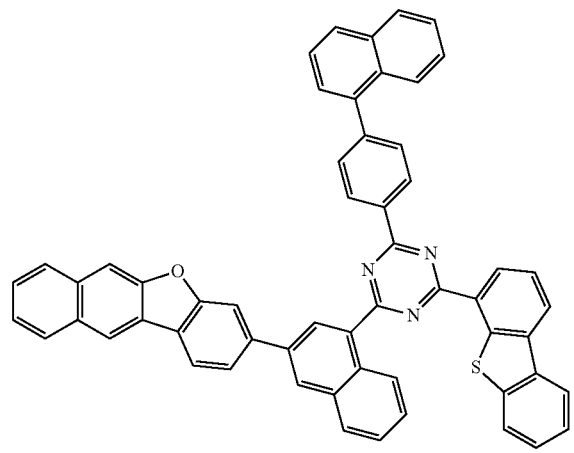

1-105
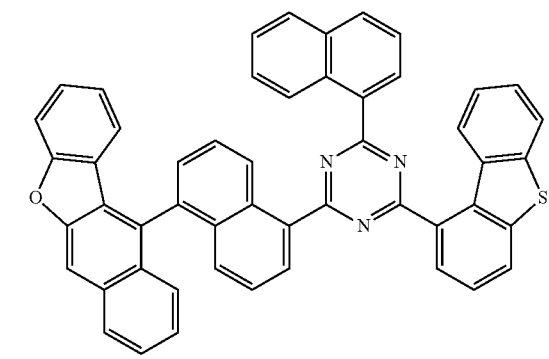
1-106
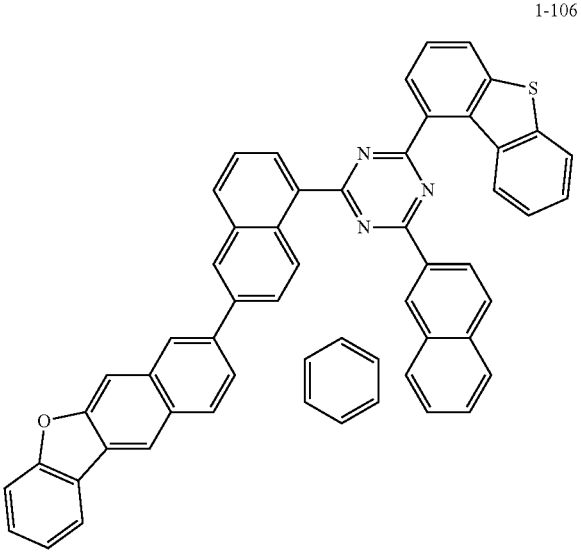
1-107
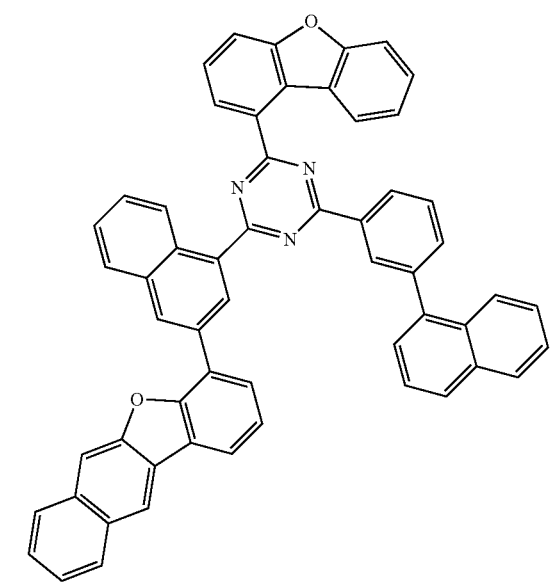
1-108
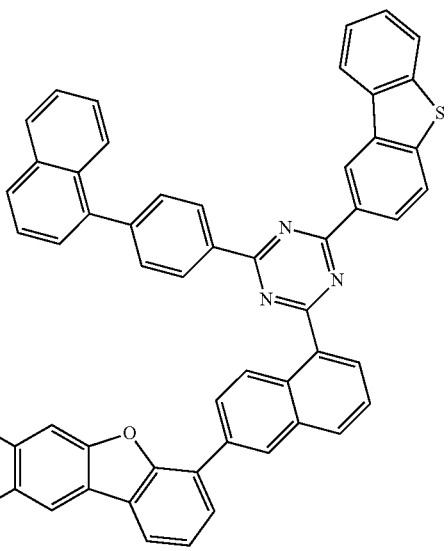
1-109
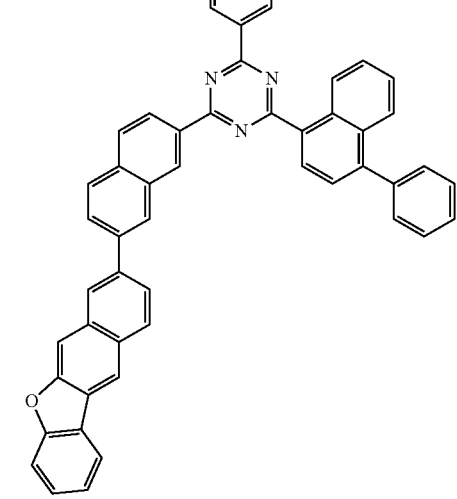
1-110
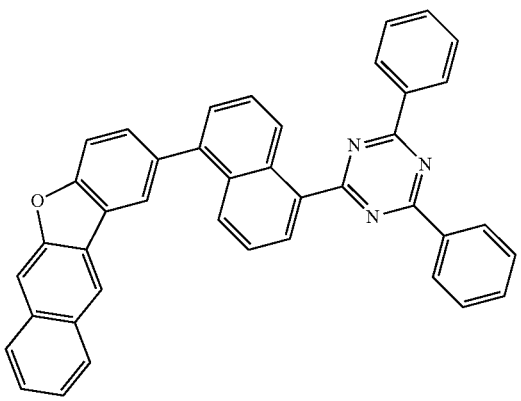

1-111
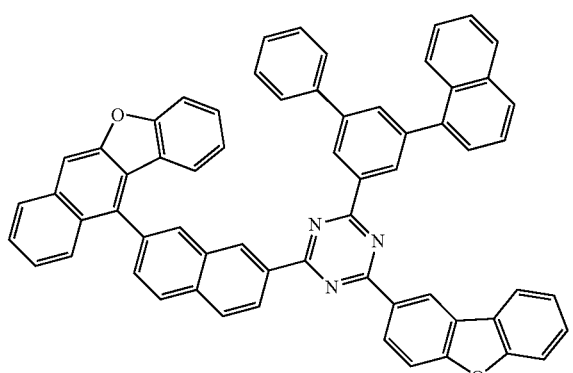
1-112
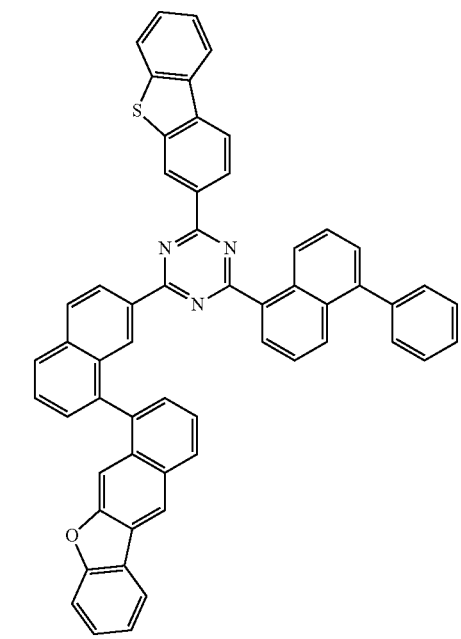
1-113
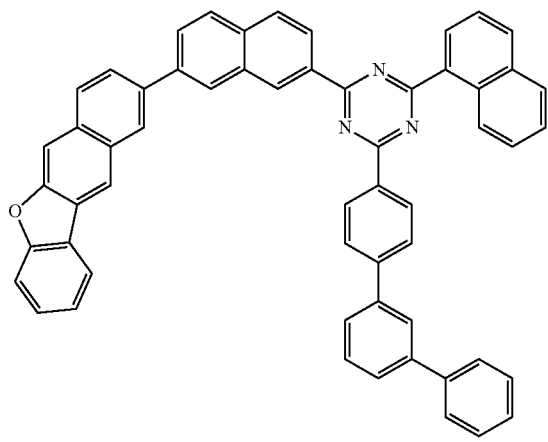
1-114
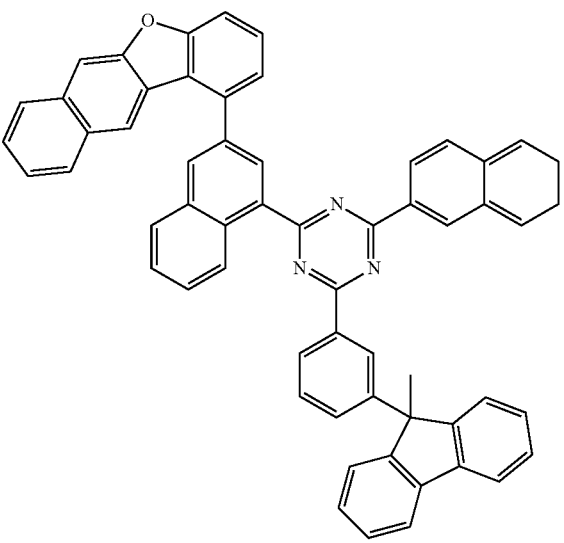
1-115
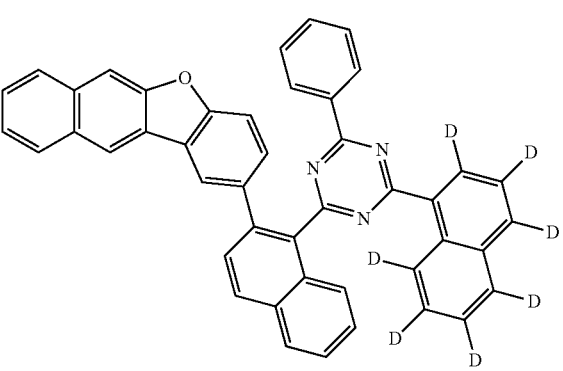
1-116
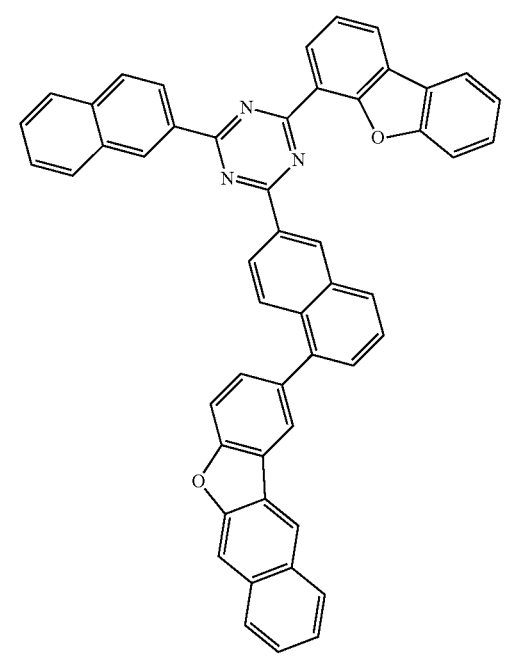

1-117
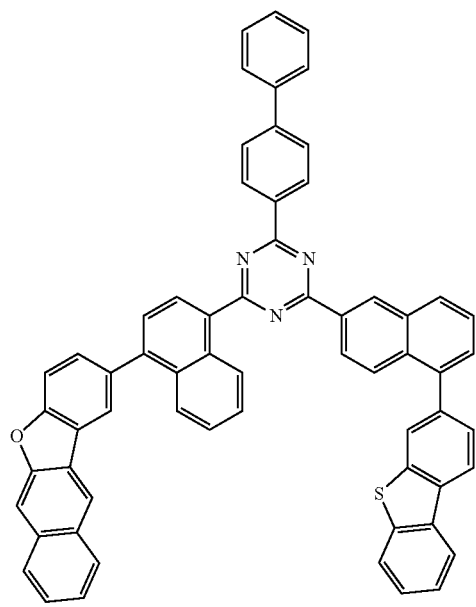
1-119
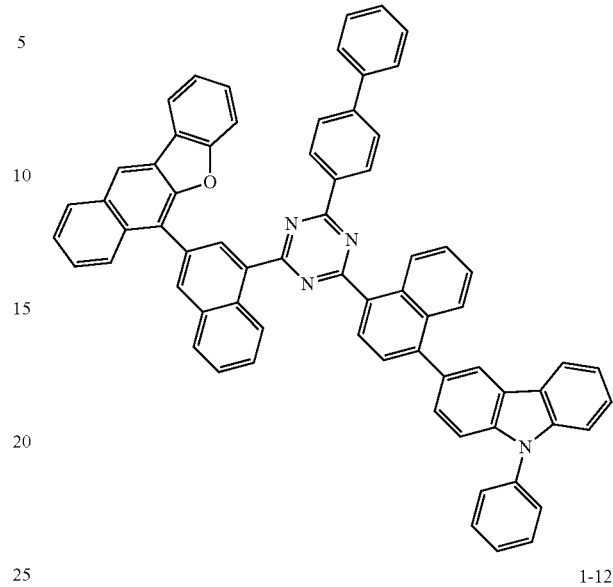
1-120
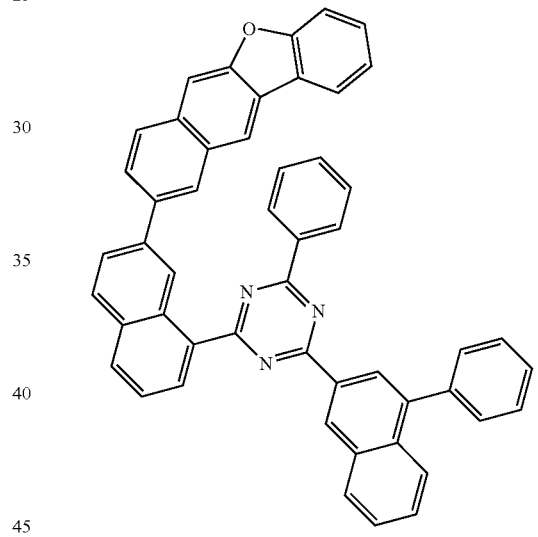
1-118
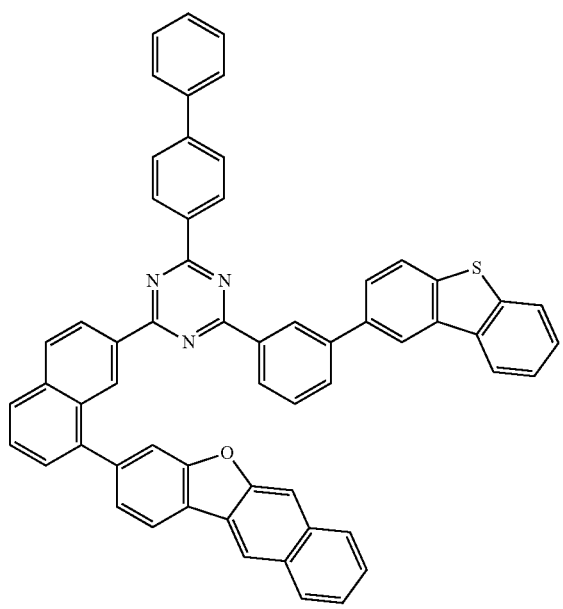
1-121
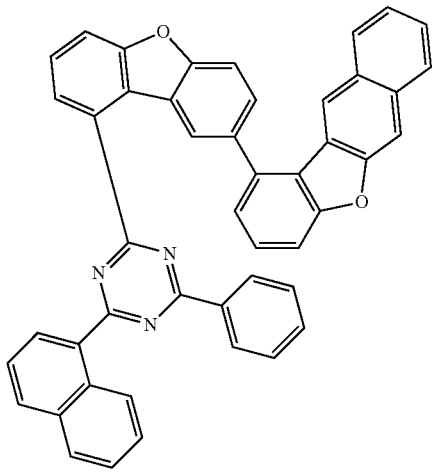

1-122
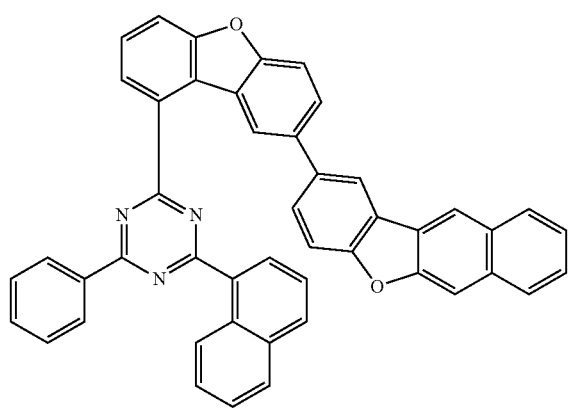
1-123
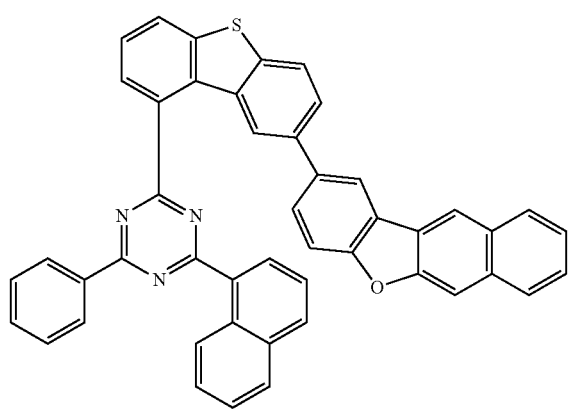
1-124
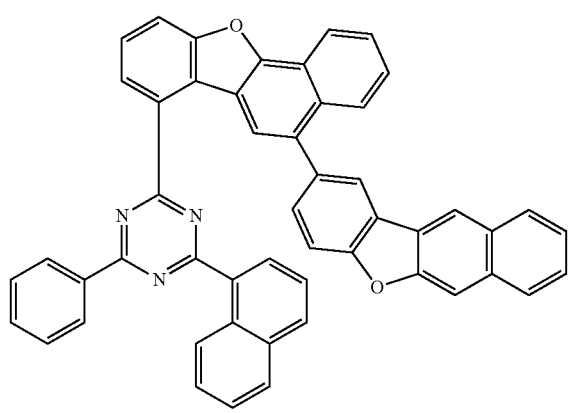
1-125
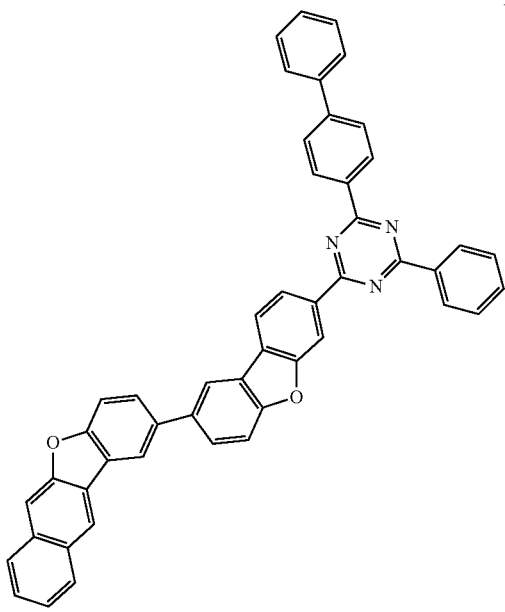
1-126
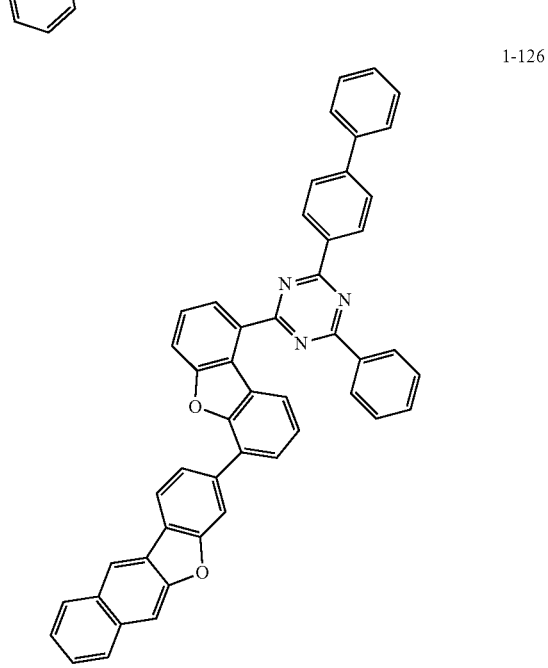
1-128
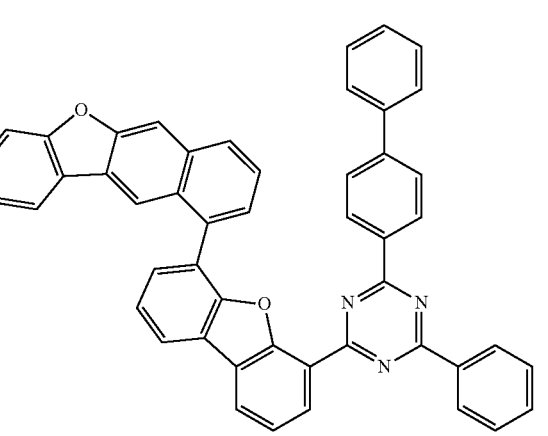

1-129
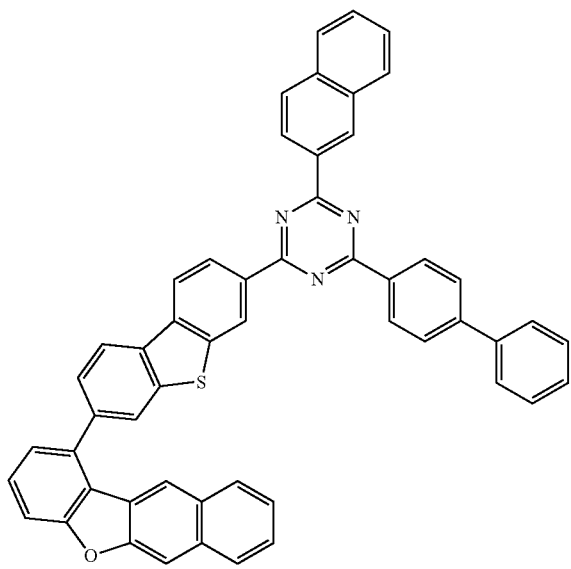
1-130
1-131
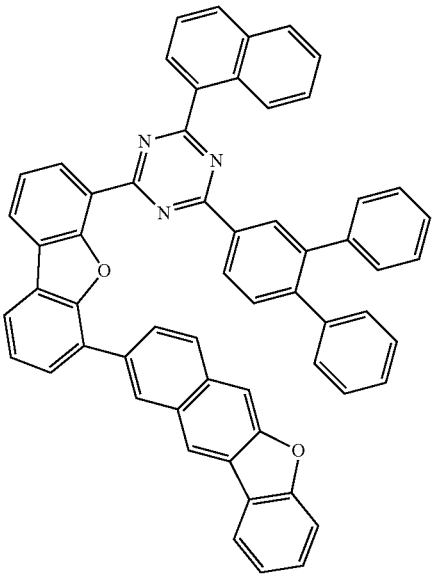
1-132

1-133
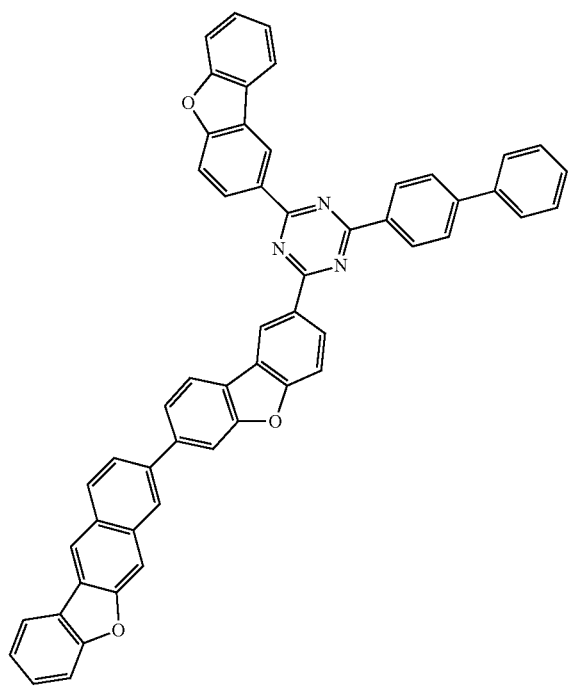
1-136
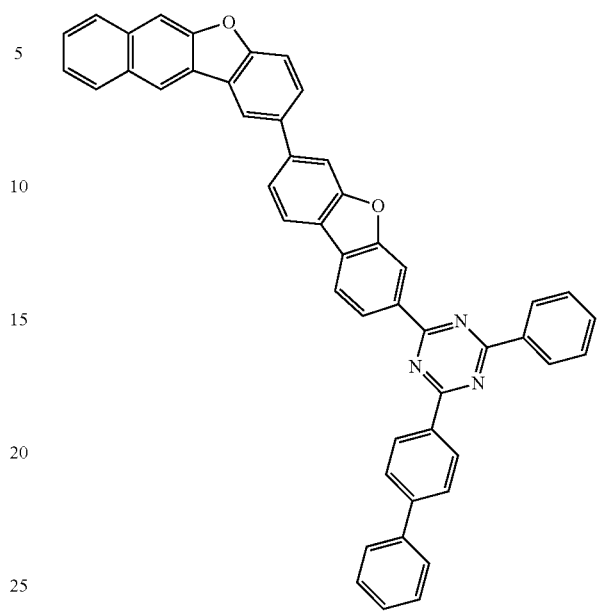
1-137
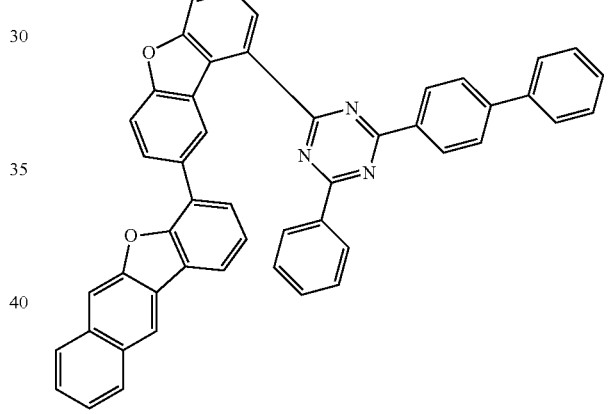
1-134
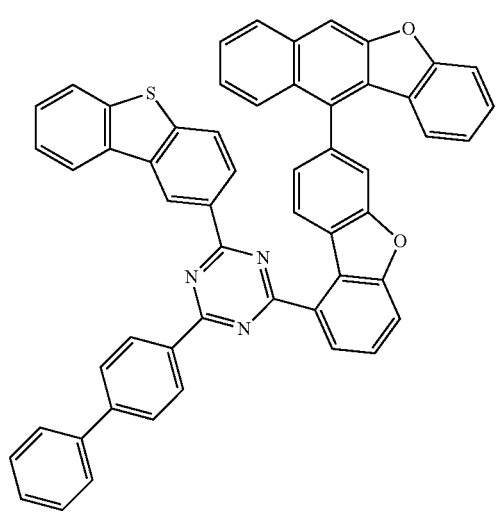
1-138
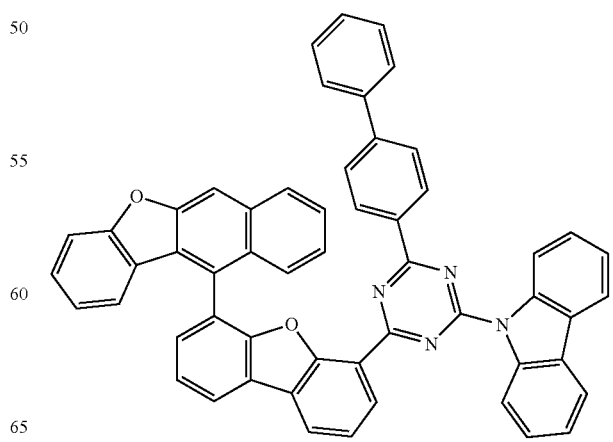

1-139
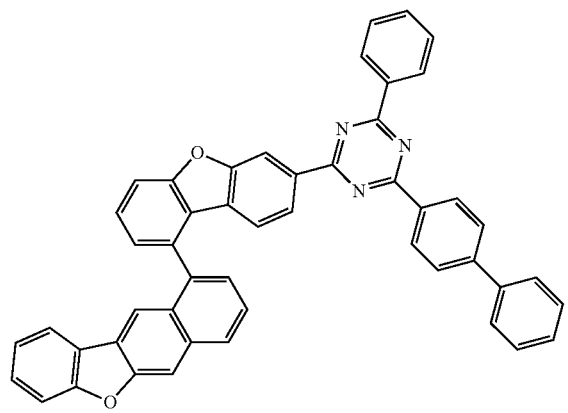
1-140
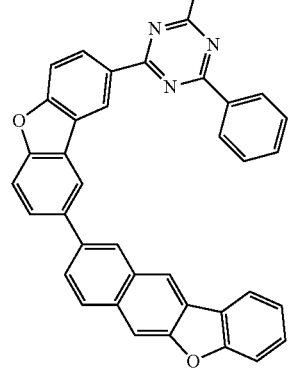
1-141
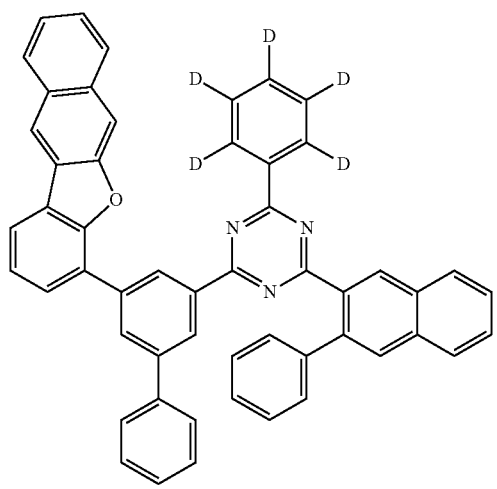
1-142
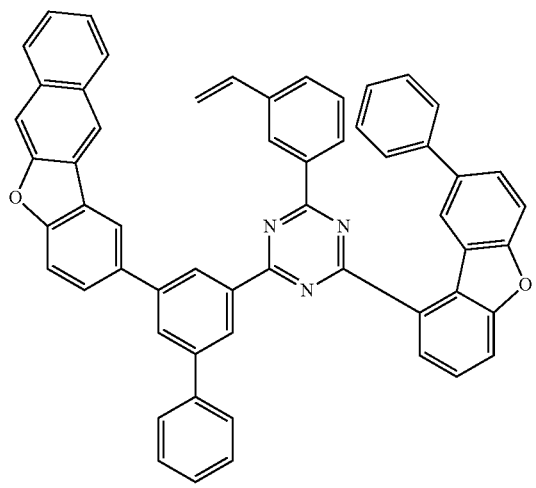
1-143
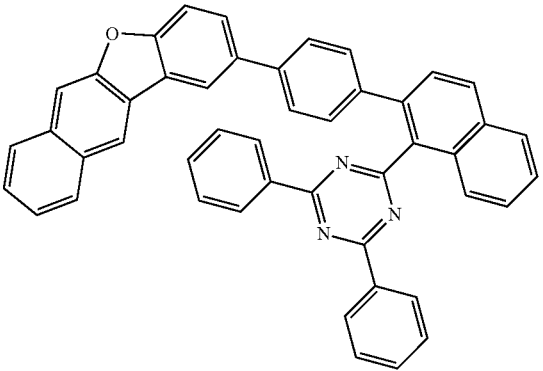
1-144
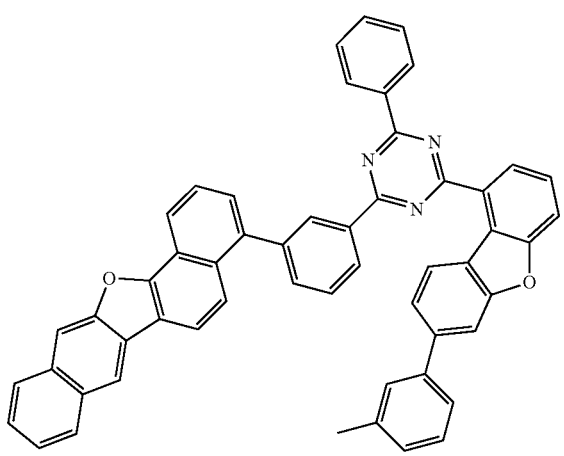

1-145
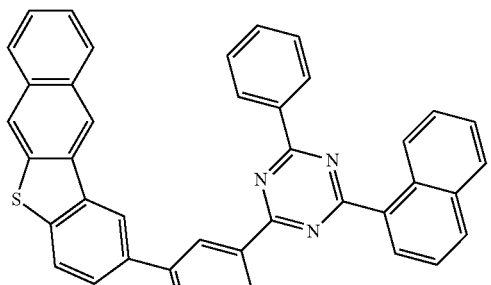
1-146
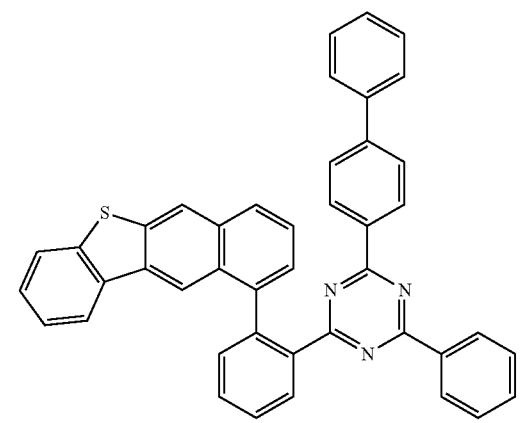
1-147
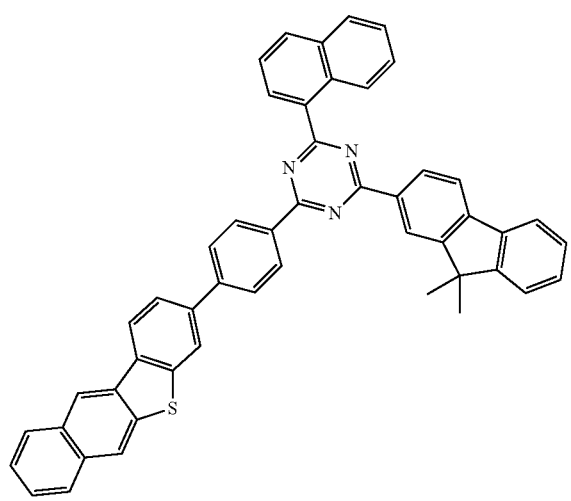
1-148
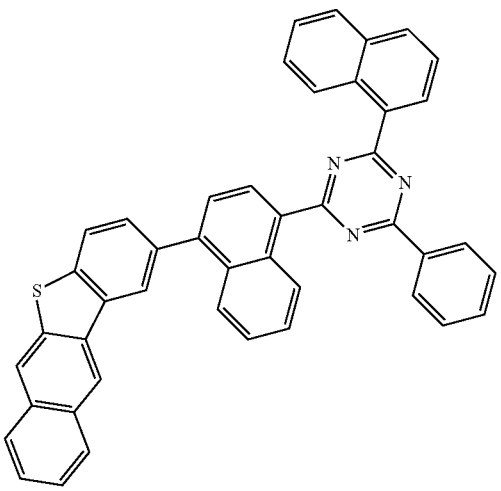
1-149
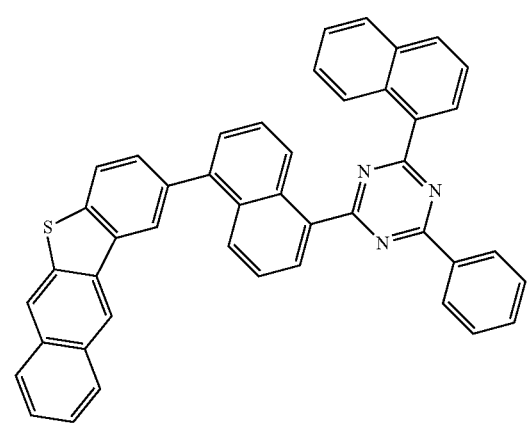
1-150
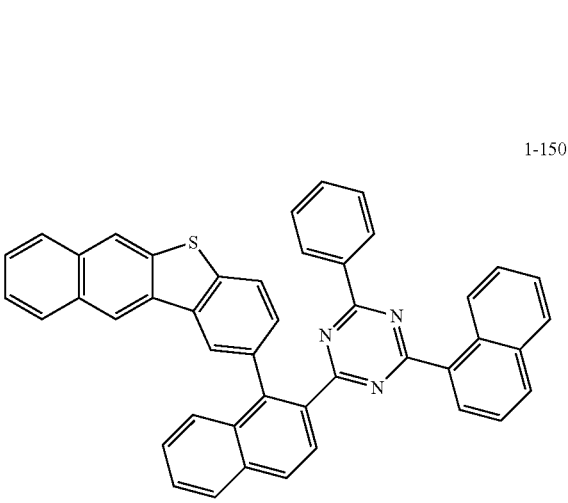

1-151
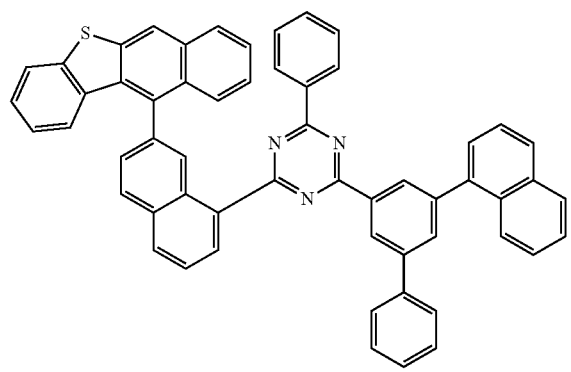
1-152
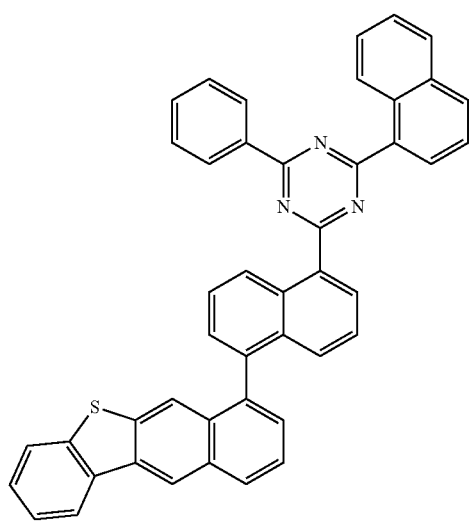
1-153
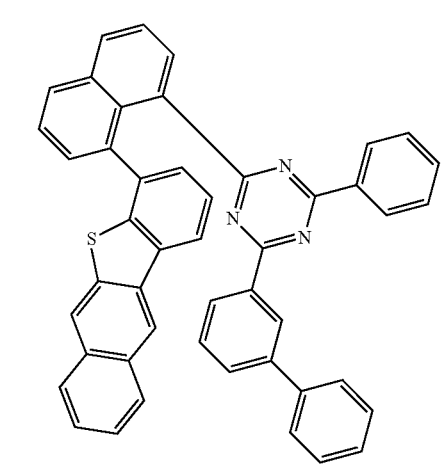
1-154
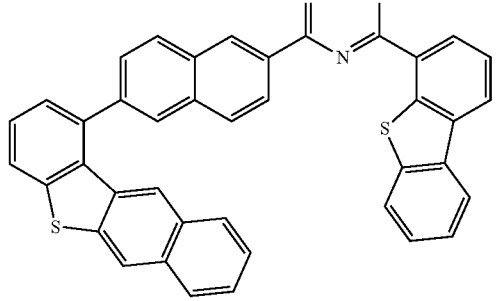
1-155
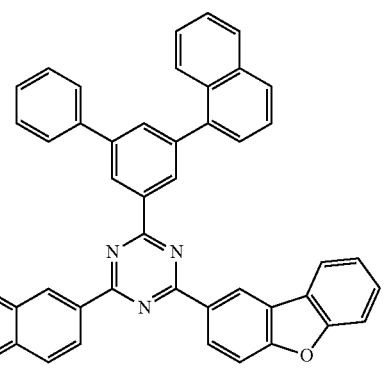
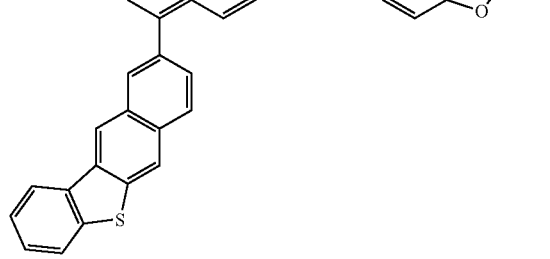
1-156
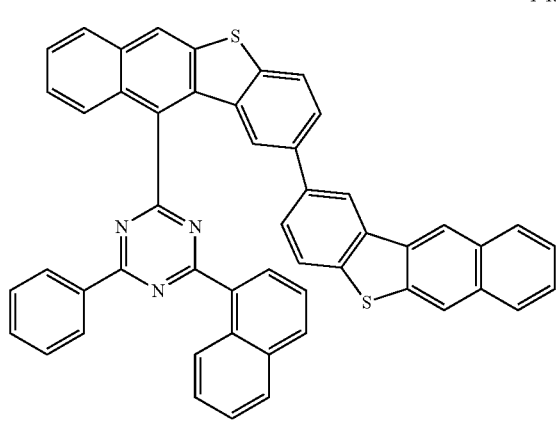

1-157
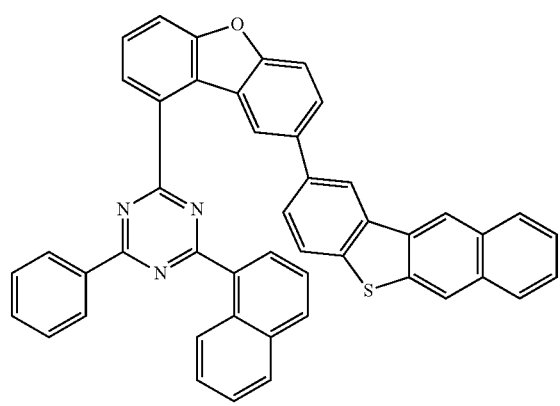
1-160
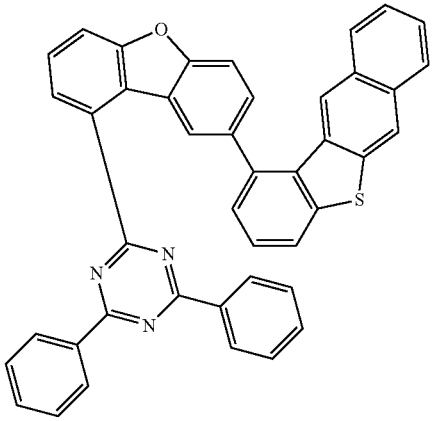
1-158
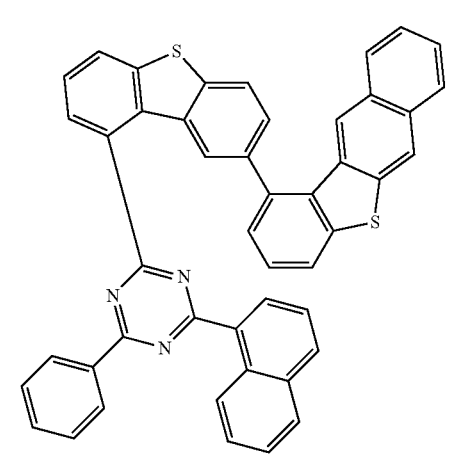
1-162
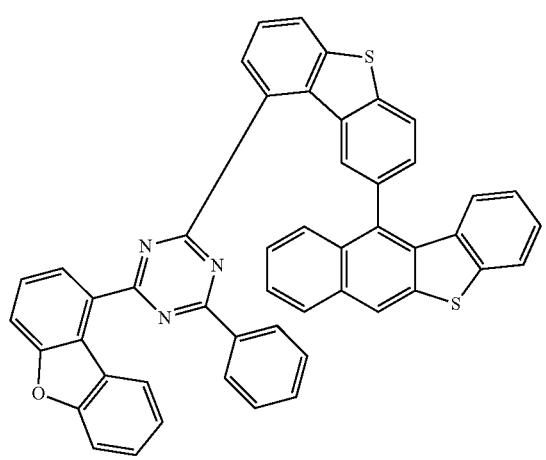
1-159
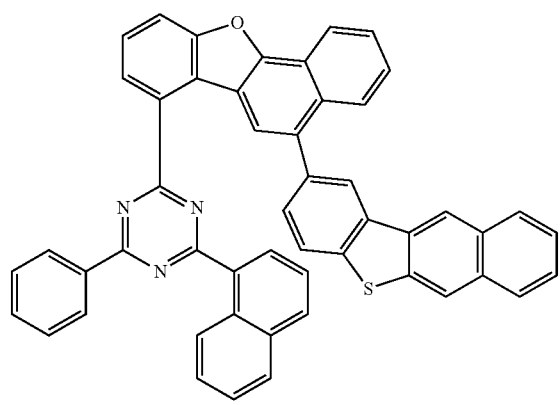
1-163
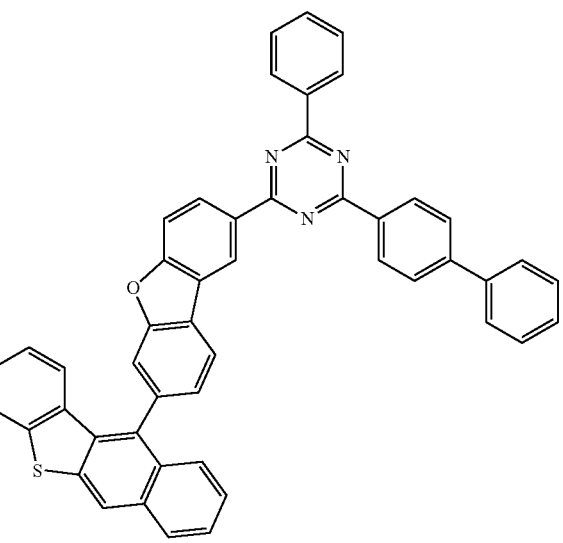

1-164
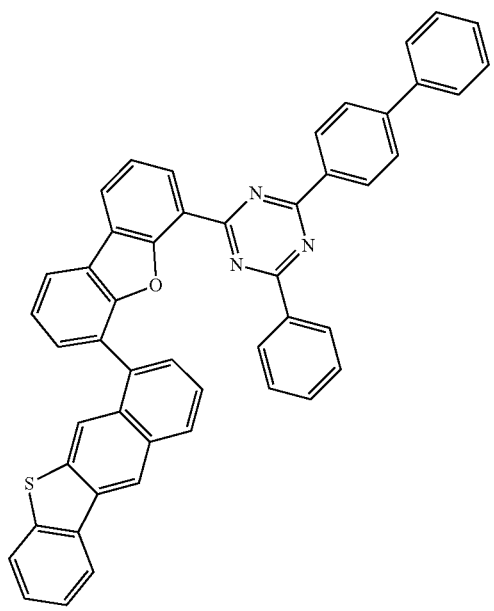
1-166
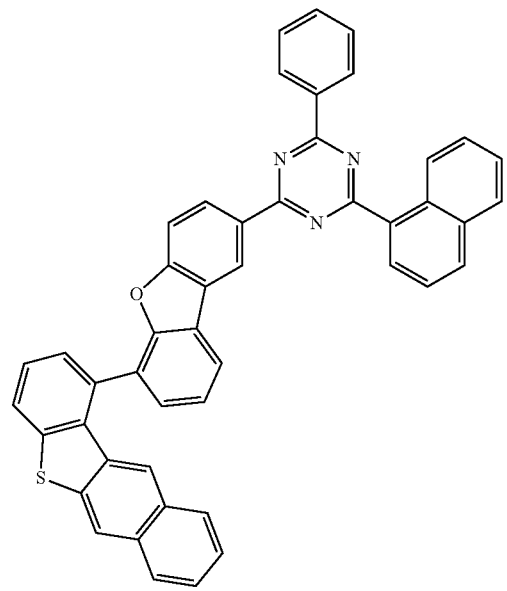
1-165
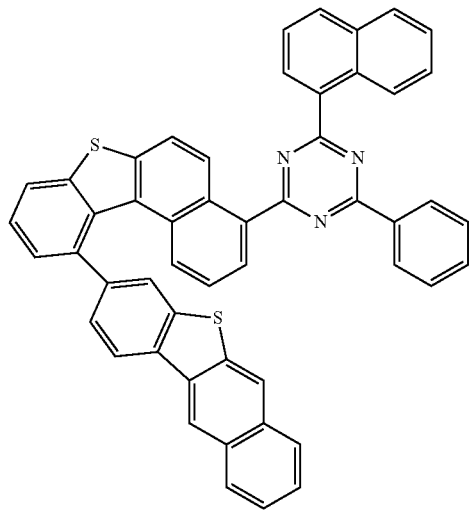
1-167
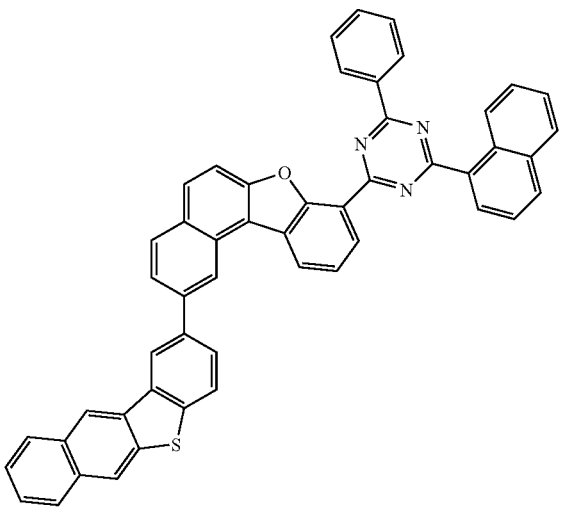

1-168
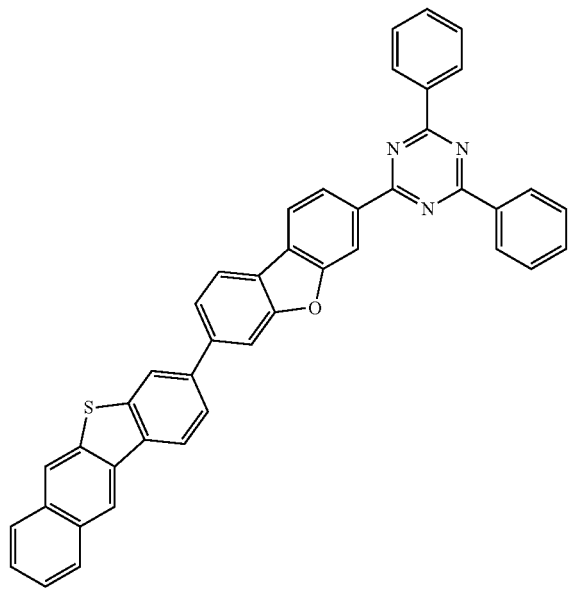
1-171
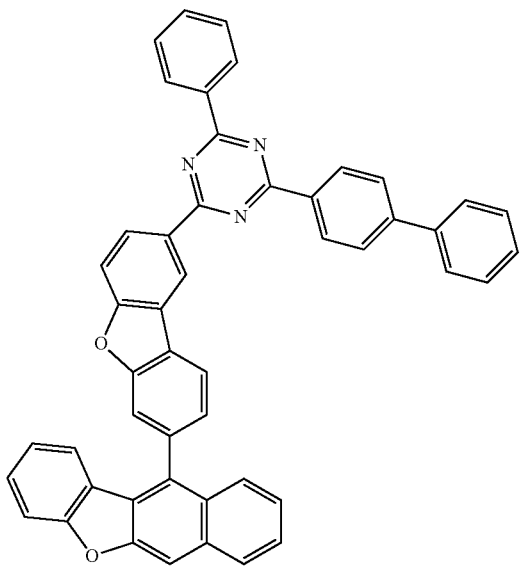
1-169
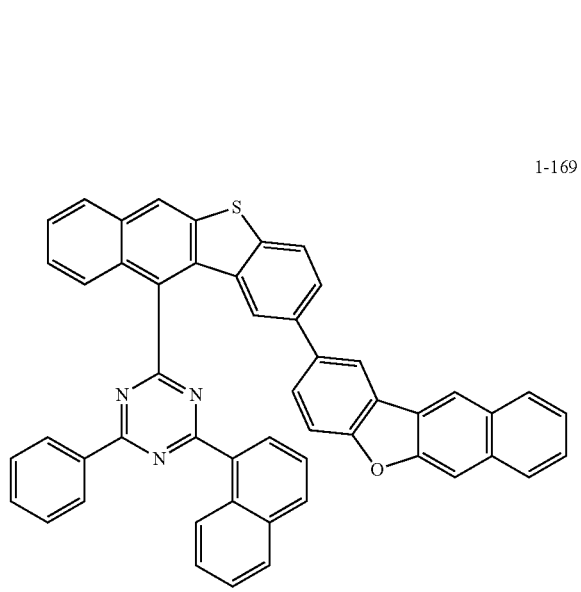
1-172
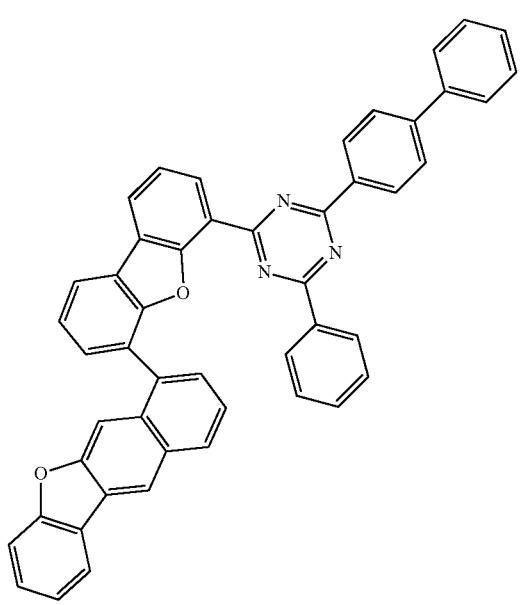
1-170
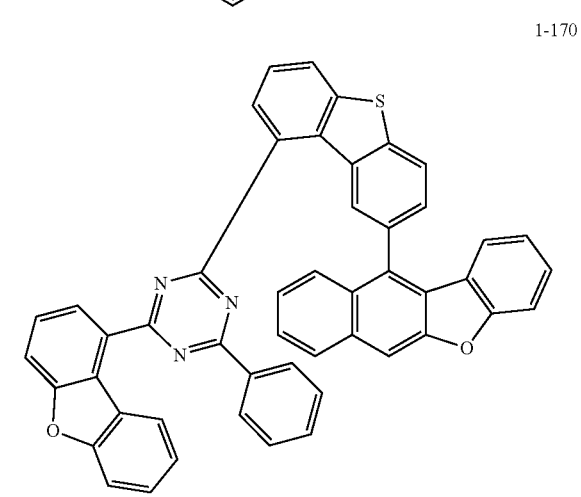
1-173
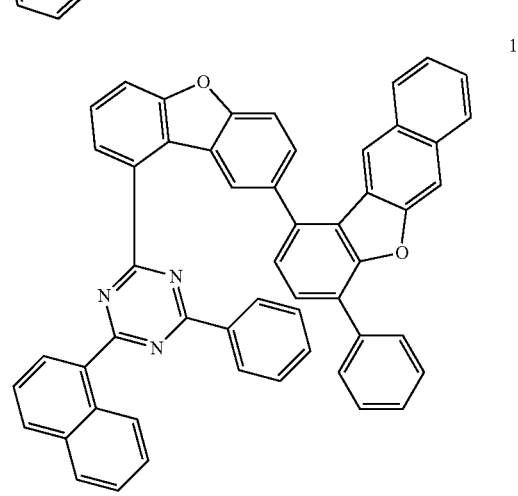

-continued 1-174
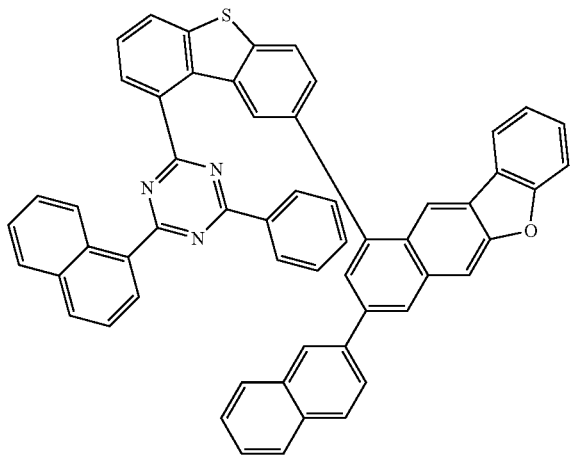

1-175
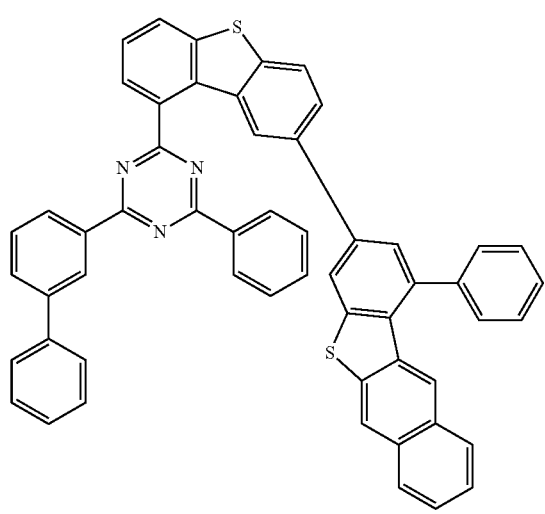

1-176
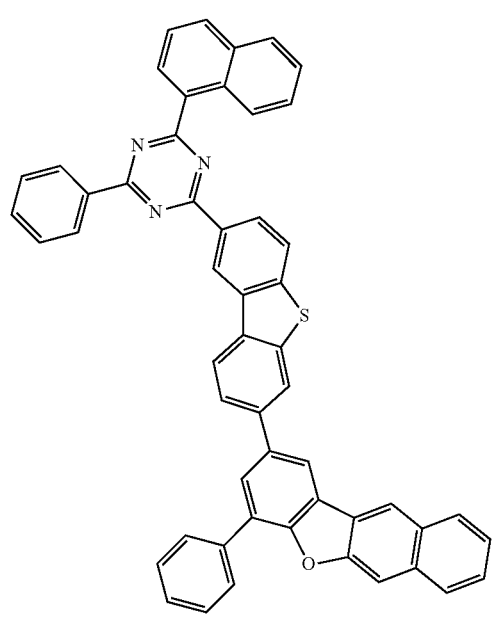

Next, Formula 2 is described in detail.

In Formula 2, each of symbols may be defined as follows: $W^1$ and $W^2$ are each independently a single bond, N-L'-(Ar$^4$), O, S or C(R')(R''), with the proviso that the case where both $W^1$ and $W^2$ are a single bond is excluded.

Ar$^3$ and Ar$^4$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

Where Ar$^3$ and Ar$^4$ are each an aryl group, the aryl group may be preferably a $C_6$-$C_{30}$ aryl group, more preferably a $C_6$-$C_{18}$ aryl group, for example, phenyl, biphenyl, naphthyl, phenanthrene, terphenyl, phenalene, triphenylene and the like.

Where Ar$^3$ and Ar$^4$ are each a heterocyclic group, the heterocyclic group may be preferably a $C_2$-$C_{30}$ heterocyclic group, more preferably a $C_2$-$C_{16}$ heterocyclic group, for example, pyridine, pyrimidine, triazine, quinazoline, benzoquinazoline, dibenzoquinazoline, quinoxaline, benzothienopyrimidine, benzofuropyrimidine, thienopyrimidine, furopyrimidine, naphthofuropyrimidine, naphthofuropyrazine, benzothiophene, dibenzothiophene, benzonaphthothiophene, benzofuran, dibenzofuran, benzonaphthofuran and the like.

Where Ar$^3$ and Ar$^4$ are each a fluorenyl group, the fluorenyl group may be 9,9-dimethyl-9H-fluorene, 9,9-diphenyl-9H-fluorene, 9,9'-spirobifluorene and the like.

$R^2$ to $R^4$ are each independently selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N(R$_a$)(R$_b$), and adjacent R$^2$s, adjacent R$^3$s or adjacent R$^4$s may be bonded to each other to form a ring.

The ring formed by bonding between neighboring groups may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring groups, the aromatic ring may be preferably a $C_6$-$C_{30}$ aromatic ring group, more preferably, a $C_6$-$C_{14}$ aromatic ring group, for example, benzene, naphthalene, phenanthrene or the like.

b and d are each an integer of 0-4, c is an integer of 0-2, and where each of these is an integer of 2 or more, each of a plurality of R$^2$s, each of a plurality of R$^3$s and each of a plurality of R$^4$s are the same as or different from each other.

Where $R^2$ to $R^4$ are each an aryl group, the aryl group may be preferably a $C_6$-$C_{30}$ aryl group, more preferably a $C_6$-$C_{18}$ aryl group, for example, phenyl, biphenyl, naphthyl, terphenyl and the like.

Where $R^2$ to $R^4$ are each an alkoxy group, the alkoxy group may be preferably a $C_1$-$C_{10}$ alkoxy group, for example, a methoxy group, an ethoxy group, or the like.

R' and R'' are each independently selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and R' and R" may be bonded to each other to form a ring. When R' and R" combine with each other to form a ring, a spiro compound may be formed.

Where R' and R" are each an alkyl group, the alkyl group may be preferably a $C_1$-$C_{20}$ alkyl group, more preferably a $C_1$-$C_{10}$ alkyl group, for example, methyl, ethyl, or the like.

When R' and R" are each aryl group, the aryl group may be preferably $C_6$-$C_{30}$ aryl groups, more preferably $C_6$-$C_{18}$ aryl group, for example, phenyl, biphenyl, naphthyl, terphenyl, or the like.

$L^4$ and L' are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Where $L^4$ and L' are each an arylene group, the arylene group may be preferably a $C_6$-$C_{30}$ arylene group, more preferably a $C_6$-$C_{18}$ arylene group, for example, phenyl, biphenyl, naphthyl, terphenyl, phenanthrene and the like.

Where $L^4$ and L' are each a heterocyclic group, the heterocyclic group may be preferably a $C_2$-$C_{30}$ heterocyclic group, more preferably a $C_2$-$C_{16}$ heterocyclic group, for example, pyridine, pyrimidine, triazine, quinazoline, benzoquinazoline, quinoxaline, furopyrimidine, thienopyrimidine, benzothienopyrimidine, benzofuropyrimidine, naphthofuropyrimidine, naphthothienopyrimidine, naphthofuropyrazine, benzothiophene, dibenzothiophene, benzofuran, dibenzofuran, and the like.

$R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

$R^2$ to $R^4$, $Ar^3$, $Ar^4$, $L^4$, L', $R_a$, $R_b$, R', R", and the ring formed by bonding between adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Formula 2 may be represented by one of Formulas 2-A to 2-I:

<Formula 2-A>

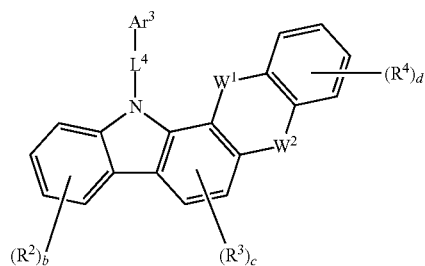

<Formula 2-B>

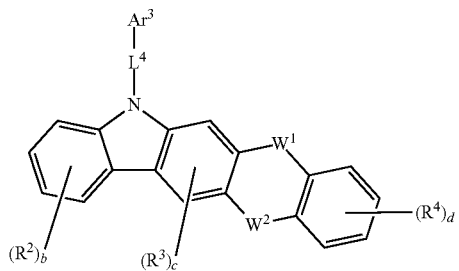

<Formula 2-C>

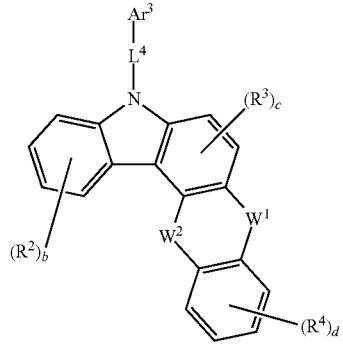

<Formula 2-D>

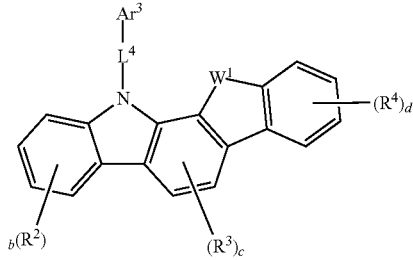

<Formula 2-E>

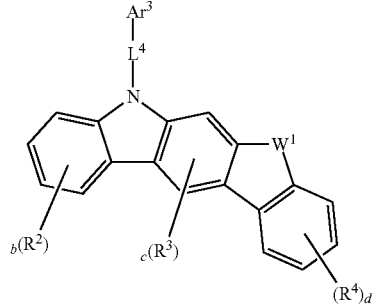

<Formula 2-F>

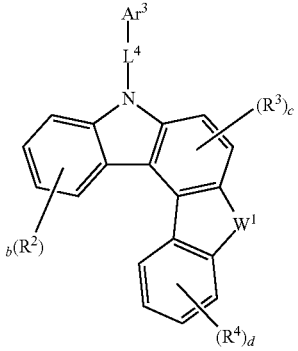

<Formula 2-G>

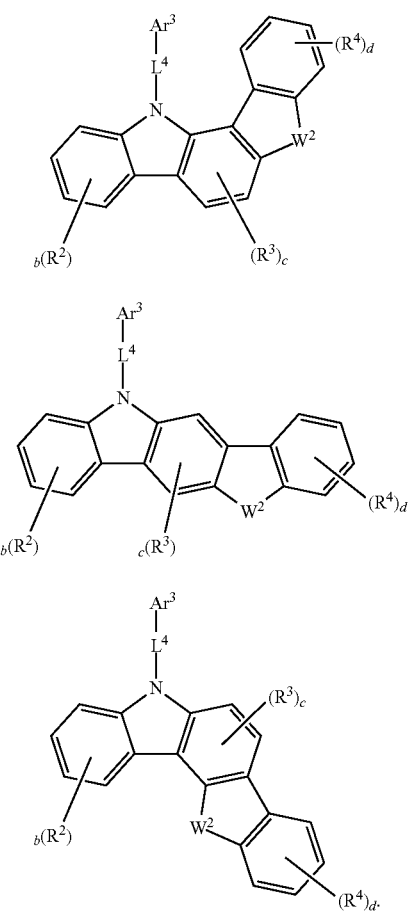

<Formula 2-H>

<Formula 2-I>

In Formulas 2-A to 2-I, $Ar^3$, $L^4$, $R^2$-$R^4$, $W^1$, $W^2$ and b to d are the same as defined for Formula 2.

In addition, Formula 2 may be represented by Formula 2-J:

<Formula 2-J>

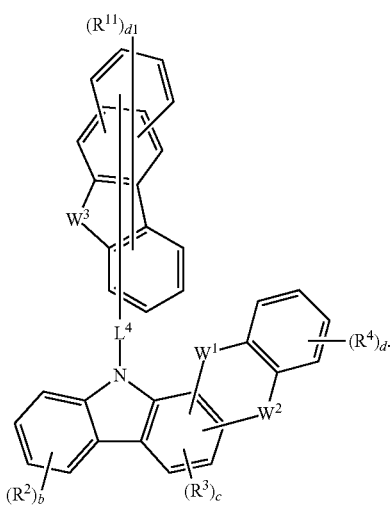

In Formula 2-J, each symbol can be defined as follows: $L^4$, $R^2$-$R^4$, $W^1$, $W^2$, b to d are the same as defined for Formula 2, and $W^3$ is O or S.

$R^{11}$ may be defined the same as $R^2$. In other words, $R^{11}$ is selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N$(R_a)(R_b)$, and adjacent $R^{11}$s may be bonded to each other to form a ring.

The ring formed by bonding between neighboring $R^{11}$s may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring $R^{11}$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

d1 is an integer of 0-9, and where d1 is an integer of 2 or more, each of a plurality of $R^{11}$s are the same as or different from each other.

Specifically, the compound represented by Formula 2 may be one of the following compounds, but it is not limited only thereto:

2-1

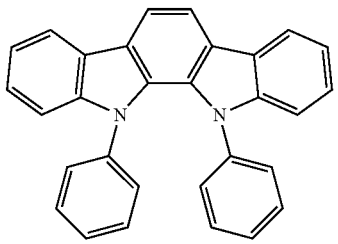

2-2

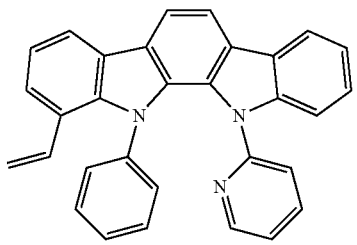

2-3

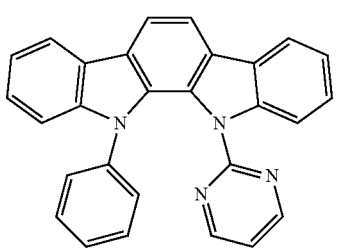

2-4
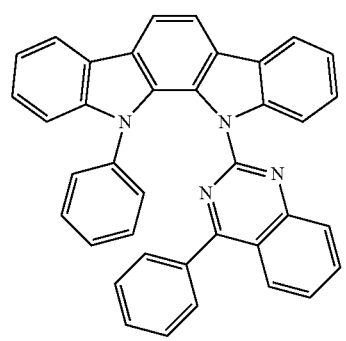
2-5
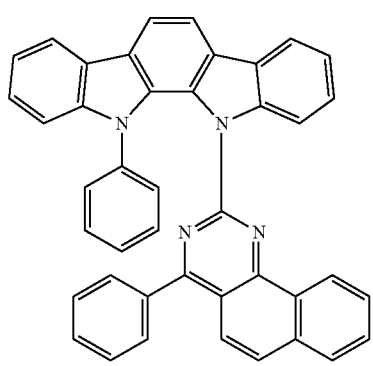
2-6
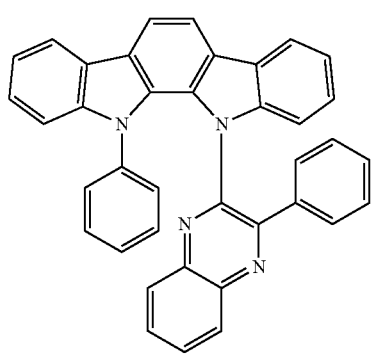
2-7
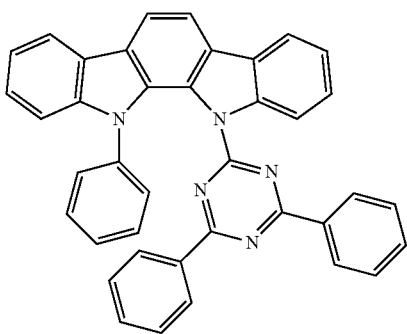
2-8
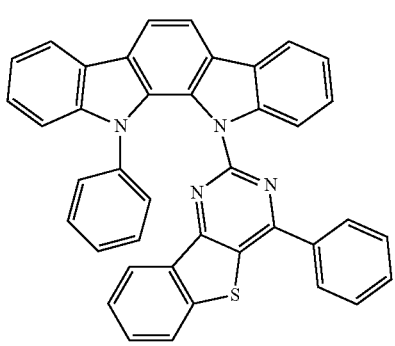
2-9
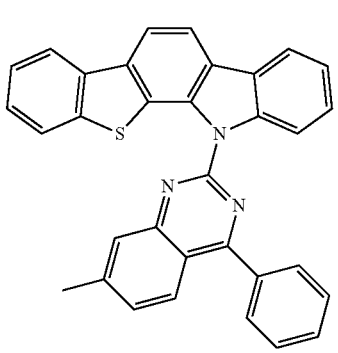
2-10
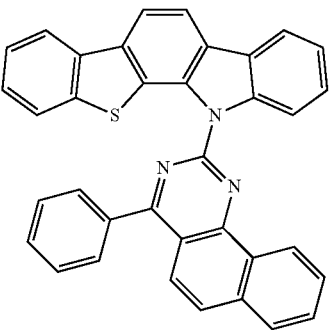
2-11
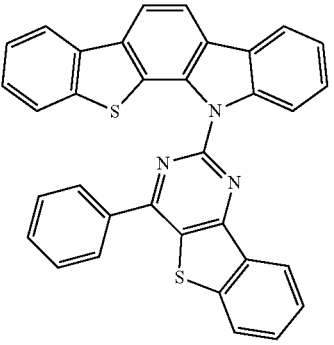

2-12
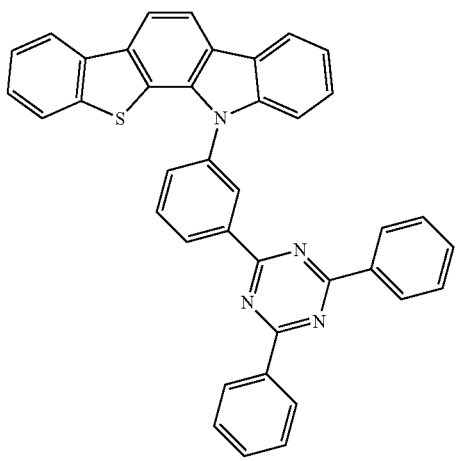
2-13
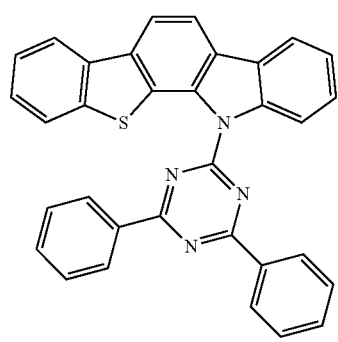
2-14
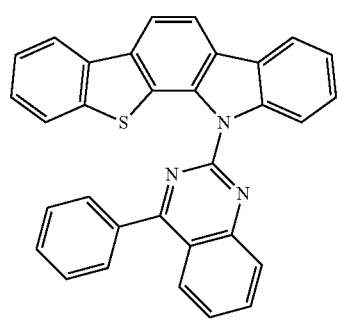
2-15
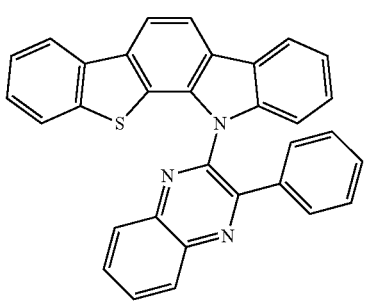
2-16
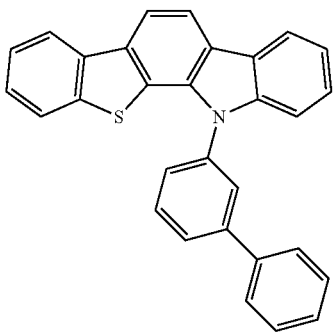
2-17
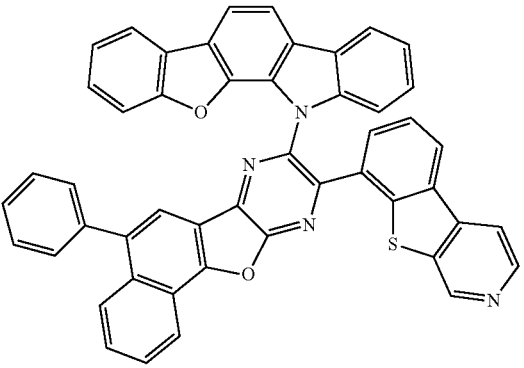
2-18
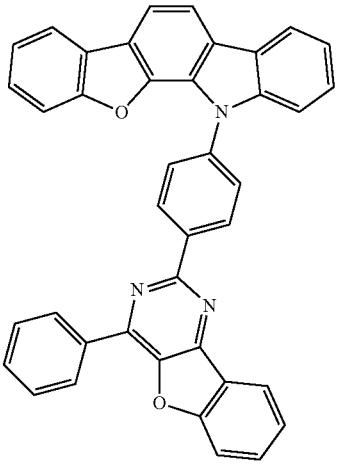
2-19
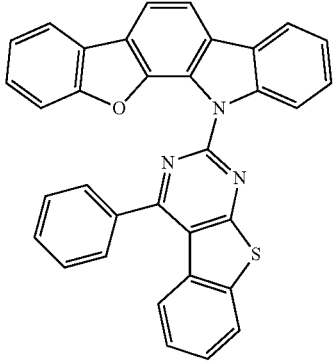

-continued
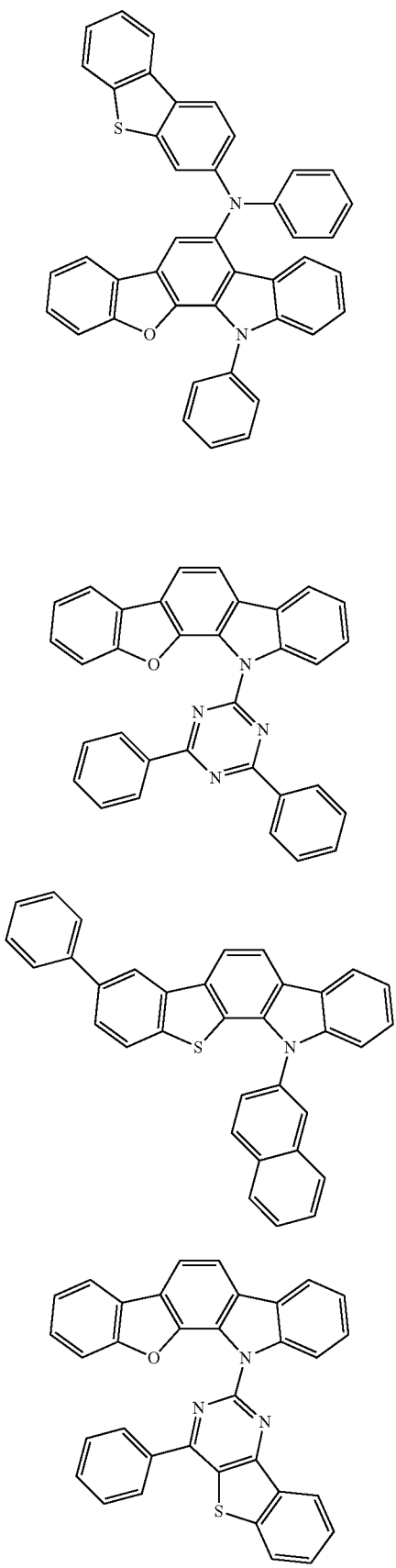
2-20
2-21
2-22
2-23
-continued
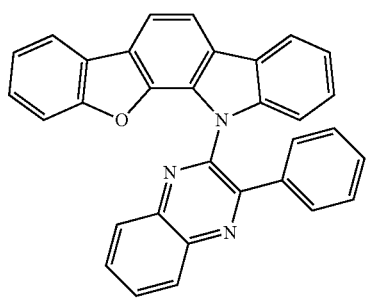
2-24
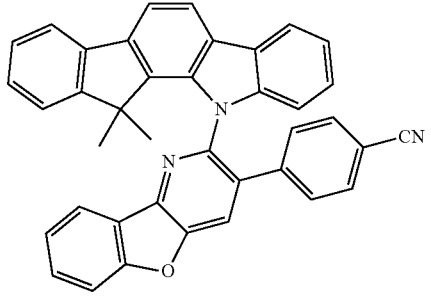
2-25
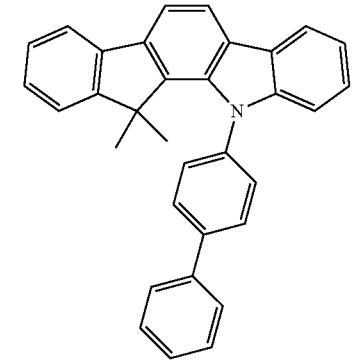
2-26
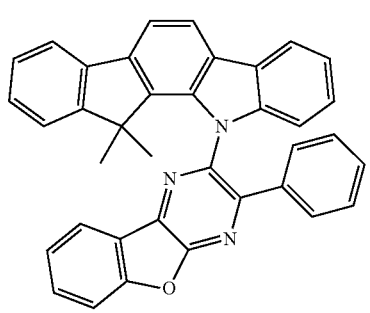
2-27
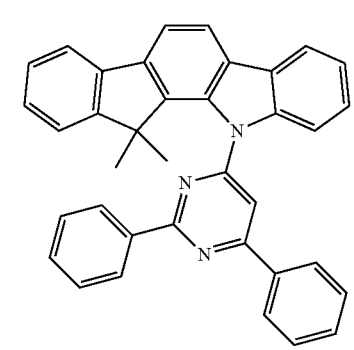
2-28

2-29
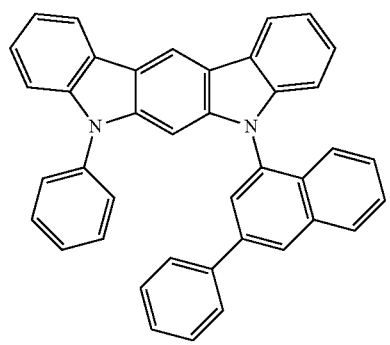
2-30
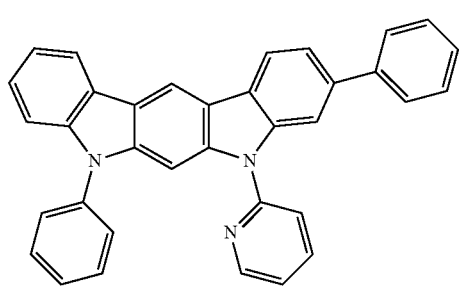
2-31
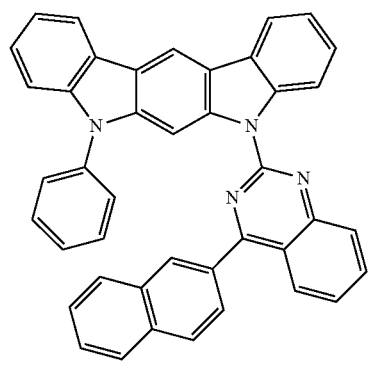
2-32
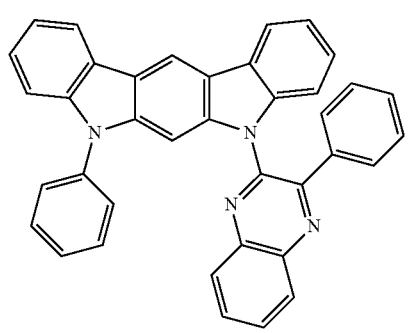
2-33
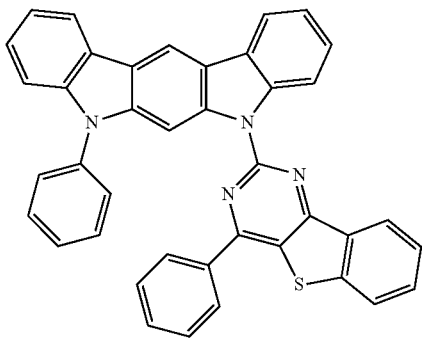
2-34
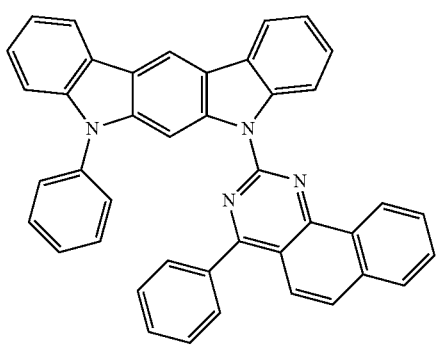
2-35
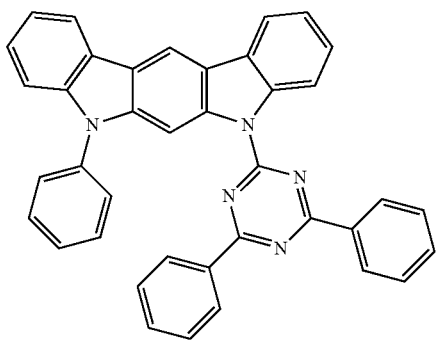
2-36
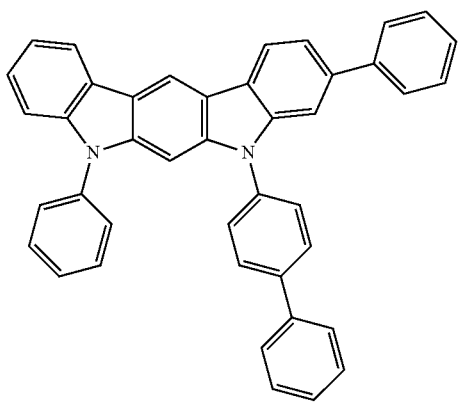

2-37
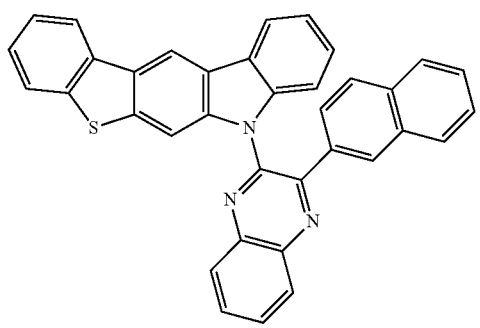
2-38
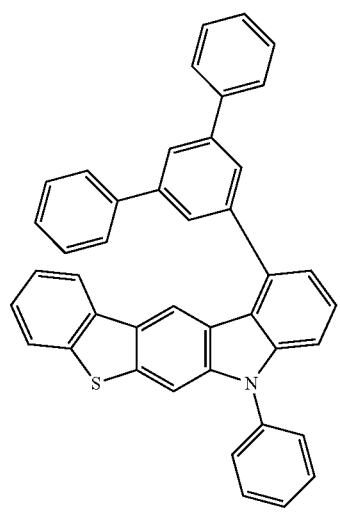
2-39
2-40
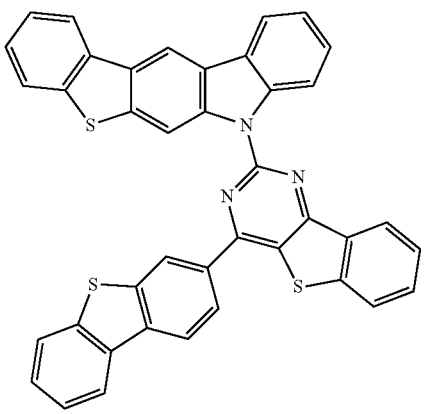
2-41
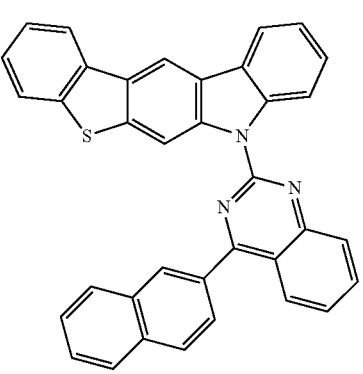
2-42
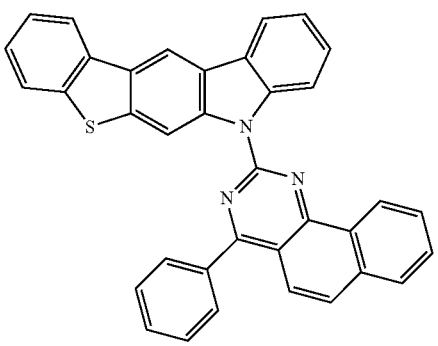
2-43
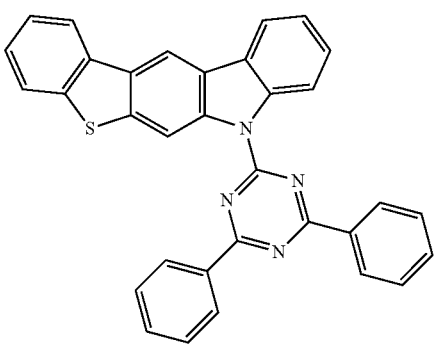

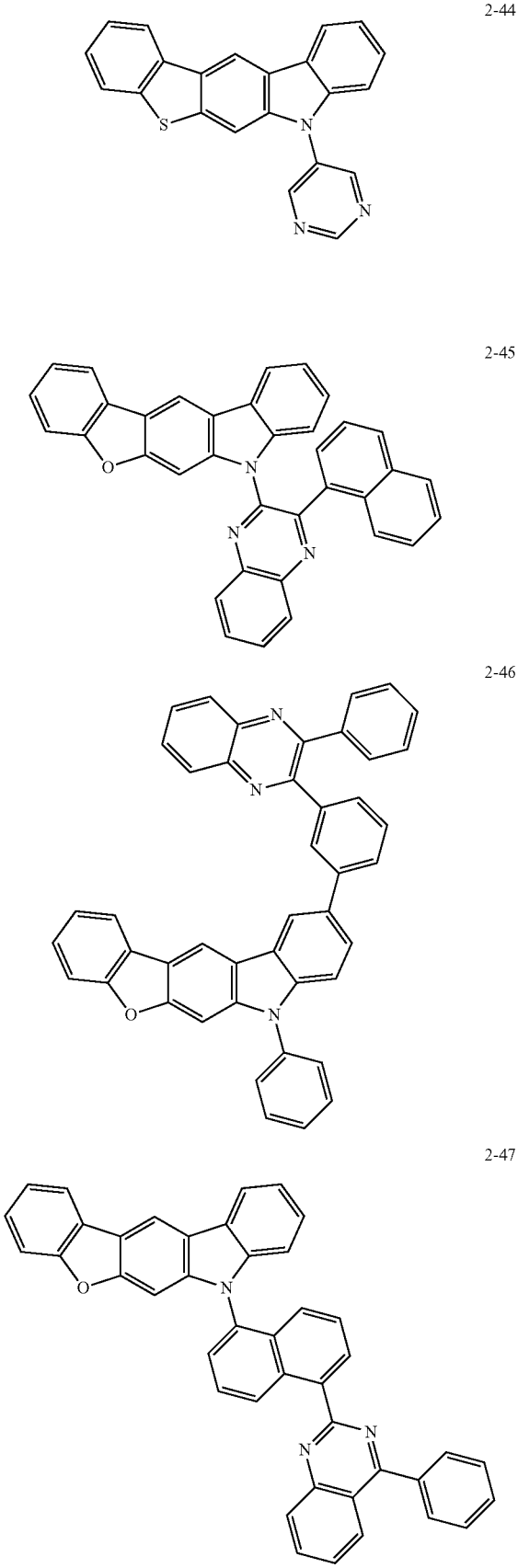
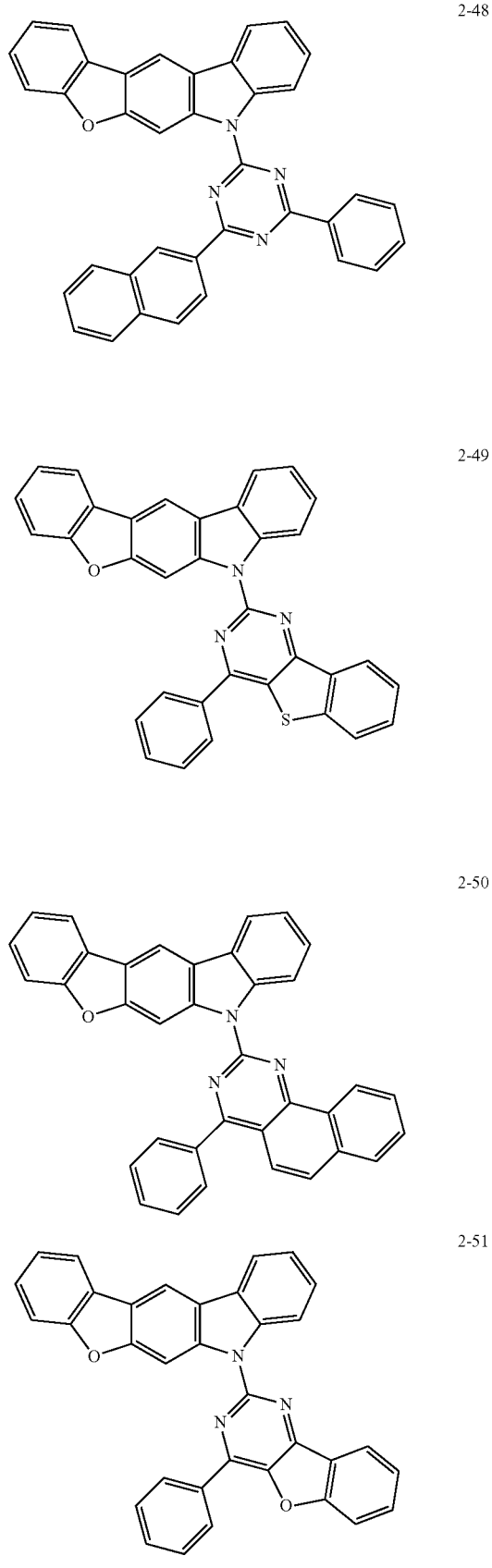

-continued
2-52
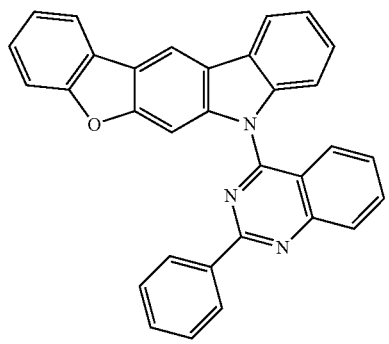
2-53
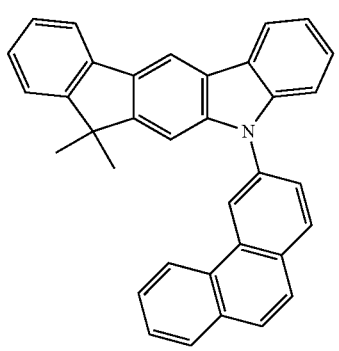
2-54
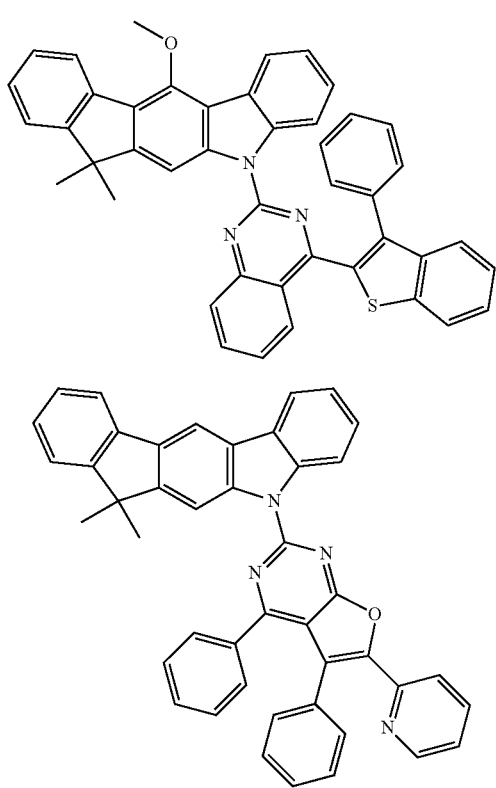
2-55
-continued
2-56
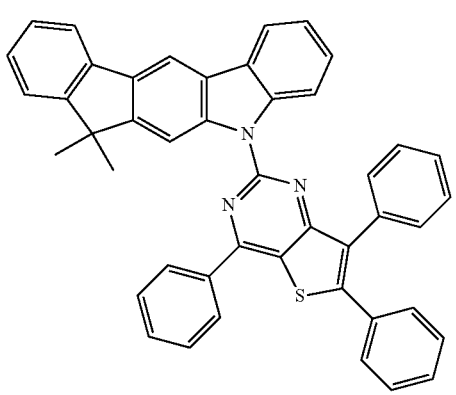
2-57
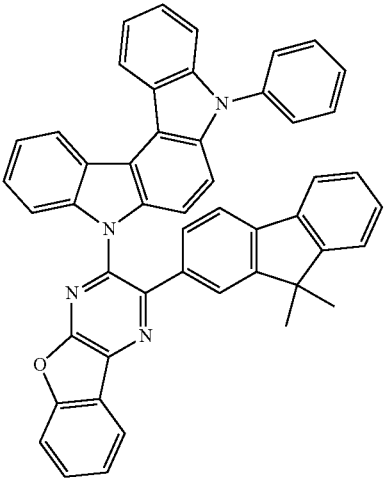
2-58
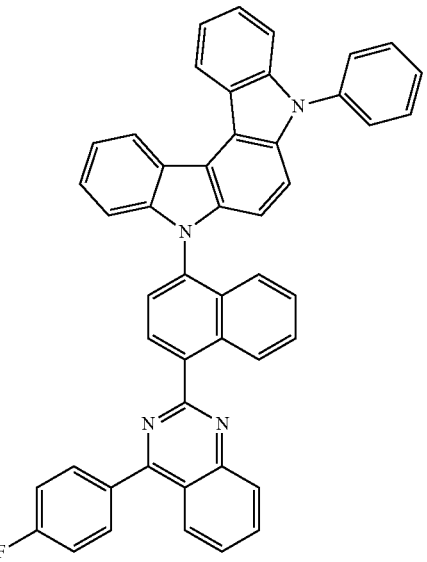

2-59
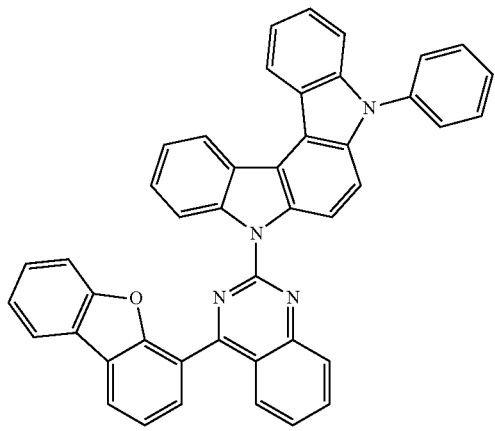
2-60
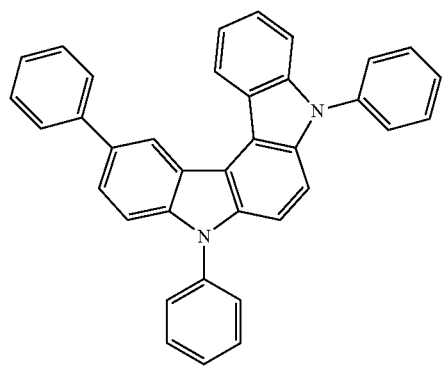
2-61
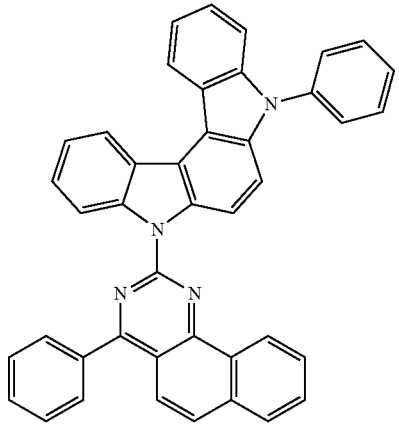
2-62
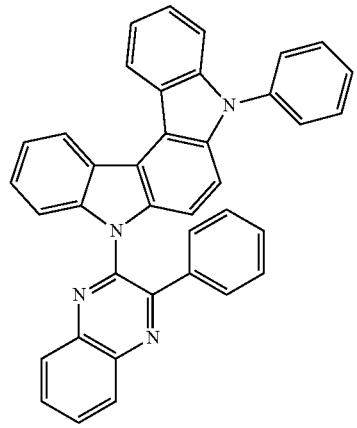
2-63
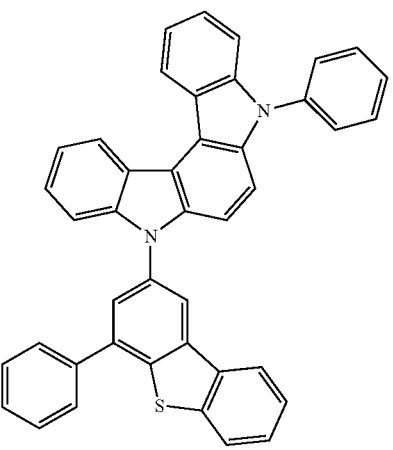
2-64
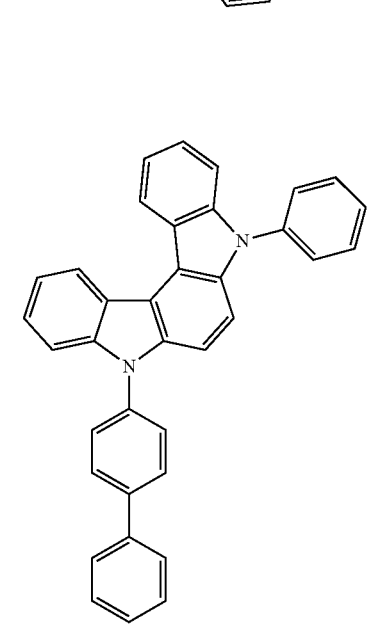
2-65
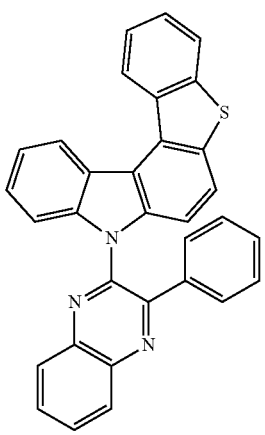

2-66 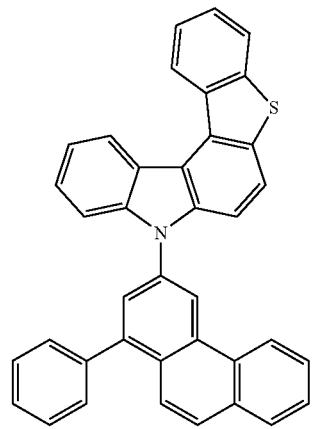
2-67 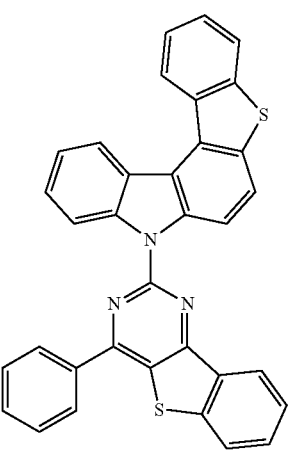
2-68 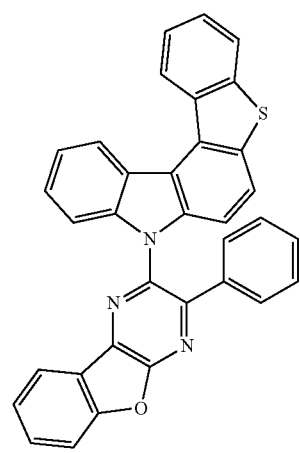
2-69 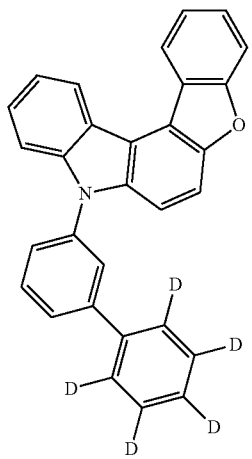
2-70 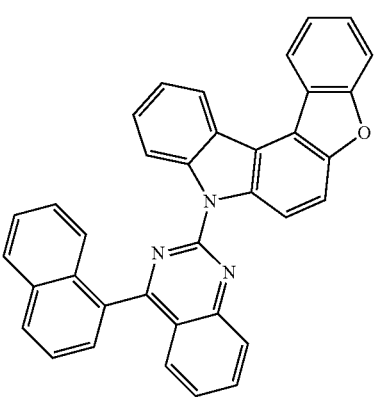
2-71

2-72
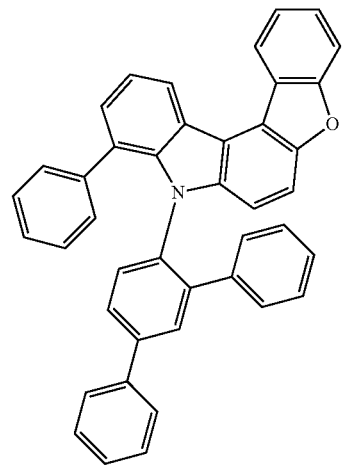
2-73
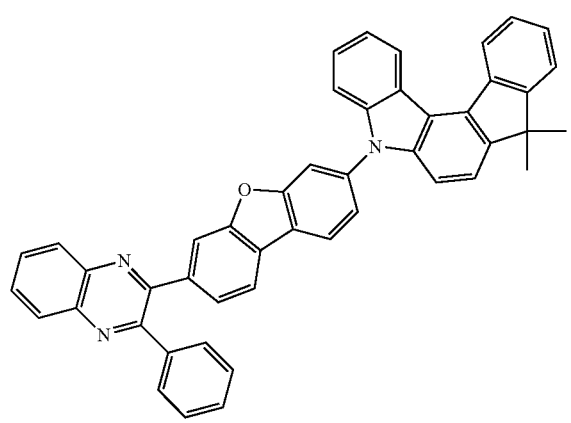
2-74
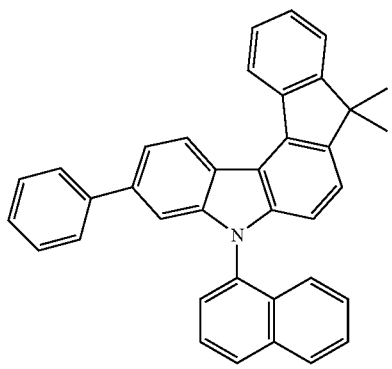
2-75
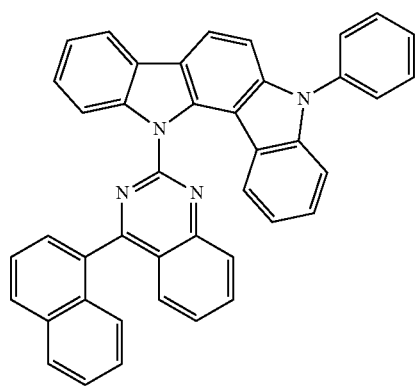
2-76
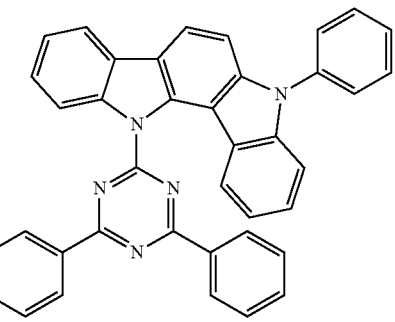
2-77
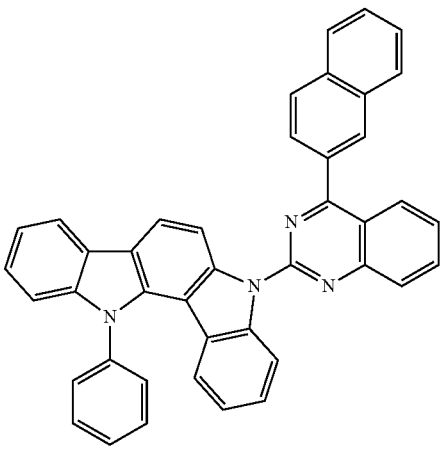
2-78
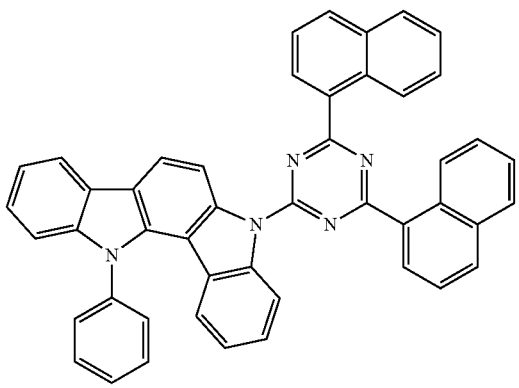
2-79
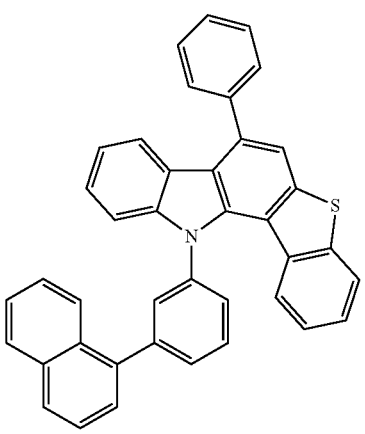

2-80
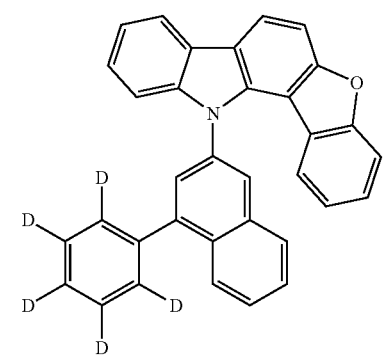
2-81
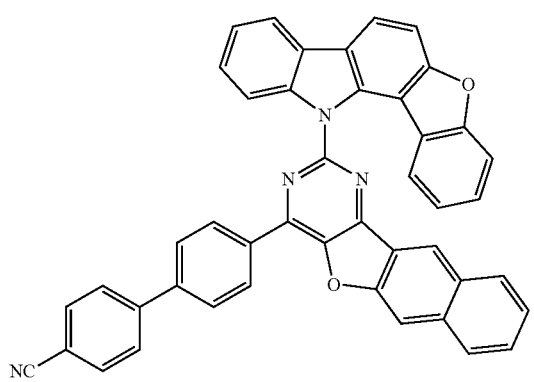
2-82
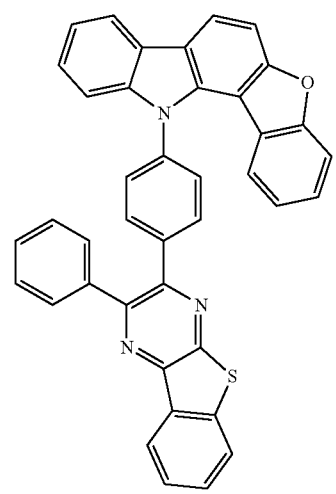
2-83
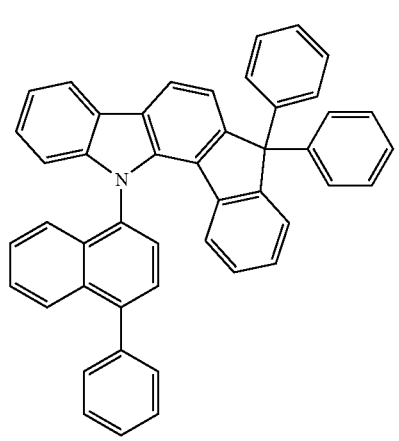
2-84
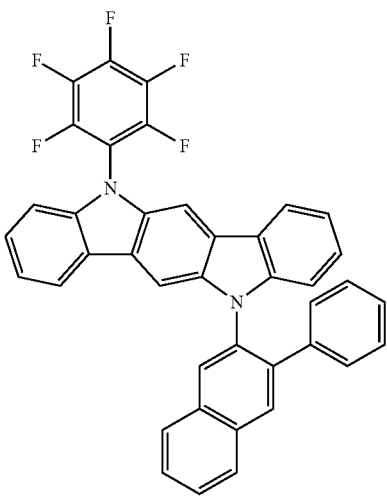
2-85
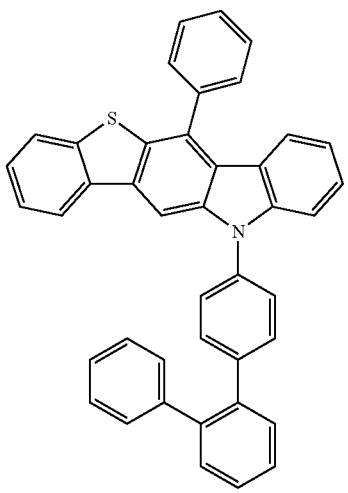
2-86
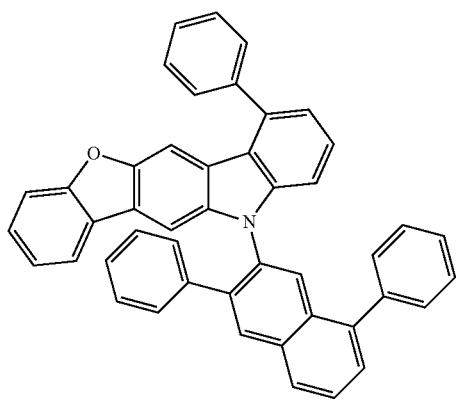

2-87
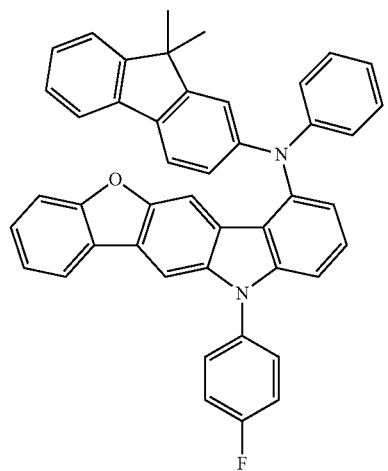
2-88
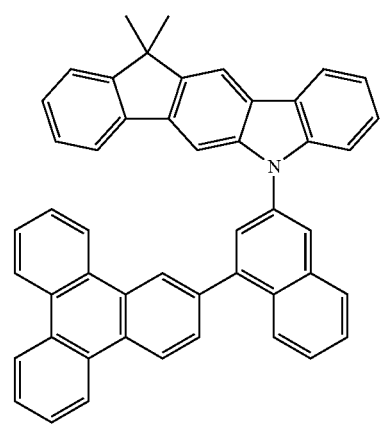
2-89
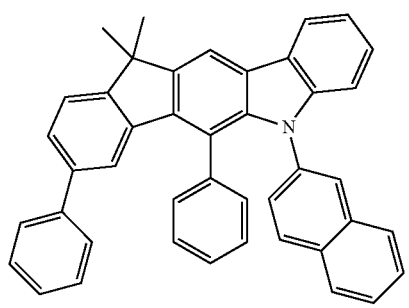
2-90
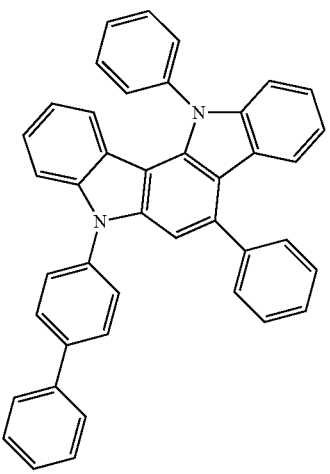
2-91
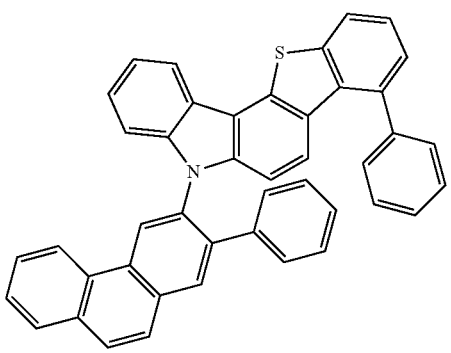
2-92
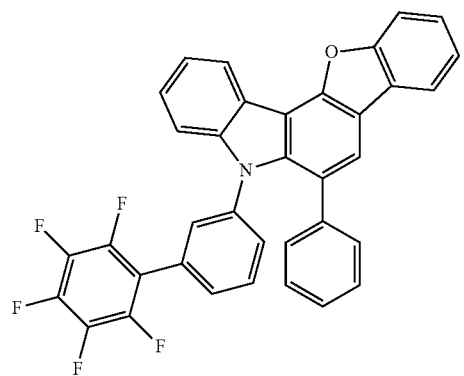

2-93
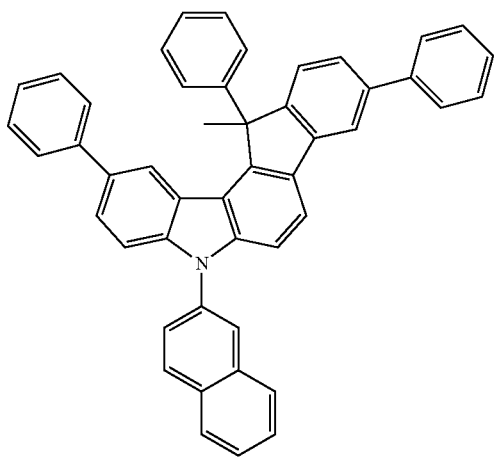
2-94
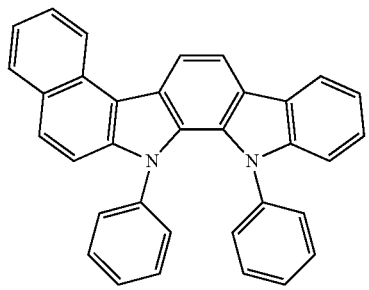
2-95
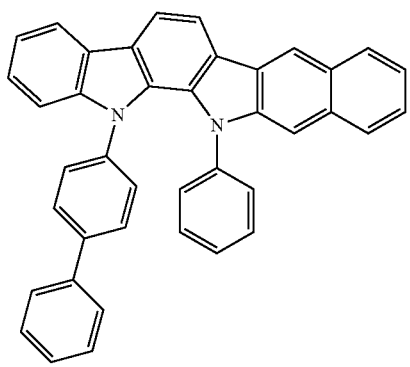
2-96
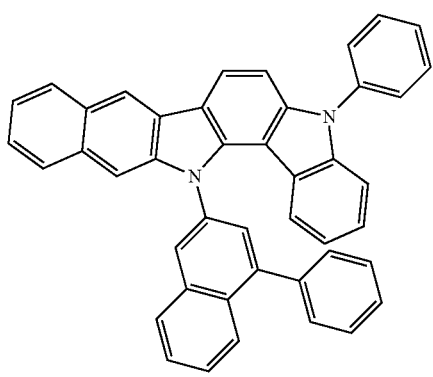
2-97
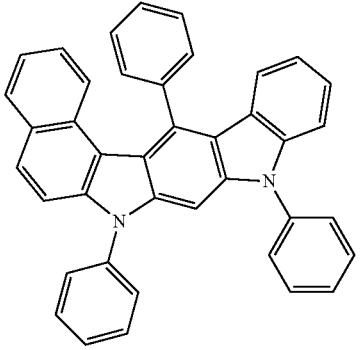
2-98
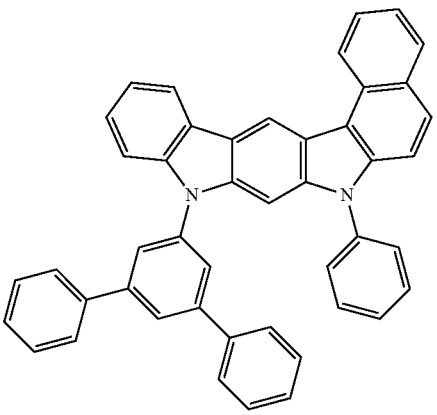
2-99
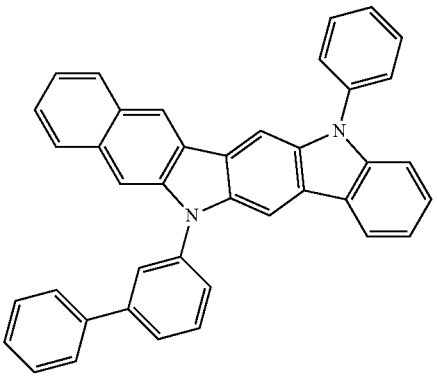
2-100
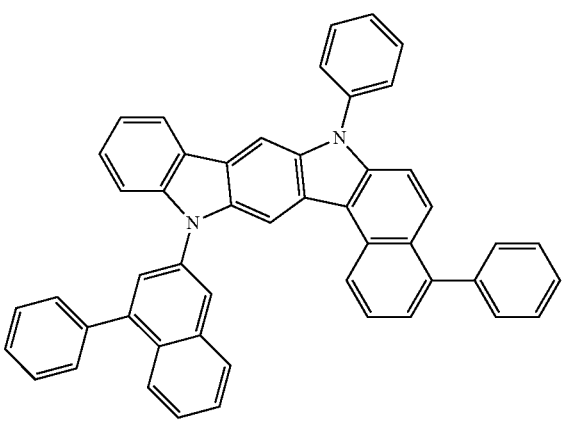

2-101 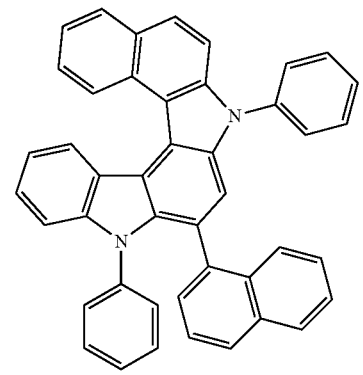
2-102 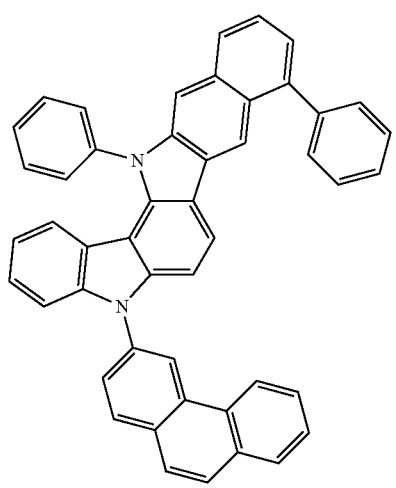
2-103 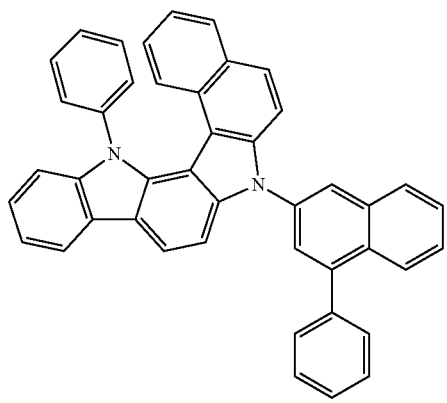
2-104 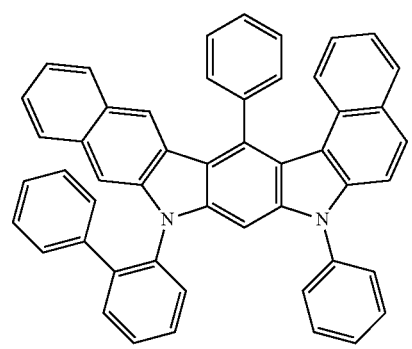
2-105 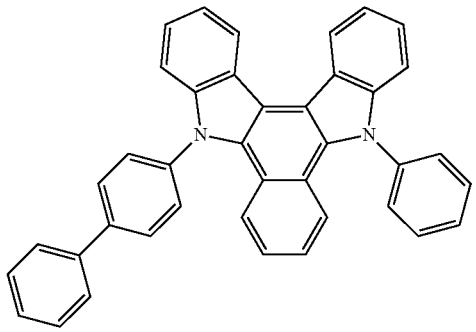
2-106 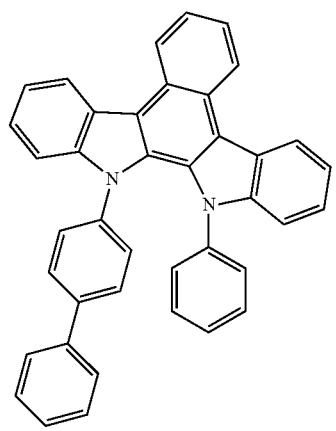
2-107 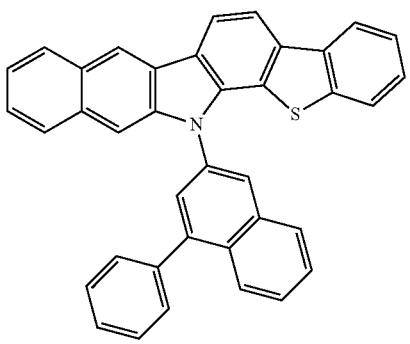
2-108 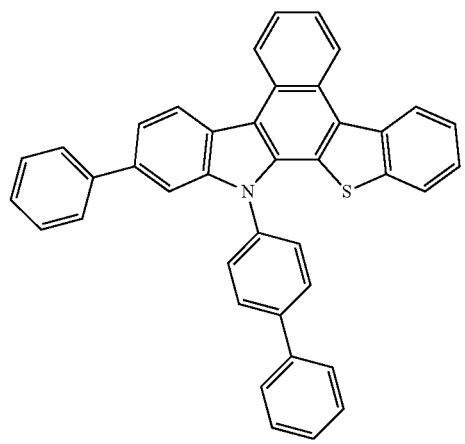

2-109
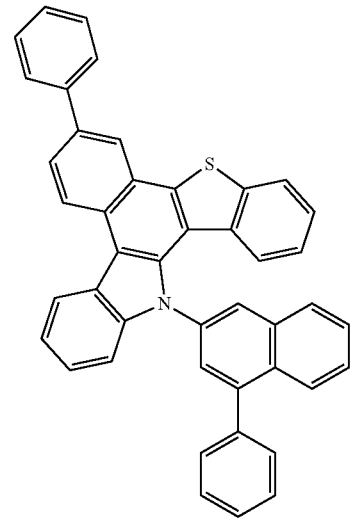
2-110
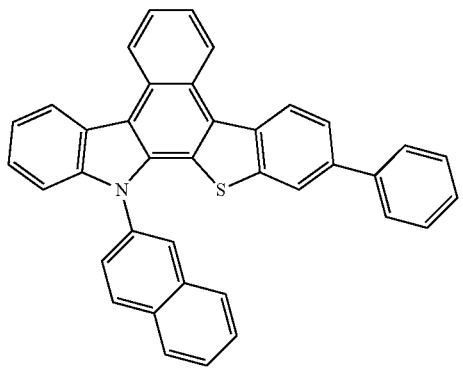
2-111
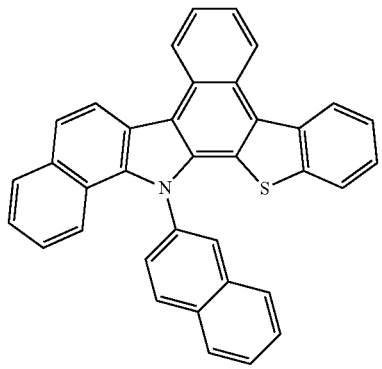
2-112
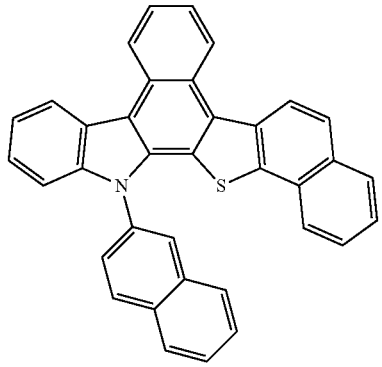
2-113
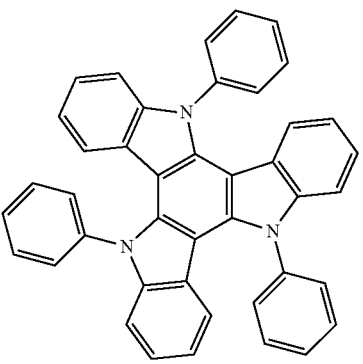
2-114
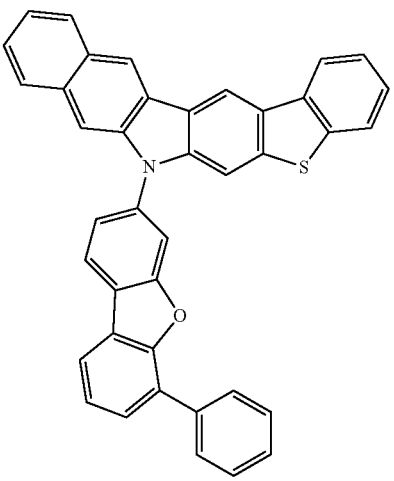
2-115
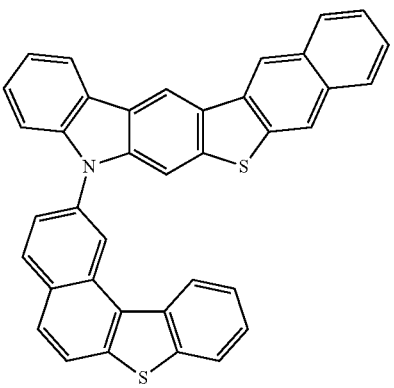
2-116
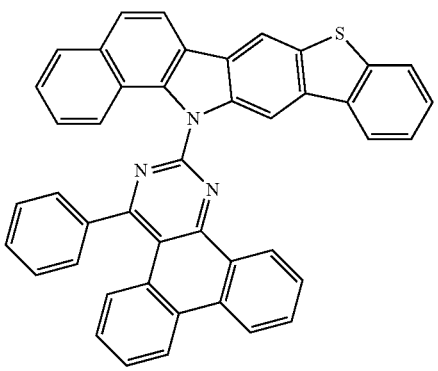

2-117
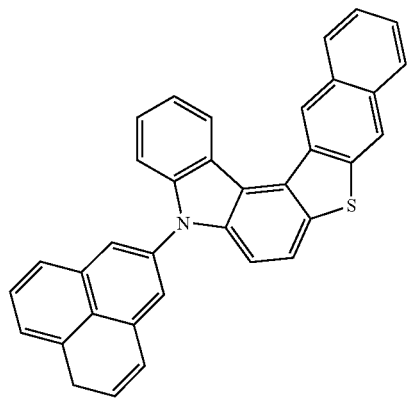
2-118
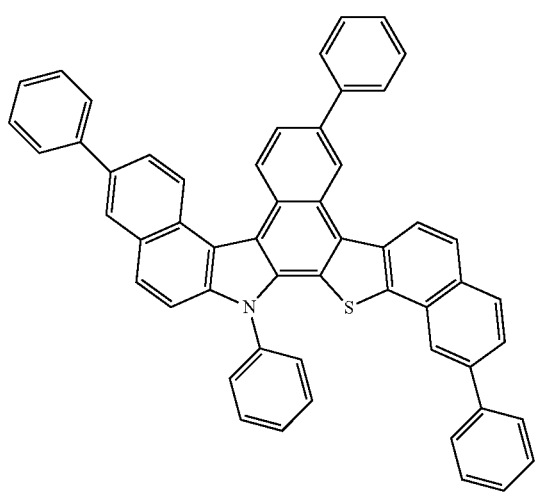
2-119
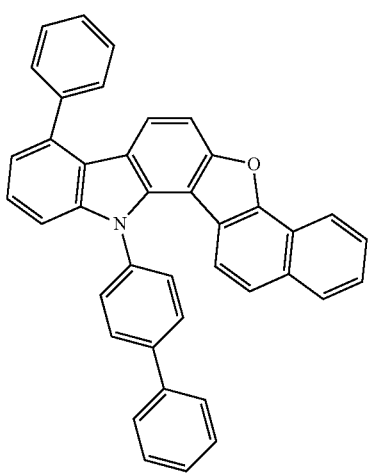
2-120
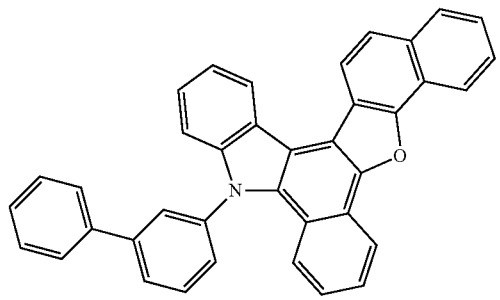
2-121
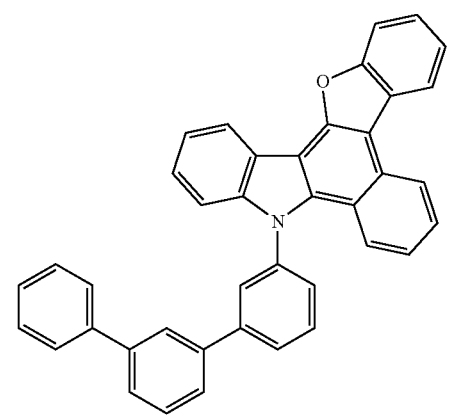
2-122
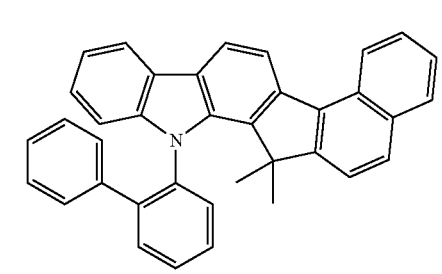
2-123
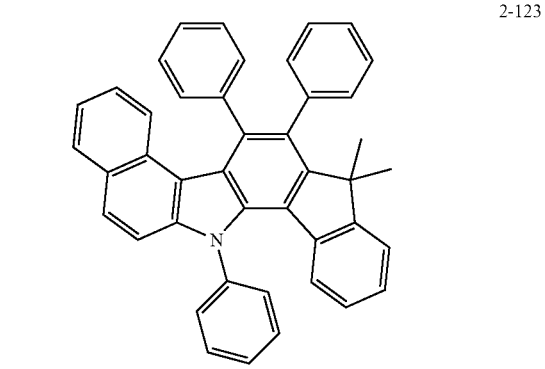

2-124
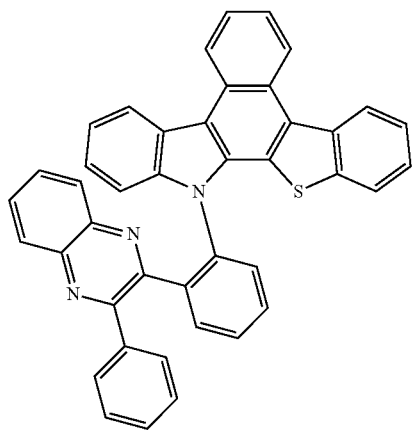
2-127
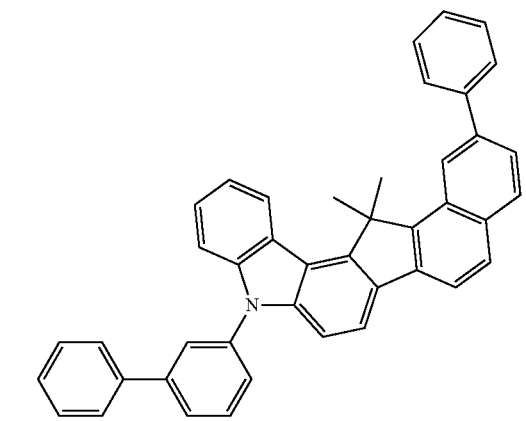
2-125
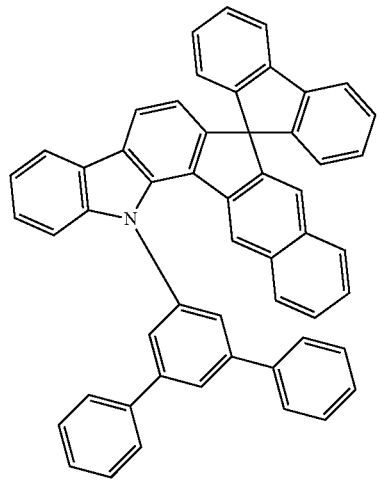
2-128
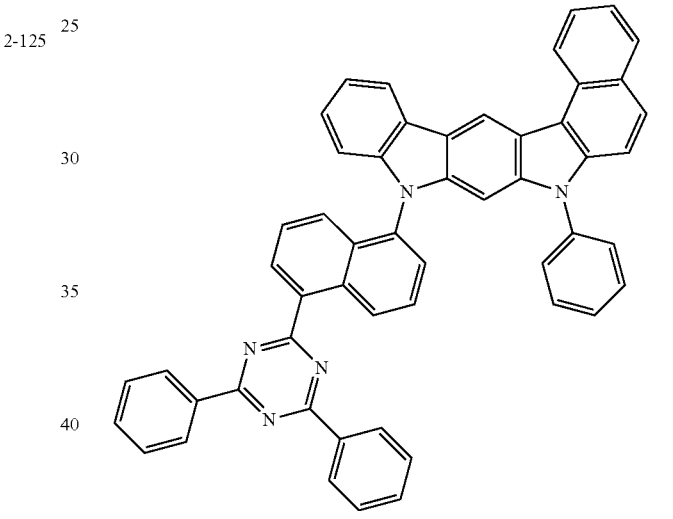
2-126
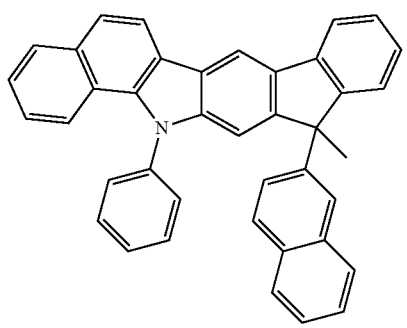
2-129
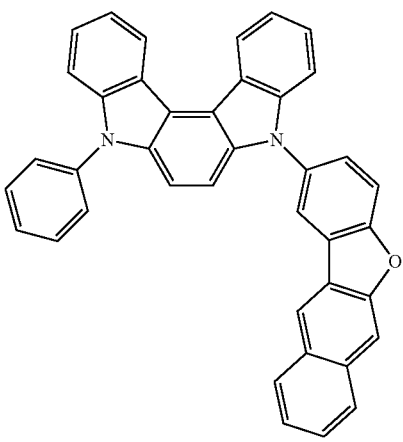

2-130
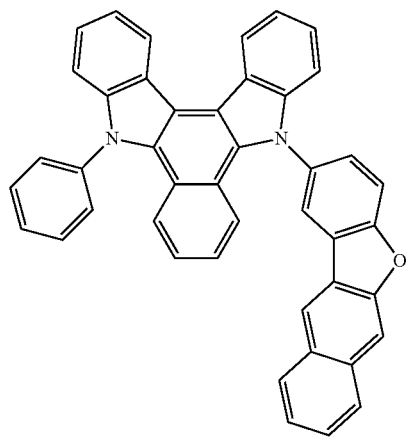
2-131
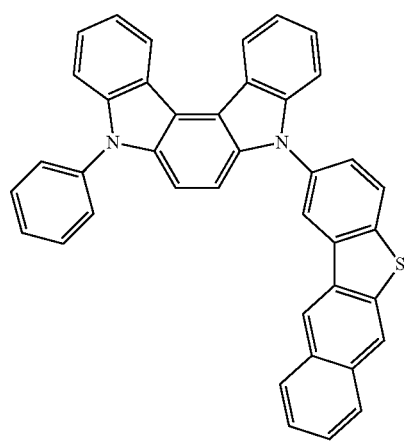
2-132
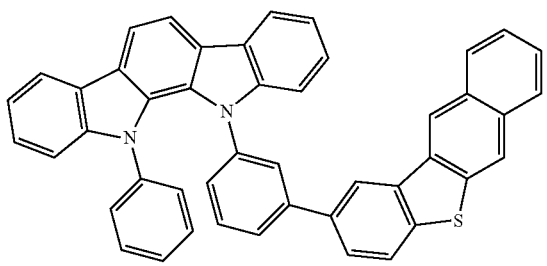
2-133
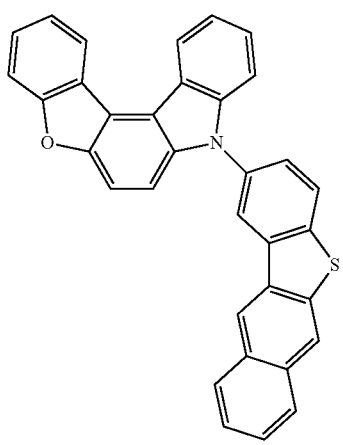
2-134
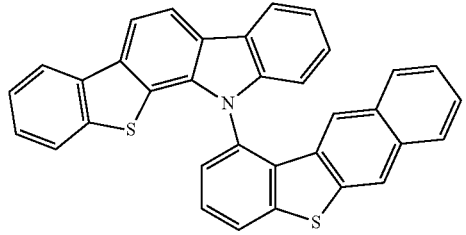
2-135
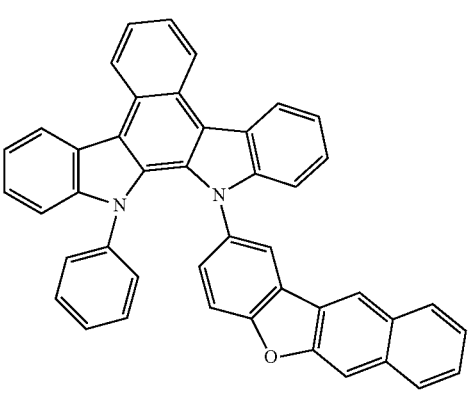
2-136
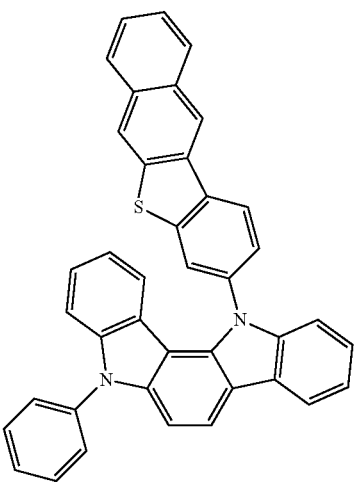
2-137
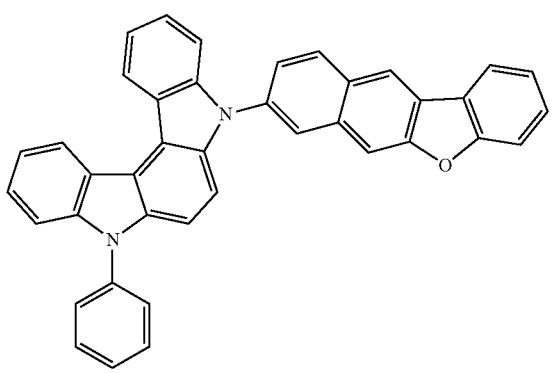

-continued
2-138
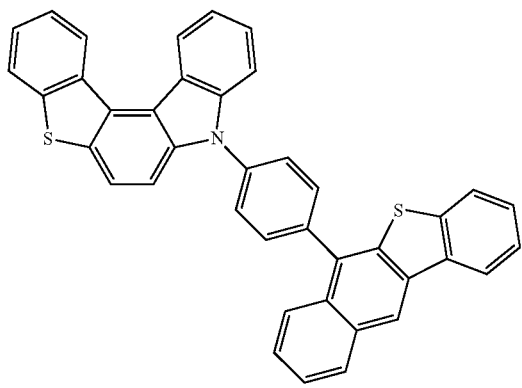
2-139
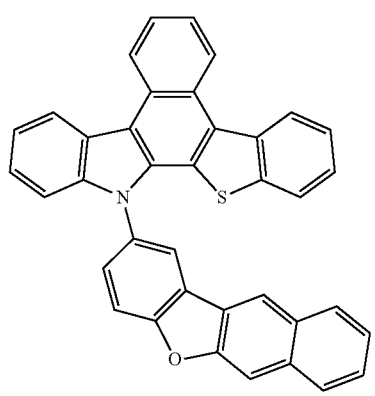
2-140
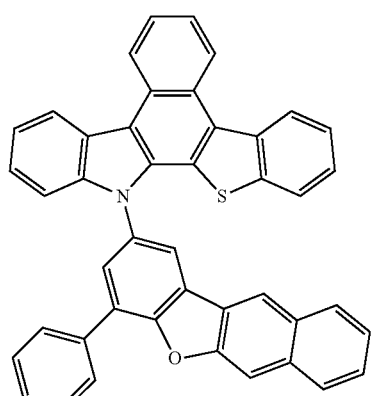
2-141
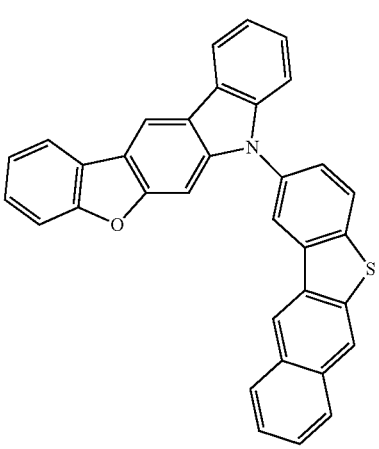
-continued
2-142
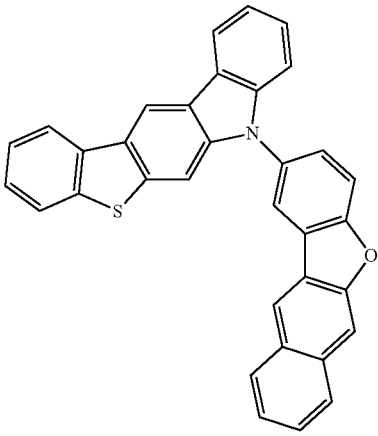
2-143
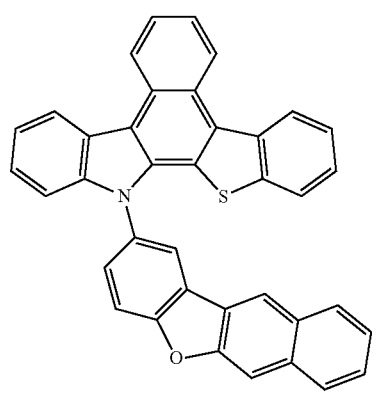
2-144
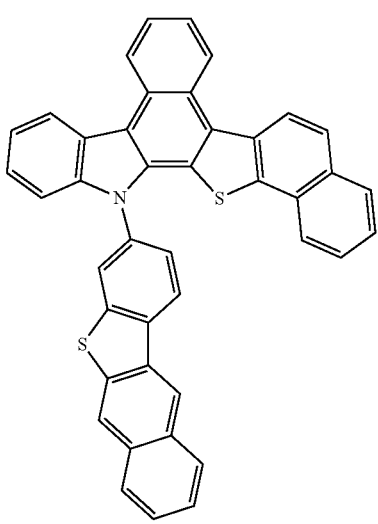

2-145
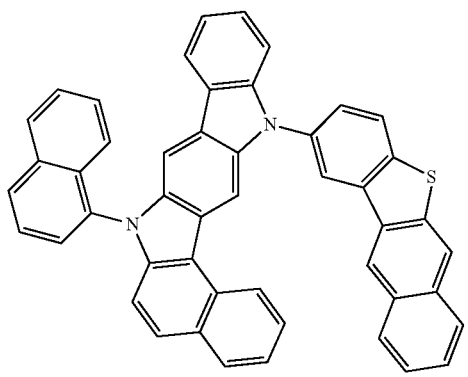
2-146
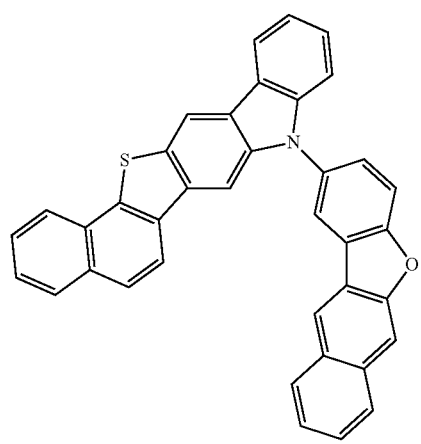
2-147
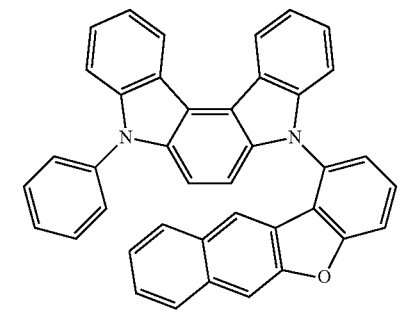
2-148
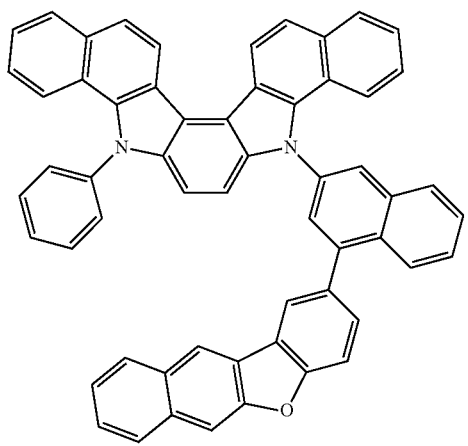
2-149
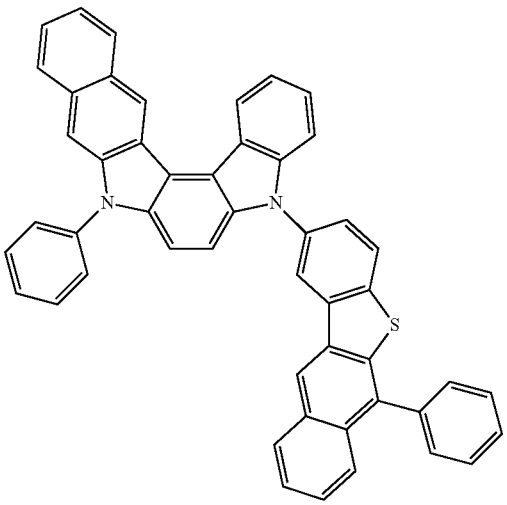
2-150
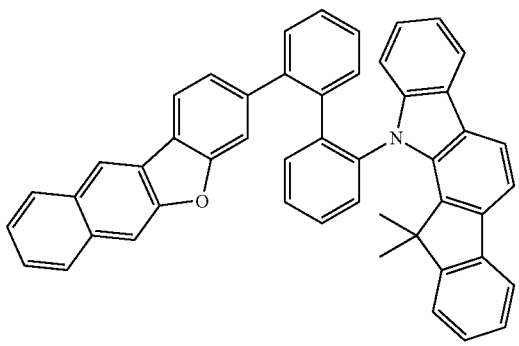
2-151
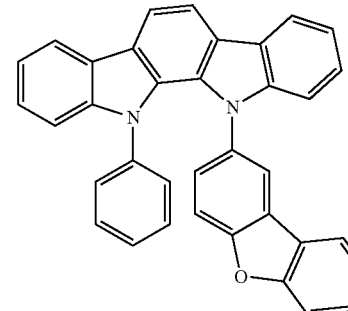
2-152
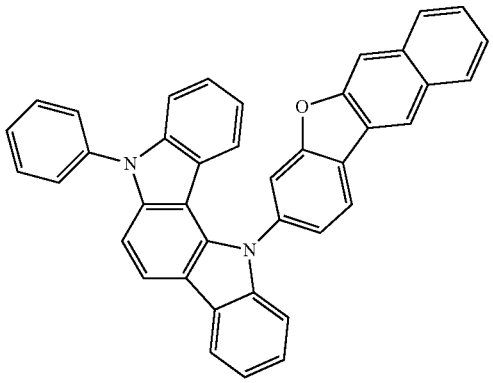

2-153
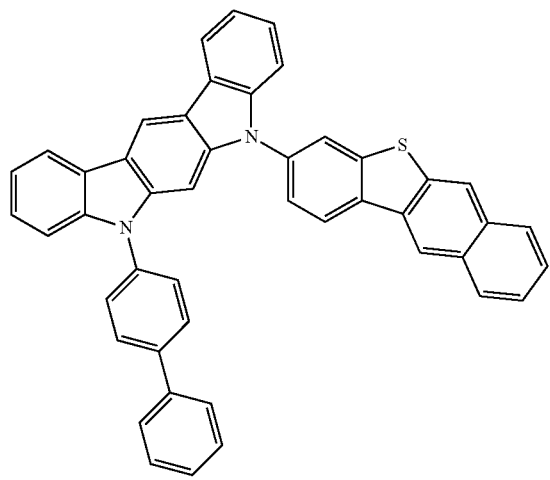
2-154
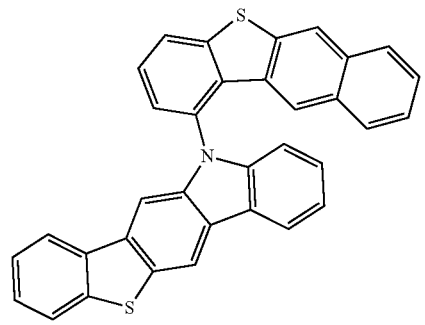
2-155
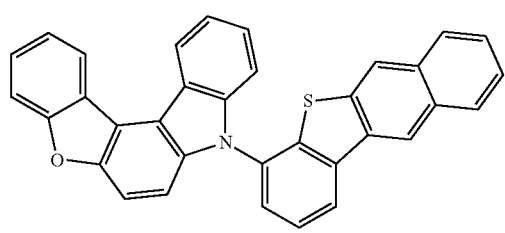
2-156
2-157
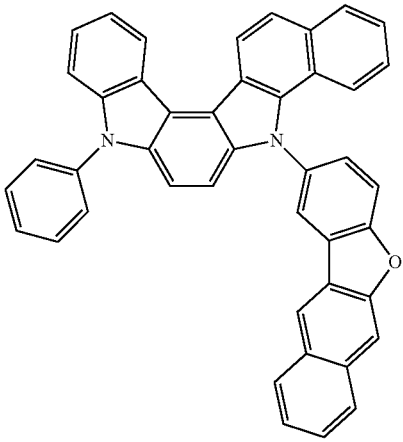
2-158
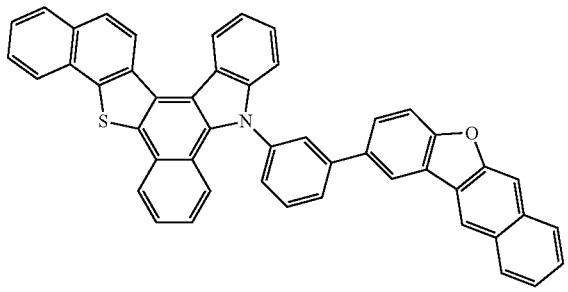
2-159
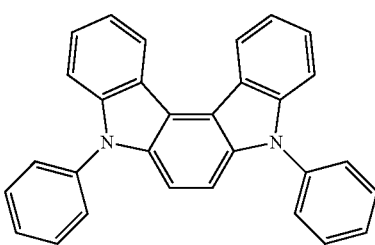
2-160
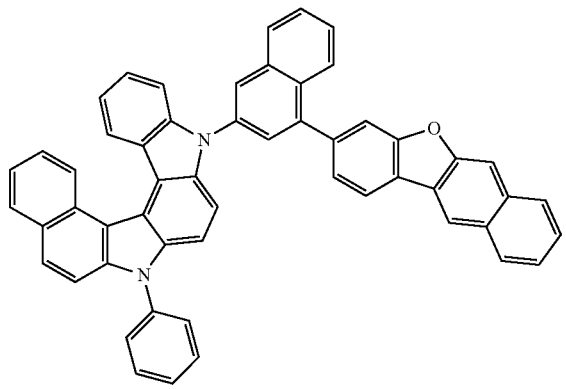

2-161
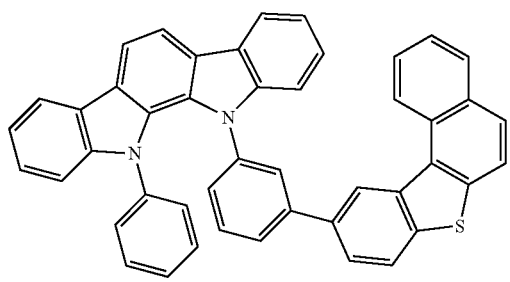
2-162
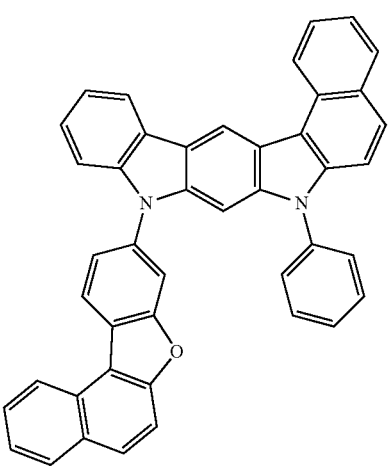
2-163
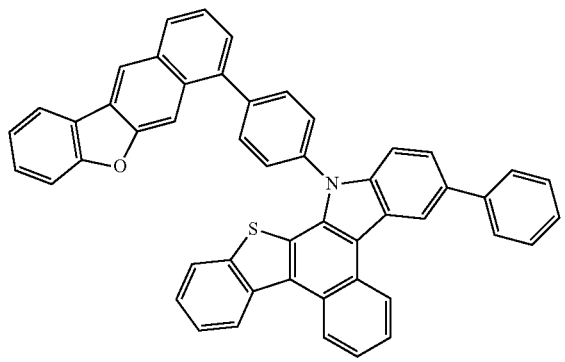
2-164
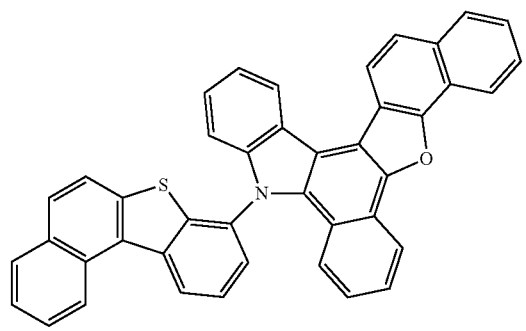
2-165
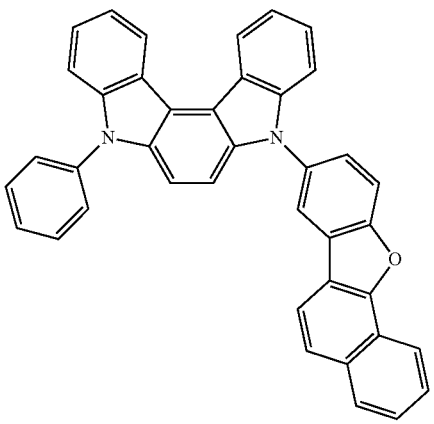
2-166
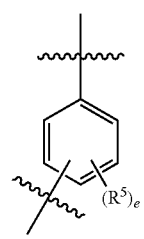
Preferably, in Formulas 1 and 2, $L^1$ to $L^4$ may be each independently one of the following Formulas b-1 to b-13:
<Formula b-1>
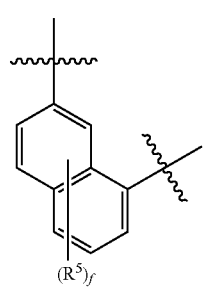
<Formula b-2>

<Formula b-3>
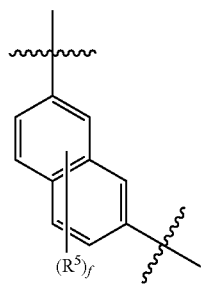

<Formula b-4>
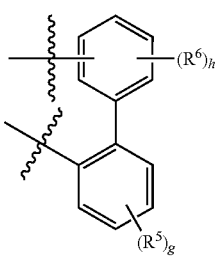

<Formula b-5>
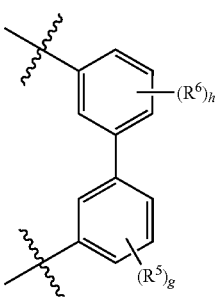

<Formula b-6>
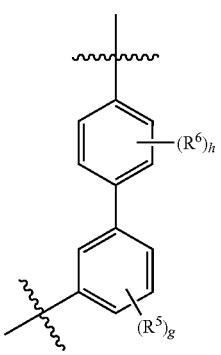

<Formula b-7>
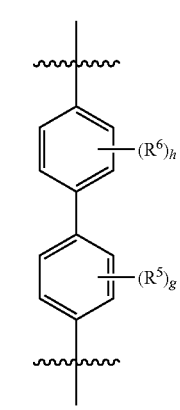

<Formula b-8>
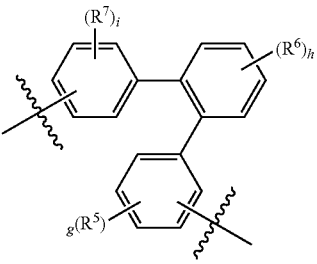

<Formula b-9>
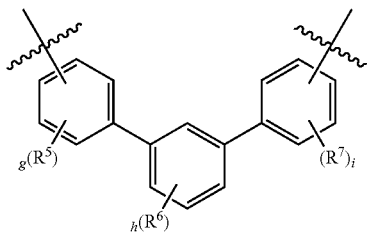

<Formula b-10>
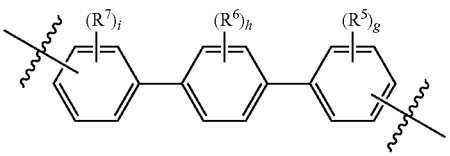

<Formula b-11>
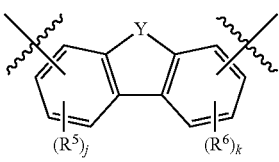

<Formula b-12>
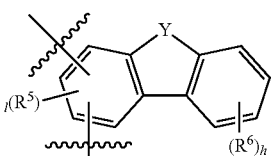

<Formula b-13>
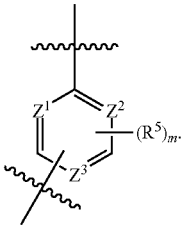

In Formulas b-1 to b-13, each of symbols may be defined as follows:

$R^5$ to $R^7$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group and -$L^a$-N($R^a$)($R^b$), and adjacent groups may be bonded to each other to form a ring.

'The ring formed by bonding between neighboring groups' may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring $R^4$s, or neighboring $R^5$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

Y is N-($L^a$-$Ar^a$), O, S or C(R')(R").

$Z^1$ to $Z^3$ are each independently C, C(R') or N, and at least one of $Z^1$ to $Z^3$ is N.

f is an integer of 0-6, e, g, h and i are each an integer of 0-4, j and k are each an integer of 0-3, l is an integer of 0-2, m is an integer of 0-3, and where each of these is an integer of 2 or more, each of a plurality of $R^5$, each of a plurality of $R^6$, and each of a plurality of $R^7$ are the same as or different from each other.

R' and R" are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group, and -$L^a$-N($R^a$)($R^b$).

R' and R" in C(R')(R") may be linked to each other to form a ring, and adjacent R's in C(R') may be linked to each other to form a ring.

$Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R^b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^5$ to $R^7$, $L^a$, $Ar^a$, R', R", $R^a$, $R^b$ and the ring formed by bonding between adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

In another aspect of the present invention, the present invention provides a compound represented by Formula 2-K:

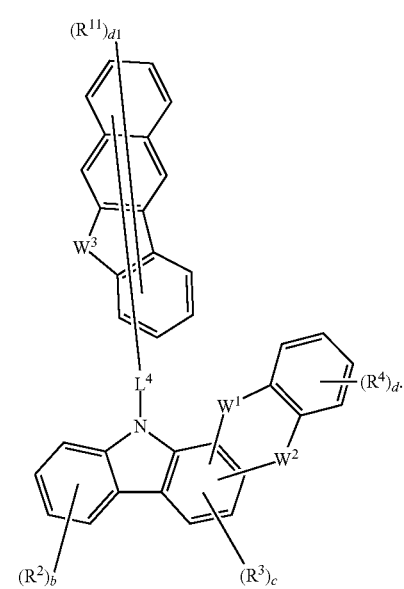

<Formula 2-K>

In Formula 2-K, $R^2$-$R^4$, $R^{11}$, $W^1$, $W^2$, $W^3$, b-d and d1 are the same as defined for Formula 2-J, $L^4$ is a single bond or a $C_6$-$C_{12}$ arylene group.

Preferably, Formula 2-K may be represented by Formula 2-K-1 or Formula 2-K-2:

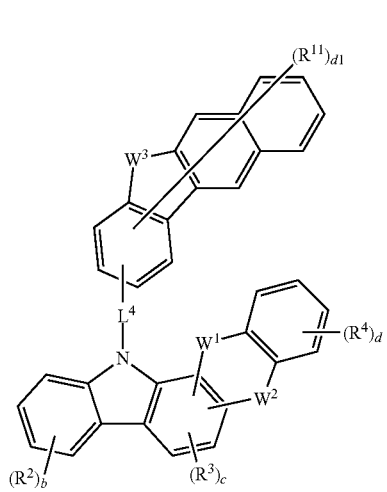

<Formula 2-K-1>

-continued

<Formula 2-K-2>

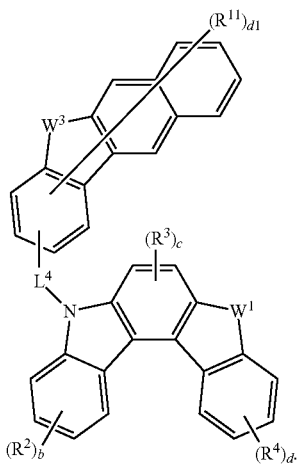

In Formulas above, $W^1$-$W^3$, $R^2$-$R^4$, $R^{11}$, $L^4$, b-d and d1 are the same as defined for Formula 2-K.

$R^2$ to $R^4$, $R^{11}$ and $L^4$ may be each further substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Specifically, the compound represented by Formula 2-K may be one of the following compounds, but it is not limited only thereto:

2-129

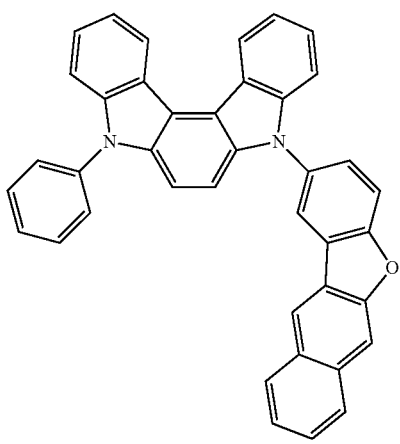

2-130

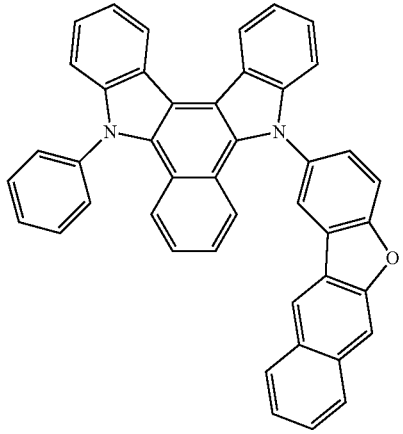

2-131

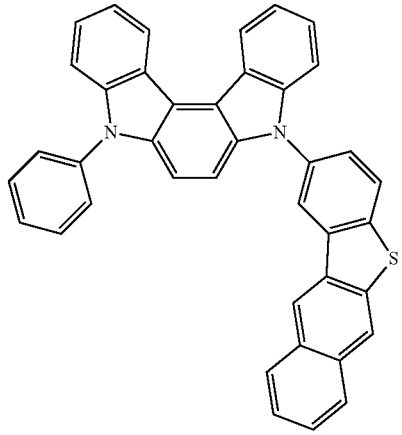

2-132

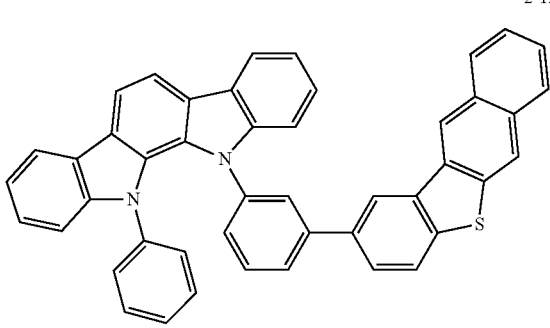

2-133

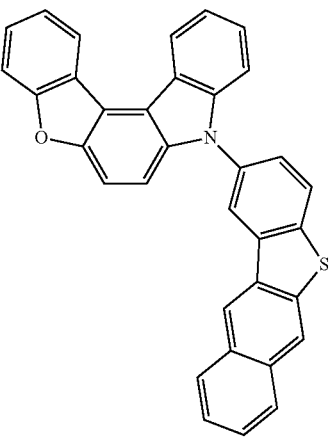

2-134
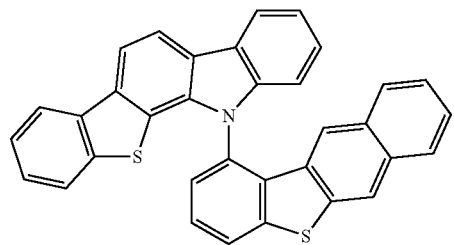
2-135
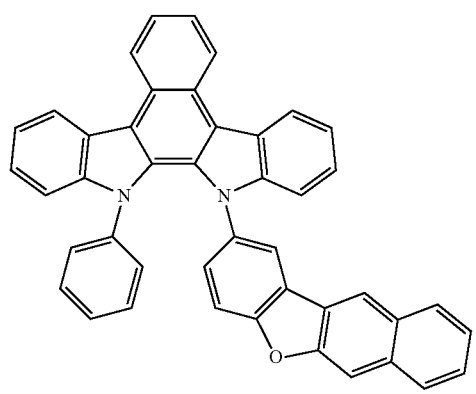
2-136
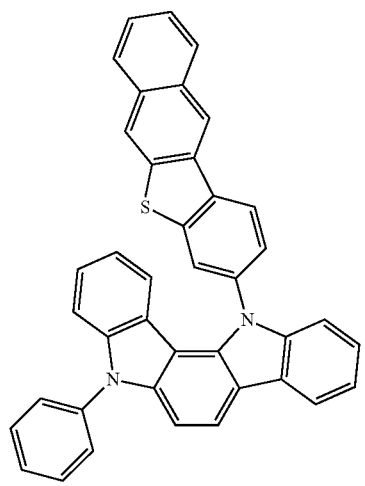
2-137
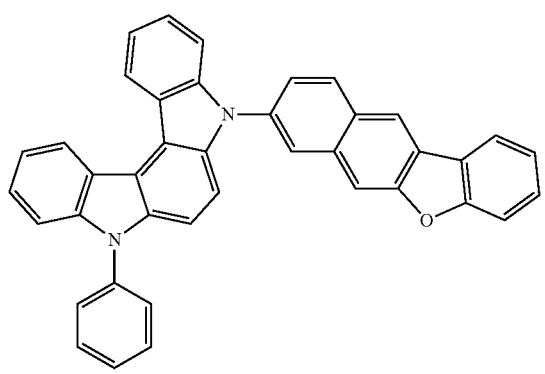
2-138
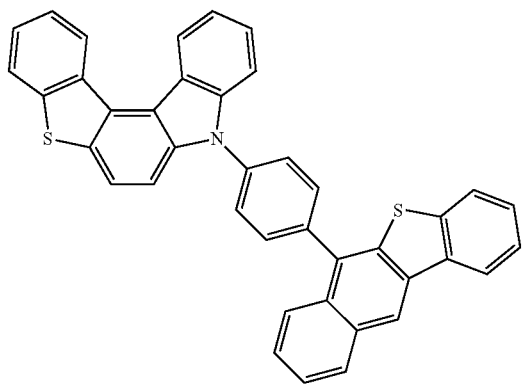
2-139
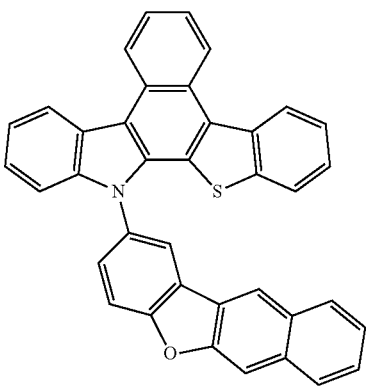
2-140
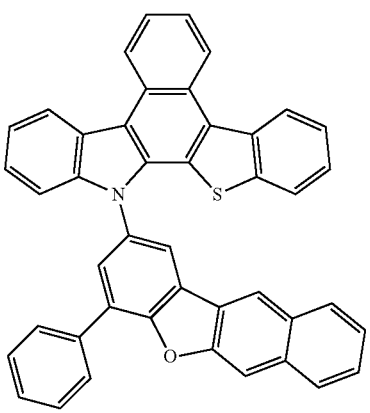
2-141
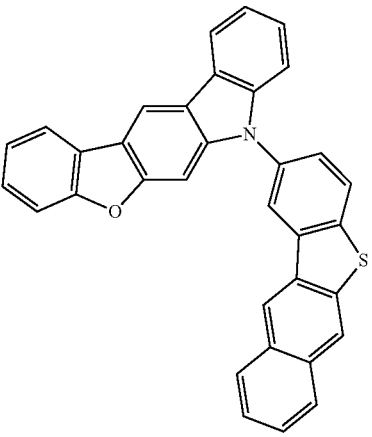

2-142
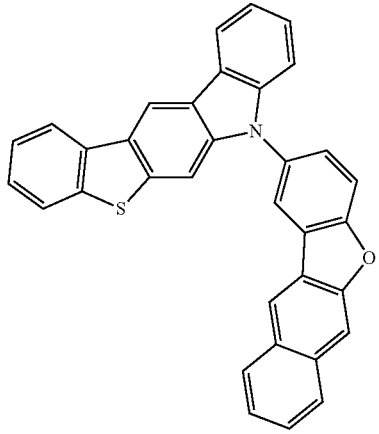
2-143
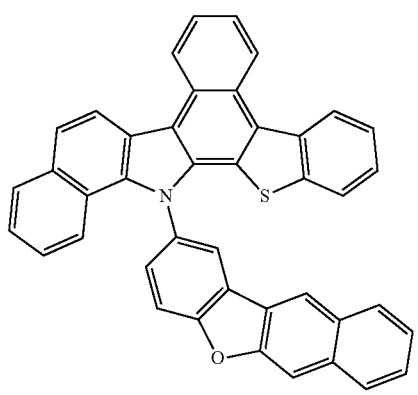
2-144
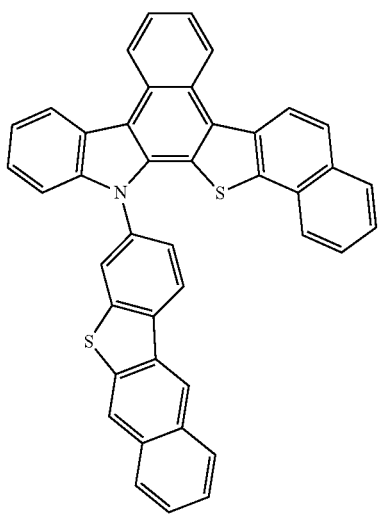
2-145
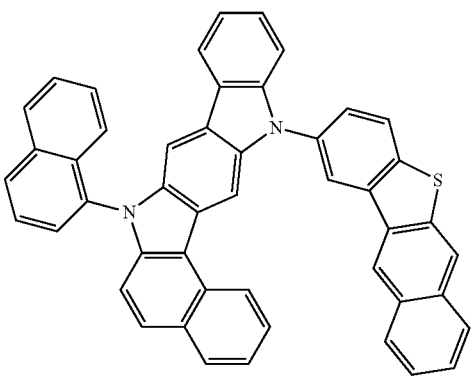
2-146
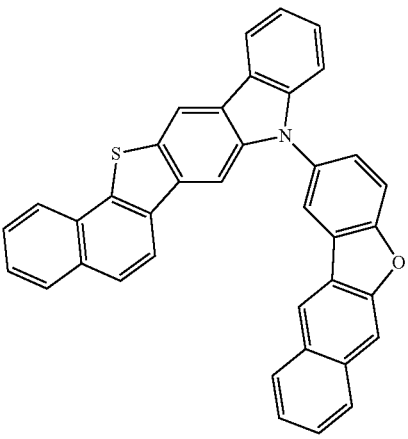
2-147
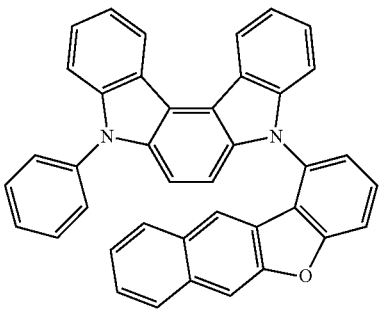
2-148
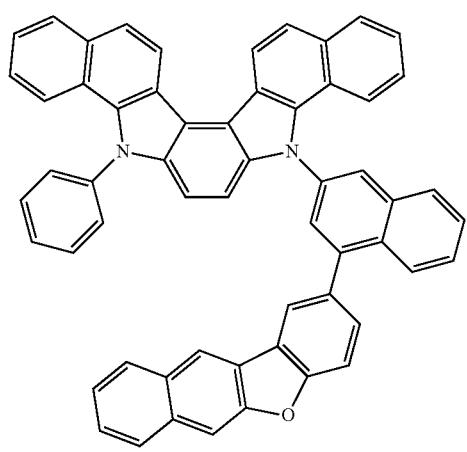

2-149
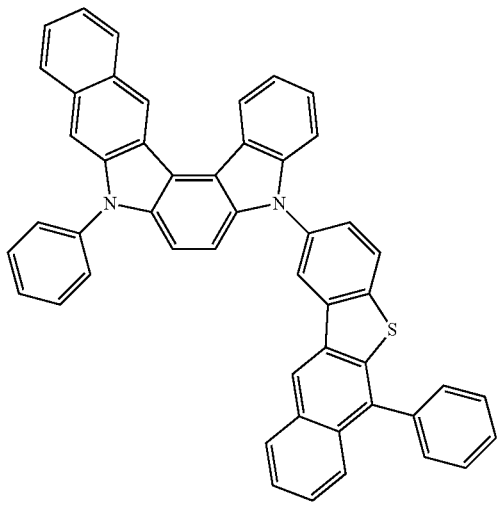
2-150
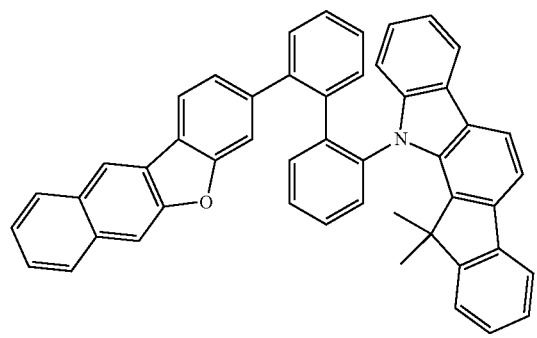
2-151
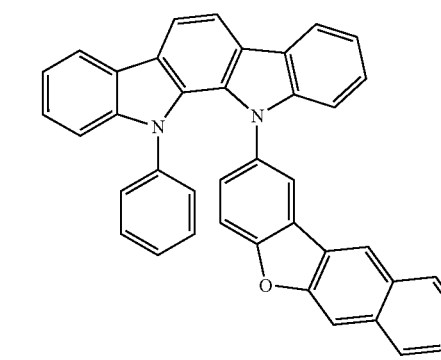
2-152
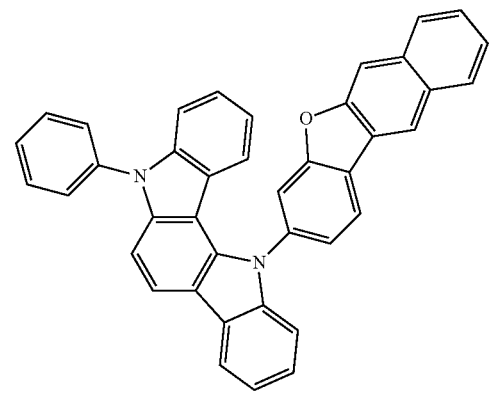
2-153
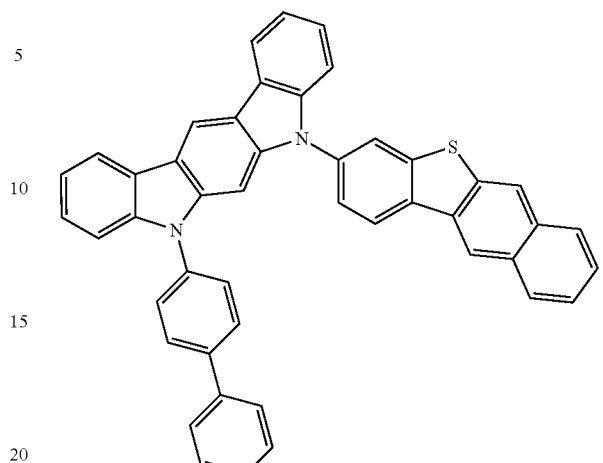
2-154
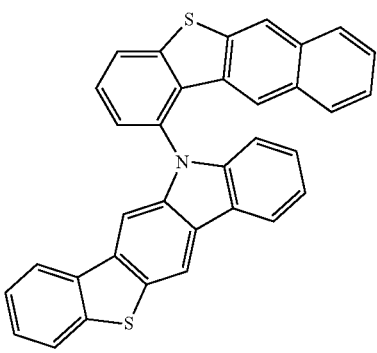
2-155
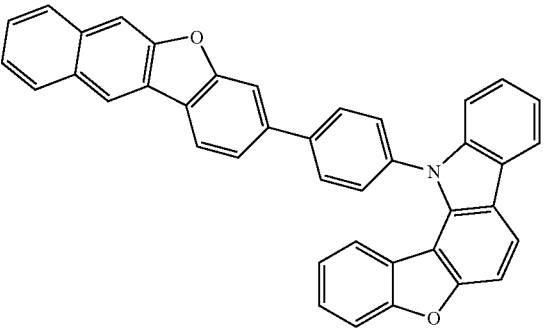
2-156
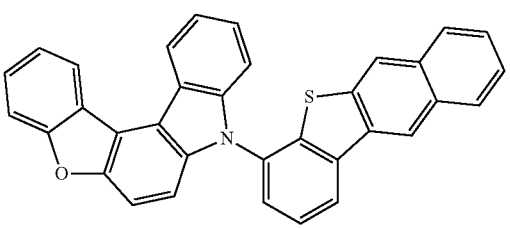

131
-continued
2-157
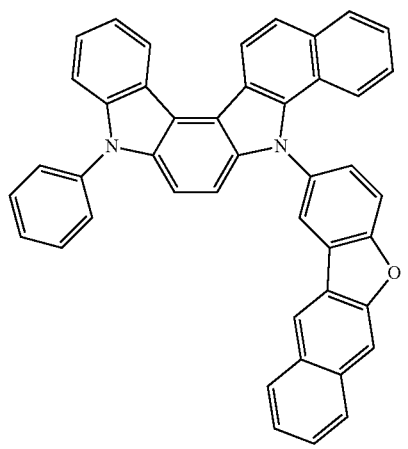
2-158
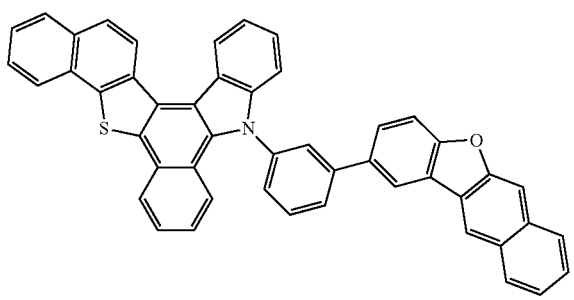
2-159
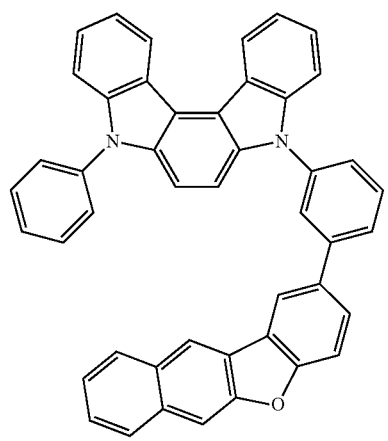
2-160
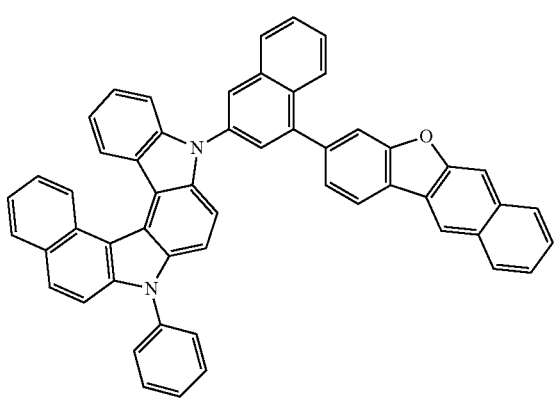
132
-continued
2-161
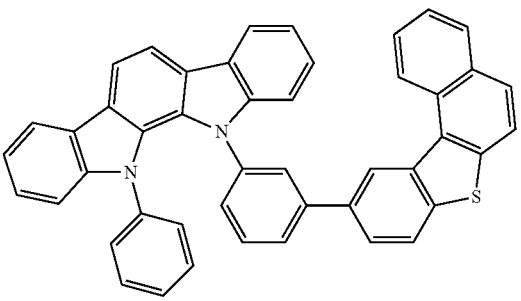
2-162
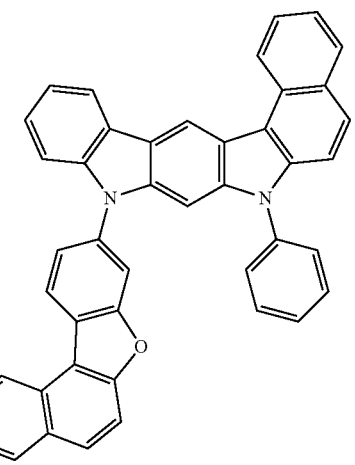
2-163
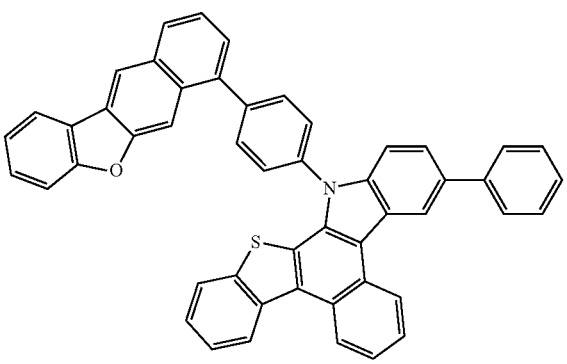
2-164
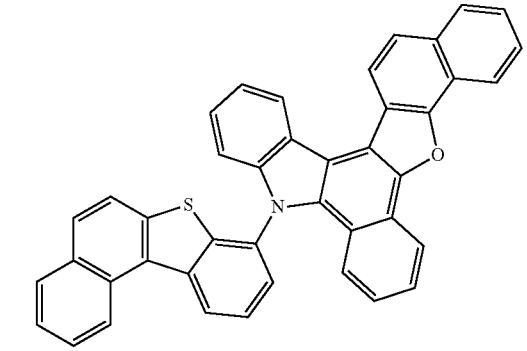

2-165

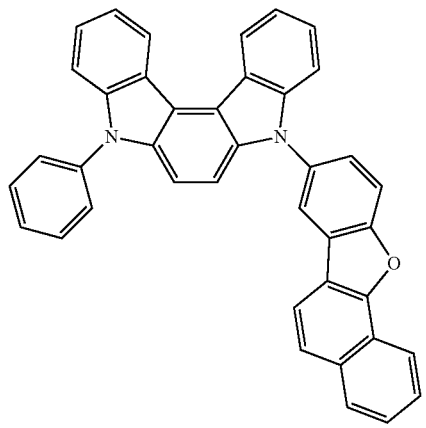

2-166

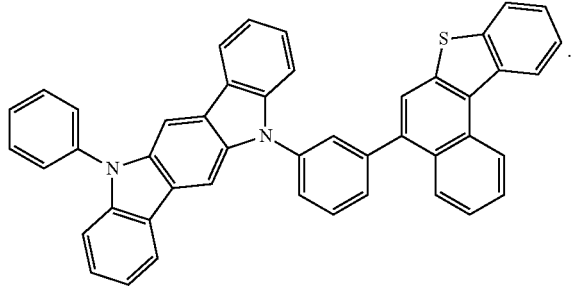

In another aspect, the present invention provides an organic electric element comprising a first electrode, a second electrode, and an organic material layer formed between the first electrode and the second electrode, wherein the organic material layer comprises compound represented by Formula 2-K. Preferably, the organic material layer comprises a light emitting layer which comprises a compound represented by Formula 2-K.

Hereinafter, examples for synthesizing the compounds represented by Formulas 1 and 2 according to the present invention and examples for preparing an organic electric element according to the present invention will be described in detail with reference to examples, but the present invention is not limited to the following examples.

[Synthesis Example 1] Formula 1

The compound represented by Formula 1 according to the present invention can be synthesized by reacting Sub 1 and Sub 2 as shown in Reaction Scheme 1, but there is no limitation thereto.

<Reaction Scheme 1>

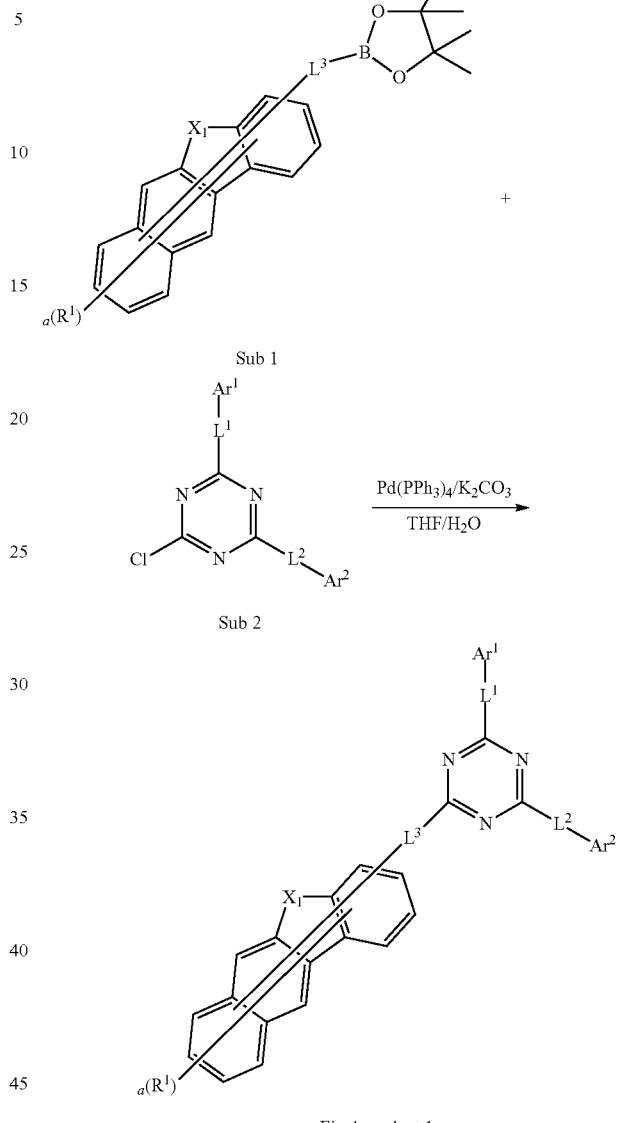

Final product 1

1. Exemplary Compounds and Synthesis Examples of Sub 1

Compounds belong to Sub 1 of Reaction Scheme 1 are as follows, but there is no limitation thereto.

Sub 1-1

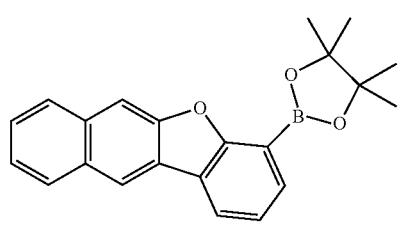

Sub 1-2
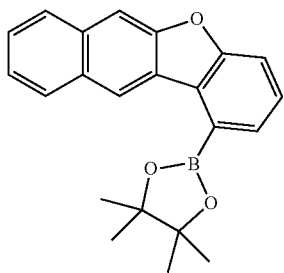
Sub 1-3
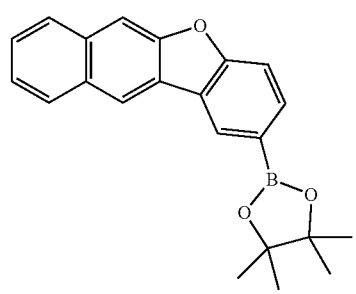
Sub 1-4
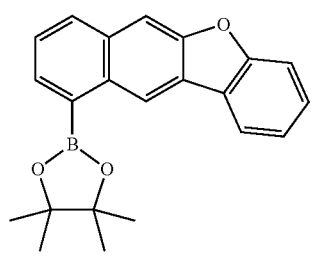
Sub 1-5
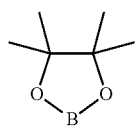
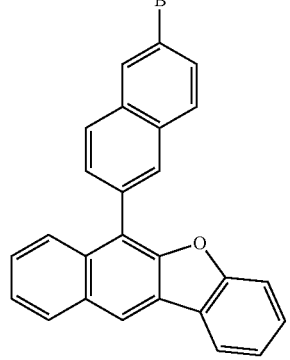
Sub 1-6
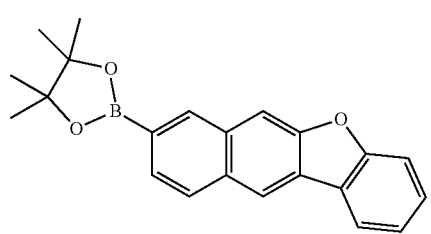
Sub 1-7
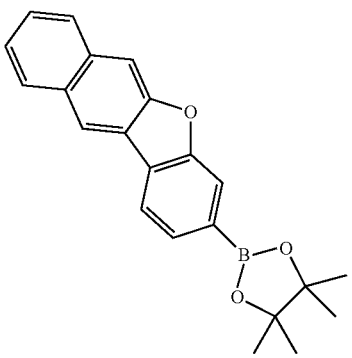
Sub 1-8
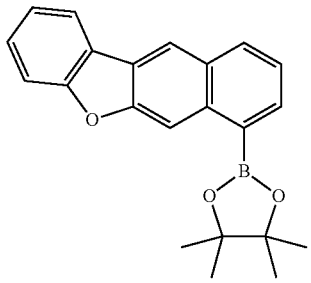
Sub 1-9
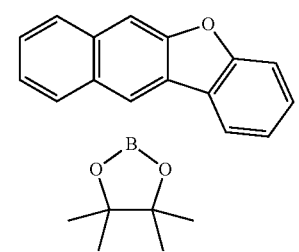
Sub 1-10
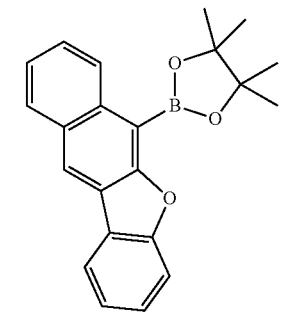
Sub 1-11
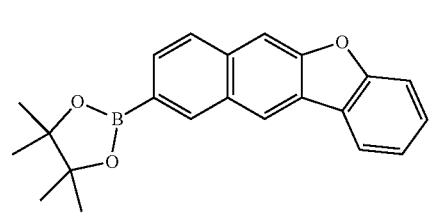

-continued
Sub 1-12
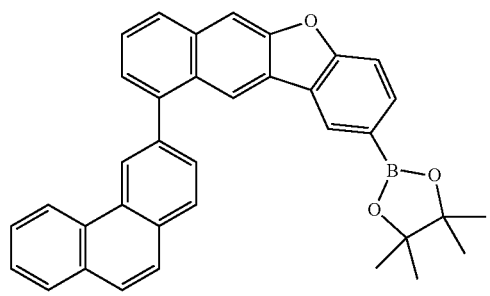
Sub 1-13
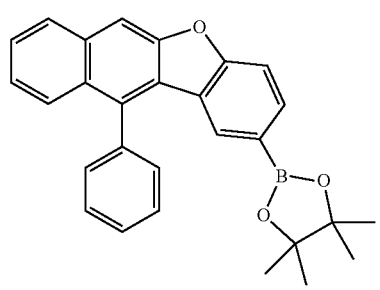
Sub 1-14
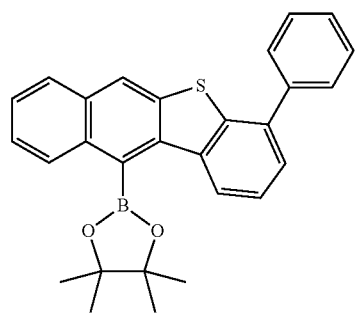
Sub 1-15
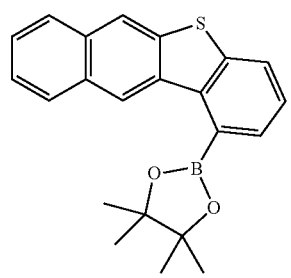
Sub 1-16
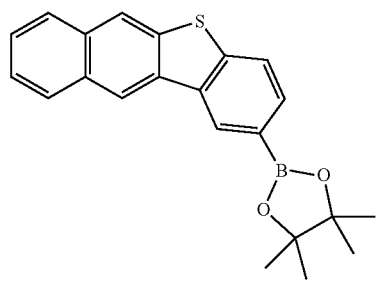
-continued
Sub 1-17
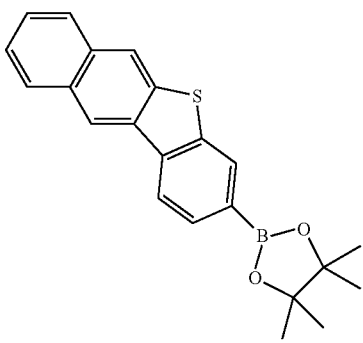
Sub 1-18
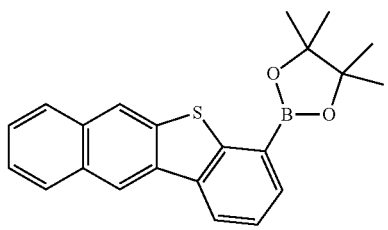
Sub 1-19
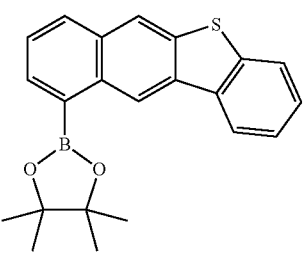
Sub 1-20
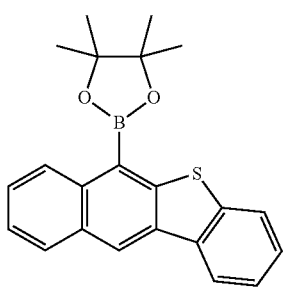
Sub 1-21
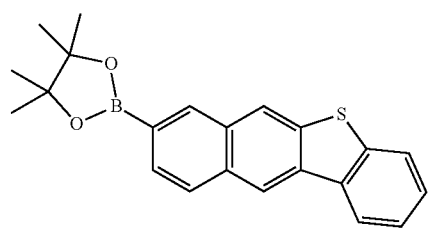

Sub 1-22
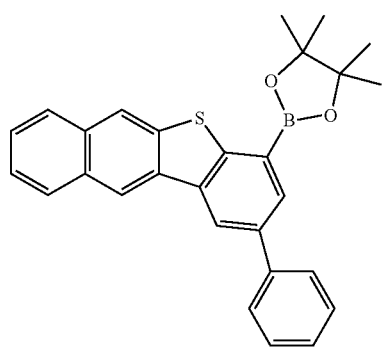
Sub 1-23
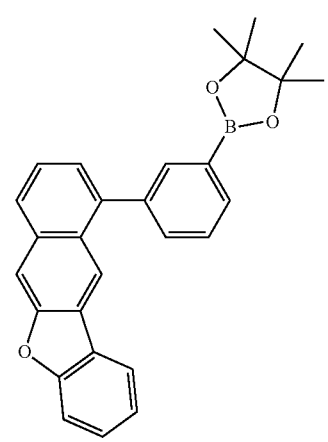
Sub 1-24
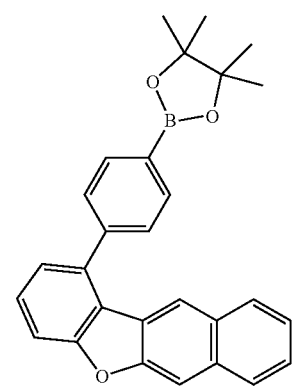
Sub 1-25
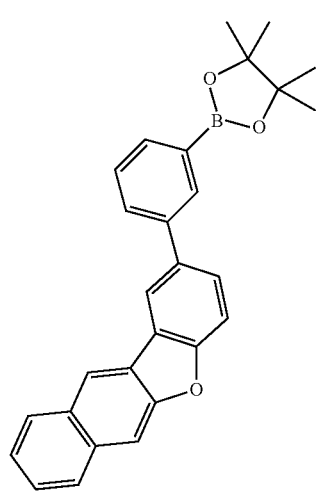
Sub 1-26
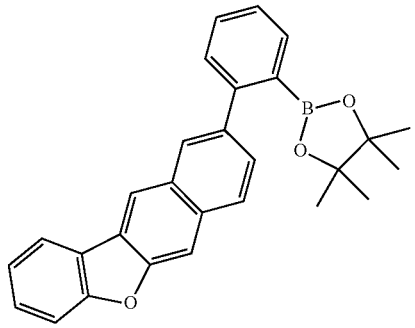
Sub 1-27
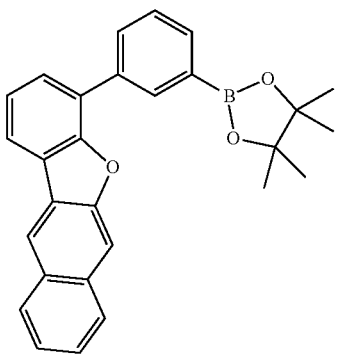
Sub 1-28
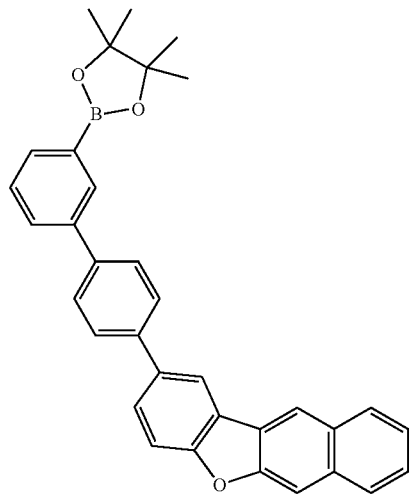
Sub 1-29
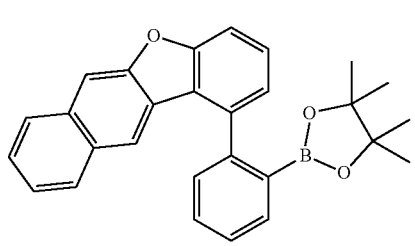

Sub 1-30
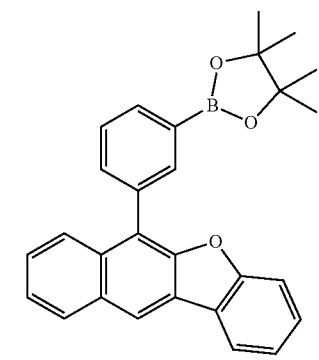
Sub 1-31
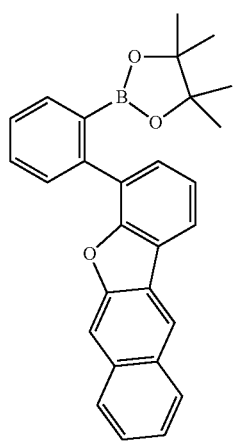
Sub 1-32
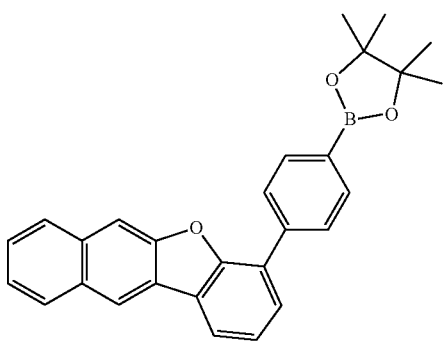
Sub 1-33
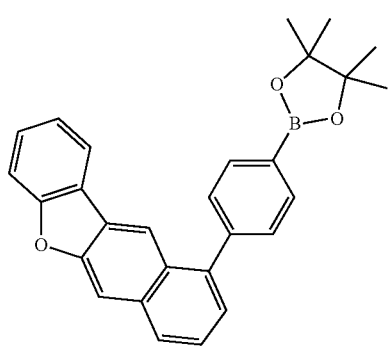
Sub 1-34
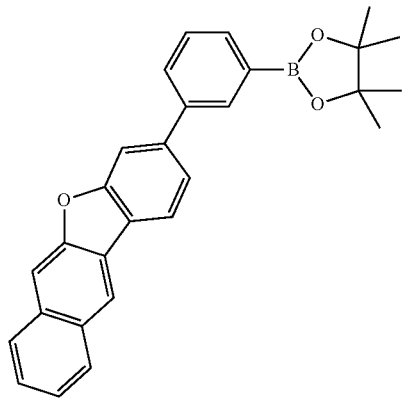
Sub 1-35
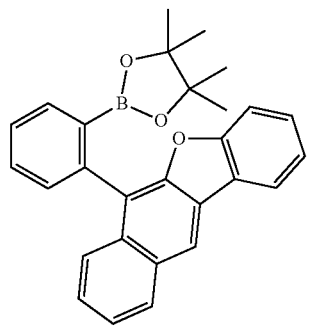
Sub 1-36
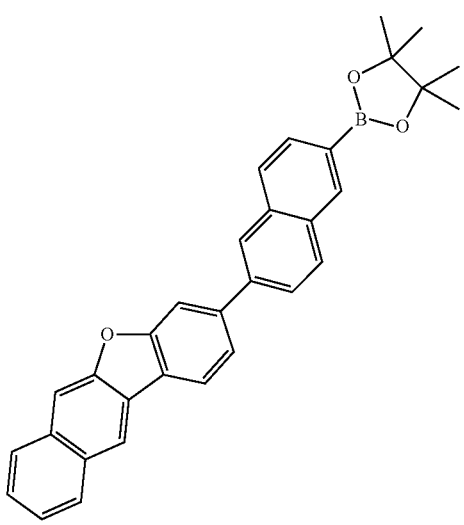
Sub 1-37
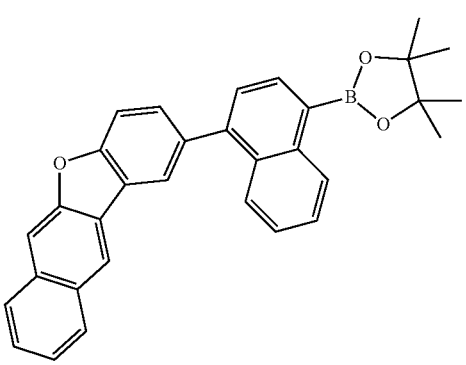

Sub 1-38
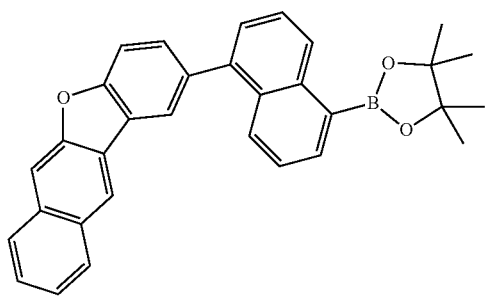
Sub 1-39
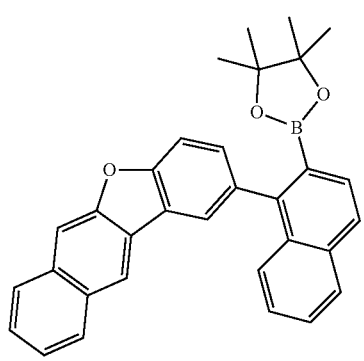
Sub 1-40
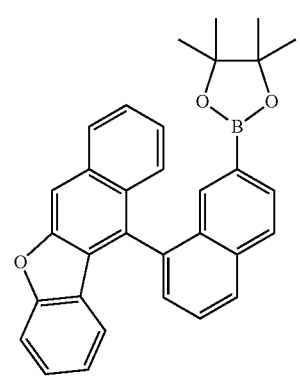
Sub 1-41
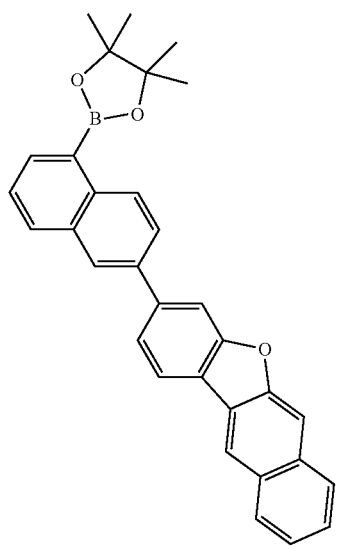
Sub 1-42
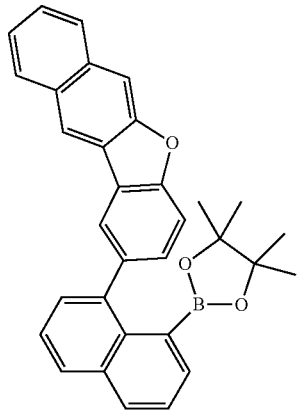
Sub 1-43
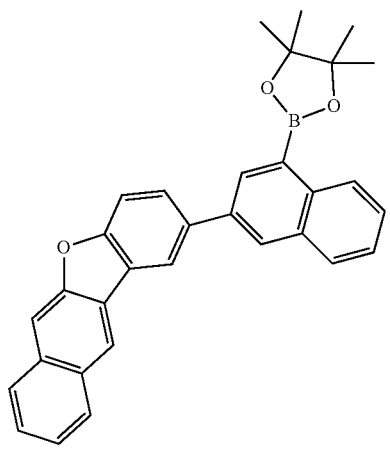
Sub 1-44
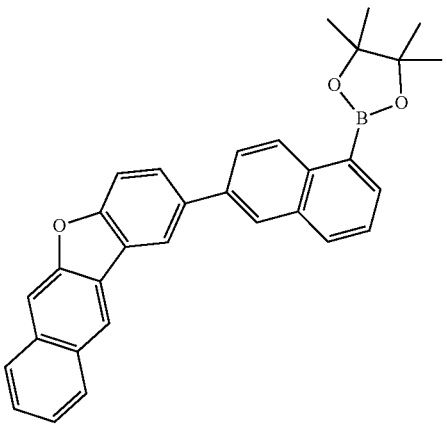
Sub 1-45
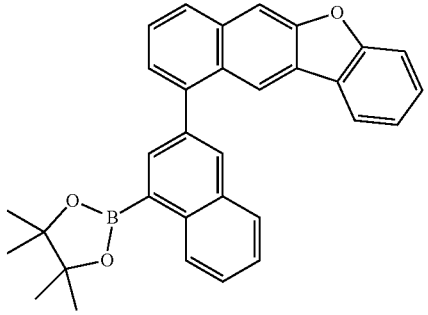

Sub 1-46
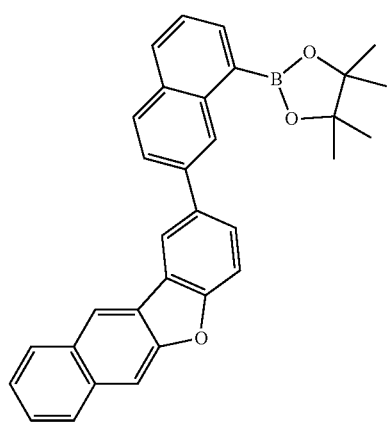
Sub 1-49
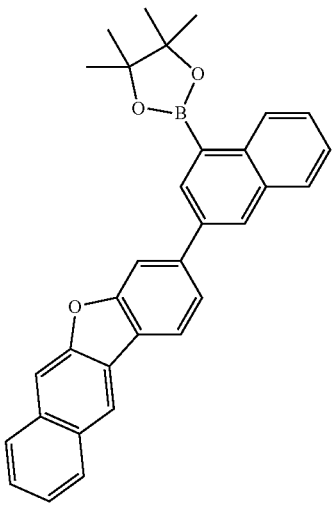
Sub 1-47
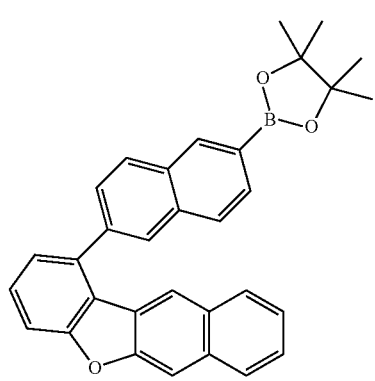
Sub 1-50
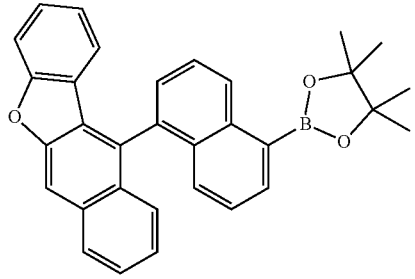
Sub 1-48
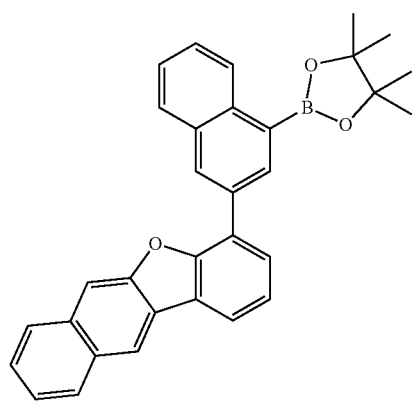
Sub 1-51
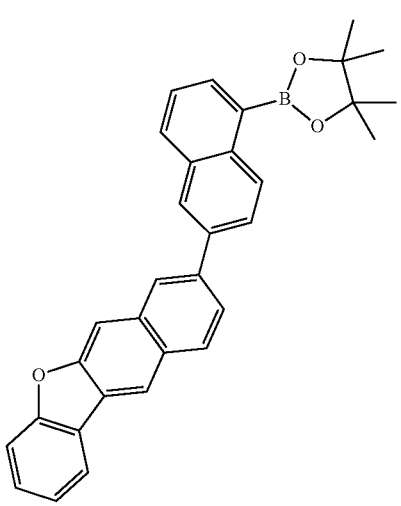

Sub 1-52
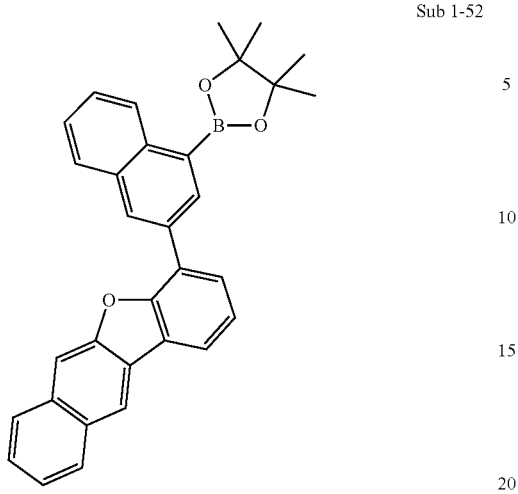
Sub 1-55
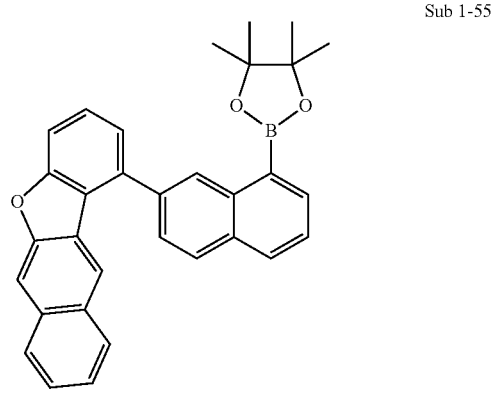
Sub 1-53
Sub 1-56
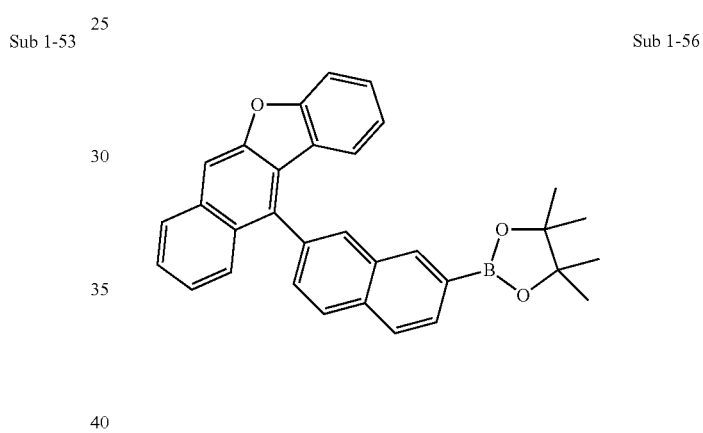
Sub 1-54
Sub 1-57
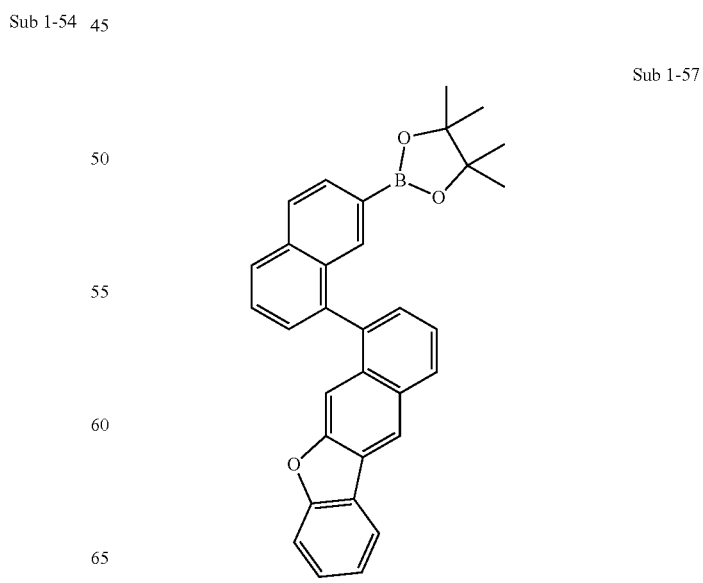

149
-continued
Sub 1-58
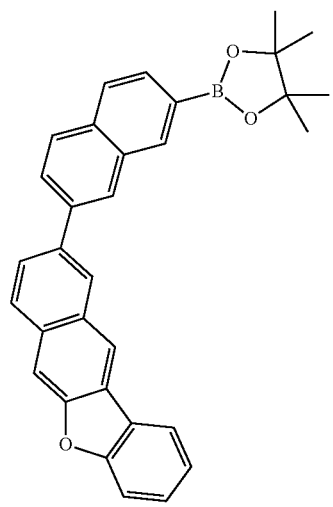
Sub 1-59
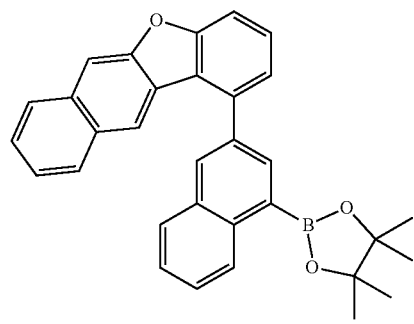
Sub 1-60
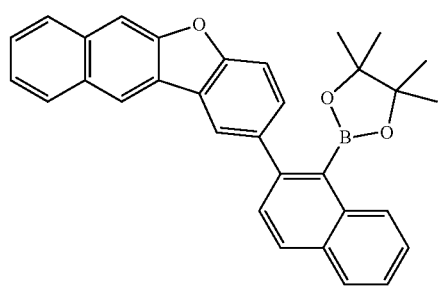
150
-continued
Sub 1-61
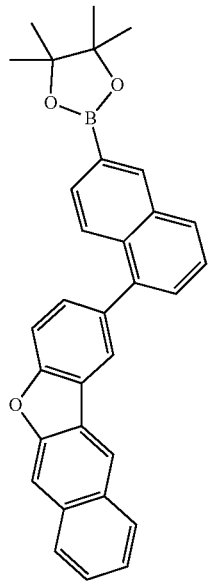
Sub 1-62
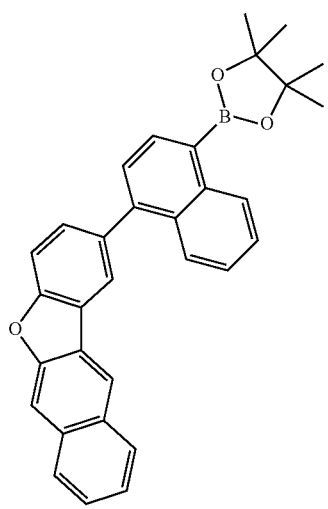
Sub 1-63
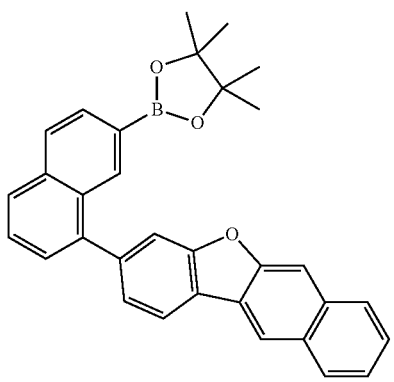

Sub 1-64
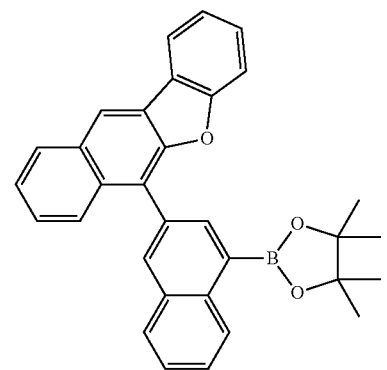
Sub 1-65
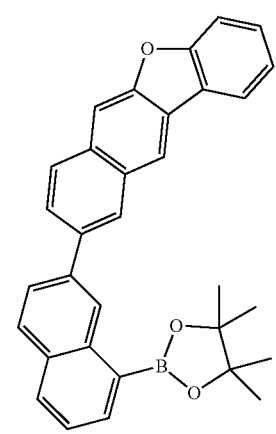
Sub 1-66
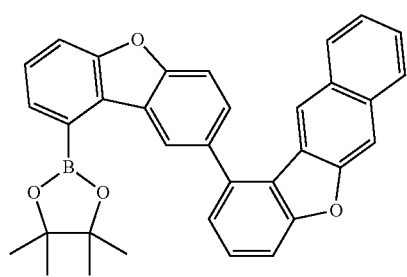
Sub 1-67
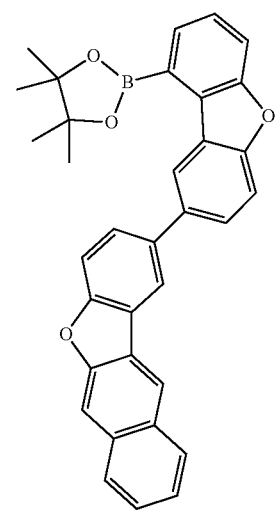
Sub 1-68
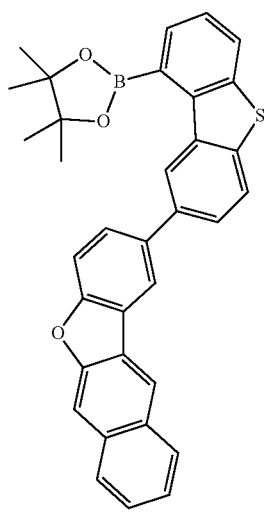
Sub 1-69
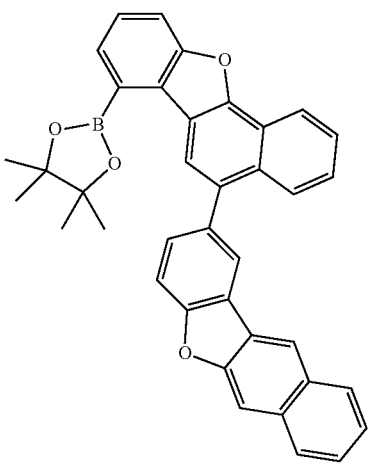
Sub 1-70
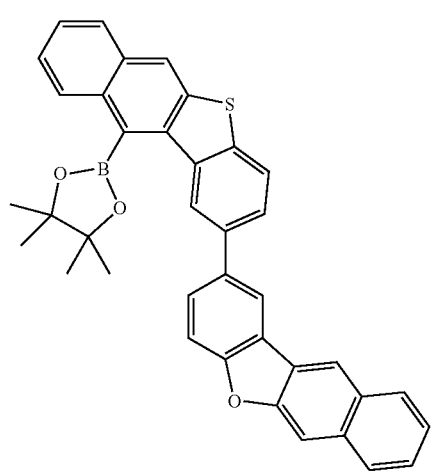

Sub 1-71
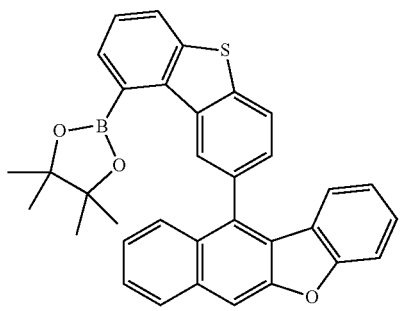
Sub 1-72
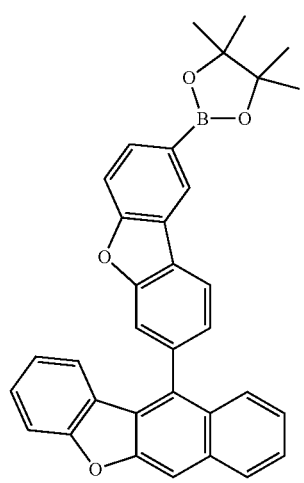
Sub 1-73
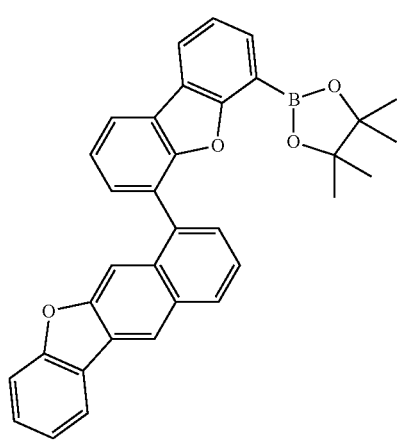
Sub 1-74
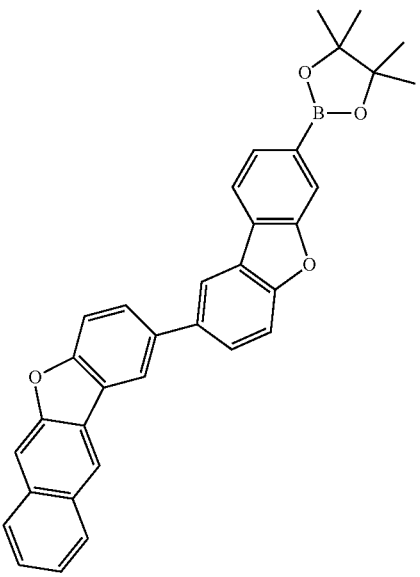
Sub 1-75
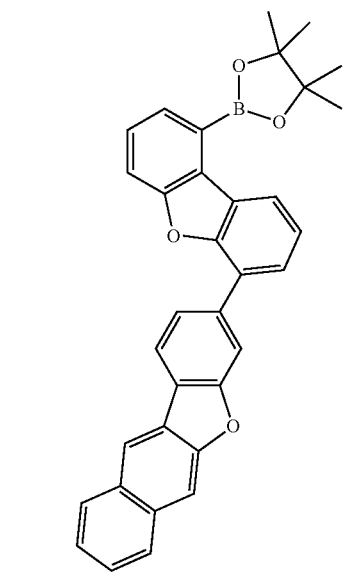
Sub 1-76
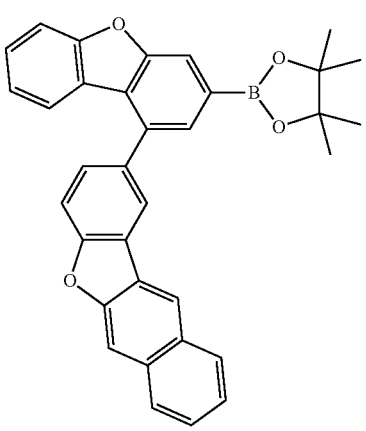

Sub 1-77
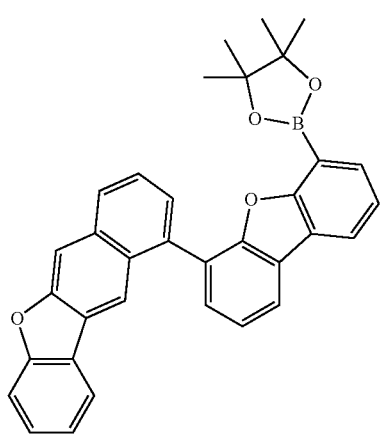
Sub 1-78
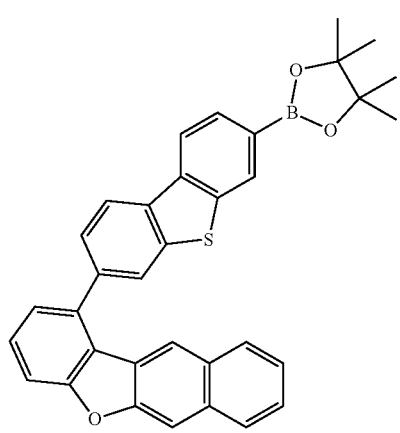
Sub 1-79
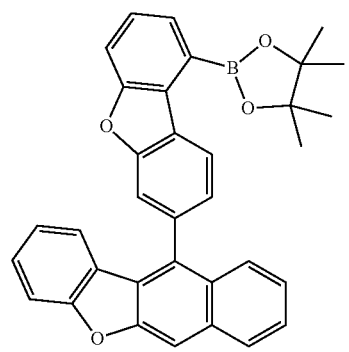
Sub 1-80
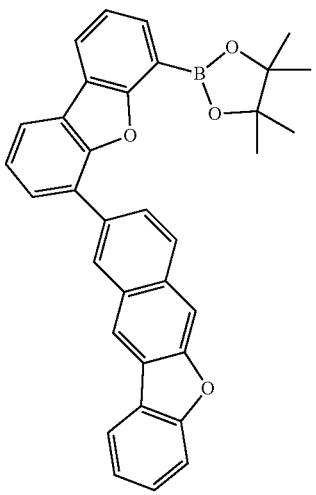
Sub 1-81
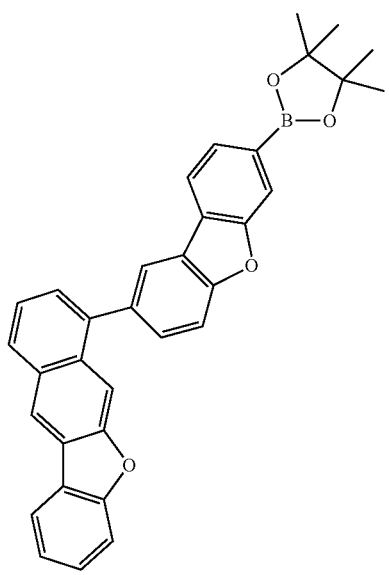
Sub 1-82
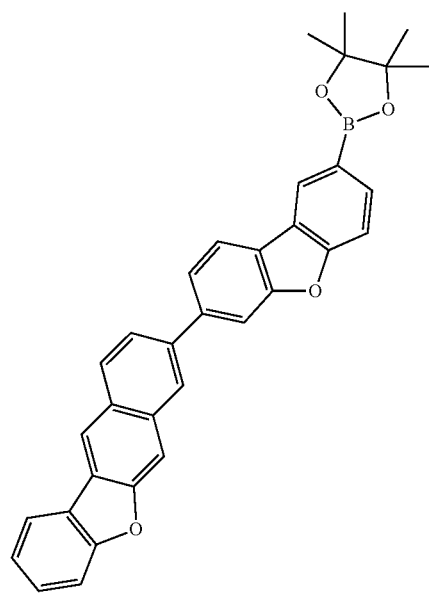

Sub 1-83
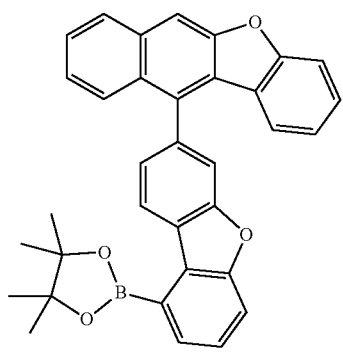
Sub 1-86
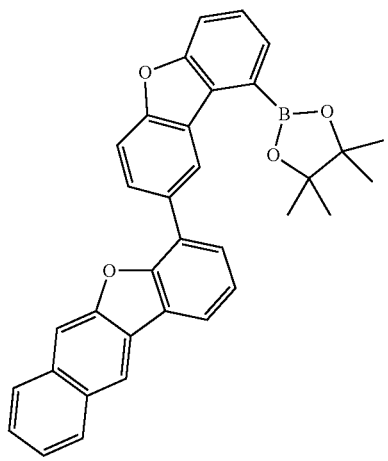
Sub 1-84
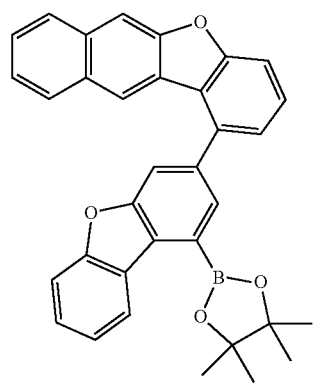
Sub 1-87
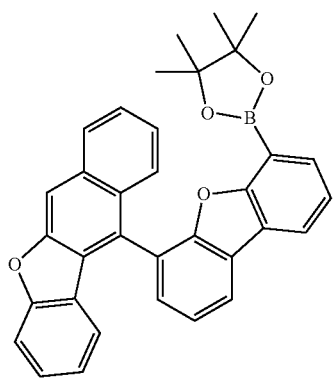
Sub 1-85
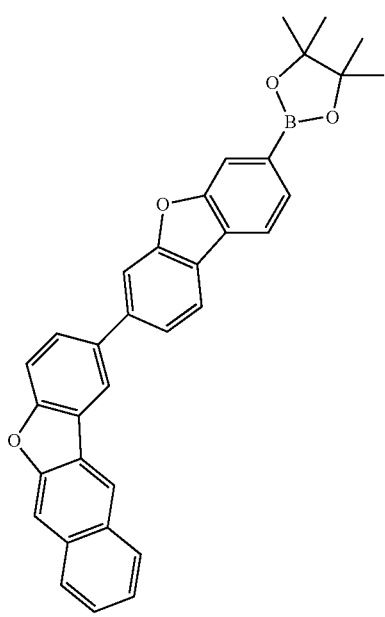
Sub 1-88
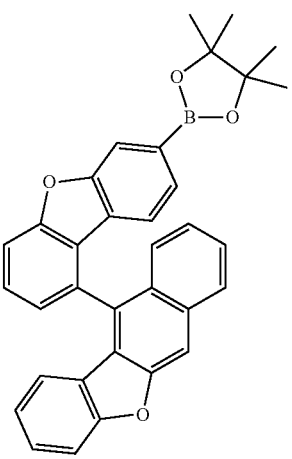

Sub 1-89
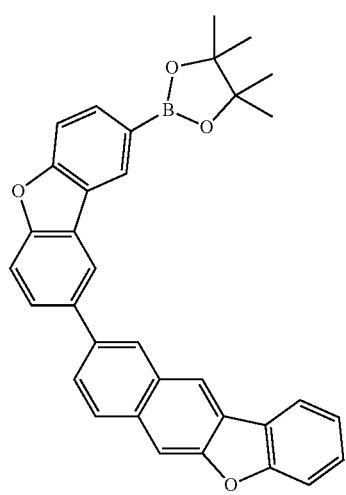
Sub 1-92
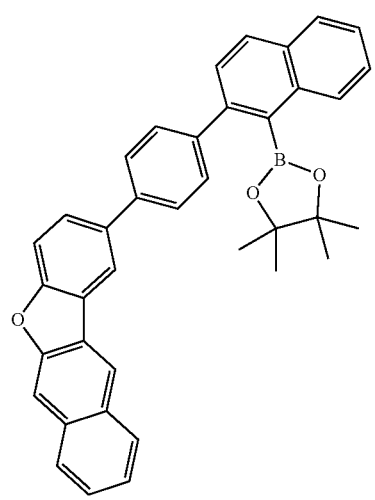
Sub 1-90
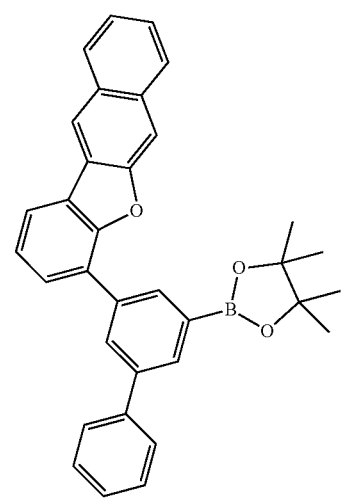
Sub 1-93
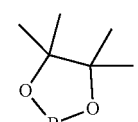
Sub 1-91
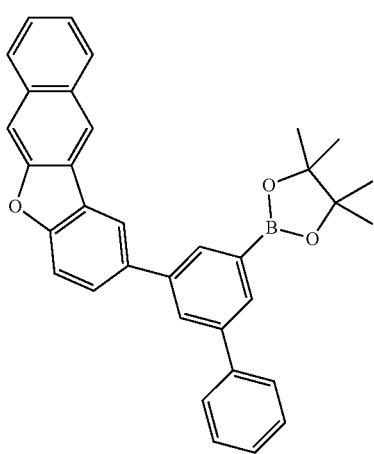
Sub 1-94
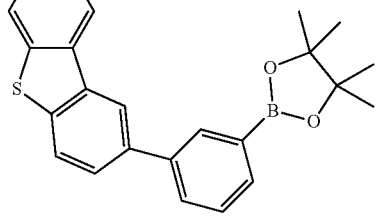
Sub 1-95
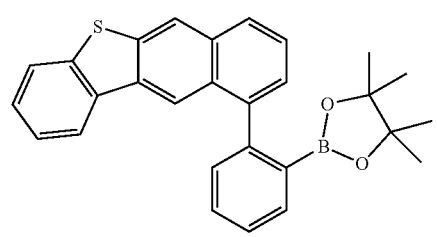

-continued
Sub 1-96
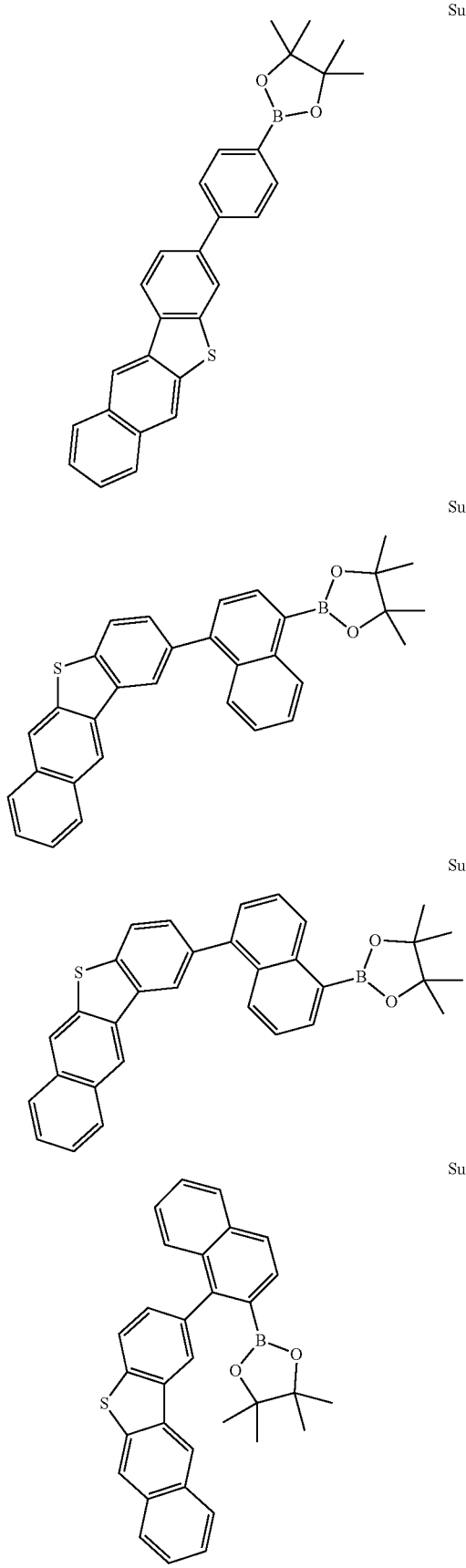
Sub 1-97
Sub 1-98
Sub 1-99
-continued
Sub 1-100
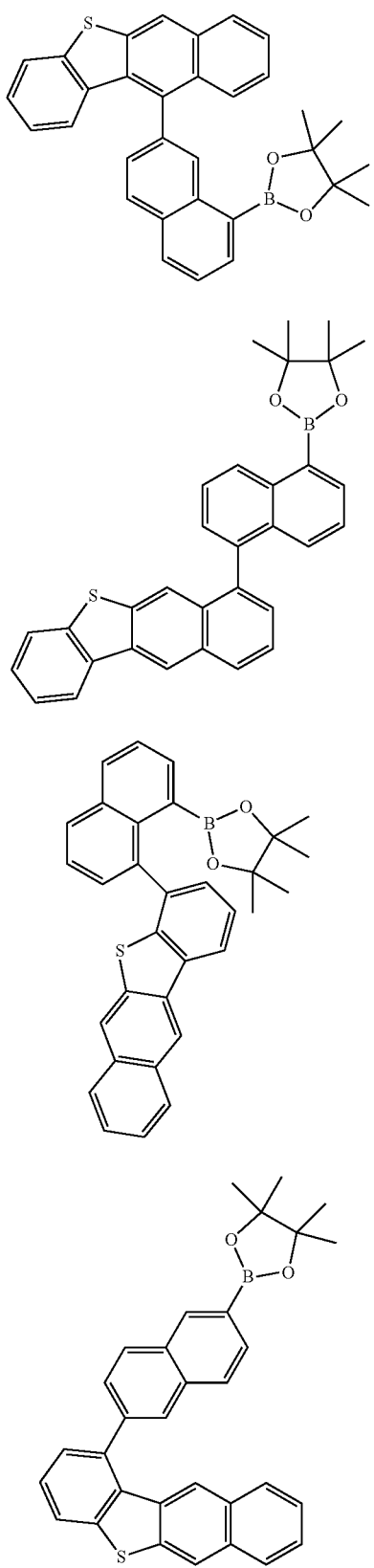
Sub 1-101
Sub 1-102
Sub 1-103

Sub 1-104
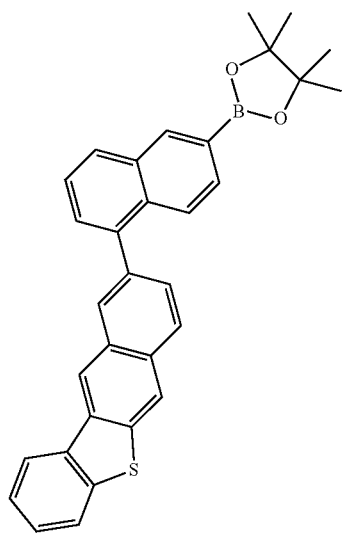
Sub 1-105
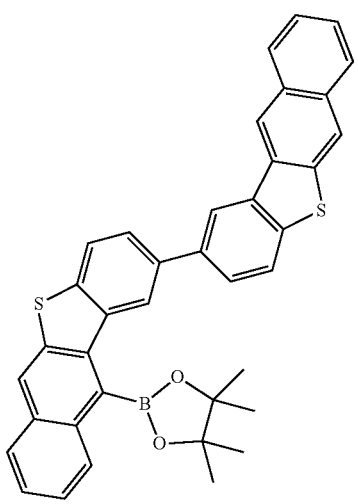
Sub 1-106
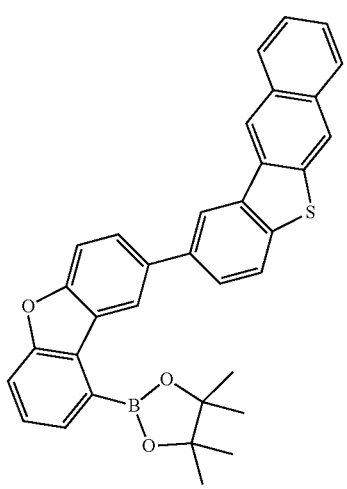
Sub 1-107
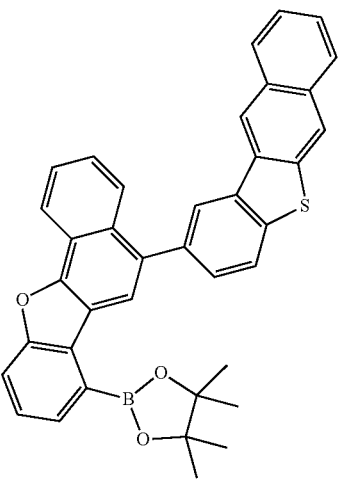
Sub 1-108
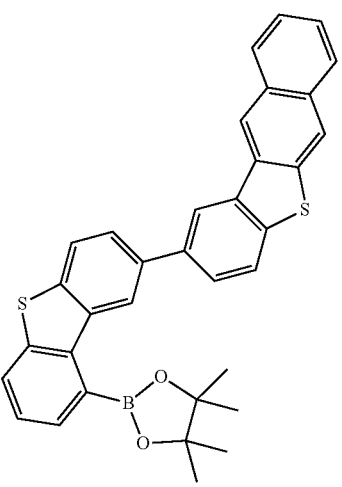
Sub 1-109
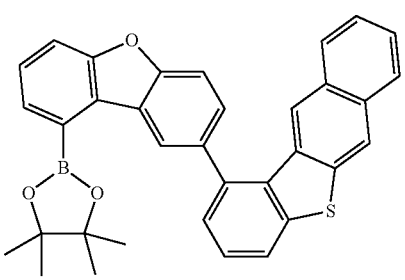
Sub 1-110
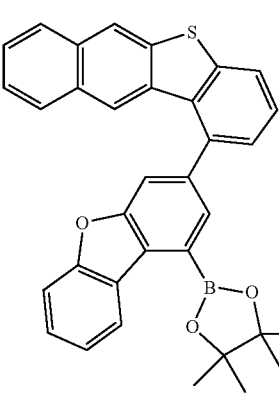

Sub 1-111
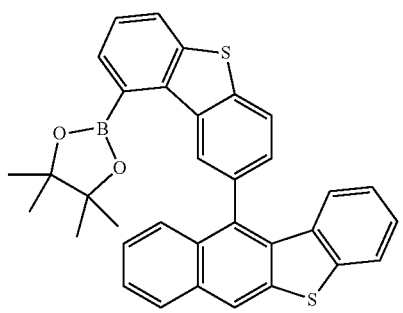
Sub 1-112
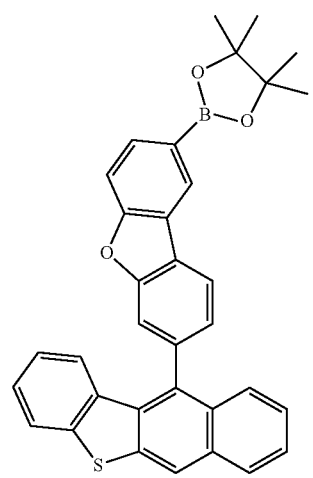
Sub 1-113
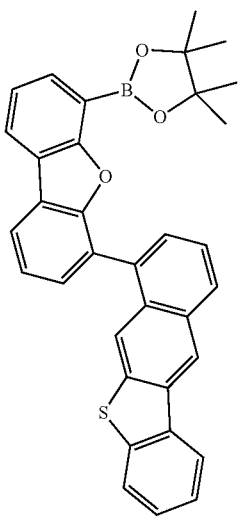
Sub 1-114
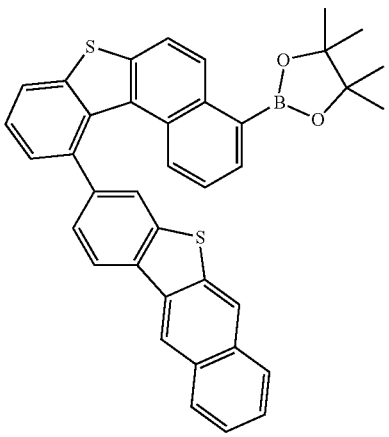
Sub 1-115
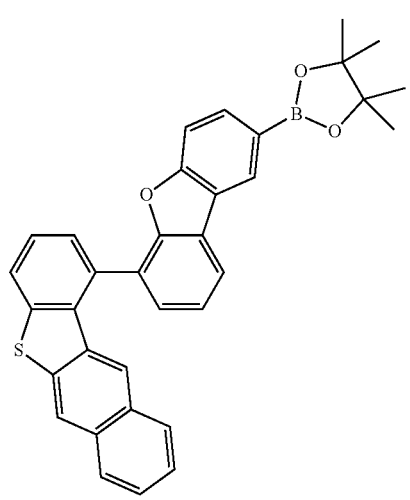
Sub 1-116
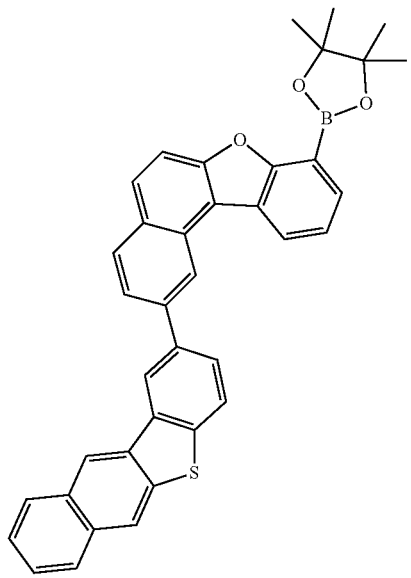

Sub 1-117
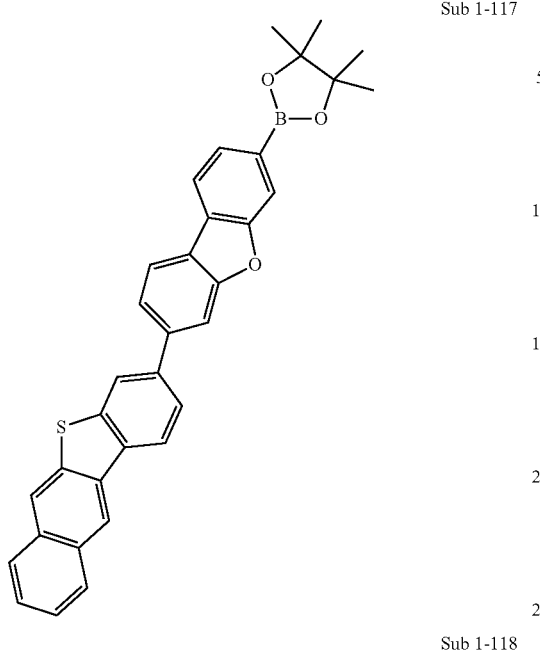
Sub 1-118
Sub 1-119
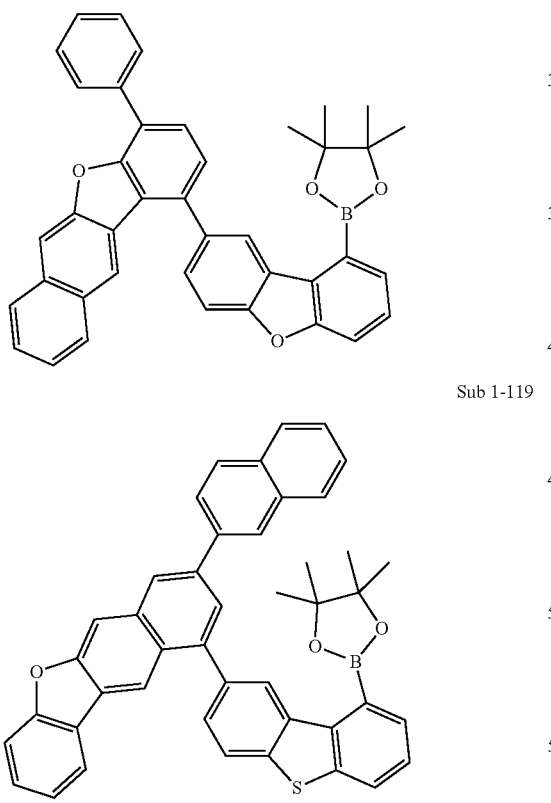
Sub 1-120
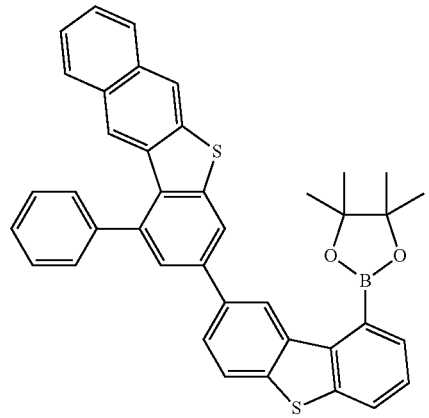
Sub 1-121
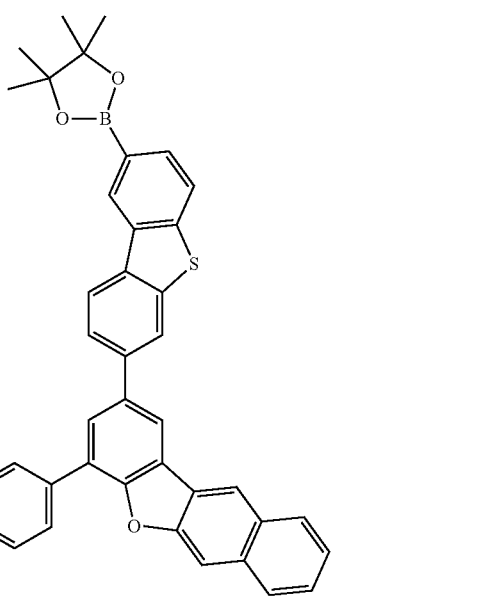
FD-MS (Field Desorption-Mass Spectrometry) values of compounds belong to Sub 1 are shown in Table 1 below.
TABLE 1
| Compound | FD-MS | Compound | FD-MS |
|---|---|---|---|
| Sub 1-1 | m/z = 344.16($C_{22}H_{21}BO_3$ = 344.22) | Sub 1-2 | m/z = 344.16($C_{22}H_{21}BO_3$ = 344.22) |
| Sub 1-3 | m/z = 344.16($C_{22}H_{21}BO_3$ = 344.22) | Sub 1-4 | m/z = 344.16($C_{22}H_{21}BO_3$ = 344.22) |
| Sub 1-5 | m/z = 470.21($C_{32}H_{27}BO_3$ = 470.38) | Sub 1-6 | m/z = 344.16($C_{22}H_{21}BO_3$ = 344.22) |
| Sub 1-7 | m/z = 344.16($C_{22}H_{21}BO_3$ = 344.22) | Sub 1-8 | m/z = 344.16($C_{22}H_{21}BO_3$ = 344.22) |
| Sub 1-9 | m/z = 344.16($C_{22}H_{21}BO_3$ = 344.22) | Sub 1-10 | m/z = 344.16($C_{22}H_{21}BO_3$ = 344.22) |

TABLE 1-continued

| Compound | FD-MS | Compound | FD-MS |
|---|---|---|---|
| Sub 1-11 | m/z = 344.16($C_{22}H_{21}BO_3$ = 344.22) | Sub 1-12 | m/z = 520.22($C_{36}H_{29}BO_3$ = 520.44) |
| Sub 1-13 | m/z = 420.19($C_{28}H_{26}BO_3$ = 420.32) | Sub 1-14 | m/z = 436.17($C_{28}H_{25}BO_2S$ = 436.38) |
| Sub 1-15 | m/z = 360.14($C_{22}H_{21}BO_2S$ = 360.28) | Sub 1-16 | m/z = 360.14($C_{22}H_{21}BO_2S$ = 360.28) |
| Sub 1-17 | m/z = 360.14($C_{22}H_{21}BO_2S$ = 360.28) | Sub 1-18 | m/z = 360.14($C_{22}H_{21}BO_2S$ = 360.28) |
| Sub 1-28 | m/z = 496.22($C_{34}H_{29}BO_3$ = 496.41) | Sub 1-30 | m/z = 420.19($C_{28}H_{25}BO_3$ = 420.32) |
| Sub 1-36 | m/z = 470.21($C_{32}H_{27}BO_3$ = 470.38) | Sub 1-66 | m/z = 510.2($C_{34}H_{27}BO_4$ = 510.4) |
| Sub 1-68 | m/z = 526.18($C_{34}H_{27}BO_3S$ = 526.46) | Sub 1-69 | m/z = 560.22($C_{38}H_{29}BO_4$ = 560.46) |
| Sub 1-70 | m/z = 576.19($C_{38}H_{29}BO_3S$ = 576.52) | Sub 1-90 | m/z = 496.22($C_{34}H_{29}BO_3$ = 496.41) |
| Sub 1-92 | m/z = 546.24($C_{38}H_{31}BO_3$ = 546.47) | Sub 1-93 | m/z = 470.21($C_{32}H_{27}BO_3$ = 470.38) |
| Sub 1-94 | m/z = 436.17($C_{28}H_{25}BO_2S$ = 436.38) | Sub 1-97 | m/z = 486.18($C_{32}H_{27}BO_2S$ = 486.44) |
| Sub 1-105 | m/z = 592.17($C_{38}H_{29}BO_2S_2$ = 592.58) | Sub 1-106 | m/z = 526.18($C_{34}H_{27}BO_3S$ = 526.46) |
| Sub 1-107 | m/z = 576.19($C_{38}H_{29}BO_3S$ = 576.52) | Sub 1-108 | m/z = 542.15($C_{34}H_{27}BO_2S_2$ = 542.52) |
| Sub 1-118 | m/z = 586.23($C_{40}H_{31}BO_4$ = 586.49) | Sub 1-119 | m/z = 652.22($C_{44}H_{33}BO_3S$ = 652.62) |
| Sub 1-120 | m/z = 618.19($C_{40}H_{31}BO_2S_2$ = 618.62) | Sub 1-121 | m/z = 602.21($C_{40}H_{31}BO_3S$ = 602.56) |

Sub 1 of Reaction Scheme 1 may be synthesized by the reaction route of the following Reaction Scheme 2, but are not limited thereto.

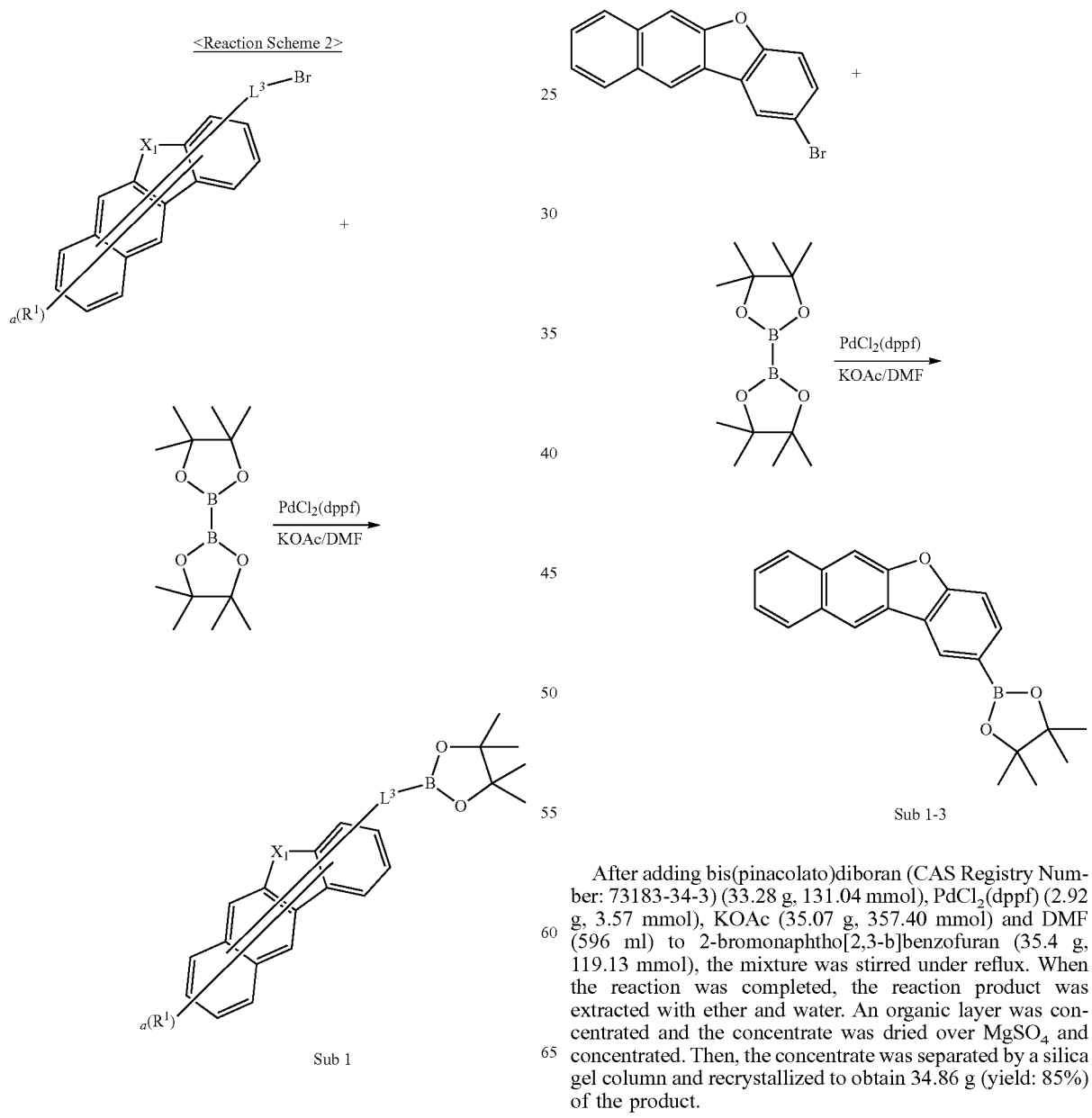

Synthesis Example of Sub 1-3

After adding bis(pinacolato)diboran (CAS Registry Number: 73183-34-3) (33.28 g, 131.04 mmol), PdCl$_2$(dppf) (2.92 g, 3.57 mmol), KOAc (35.07 g, 357.40 mmol) and DMF (596 ml) to 2-bromonaphtho[2,3-b]benzofuran (35.4 g, 119.13 mmol), the mixture was stirred under reflux. When the reaction was completed, the reaction product was extracted with ether and water. An organic layer was concentrated and the concentrate was dried over MgSO$_4$ and concentrated. Then, the concentrate was separated by a silica gel column and recrystallized to obtain 34.86 g (yield: 85%) of the product.

Synthesis Example of Sub 1-21

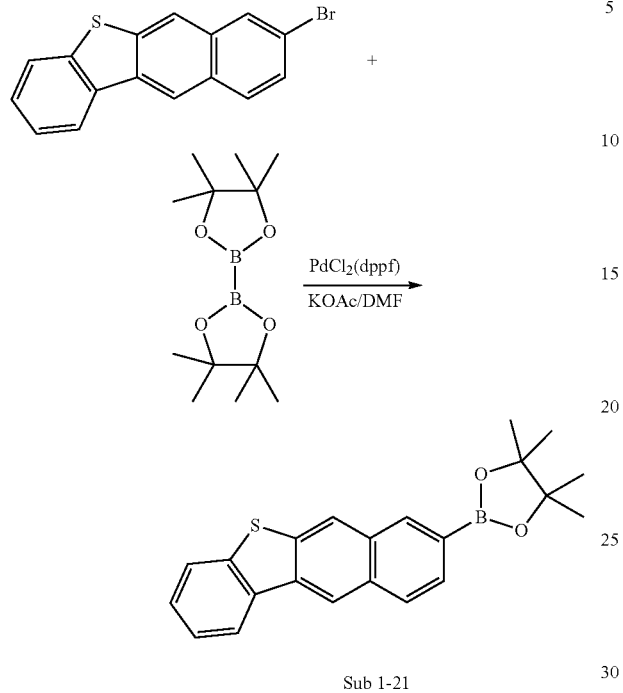

Sub 1-21

Bis(pinacolato)diboran (CAS Registry Number: 73183-34-3) (31.57 g, 124.33 mmol), PdCl$_2$(dppf) (2.77 g, 3.39 mmol), KOAc (33.28 g, 339.07 mmol) and DMF (565 ml) were added to 8-bromobenzo[b]naphtho[2,3-d]thiophene (35.40 g, 113.02 mmol), and the reaction was carried out in the same manner as in the synthesis method of 1-3 to obtain 33.39 g (yield: 82%) of the product.

Synthesis Example of Sub 1-37

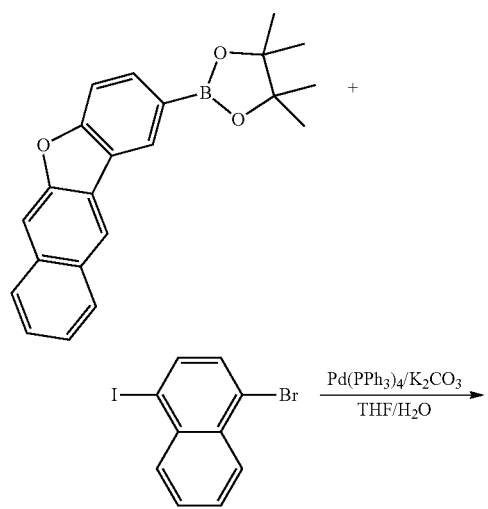

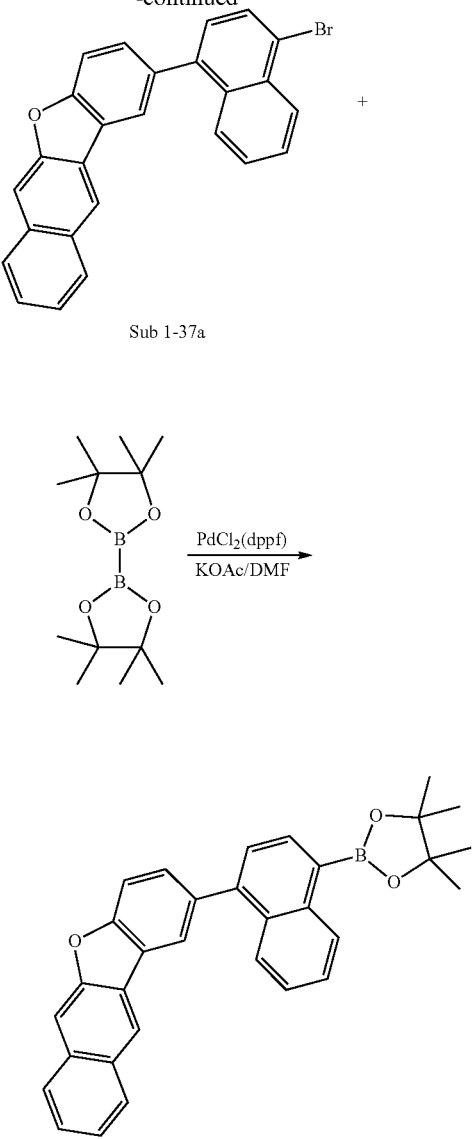

Sub 1-37a

Sub 1-37

(1) Synthesis of Sub 1-37a

After adding 1-bromo-4-iodonaphthalene (69.65 g, 209.17 mmol), Pd(PPh$_3$)$_4$ (8.06 g, 6.97 mmol), K$_2$CO$_3$ (72.27 g, 522.92 mmol), THF (639 ml) and water (320 ml) to 4,4,5,5-tetramethyl-2-(naphtho[2,3-b]benzofuran-2-yl)-1,3,2-dioxaborolane (60 g, 174.31 mmol), the mixture was stirred under reflux. When the reaction was completed, the reaction product was extracted with ether and water. An organic layer was concentrated and the concentrate was dried over MgSO$_4$ and concentrated. Then, the concentrate was separated by a silica gel column and recrystallized to obtain 45.01 g (yield: 61%) of the product.

(2) Synthesis of Sub 1-37

Bis(pinacolato)diboran (CAS Registry Number: 73183-34-3) (29.70 g, 116.96 mmol), PdCl$_2$(dppf) (2.60 g, 3.19 mmol), KOAc (31.31 g, 318.99 mmol) and DMF (532 ml) were added to Sub 1-37a (45.01 g, 106.33 mmol), and the reaction was carried out in the same manner as in the synthesis method of 1-3 to obtain 39.01 g (yield: 78%) of the product.

Synthesis Example of Sub 1-68

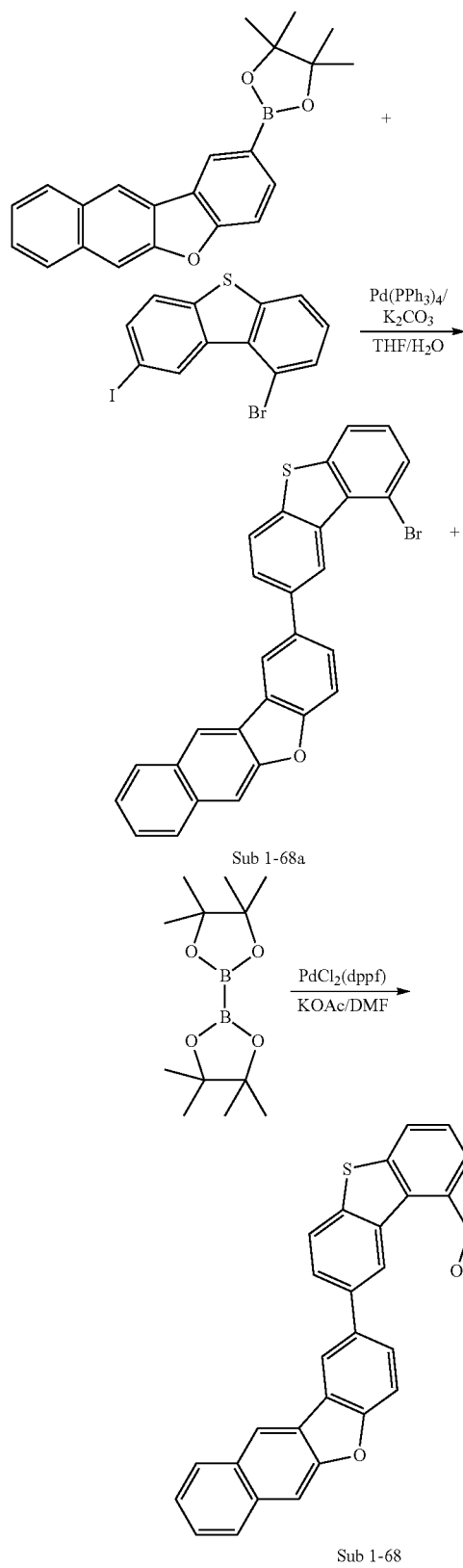

Sub 1-68a

Sub 1-68

(1) Synthesis of Sub 1-68a 1-bromo-8-iododibenzo[b,d]thiophene (81.38 g, 209.17 mmol), Pd(PPh₃)₄ (8.06 g, 6.97 mmol), K₂CO₃ (72.27 g, 522.92 mmol), THF (639 ml) and water (320 ml) were added to 4,4,5,5-tetramethyl-2-(naphtho[2,3-b]benzofuran-2-yl)-1,3,2-dioxaborolane (60 g, 174.31 mmol), and the reaction was carried out in the same manner as in the synthesis method of Sub 1-37a to obtain 56.82 g (yield: 68%) of the product.

(2) Synthesis of Sub 1-68

Bis(pinacolato)diboran (CAS Registry Number: 73183-34-3) (33.11 g, 130.38 mmol), PdCl₂(dppf) (2.90 g, 3.56 mmol), KOAc (34.90 g, 355.58 mmol) and DMF (593 ml) were added to Sub 1-68a (56.82 g, 118.53 mmol), and the reaction was carried out in the same manner as in the synthesis method of 1-3 to obtain 46.80 g (yield: 75%) of the product.

Synthesis Example of Sub 1-98

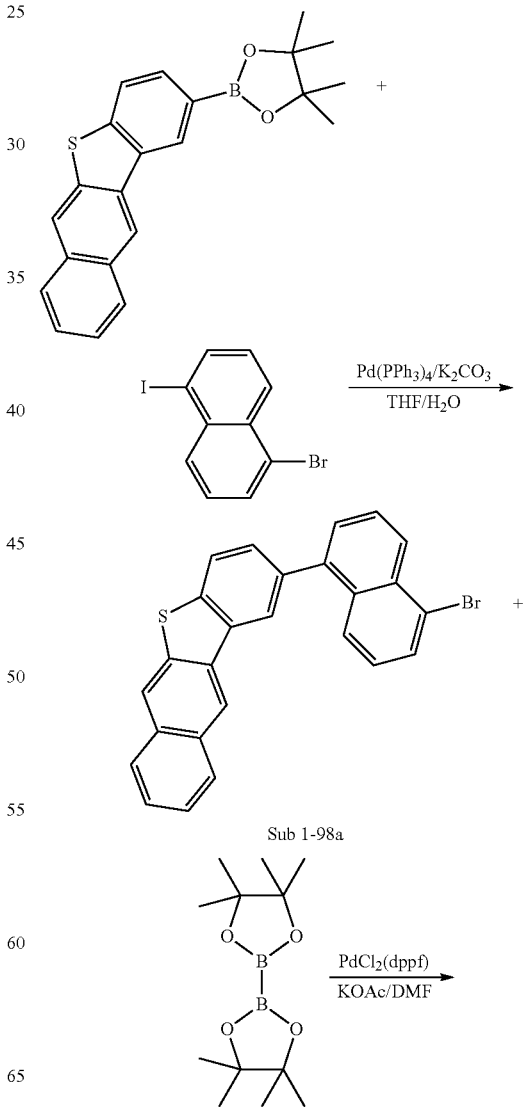

Sub 1-98a

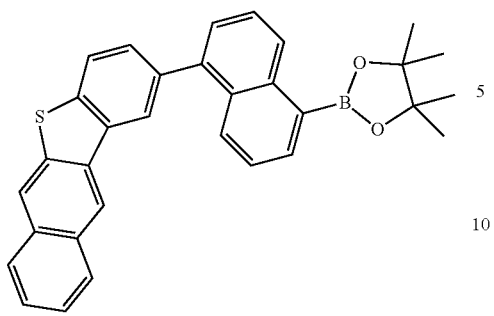

Sub 1-98

(1) Synthesis of Sub 1-98a 1-bromo-5-iodonaphthalene (66.54 g, 199.84 mmol), Pd(PPh$_3$)$_4$ (7.70 g, 6.66 mmol), K$_2$CO$_3$ (69.05 g, 499.61 mmol), THF (611 ml) and water (305 ml) were added to 2-(benzo[b]naphtho[2,3-d]thiophen-2-yl)-4,4,5,5-tetramethyl-1,3,2-dioxaborolane (60 g, 166.54 mmol), and the reaction was carried out in the same manner as in the synthesis method of Sub 1-37a to obtain 46.83 g (yield: 64%) of the product.

(2) Synthesis of Sub 1-98

Bis(pinacolato)diboran (CAS Registry Number: 73183-34-3) (29.77 g, 117.24 mmol), PdCl$_2$(dppf) (2.61 g, 3.20 mmol), KOAc (31.38 g, 319.75 mmol) and DMF (533 ml) were added to 1-98a (46.83 g, 106.58 mmol), and the reaction was carried out in the same manner as in the synthesis method of 1-3 to obtain 37.33 g (yield: 72%) of the product.

6. Synthesis Example of Sub 1-111

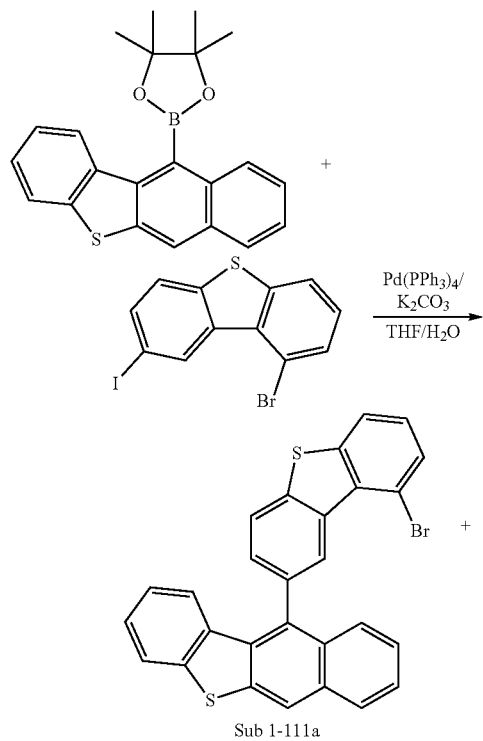

Sub 1-111a

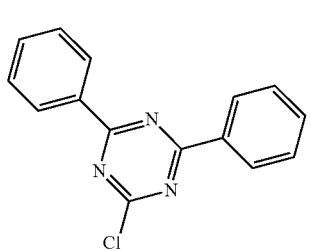

Sub 1-111

(1) Synthesis of Sub 1-111a 1-bromo-8-iododibenzo[b,d]thiophene (77.75 g, 199.84 mmol), Pd(PPh$_3$)$_4$ (7.70 g, 6.66 mmol), K$_2$CO$_3$ (69.05 g, 499.61 mmol), THF (611 ml) and water (305 ml) were added to 2-(benzo[b]naphtho[2,3-d]thiophen-11-yl)-4,4,5,5-tetramethyl-1,3,2-dioxaborolane (60 g, 166.54 mmol), and the reaction was carried out in the same manner as in the synthesis method of Sub 1-37a to obtain 54.46 g (yield: 66%) of the product.

(2) Synthesis of Sub 1-111

Bis(pinacolato)diboran (CAS Registry Number: 73183-34-3) (30.70 g, 120.91 mmol), PdCl$_2$(dppf) (2.69 g, 3.30 mmol), KOAc (32.36 g, 329.76 mmol) and DMF (550 ml) were added to Sub 1-111a (54.46 g, 109.92 mmol), and the reaction was carried out in the same manner as in the synthesis method of 1-3 to obtain 41.15 g (yield: 69%) of the product.

2. Exemplary Compounds and Synthesis Examples of Sub 2

Compounds belong to Sub 2 of Reaction Scheme 1 are as follows, but are not limited thereto.

Sub 2-1

-continued
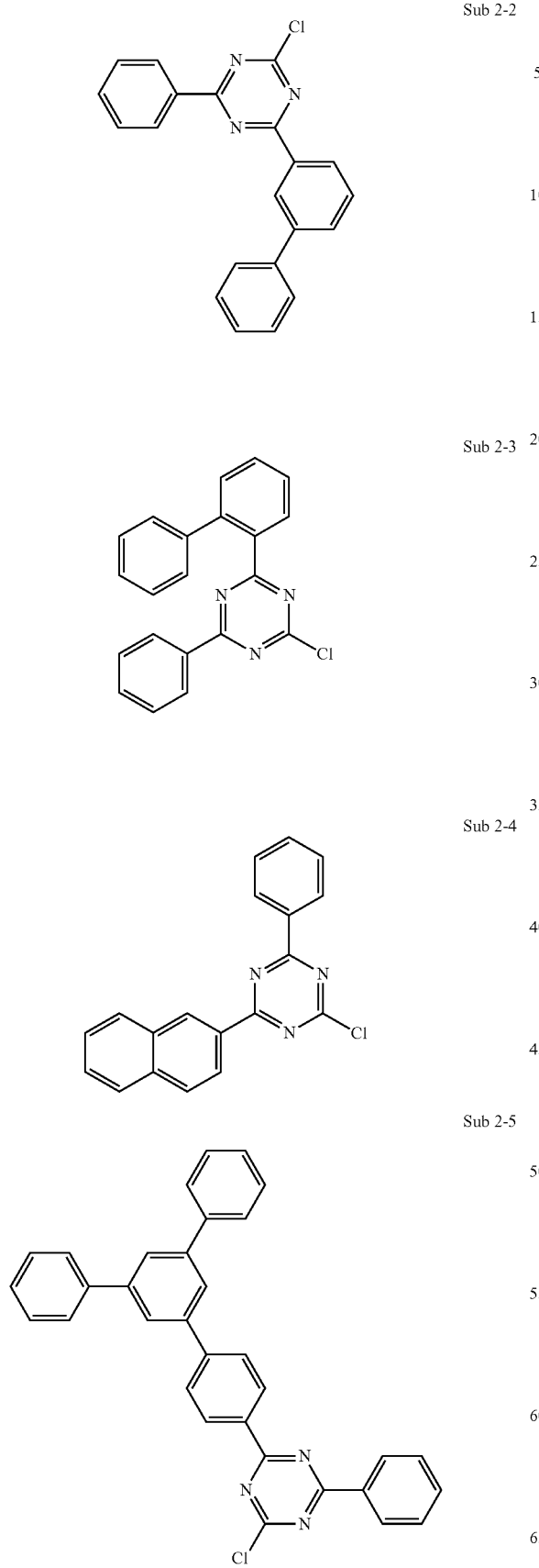
Sub 2-2
Sub 2-3
Sub 2-4
Sub 2-5
-continued
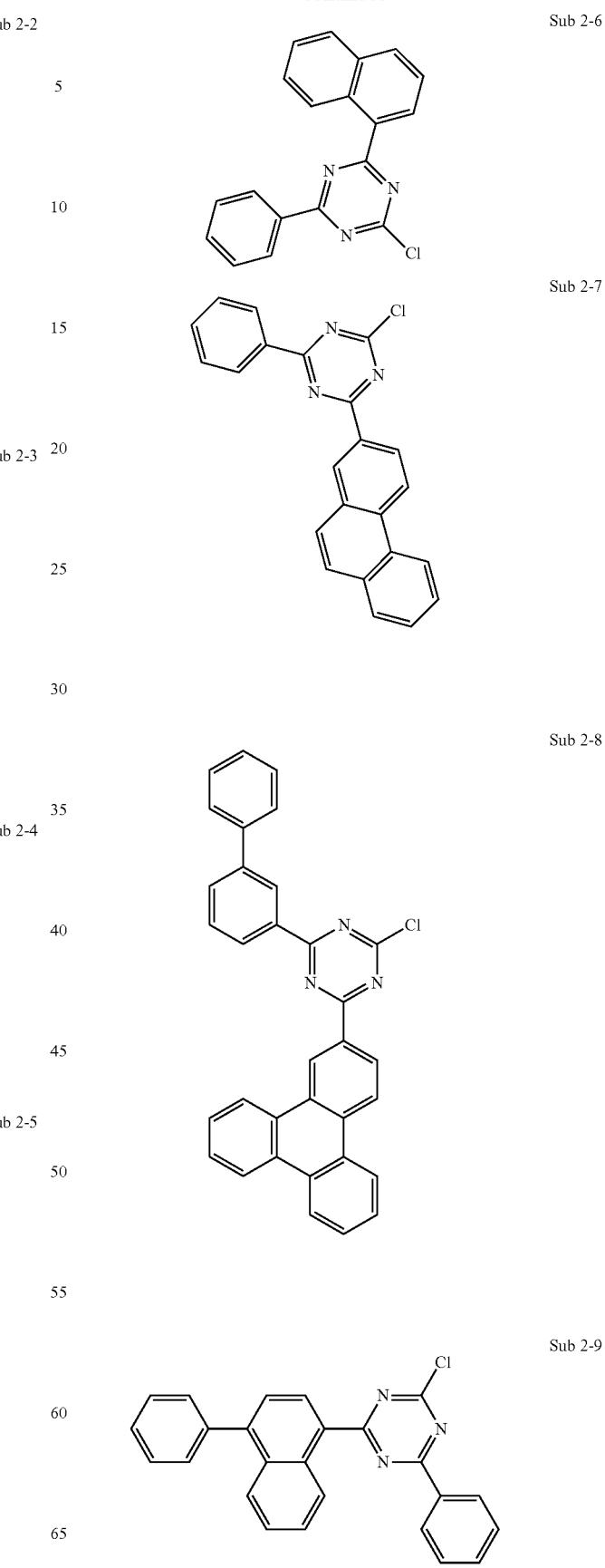
Sub 2-6
Sub 2-7
Sub 2-8
Sub 2-9

Sub 2-10
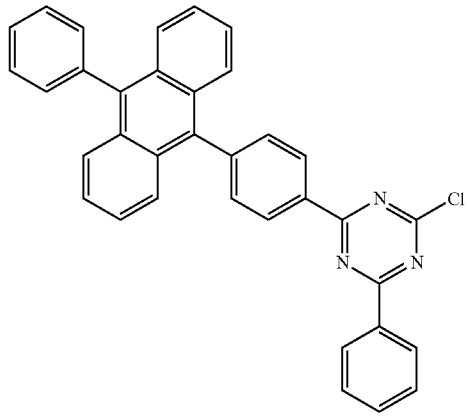
Sub 2-13
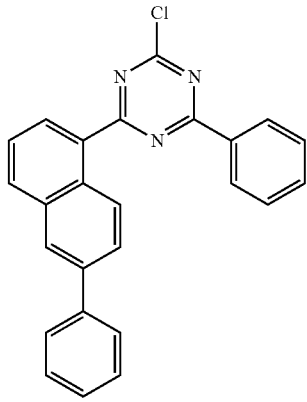
Sub 2-11
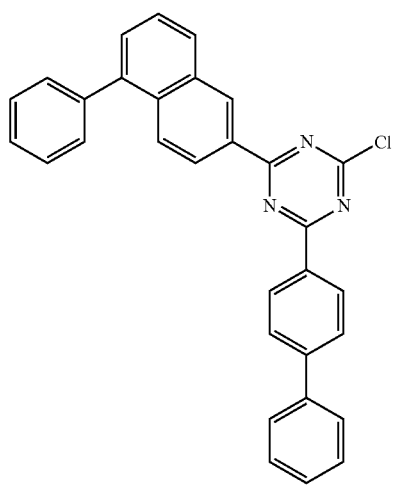
Sub 2-14
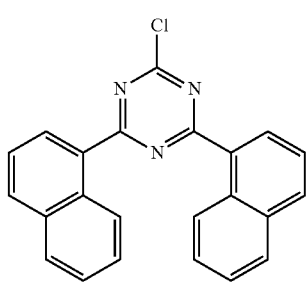
Sub 2-15
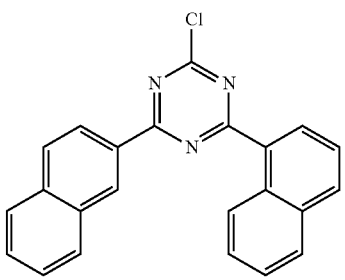
Sub 2-16
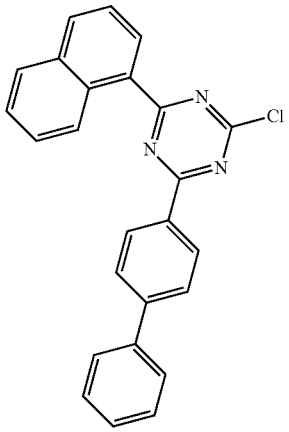
Sub 2-12
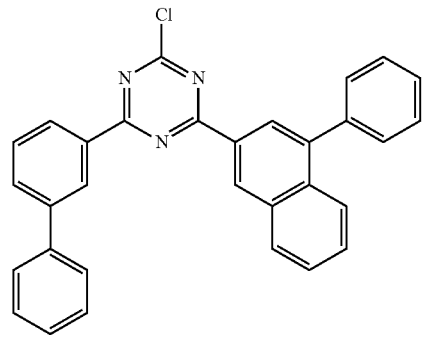

-continued
Sub 2-17
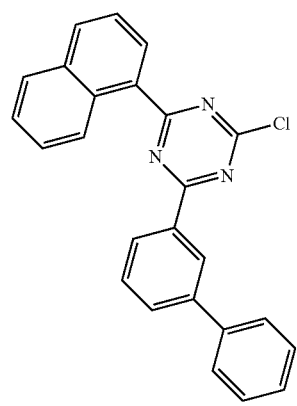
Sub 2-18
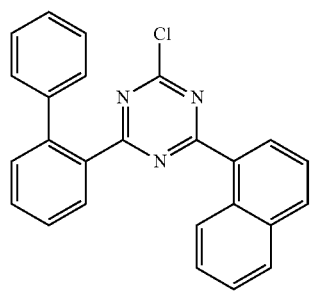
Sub 2-19
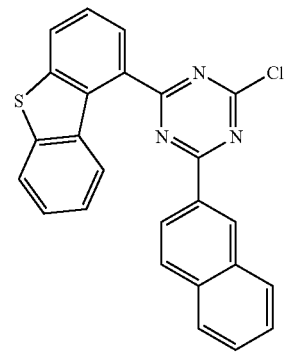
Sub 2-20
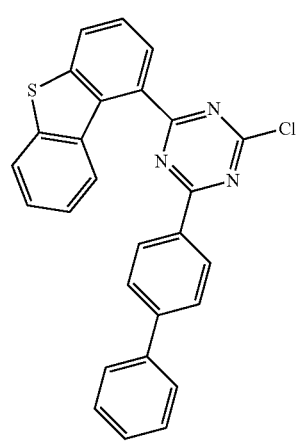
Sub 2-21
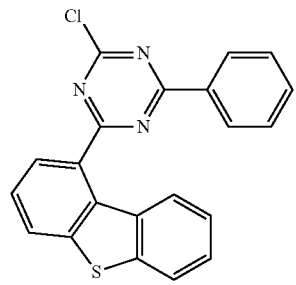
Sub 2-22
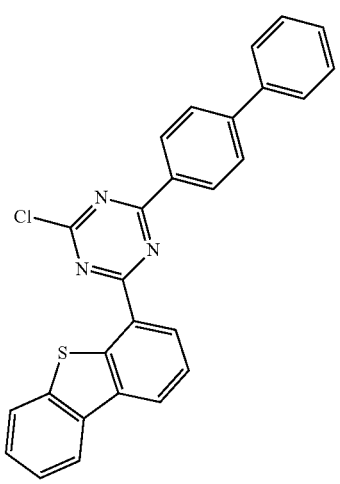
Sub 2-23
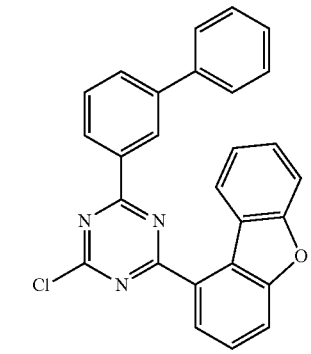
Sub 2-24
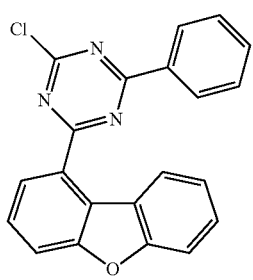

Sub 2-25
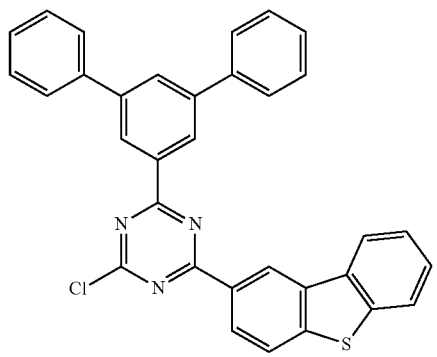
Sub 2-26
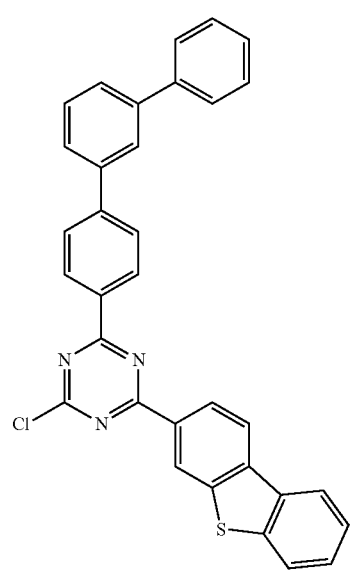
Sub 2-27
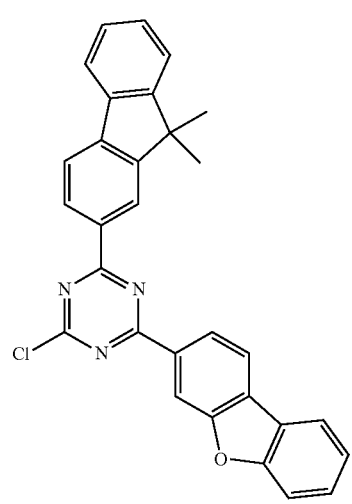
Sub 2-28
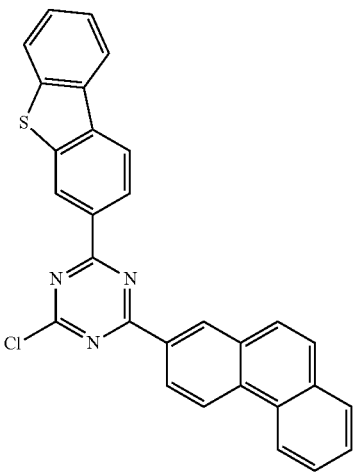
Sub 2-29
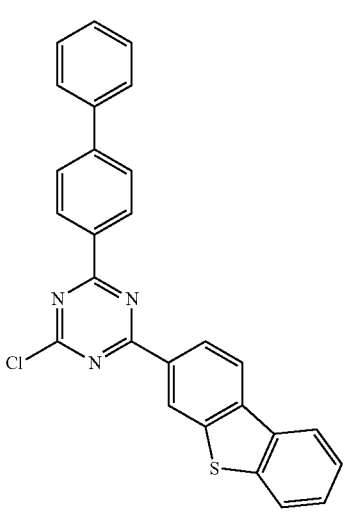
Sub 2-30
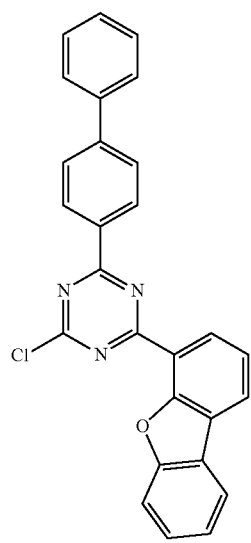

Sub 2-31
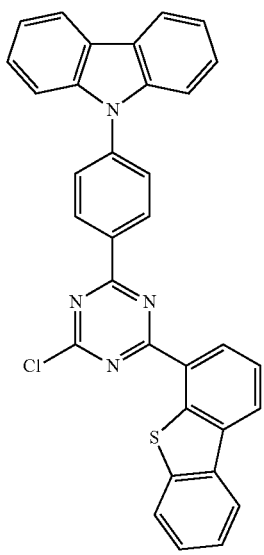
Sub 2-32
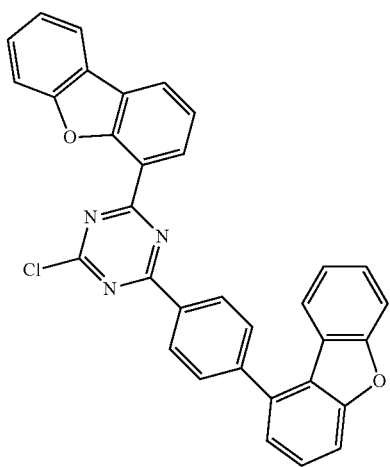
Sub 2-33
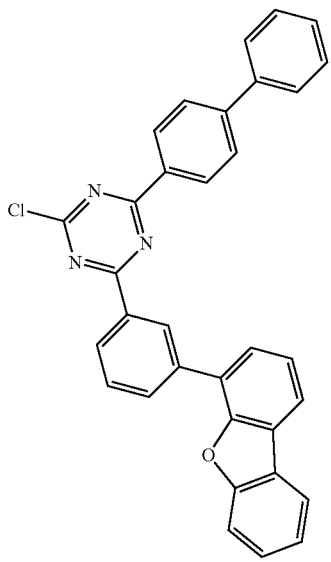
Sub 2-34
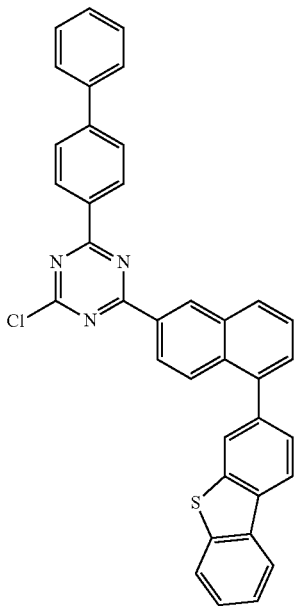
Sub 2-35
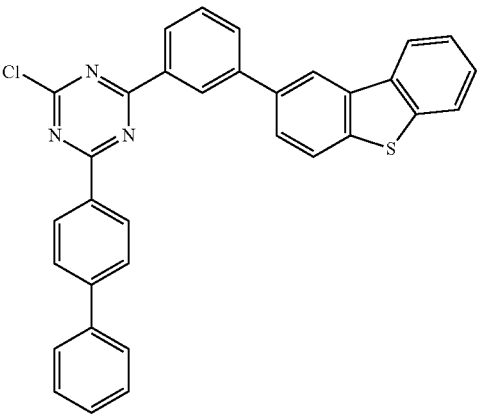
Sub 2-36
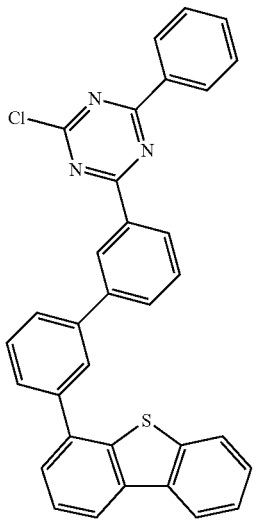

Sub 2-37
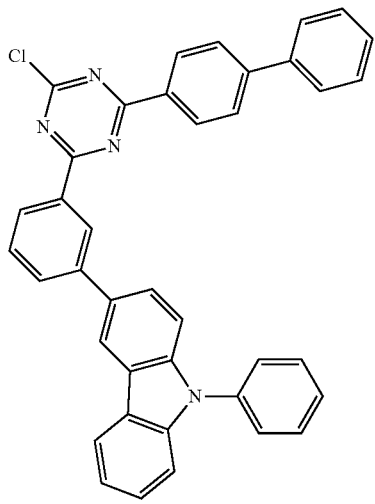
Sub 2-38
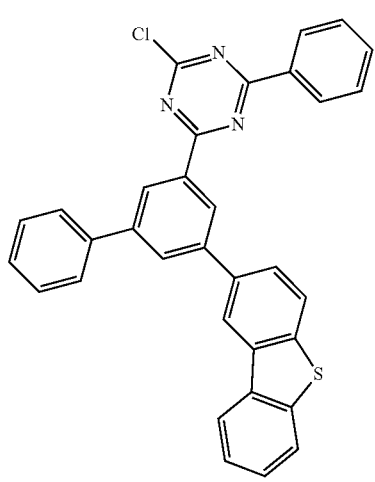
Sub 2-39
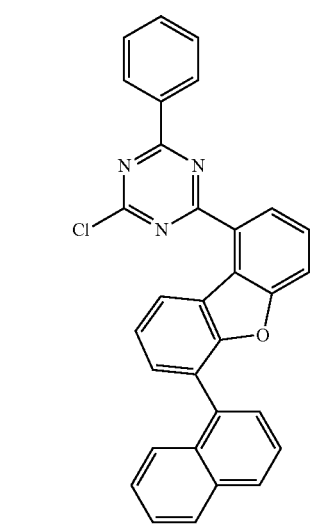
Sub 2-40
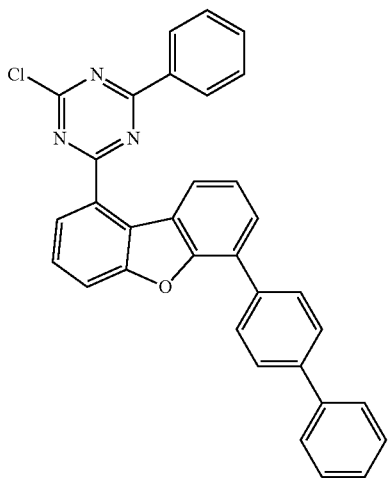
Sub 2-41
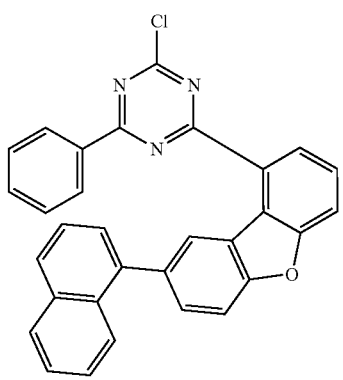
Sub 2-42
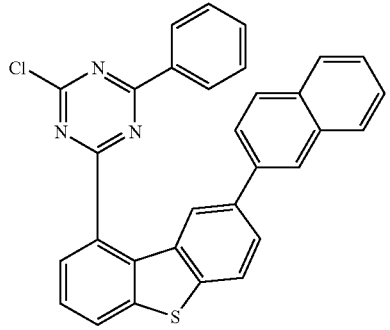
Sub 2-43
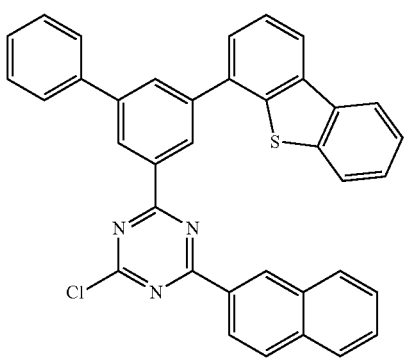

Sub 2-44
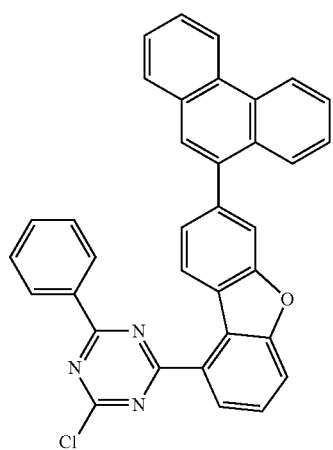
Sub 2-45
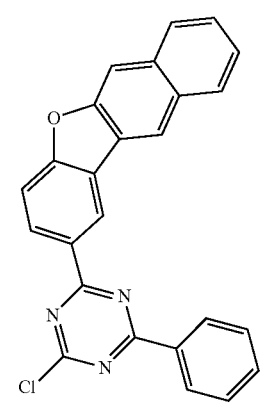
Sub 2-46
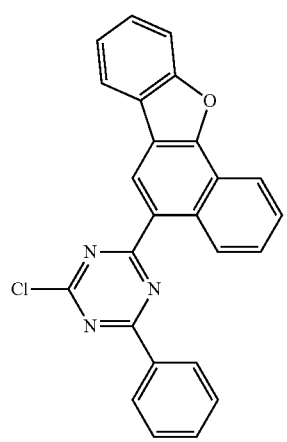
Sub 2-47
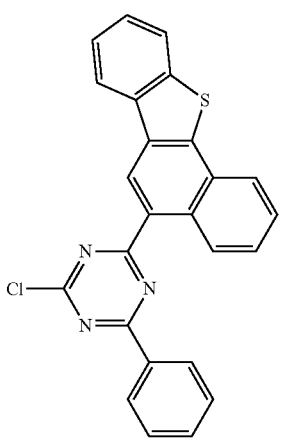
Sub 2-48
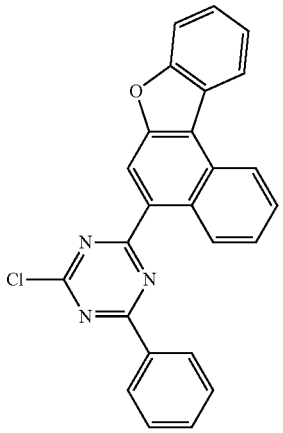
Sub 2-49
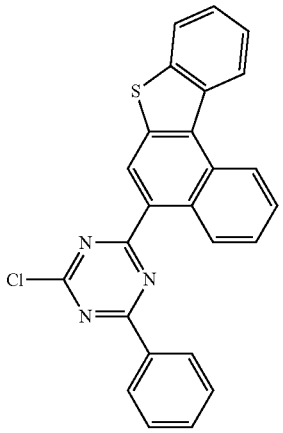

Sub 2-50
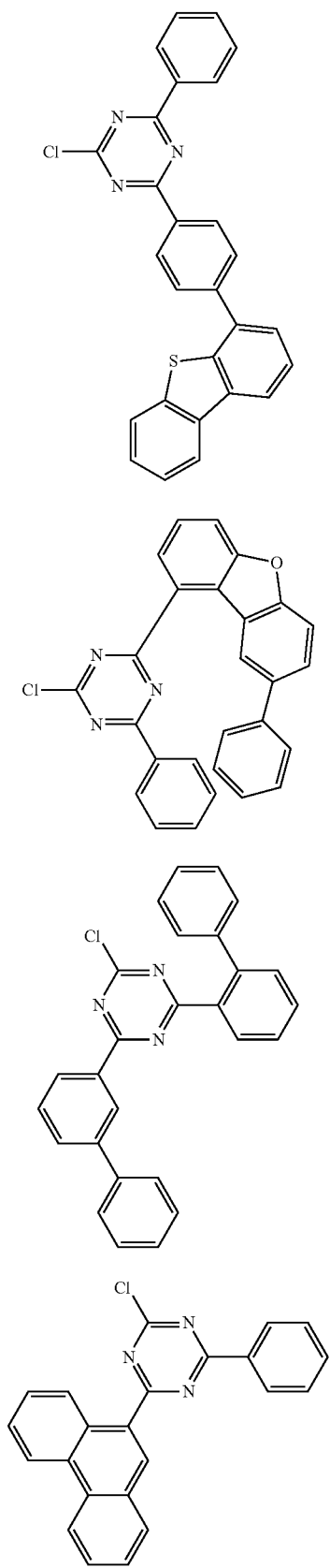
Sub 2-51
Sub 2-52
Sub 2-53
Sub 2-54
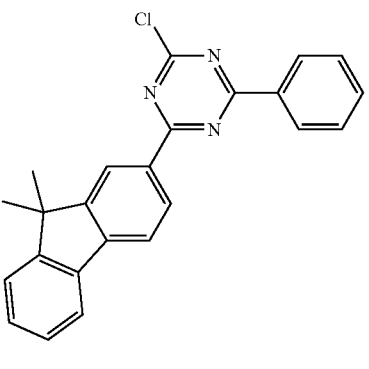
Sub 2-55
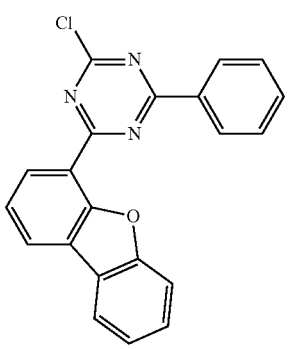
Sub 2-56
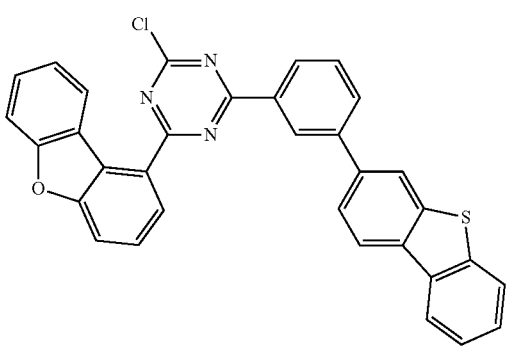
Sub 2-57
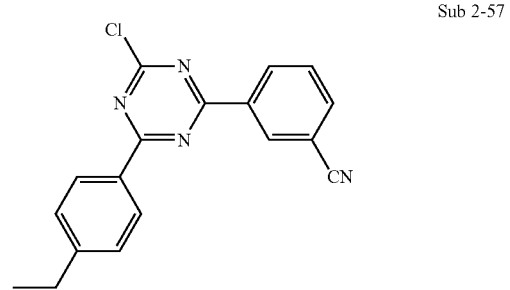

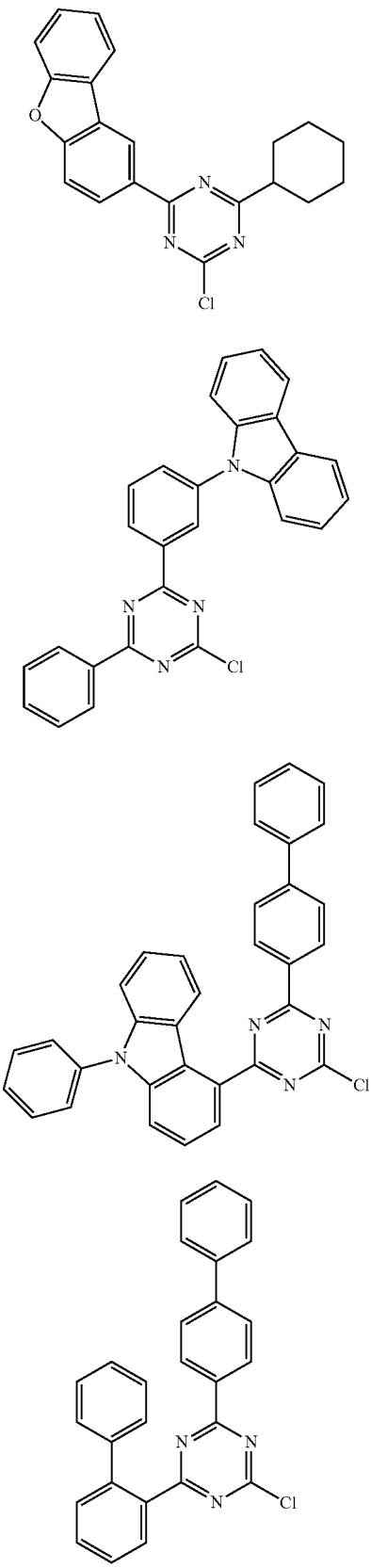
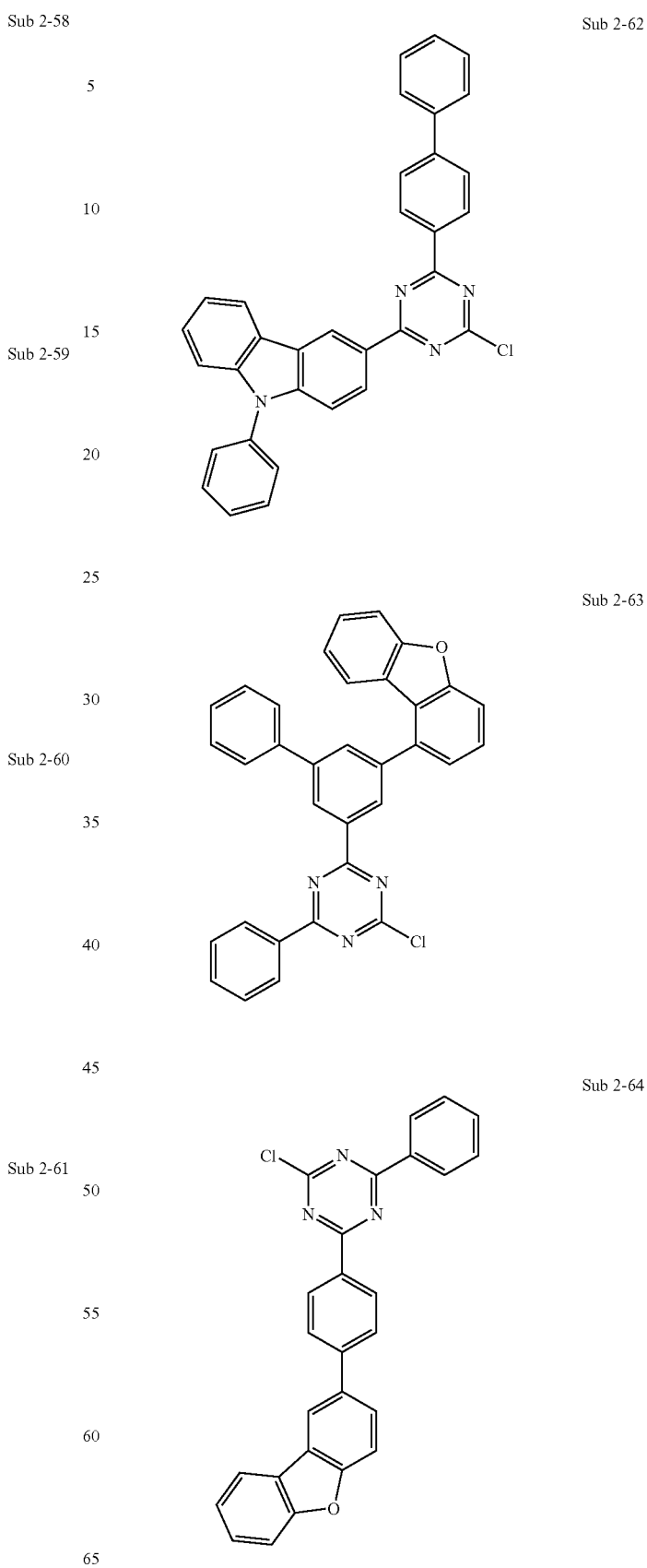

Sub 2-65
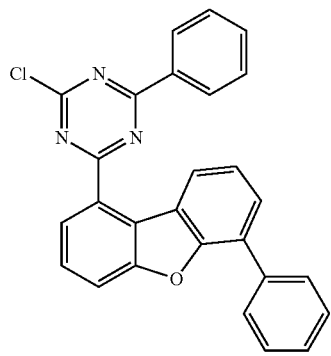
Sub 2-68
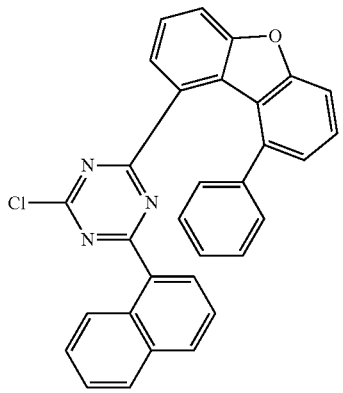
Sub 2-66
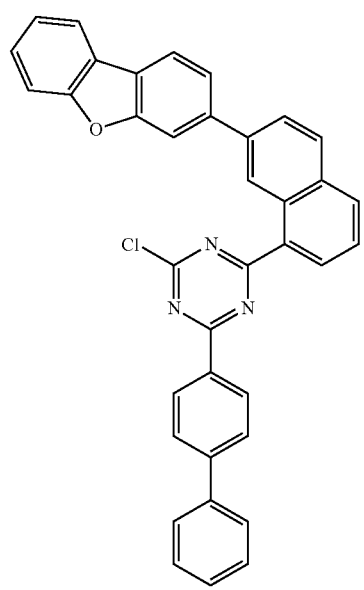
Sub 2-69
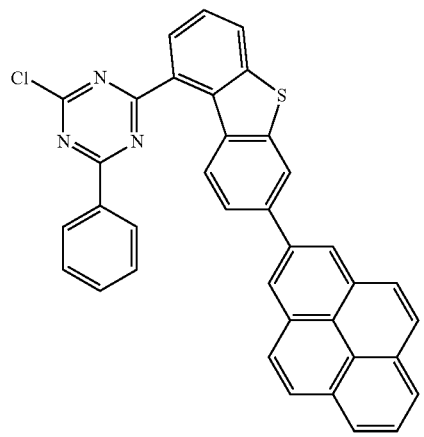
Sub 2-70
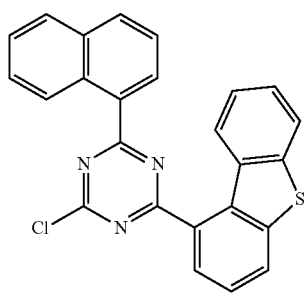
Sub 2-67
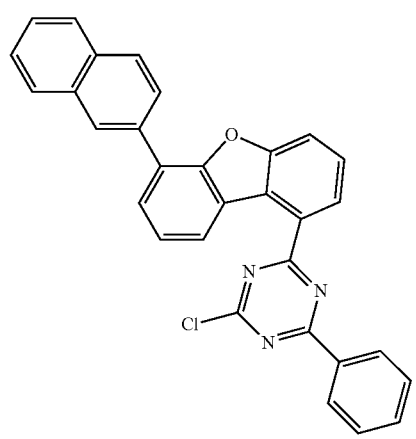
Sub 2-71
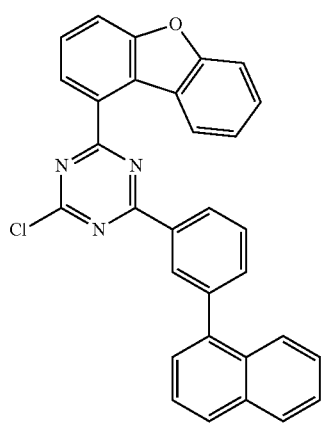

Sub 2-72
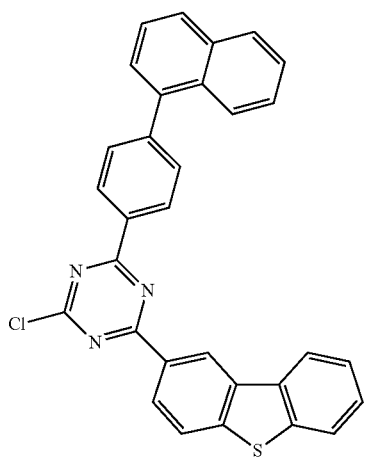
Sub 2-75
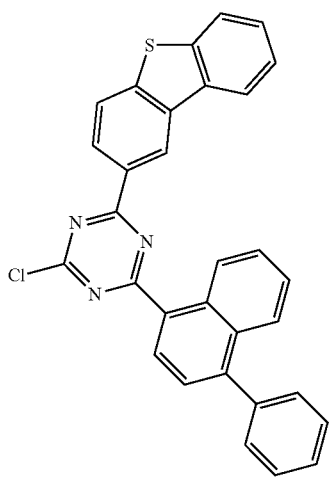
Sub 2-73
Sub 2-76
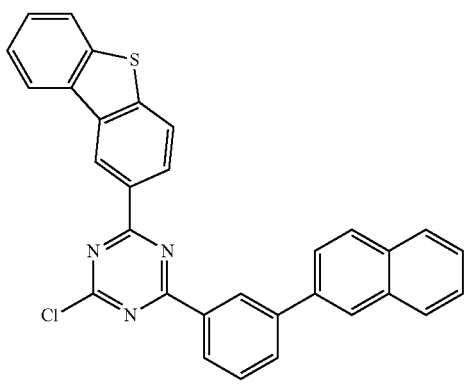
Sub 2-74
Sub 2-77
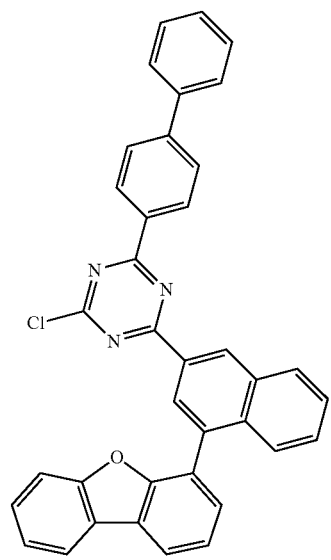

-continued
Sub 2-78
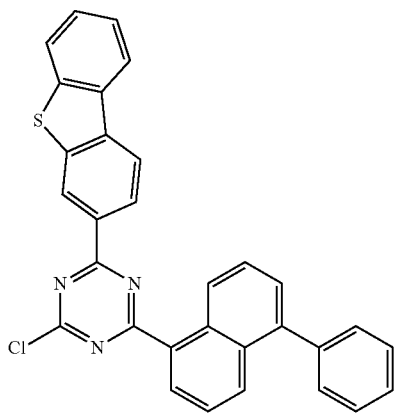
Sub 2-79
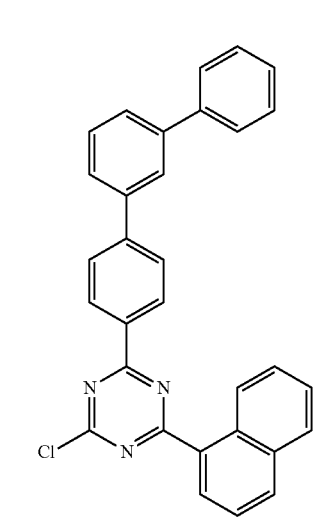
Sub 2-80
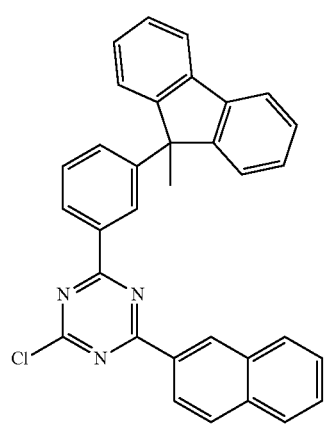
-continued
Sub 2-81
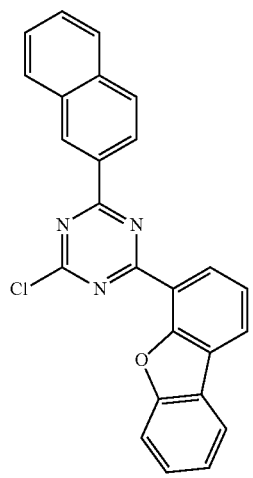
Sub 2-82
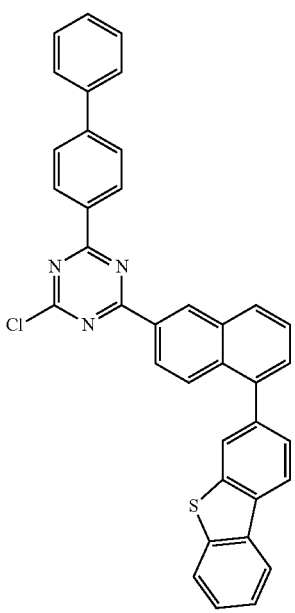
Sub 2-83
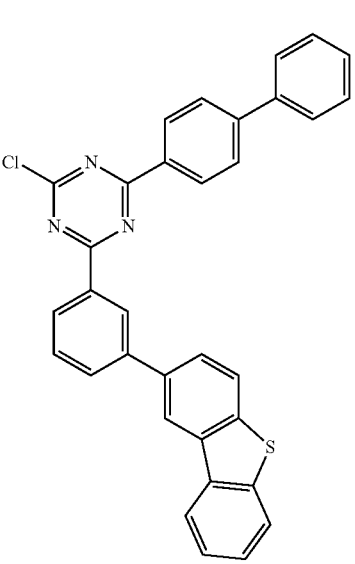

Sub 2-84
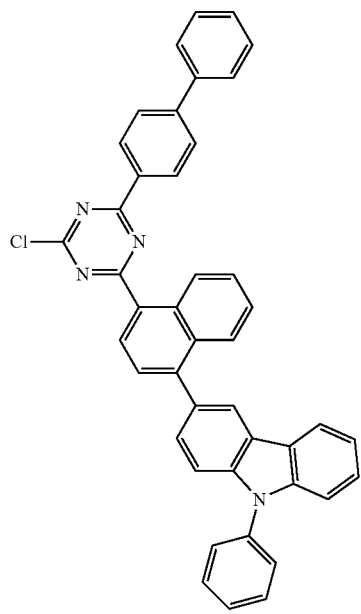
Sub 2-85
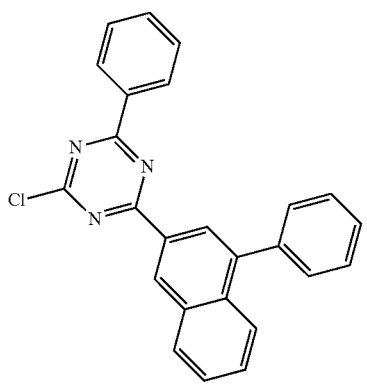
Sub 2-86
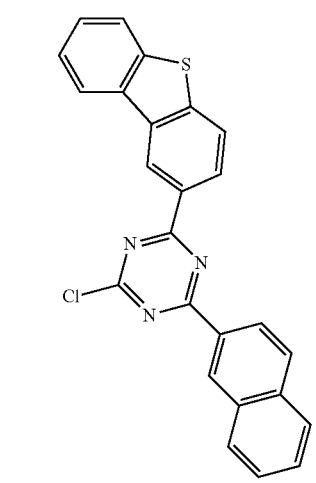
Sub 2-87
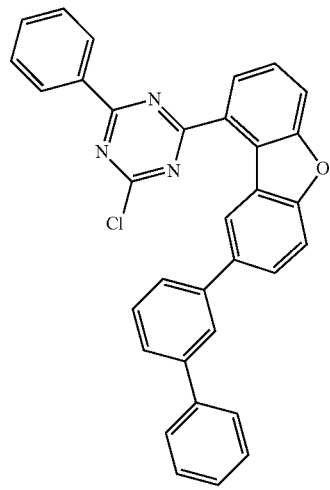
Sub 2-88
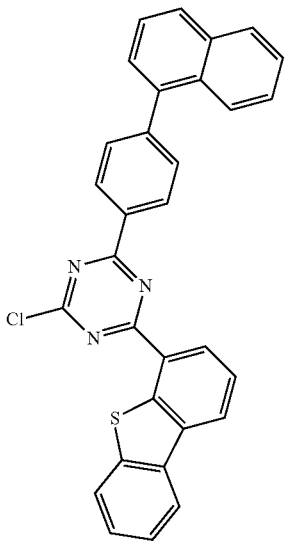
Sub 2-89
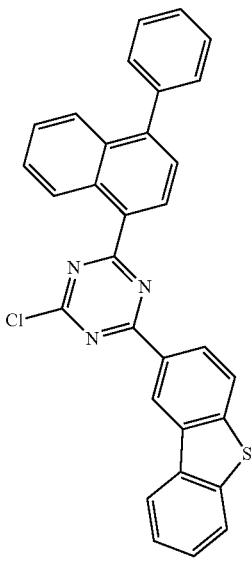

Sub 2-90
Sub 2-91
Sub 2-92
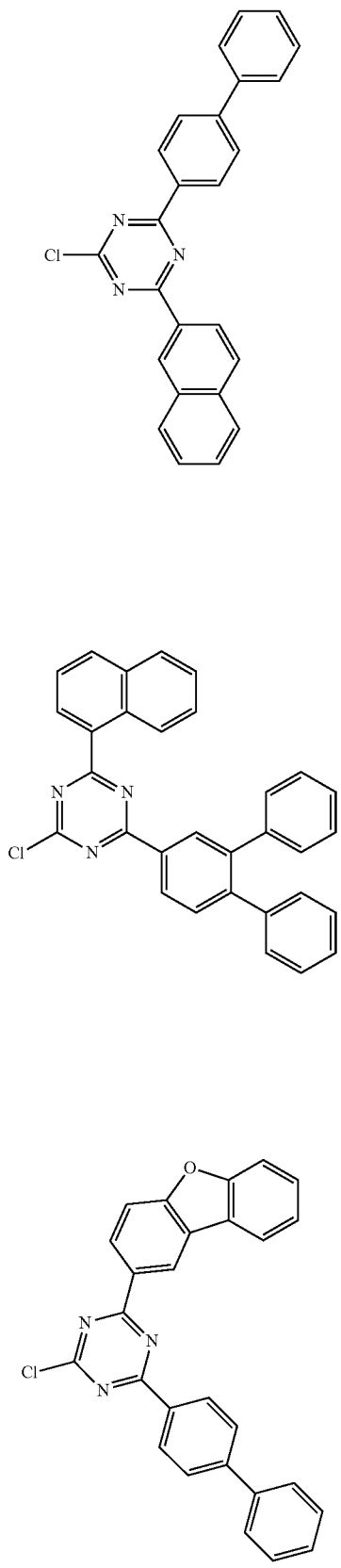
Sub 2-93
Sub 2-94
Sub 2-95
Sub 2-96
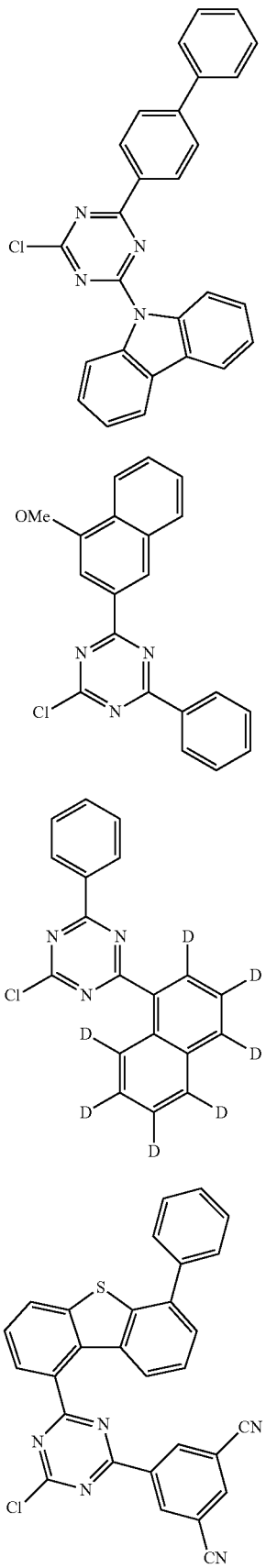

Sub 2-97
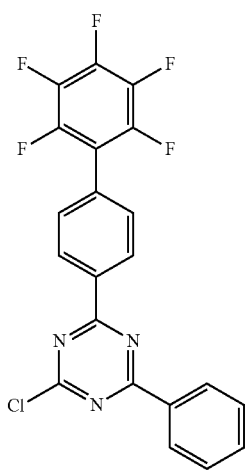
Sub 2-98
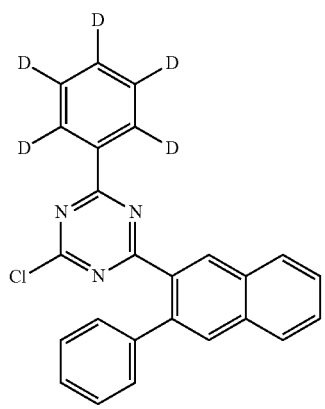
Sub 2-99
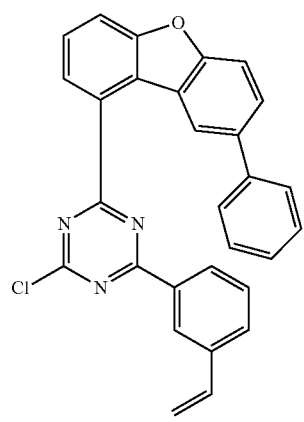
Sub 2-100
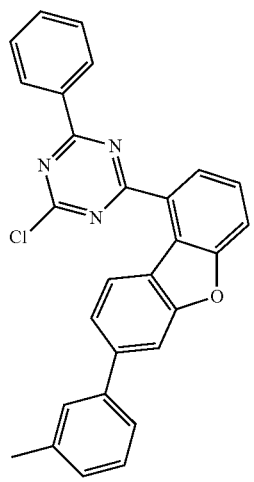
Sub 2-101
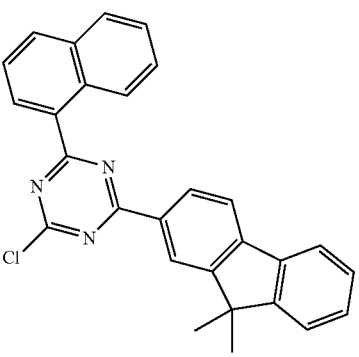
Sub 2-102
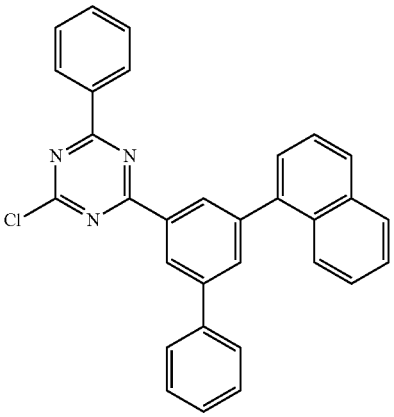

-continued

Sub 2-103

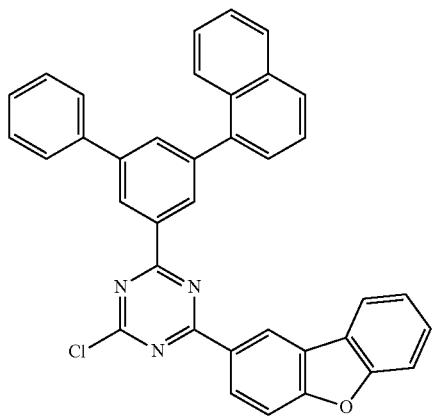

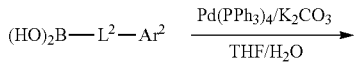

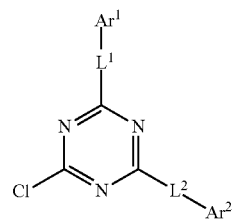

Sub2

FD-MS values of compounds belong to Sub 2 are shown in Table 2 below.

TABLE 2

| Compound | FD-MS | Compound | FD-MS |
| --- | --- | --- | --- |
| Sub 2-1 | m/z = 267.06($C_{15}H_{10}ClN_3$ = 267.72) | Sub 2-2 | m/z = 343.09($C_{21}H_{14}ClN_3$ = 343.81) |
| Sub 2-4 | m/z = 317.07($C_{19}H_{12}ClN_3$ = 317.78) | Sub 2-5 | m/z = 495.15($C_{33}H_{22}ClN_3$ = 496.01) |
| Sub 2-7 | m/z = 367.09($C_{23}H_{14}ClN_3$ = 367.84) | Sub 2-8 | m/z = 493.13($C_{33}H_{20}ClN_3$ = 493.99) |
| Sub 2-9 | m/z = 393.1($C_{25}H_{16}ClN_3$ = 393.87) | Sub 2-10 | m/z = 519.15($C_{35}H_{22}ClN_3$ = 520.03) |
| Sub 2-11 | m/z = 469.13($C_{31}H_{20}ClN_3$ = 469.97) | Sub 2-12 | m/z = 393.1($C_{25}H_{16}ClN_3$ = 393.87) |
| Sub 2-14 | m/z = 367.09($C_{23}H_{14}ClN_3$ = 367.84) | Sub 2-19 | m/z = 423.06($C_{25}H_{14}ClN_3S$ = 423.92) |
| Sub 2-20 | m/z = 449.08($C_{27}H_{16}ClN_3S$ = 449.96) | Sub 2-21 | m/z = 373.04($C_{21}H_{12}ClN_3S$ = 373.86) |
| Sub 2-22 | m/z = 433.1($C_{27}H_{16}ClN_3O$ = 433.9) | Sub 2-24 | m/z = 357.07($C_{21}H_{12}ClN_3O$ = 357.8) |
| Sub 2-25 | m/z = 525.11($C_{33}H_{20}ClN_3S$ = 526.05) | Sub 2-27 | m/z = 473.13($C_{30}H_{20}ClN_3O$ = 473.96) |
| Sub 2-28 | m/z = 473.08($C_{29}H_{16}ClN_3S$ = 473.98) | Sub 2-31 | m/z = 538.1($C_{33}H_{19}ClN_4S$ = 539.05) |
| Sub 2-32 | m/z = 523.11($C_{33}H_{18}ClN_3O_2$ = 523.98) | Sub 2-33 | m/z = 509.13($C_{33}H_{20}ClN_3O$ = 509.99) |
| Sub 2-34 | m/z = 575.12($C_{37}H_{22}ClN_3S$ = 576.11) | Sub 2-37 | m/z = 584.18($C_{39}H_{25}ClN_4$ = 585.11) |
| Sub 2-39 | m/z = 483.11($C_{31}H_{18}ClN_3O$ = 483.96) | Sub 2-40 | m/z = 509.13($C_{33}H_{20}ClN_3O$ = 509.99) |
| Sub 2-42 | m/z = 499.09($C_{31}H_{18}ClN_3S$ = 500.02) | Sub 2-43 | m/z = 575.12($C_{37}H_{22}ClN_3S$ = 576.11) |
| Sub 2-44 | m/z = 533.13($C_{35}H_{20}ClN_3O$ = 534.02) | Sub 2-45 | m/z = 407.08($C_{25}H_{14}ClN_3O$ = 407.86) |
| Sub 2-47 | m/z = 423.06($C_{25}H_{14}ClN_3S$ = 423.92) | Sub 2-50 | m/z = 449.08($C_{27}H_{16}ClN_3S$ = 449.96) |
| Sub 2-51 | m/z = 433.1($C_{27}H_{16}ClN_3O$ = 433.9) | Sub 2-52 | m/z = 419.12($C_{27}H_{18}ClN_3$ = 419.91) |
| Sub 2-54 | m/z = 383.12($C_{24}H_{18}ClN_3$ = 383.88) | Sub 2-55 | m/z = 357.07($C_{21}H_{12}ClN_3O$ = 357.8) |
| Sub 2-56 | m/z = 539.09($C_{33}H_{18}ClN_3OS$ = 540.04) | Sub 2-57 | m/z = 320.08($C_{18}H_{13}ClN_4$ = 320.78) |
| Sub 2-58 | m/z = 363.11($C_{21}H_{18}ClN_3O$ = 363.85) | Sub 2-59 | m/z = 432.11($C_{27}H_{17}ClN_4$ = 432.91) |
| Sub 2-60 | m/z = 508.15($C_{33}H_{21}ClN_4$ = 509.01) | Sub 2-64 | m/z = 433.1($C_{27}H_{16}ClN_3O$ = 433.9) |
| Sub 2-66 | m/z = 559.15($C_{37}H_{22}ClN_3O$ = 560.05) | Sub 2-67 | m/z = 483.11($C_{31}H_{13}ClN_3O$ = 483.96) |
| Sub 2-69 | m/z = 573.11($C_{37}H_{20}ClN_3S$ = 574.1) | Sub 2-80 | m/z = 495.15($C_{33}H_{22}ClN_3$ = 496.01) |
| Sub 2-84 | m/z = 634.19($C_{43}H_{27}ClN_4$ = 635.17) | Sub 2-94 | m/z = 347.08($C_{20}H_{14}ClN_3O$ = 347.8) |
| Sub 2-95 | m/z = 324.12($C_{19}H_5D_7ClN_3$ = 324.82) | Sub 2-96 | m/z = 499.07($C_{29}H_{14}ClN_5S$ = 499.98) |
| Sub 2-97 | m/z = 433.04($C_{21}H_9ClF_5N_3$ = 433.77) | Sub 2-98 | m/z = 398.13($C_{25}H_{11}D_5ClN_3$ = 398.9) |
| Sub 2-99 | m/z = 459.11($C_{29}H_{18}ClN_3O$ = 459.93) | Sub 2-100 | m/z = 447.11($C_{28}H_{18}ClN_3O$ = 447.92) |
| Sub 2-101 | m/z = 433.13($C_{28}H_{20}ClN_3$ = 433.94) | Sub 2-102 | m/z = 469.13($C_{31}H_{20}ClN_3$ = 469.97) |
| Sub 2-103 | m/z = 559.15($C_{37}H_{22}ClN_3O$ = 560.05) | | |

Sub 2 of Reaction Scheme 1 may be synthesized by the reaction route of the following Reaction Scheme 3, but are not limited thereto.

Synthesis Example of Sub 2-2

<Reaction Scheme 3>

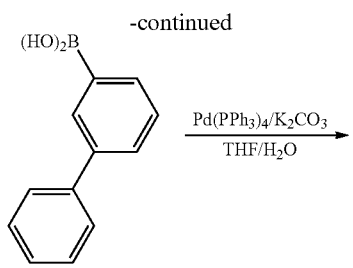

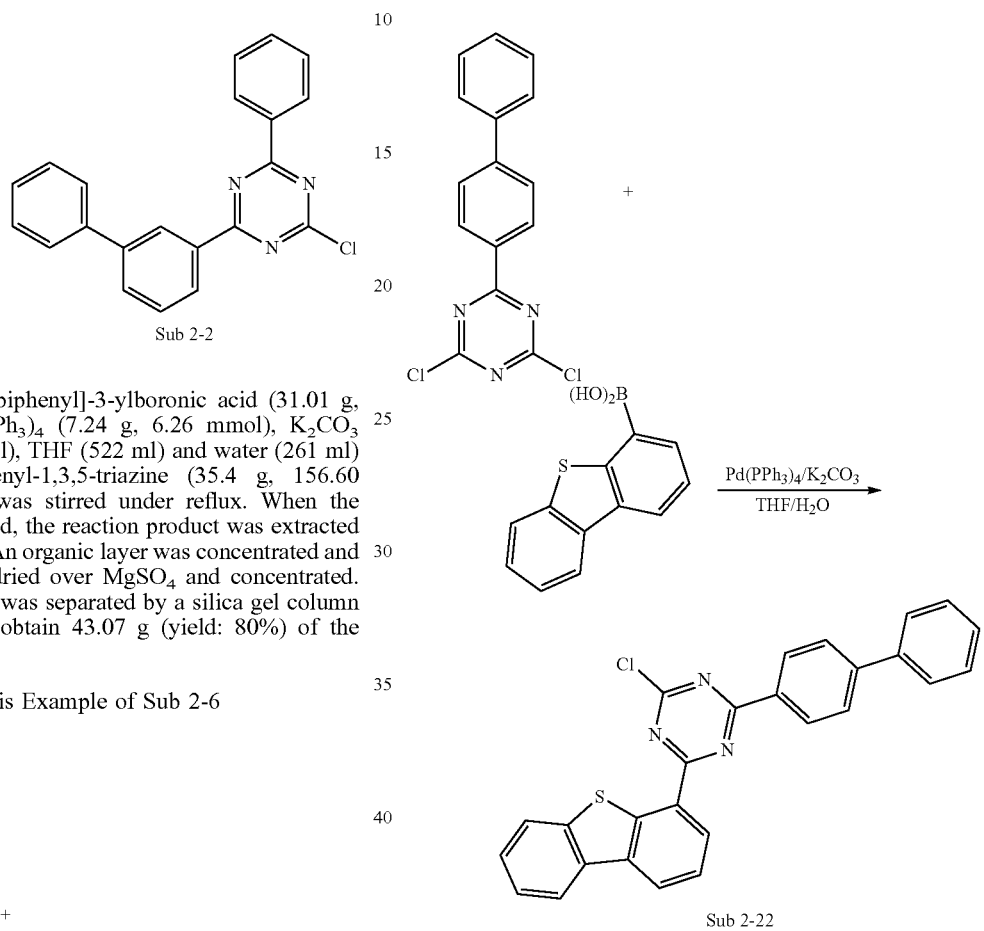

After adding [1,1'-biphenyl]-3-ylboronic acid (31.01 g, 156.60 mmol), Pd(PPh₃)₄ (7.24 g, 6.26 mmol), K₂CO₃ (64.93 g, 469.79 mmol), THF (522 ml) and water (261 ml) to 2,4-dichloro-6-phenyl-1,3,5-triazine (35.4 g, 156.60 mmol), the mixture was stirred under reflux. When the reaction was completed, the reaction product was extracted with ether and water. An organic layer was concentrated and the concentrate was dried over MgSO₄ and concentrated. Then, the concentrate was separated by a silica gel column and recrystallized to obtain 43.07 g (yield: 80%) of the product.

Synthesis Example of Sub 2-6

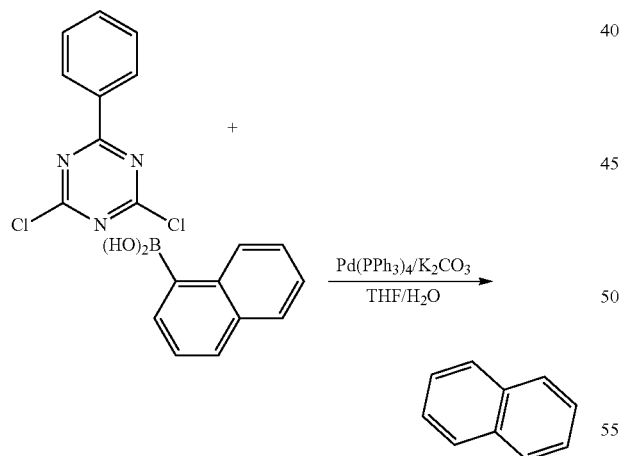

Naphthalen-1-ylboronic acid (26.93 g, 156.60 mmol), Pd(PPh₃)₄ (7.24 g, 6.26 mmol), K₂CO₃ (64.93 g, 469.79 mmol), THF (522 ml) and water (261 ml) were added to 2,4-dichloro-6-phenyl-1,3,5-triazine (35.4 g, 156.60 mmol), and the reaction was carried out in the same manner as in the synthesis method of Sub 2-2 to obtain 36.82 g (yield: 74%) of the product.

Synthesis Example of Sub 2-22

Dibenzo[b,d]thiophen-4-ylboronic acid (26.72 g, 117.16 mmol), Pd(PPh₃)₄ (5.42 g, 4.69 mmol), K₂CO₃ (48.58 g, 351.47 mmol), THF (391 ml) and water (195 ml) were added to 2-([1,1'-biphenyl]-4-yl)-4,6-dichloro-1,3,5-triazine (35.4 g, 117.16 mmol), and the reaction was carried out in the same manner as in the synthesis method of Sub 2-2 to obtain 40.06 g (yield: 76%) of the product.

Synthesis Example of Sub 2-24

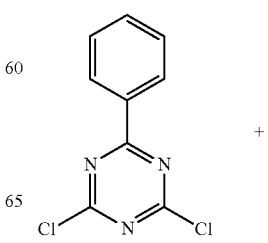

211
-continued

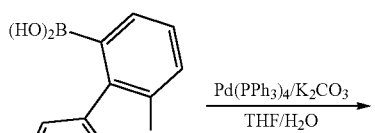

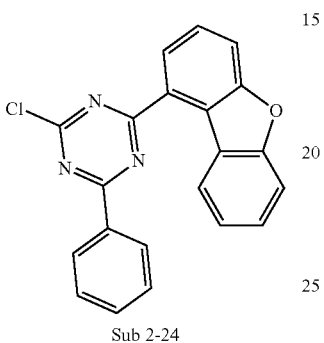

Sub 2-24

Dibenzo[b,d]furan-1-ylboronic acid (33.20 g, 156.60 mmol), Pd(PPh$_3$)$_4$ (7.24 g, 6.26 mmol), K$_2$CO$_3$ (64.93 g, 469.79 mmol), THF (522 ml) and water (261 ml) were added to 2,4-dichloro-6-phenyl-1,3,5-triazine (35.4 g, 156.60 mmol), and the reaction was carried out in the same manner as in the synthesis method of Sub 2-2 to obtain 38.66 g (yield: 69%) of the product.

Synthesis Example of Sub 2-47

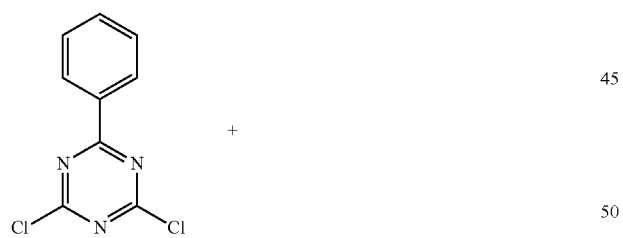

212
-continued

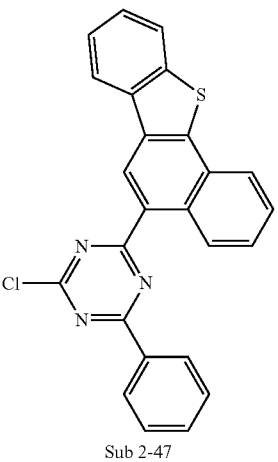

Sub 2-47

Benzo[b]naphtho[2,1-d]thiophen-5-ylboronic acid (43.55 g, 156.60 mmol), Pd(PPh$_3$)$_4$ (7.24 g, 6.26 mmol), K$_2$CO$_3$ (64.93 g, 469.79 mmol), THF (522 ml) and water (261 ml) were added to 2,4-dichloro-6-phenyl-1,3,5-triazine (35.4 g, 156.60 mmol), and the reaction was carried out in the same manner as in the synthesis method of Sub 2-2 to obtain 19.58 g (yield: 45%) of the product.

3. Synthesis Example of Final Compound

Synthesis Example of 1-6

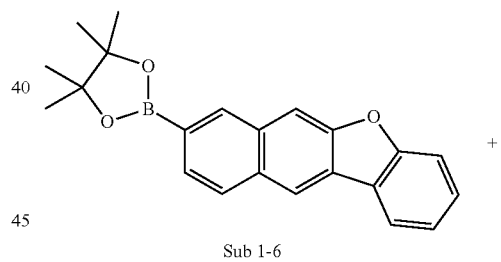

Sub 1-6

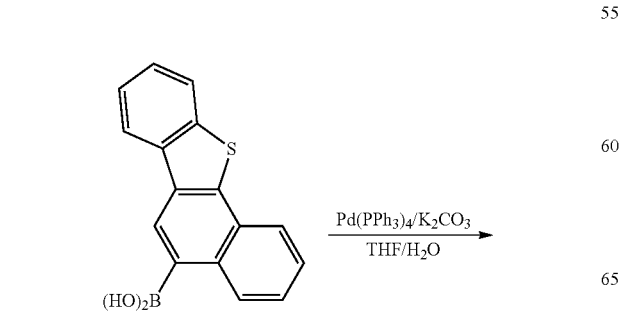

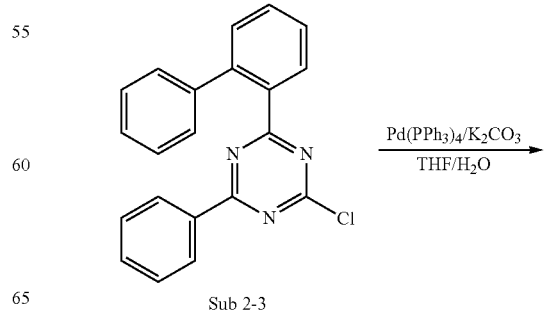

Sub 2-3

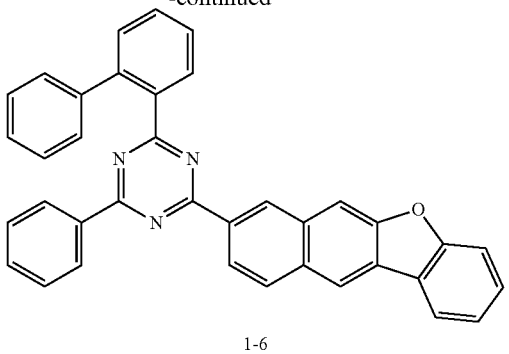

1-6

Sub 1-6 (56.7 g, 164.72 mmol) was placed in a round bottom flask and dissolved in THF (604 ml). Sub 2-3 (67.96 g, 197.66 mmol), Pd(PPh$_3$)$_4$ (7.61 g, 6.59 mmol), K$_2$CO$_3$ (68.30 g, 494.16 mmol) and water (302 ml) were added to the solution and the mixture was stirred under reflux. When the reaction was completed, the reaction product was extracted by using ether and water. An organic layer was dried over MgSO$_4$ and concentrated. Then, the concentrate was separated by a silica gel column and recrystallized to obtain 64.93 g (yield: 75%) of the product.

Synthesis Example of 1-46

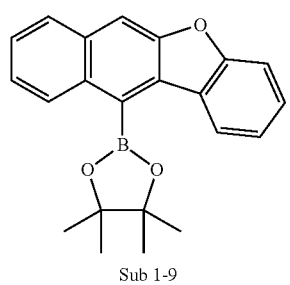

Sub 1-9

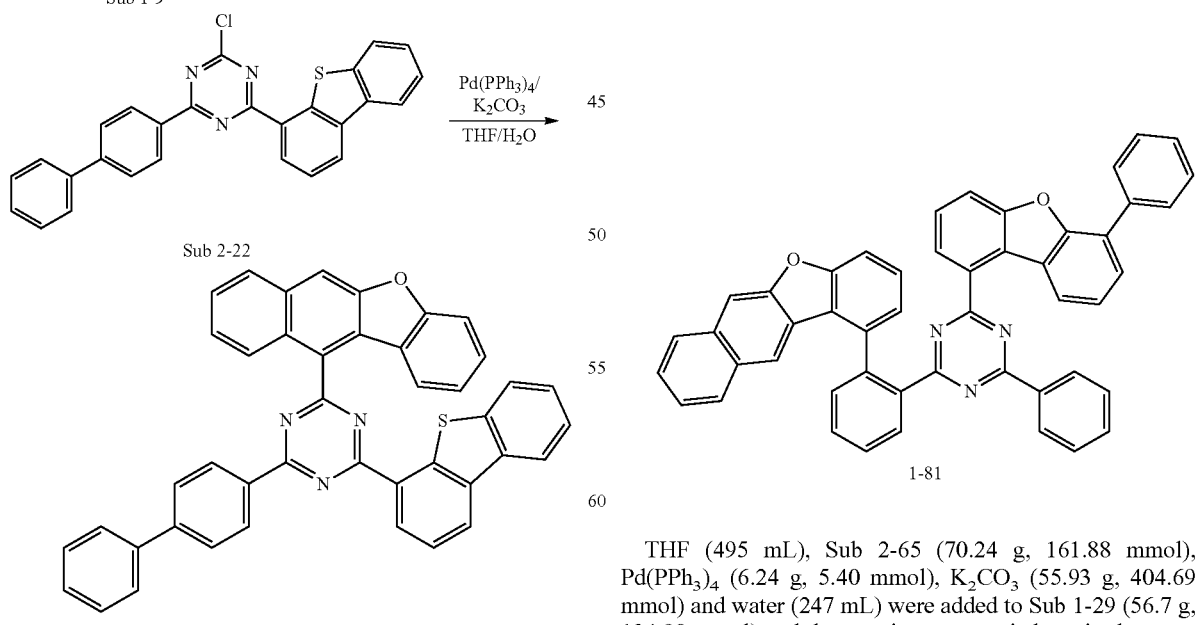

1-46

THF (604 mL), Sub 2-22 (88.94 g, 197.66 mmol), Pd(PPh$_3$)$_4$ (7.61 g, 6.59 mmol), K$_2$CO$_3$ (68.30 g, 494.16 mmol) and water (302 mL) were added to Sub 1-9 (56.7 g, 164.72 mmol) and the reaction was carried out in the same manner as in the synthesis method of 1-6 to obtain 81.17 g (yield: 73%) of the product.

Synthesis Example of 1-81

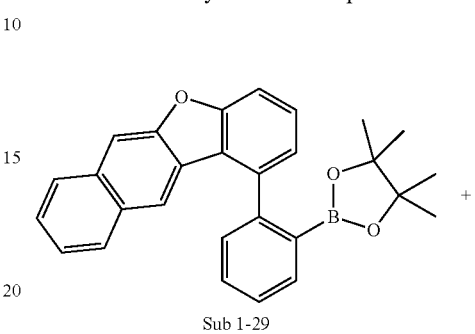

Sub 1-29

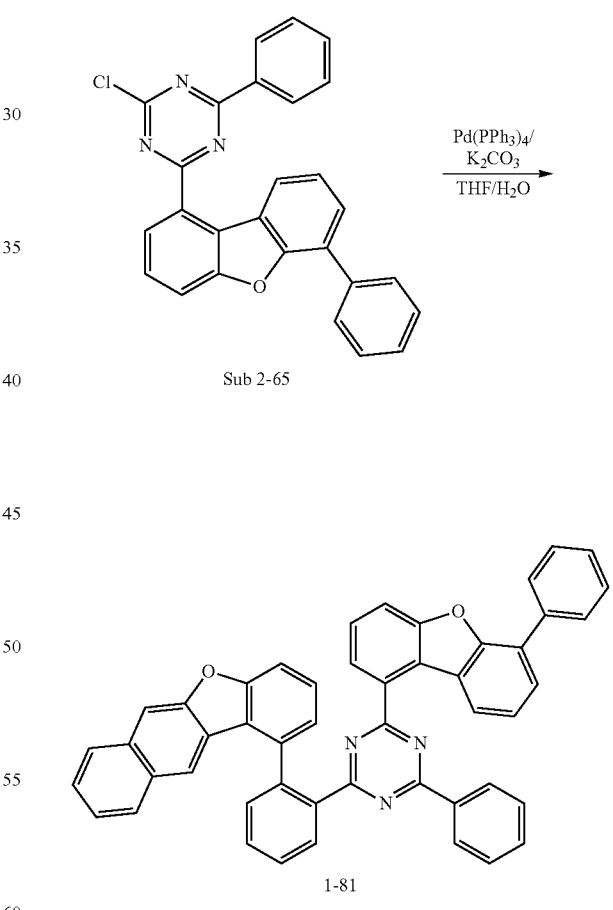

1-81

THF (495 mL), Sub 2-65 (70.24 g, 161.88 mmol), Pd(PPh$_3$)$_4$ (6.24 g, 5.40 mmol), K$_2$CO$_3$ (55.93 g, 404.69 mmol) and water (247 mL) were added to Sub 1-29 (56.7 g, 134.90 mmol) and the reaction was carried out in the same manner as in the synthesis method of 1-6 to obtain 59.73 g (yield: 64%) of the product.

Synthesis Example of 1-92

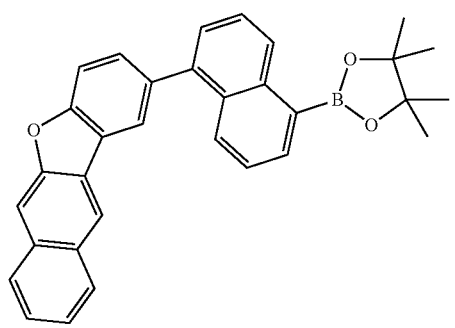
Sub 1-38

+

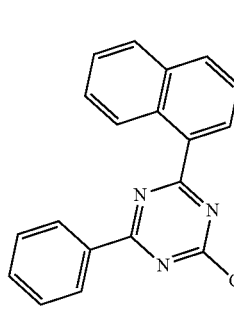
Sub 2-6

$\xrightarrow{\text{Pd(PPh}_3)_4/\text{K}_2\text{CO}_3}{\text{THF/H}_2\text{O}}$

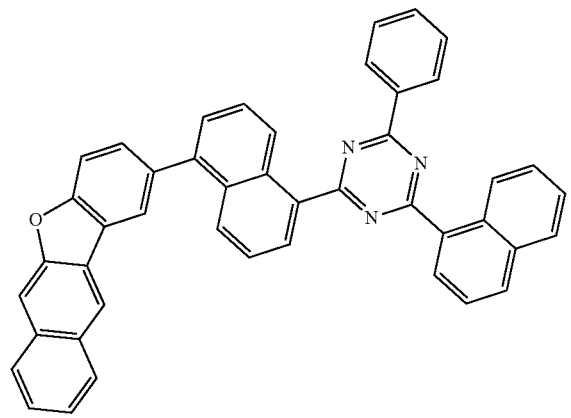
1-92

THF (442 mL), Sub 2-6 (45.97 g, 144.65 mmol), Pd(PPh$_3$)$_4$ (5.57 g, 4.82 mmol), K$_2$CO$_3$ (49.98 g, 361.62 mmol) and water (221 mL) were added to Sub 1-38 (56.7 g, 120.54 mmol) and the reaction was carried out in the same manner as in the synthesis method of 1-6 to obtain 65.62 g (yield: 87%) of the product.

Synthesis Example of 1-122

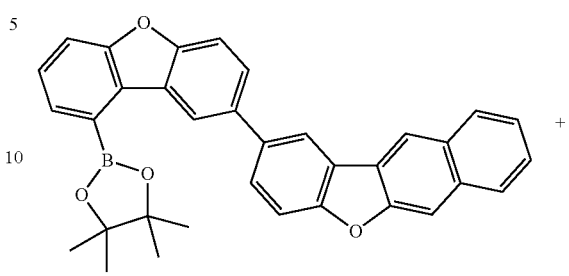
Sub 1-67

+

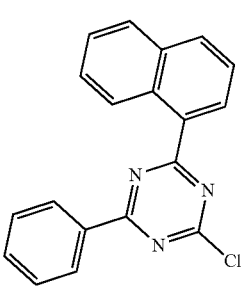
Sub 2-6

$\xrightarrow{\text{Pd(PPh}_3)_4/\text{K}_2\text{CO}_3}{\text{THF/H}_2\text{O}}$

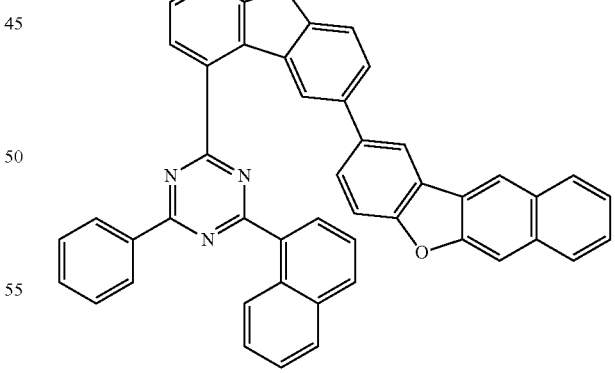
1-122

THF (407 mL), Sub 2-6 (42.36 g, 133.31 mmol), Pd(PPh$_3$)$_4$ (5.13 g, 4.44 mmol), K$_2$CO$_3$ (46.06 g, 333.27 mmol) and water (204 mL) were added to Sub 1-67 (56.7 g, 111.09 mmol) and the reaction was carried out in the same manner as in the synthesis method of 1-6 to obtain 59.17 g (yield: 80%) of the product.

Synthesis Example of 1-148

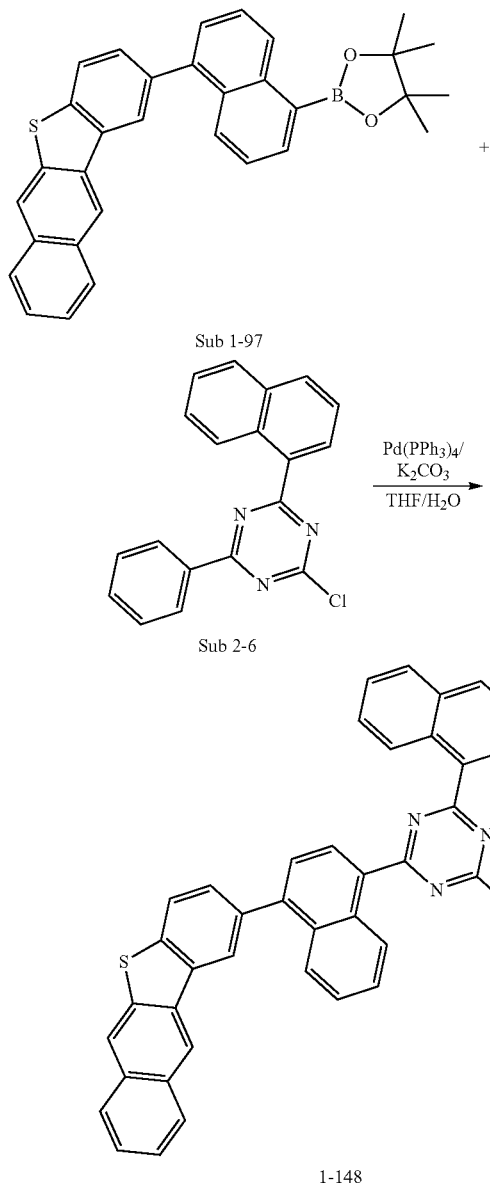

1-148

THF (427 mL), Sub 2-6 (44.45 g, 139.87 mmol), Pd(PPh$_3$)$_4$ (5.39 g, 4.66 mmol), K$_2$CO$_3$ (48.33 g, 349.68 mmol) and water (214 mL) were added to Sub 1-97 (56.7 g, 116.56 mmol) and the reaction was carried out in the same manner as in the synthesis method of 1-6 to obtain 62.84 g (yield: 84%) of the product.

Synthesis Example of 1-157

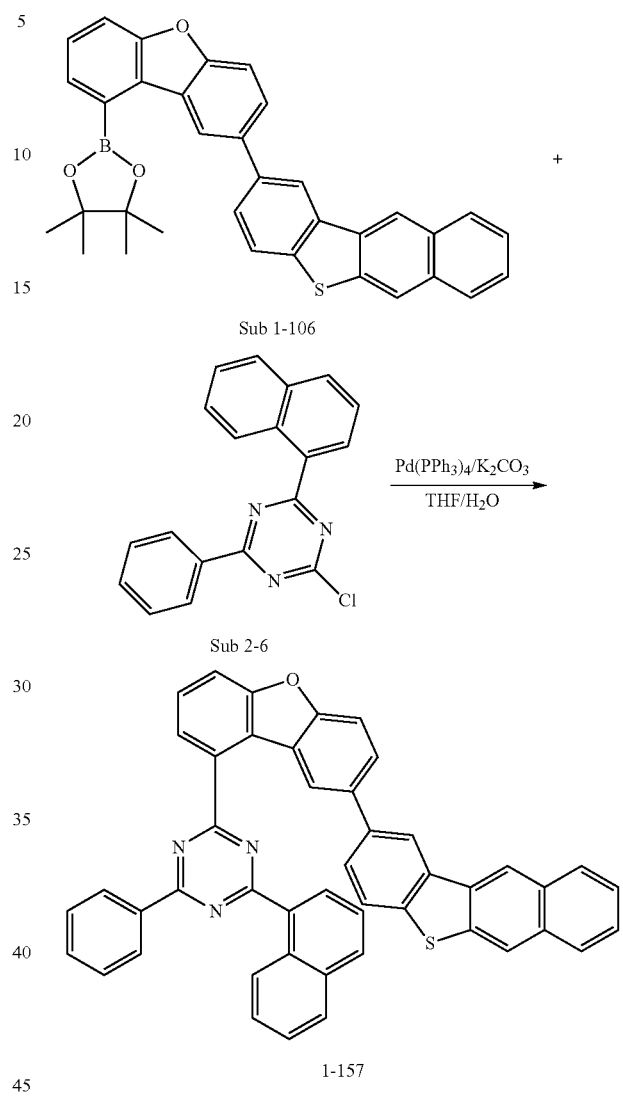

1-157

THF (395 mL), Sub 2-6 (41.07 g, 129.24 mmol), Pd(PPh$_3$)$_4$ (4.98 g, 4.31 mmol), K$_2$CO$_3$ (44.66 g, 323.10 mmol) and water (197 mL) were added to Sub 1-106 (56.7 g, 107.70 mmol) and the reaction was carried out in the same manner as in the synthesis method of 1-6 to obtain 59.48 g (yield: 81%) of the product.

The FD-MS values of compounds 1-1 to 1-176 of the present invention synthesized by the same method as in Synthesis Example are shown in Table 3 below.

TABLE 3

| Compound | FD-MS | Compound | FD-MS |
|---|---|---|---|
| 1-1 | m/z = 449.15(C$_{31}$H$_{19}$N$_3$O = 449.51) | 1-2 | m/z = 525.18(C$_{37}$H$_{23}$N$_3$O = 525.61) |
| 1-3 | m/z = 449.15(C$_{31}$H$_{19}$N$_3$O = 449.51) | 1-4 | m/z = 449.15(C$_{31}$H$_{19}$N$_3$O = 449.51) |
| 1-5 | m/z = 575.2(C$_{41}$H$_{25}$N$_3$O = 575.67) | 1-6 | m/z = 525.18(C$_{37}$H$_{23}$N$_3$O = 525.61) |
| 1-7 | m/z = 499.17(C$_{35}$H$_{21}$N$_3$O = 499.57) | 1-8 | m/z = 677.25(C$_{49}$H$_{31}$N$_3$O = 677.81) |
| 1-9 | m/z = 499.17(C$_{35}$H$_{21}$N$_3$O = 499.57) | 1-10 | m/z = 549.18(C$_{39}$H$_{23}$N$_3$O = 549.63) |
| 1-11 | m/z = 675.23(C$_{49}$H$_{29}$N$_3$O = 675.79) | 1-12 | m/z = 575.2(C$_{41}$H$_{25}$N$_3$O = 575.67) |
| 1-13 | m/z = 701.25(C$_{51}$H$_{31}$N$_3$O = 701.83) | 1-14 | m/z = 651.23(C$_{47}$H$_{29}$N$_3$O = 651.77) |

TABLE 3-continued

| Compound | FD-MS | Compound | FD-MS |
|---|---|---|---|
| 1-15 | m/z = 651.23($C_{47}H_{29}N_3O$ = 651.77) | 1-16 | m/z = 575.2($C_{41}H_{25}N_3O$ = 575.67) |
| 1-17 | m/z = 549.18($C_{39}H_{23}N_3O$ = 549.63) | 1-18 | m/z = 549.18($C_{39}H_{23}N_3O$ = 549.63) |
| 1-19 | m/z = 575.2($C_{41}H_{25}N_3O$ = 575.67) | 1-20 | m/z = 575.2($C_{41}H_{25}N_3O$ = 575.67) |
| 1-21 | m/z = 575.2($C_{41}H_{25}N_3O$ = 575.67) | 1-22 | m/z = 555.14($C_{37}H_{21}N_3OS$ = 555.66) |
| 1-23 | m/z = 605.16($C_{41}H_{23}N_3OS$ = 605.72) | 1-24 | m/z = 631.17($C_{43}H_{25}N_3OS$ = 631.75) |
| 1-25 | m/z = 631.17($C_{43}H_{25}N_3OS$ = 631.75) | 1-26 | m/z = 615.19($C_{43}H_{25}N_3O_2$ = 615.69) |
| 1-27 | m/z = 539.16($C_{37}H_{21}N_3O_2$ = 539.59) | 1-28 | m/z = 707.2($C_{49}H_{29}N_3OS$ = 707.85) |
| 1-29 | m/z = 707.2($C_{49}H_{29}N_3OS$ = 707.85) | 1-30 | m/z = 655.23($C_{46}H_{29}N_3O_2$ = 655.76) |
| 1-31 | m/z = 655.17($C_{45}H_{25}N_3OS$ = 655.78) | 1-32 | m/z = 631.17($C_{43}H_{25}N_3OS$ = 631.75) |
| 1-33 | m/z = 615.19($C_{43}H_{25}N_3O_2$ = 615.69) | 1-34 | m/z = 720.2($C_{49}H_{28}N_4OS$ = 720.85) |
| 1-35 | m/z = 705.21($C_{49}H_{27}N_3O_3$ = 705.77) | 1-36 | m/z = 691.23($C_{49}H_{29}N_3O_2$ = 691.79) |
| 1-37 | m/z = 757.22($C_{53}H_{31}N_3OS$ = 757.91) | 1-38 | m/z = 707.2($C_{49}H_{29}N_3OS$ = 707.85) |
| 1-39 | m/z = 707.2($C_{49}H_{29}N_3OS$ = 707.85) | 1-40 | m/z = 766.27($C_{55}H_{34}N_4O$ = 766.9) |
| 1-41 | m/z = 631.17($C_{43}H_{25}N_3OS$ = 631.75) | 1-42 | m/z = 631.17($C_{43}H_{25}N_3OS$ = 631.75) |
| 1-43 | m/z = 631.17($C_{43}H_{25}N_3OS$ = 631.75) | 1-44 | m/z = 707.2($C_{49}H_{29}N_3OS$ = 707.85) |
| 1-45 | m/z = 631.17($C_{43}H_{25}N_3OS$ = 631.75) | 1-46 | m/z = 631.17($C_{43}H_{25}N_3OS$ = 631.75) |
| 1-47 | m/z = 665.21($C_{47}H_{27}N_3O_2$ = 665.75) | 1-48 | m/z = 691.23($C_{49}H_{29}N_3O_2$ = 691.79) |
| 1-49 | m/z = 665.21($C_{47}H_{27}N_3O_2$ = 665.75) | 1-50 | m/z = 681.19($C_{47}H_{27}N_3OS$ = 681.81) |
| 1-51 | m/z = 757.22($C_{53}H_{31}N_3OS$ = 757.91) | 1-52 | m/z = 715.23($C_{51}H_{29}N_3O_2$ = 715.81) |
| 1-53 | m/z = 589.18($C_{41}H_{23}N_3O_2$ = 589.65) | 1-54 | m/z = 589.18($C_{41}H_{23}N_3O_2$ = 589.65) |
| 1-55 | m/z = 605.16($C_{41}H_{23}N_3OS$ = 605.72) | 1-56 | m/z = 589.18($C_{41}H_{23}N_3O_2$ = 589.65) |
| 1-57 | m/z = 605.16($C_{41}H_{23}N_3OS$ = 605.72) | 1-58 | m/z = 807.23($C_{57}H_{33}N_3OS$ = 807.97) |
| 1-59 | m/z = 691.23($C_{49}H_{29}N_3O_2$ = 691.79) | 1-60 | m/z = 591.18($C_{41}H_{25}N_3S$ = 591.73) |
| 1-61 | m/z = 515.15($C_{35}H_{21}N_3S$ = 515.63) | 1-62 | m/z = 617.19($C_{43}H_{27}N_3S$ = 617.77) |
| 1-63 | m/z = 565.16($C_{39}H_{23}N_3S$ = 565.69) | 1-64 | m/z = 565.16($C_{39}H_{23}N_3S$ = 565.69) |
| 1-65 | m/z = 581.19($C_{40}H_{27}N_3S$ = 581.74) | 1-66 | m/z = 555.14($C_{37}H_{21}N_3OS$ = 555.66) |
| 1-67 | m/z = 737.16($C_{49}H_{27}N_3OS_2$ = 737.9) | 1-68 | m/z = 518.16($C_{34}H_{22}N_4S$ = 518.64) |
| 1-69 | m/z = 515.15($C_{35}H_{21}N_3S$ = 515.63) | 1-70 | m/z = 561.19($C_{37}H_{27}N_3OS$ = 561.7) |
| 1-71 | m/z = 630.19($C_{43}H_{26}N_4S$ = 630.77) | 1-72 | m/z = 591.18($C_{41}H_{25}N_3S$ = 591.73) |
| 1-73 | m/z = 766.27($C_{55}H_{34}N_4O$ = 766.9) | 1-74 | m/z = 575.2($C_{41}H_{25}N_3O$ = 575.67) |
| 1-75 | m/z = 677.25($C_{49}H_{31}N_3OS$ = 677.81) | 1-76 | m/z = 707.2($C_{49}H_{29}N_3OS$ = 707.85) |
| 1-77 | m/z = 766.27($C_{55}H_{34}N_4O$ = 766.9) | 1-78 | m/z = 707.2($C_{49}H_{29}N_3OS$ = 707.85) |
| 1-79 | m/z = 767.26($C_{55}H_{33}N_3O_2$ = 767.89) | 1-80 | m/z = 767.26($C_{55}H_{33}N_3O_2$ = 767.89) |
| 1-81 | m/z = 691.23($C_{49}H_{29}N_3O_2$ = 691.79) | 1-82 | m/z = 817.27($C_{59}H_{35}N_3O_2$ = 817.95) |
| 1-83 | m/z = 741.24($C_{53}H_{31}N_3O_2$ = 741.85) | 1-84 | m/z = 741.24($C_{53}H_{31}N_3O_2$ = 741.85) |
| 1-85 | m/z = 831.25($C_{59}H_{33}N_3OS$ = 831.99) | 1-86 | m/z = 767.26($C_{55}H_{33}N_3O_2$ = 767.89) |
| 1-87 | m/z = 757.19($C_{51}H_{27}N_5OS$ = 757.87) | 1-88 | m/z = 601.22($C_{43}H_{27}N_3O$ = 601.71) |
| 1-89 | m/z = 757.22($C_{53}H_{31}N_3OS$ = 757.91) | 1-90 | m/z = 625.22($C_{45}H_{27}N_3O$ = 625.73) |
| 1-91 | m/z = 625.22($C_{45}H_{27}N_3O$ = 625.73) | 1-92 | m/z = 625.22($C_{45}H_{27}N_3O$ = 625.73) |
| 1-93 | m/z = 625.22($C_{45}H_{27}N_3O$ = 625.73) | 1-94 | m/z = 651.23($C_{47}H_{29}N_3O$ = 651.77) |
| 1-95 | m/z = 731.2($C_{51}H_{29}N_3OS$ = 731.87) | 1-96 | m/z = 833.25($C_{59}H_{35}N_3OS$ = 834.01) |
| 1-97 | m/z = 757.22($C_{53}H_{31}N_3OS$ = 757.91) | 1-98 | m/z = 867.29($C_{63}H_{37}N_3O_2$ = 868.01) |
| 1-99 | m/z = 757.22($C_{53}H_{31}N_3OS$ = 757.91) | 1-100 | m/z = 655.23($C_{46}H_{29}N_3O_2$ = 655.76) |
| 1-101 | m/z = 625.22($C_{45}H_{27}N_3O$ = 625.73) | 1-102 | m/z = 625.22($C_{45}H_{27}N_3O$ = 625.73) |
| 1-103 | m/z = 625.22($C_{45}H_{27}N_3O$ = 625.73) | 1-104 | m/z = 807.23($C_{57}H_{33}N_3OS$ = 807.97) |
| 1-105 | m/z = 731.2($C_{51}H_{29}N_3OS$ = 731.87) | 1-106 | m/z = 731.2($C_{51}H_{29}N_3OS$ = 731.87) |
| 1-107 | m/z = 791.26($C_{57}H_{33}N_3O_2$ = 791.91) | 1-108 | m/z = 807.23($C_{57}H_{33}N_3OS$ = 807.97) |
| 1-109 | m/z = 807.23($C_{57}H_{33}N_3OS$ = 807.97) | 1-110 | m/z = 575.20($C_{41}H_{25}N_3O$ = 575.67) |
| 1-111 | m/z = 867.29($C_{63}H_{37}N_3O_2$ = 868.01) | 1-112 | m/z = 807.23($C_{57}H_{33}N_3OS$ = 807.97) |
| 1-113 | m/z = 777.28($C_{57}H_{35}N_3O$ = 777.93) | 1-114 | m/z = 803.29($C_{59}H_{37}N_3O$ = 803.97) |
| 1-115 | m/z = 632.26($C_{45}H_{20}D_7N_3O$ = 632.77) | 1-116 | m/z = 715.23($C_{51}H_{29}N_3O_2$ = 715.81) |
| 1-117 | m/z = 883.27($C_{63}H_{37}N_3OS$ = 884.07) | 1-118 | m/z = 833.25($C_{59}H_{35}N_3OS$ = 834.01) |
| 1-119 | m/z = 942.34($C_{69}H_{42}N_4O$ = 943.12) | 1-120 | m/z = 701.25($C_{51}H_{31}N_3O$ = 701.83) |
| 1-121 | m/z = 615.19($C_{43}H_{25}N_3O_2$ = 615.69) | 1-122 | m/z = 665.21($C_{47}H_{27}N_3O_2$ = 665.75) |
| 1-123 | m/z = 681.19($C_{47}H_{27}N_3OS$ = 681.81) | 1-124 | m/z = 715.23($C_{51}H_{29}N_3O_2$ = 715.81) |
| 1-125 | m/z = 691.23($C_{49}H_{29}N_3O_2$ = 691.79) | 1-126 | m/z = 691.23($C_{49}H_{20}N_3O_2$ = 691.79) |
|  |  | 1-128 | m/z = 691.23($C_{49}H_{29}N_3O_2$ = 691.79) |
| 1-129 | m/z = 757.22($C_{53}H_{31}N_3OS$ = 757.91) | 1-130 | m/z = 691.23($C_{49}H_{29}N_3O_2$ = 691.79) |
| 1-131 | m/z = 817.27($C_{59}H_{35}N_3O_2$ = 817.95) | 1-132 | m/z = 691.23($C_{49}H_{29}N_3O_2$ = 691.79) |
| 1-133 | m/z = 781.24($C_{55}H_{31}N_3O_3$ = 781.87) | 1-134 | m/z = 797.21($C_{55}H_{31}N_3O_2S$ = 797.93) |
|  |  | 1-136 | m/z = 691.23($C_{49}H_{29}N_3O_2$ = 691.79) |
| 1-137 | m/z = 691.23($C_{49}H_{29}N_3O_2$ = 691.79) | 1-138 | m/z = 780.25($C_{55}H_{32}N_4O_2$ = 780.89) |
| 1-139 | m/z = 691.23($C_{49}H_{29}N_3O_2$ = 691.79) | 1-140 | m/z = 781.18($C_{49}H_{24}F_5N_3O_2$ = 781.74) |
| 1-141 | m/z = 732.29($C_{53}H_{28}D_5N_3O$ = 732.9) | 1-142 | m/z = 793.27($C_{57}H_{35}N_3O_2$ = 793.93) |
| 1-143 | m/z = 651.23($C_{47}H_{29}N_3O$ = 651.77) | 1-144 | m/z = 755.26($C_{54}H_{33}N_3O_2$ = 755.88) |
| 1-145 | m/z = 591.18($C_{41}H_{25}N_3S$ = 591.73) | 1-146 | m/z = 617.19($C_{43}H_{27}N_3S$ = 617.77) |
| 1-147 | m/z = 707.24($C_{50}H_{33}N_3S$ = 707.9) | 1-148 | m/z = 641.19($C_{45}H_{27}N_3S$ = 641.79) |
| 1-149 | m/z = 641.19($C_{45}H_{27}N_3S$ = 641.79) | 1-150 | m/z = 641.19($C_{45}H_{27}N_3S$ = 641.79) |
| 1-151 | m/z = 793.26($C_{57}H_{35}N_3S$ = 793.99) | 1-152 | m/z = 641.19($C_{45}H_{27}N_3S$ = 641.79) |
| 1-153 | m/z = 667.21($C_{47}H_{29}N_3S$ = 667.83) | 1-154 | m/z = 823.21($C_{57}H_{33}N_3S_2$ = 824.03) |
| 1-155 | m/z = 883.27($C_{63}H_{37}N_3OS$ = 884.07) | 1-156 | m/z = 747.18($C_{51}H_{29}N_3S_2$ = 747.93) |
| 1-157 | m/z = 681.19($C_{47}H_{27}N_3OS$ = 681.81) | 1-158 | m/z = 697.16($C_{47}H_{27}N_3S_2$ = 697.87) |
| 1-159 | m/z = 731.2($C_{51}H_{29}N_3OS$ = 731.87) | 1-160 | m/z = 631.17($C_{43}H_{25}N_3OS$ = 631.75) |
|  |  | 1-162 | m/z = 737.16($C_{49}H_{27}N_3OS_2$ = 737.9) |
| 1-163 | m/z = 707.2($C_{49}H_{29}N_3OS$ = 707.85) | 1-164 | m/z = 707.2($C_{49}H_{29}N_3OS$ = 707.85) |
| 1-165 | m/z = 747.18($C_{51}H_{29}N_3S_2$ = 747.93) | 1-166 | m/z = 681.19($C_{47}H_{27}N_3OS$ = 681.81 ) |
| 1-167 | m/z = 731.2($C_{51}H_{29}N_3OS$ = 731.87) | 1-168 | m/z = 631.17($C_{43}H_{25}N_3OS$ = 631.75) |
| 1-169 | m/z = 731.2($C_{51}H_{29}N_3OS$ = 731.87) | 1-170 | m/z = 721.18($C_{49}H_{27}N_3O_2S$ = 721.83) |

TABLE 3-continued

| Compound | FD-MS | Compound | FD-MS |
|---|---|---|---|
| 1-171 | m/z = 691.23(C$_{40}$H$_{29}$N$_3$O$_2$ = 691.79) | 1-172 | m/z = 691.23(C$_{49}$H$_{29}$N$_3$O$_2$ = 691.79) |
| 1-173 | m/z = 741.24(C$_{53}$H$_{31}$N$_3$O$_2$ = 741.85) | 1-174 | m/z = 807.23(C$_{57}$H$_{33}$N$_3$OS = 807.97) |
| 1-175 | m/z = 799.21(C$_{55}$H$_{33}$N$_3$S$_2$ = 800.01) | 1-176 | m/z = 757.22(C$_{53}$H$_{31}$N$_3$OS = 757.91) |

[Synthesis Example 2] Formula 2

The compound (Final product 2) represented by Formula 2 of the present invention may be prepared by reacting Sub 3 and Sub 4 as shown in Reaction Scheme 4 below, but is not limited thereto.

<Reaction Scheme 4>

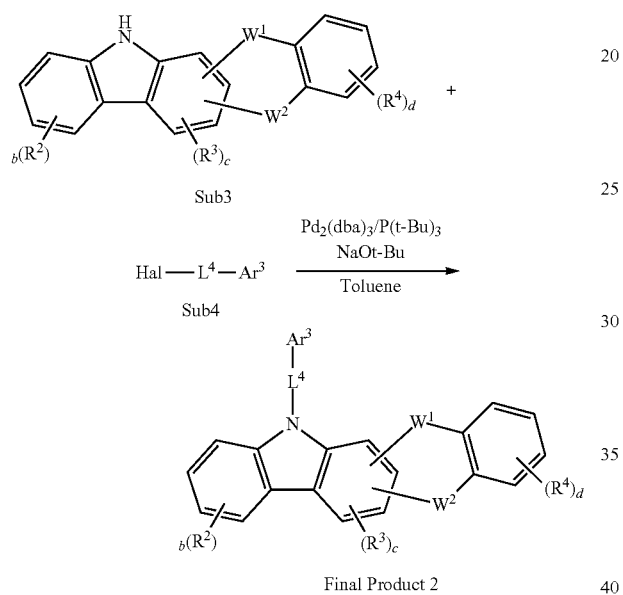

Final Product 2

1. Exemplary Compounds and Synthesis Examples of Sub 3

The compounds belonging to Sub 3 of Reaction Scheme 4 are as follows, but are not limited thereto.

Sub 3-1

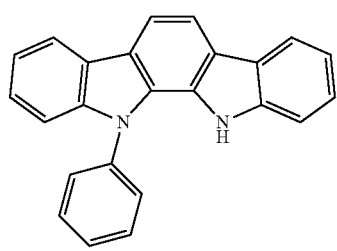

Sub 3-2

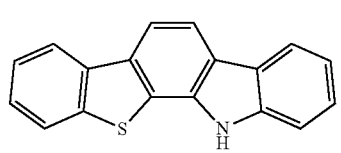

Sub 3-3

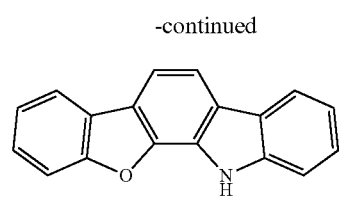

Sub 3-4

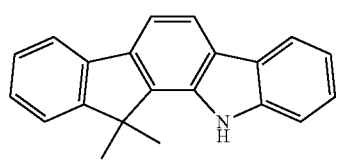

Sub 3-5

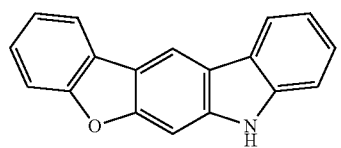

Sub 3-6

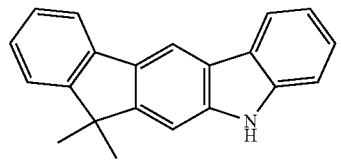

Sub 3-7

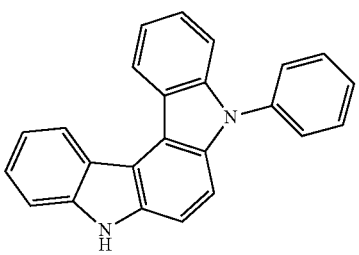

Sub 3-8

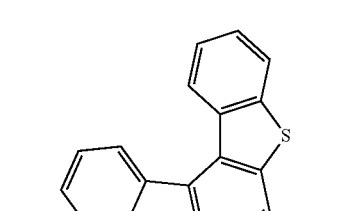

Sub 3-9

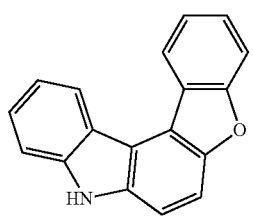

-continued
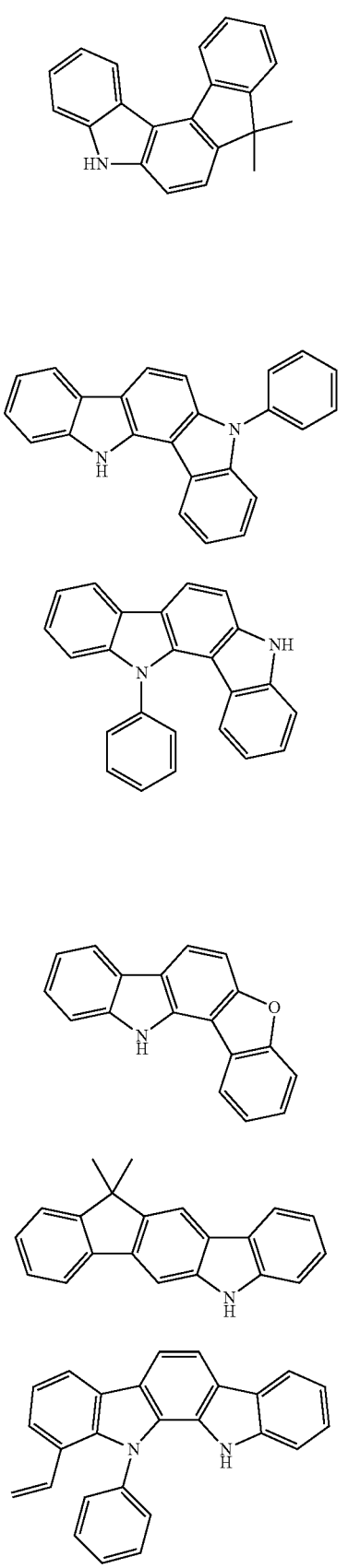
Sub 3-10
Sub 3-11
Sub 3-12
Sub 3-13
Sub 3-14
Sub 3-15
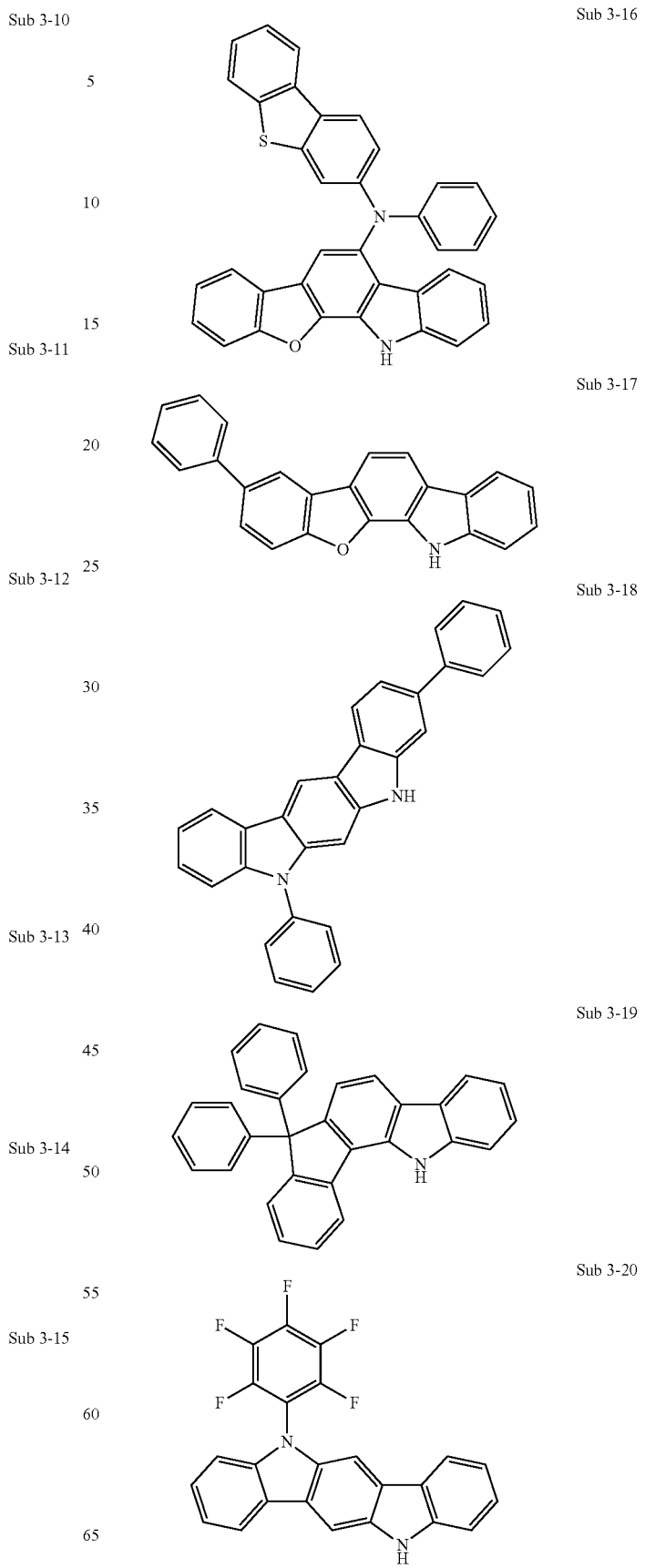
Sub 3-16
Sub 3-17
Sub 3-18
Sub 3-19
Sub 3-20

Sub 3-21
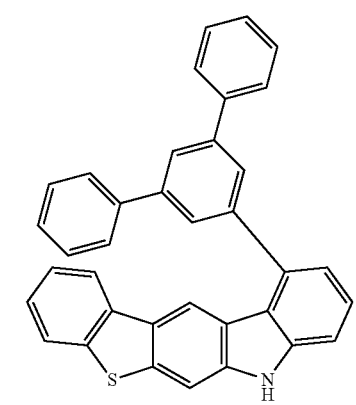
Sub 3-22
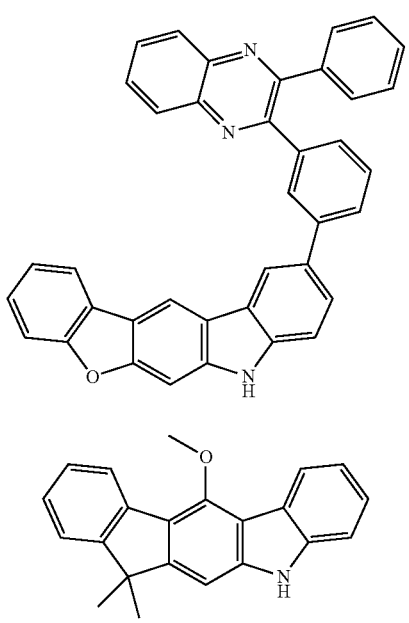
Sub 3-23
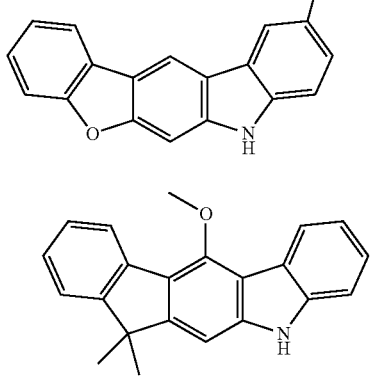
Sub 3-24
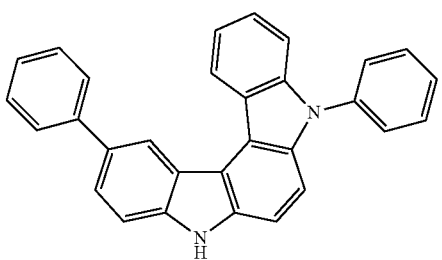
Sub 3-25
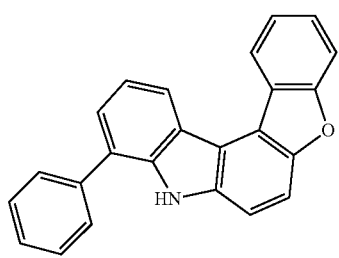
Sub 3-26
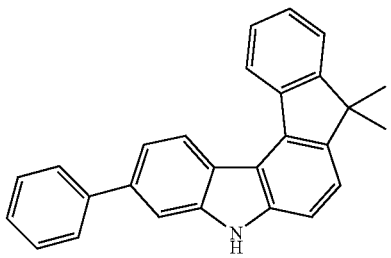
Sub 3-27
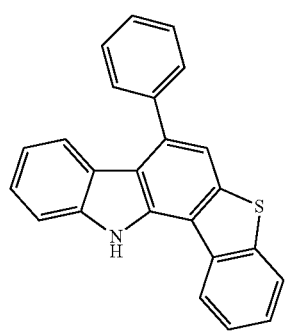
Sub 3-28
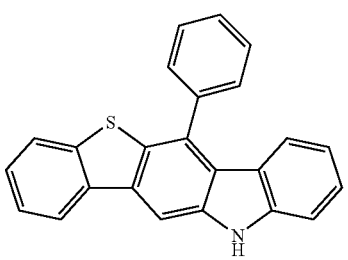
Sub 3-29
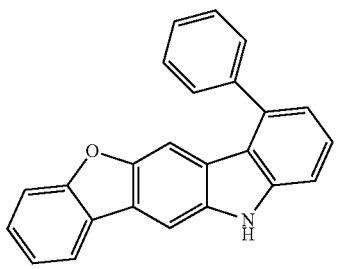
Sub 3-30
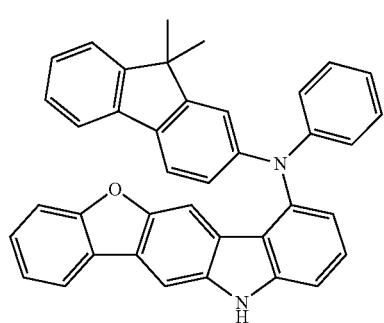

Sub 3-31
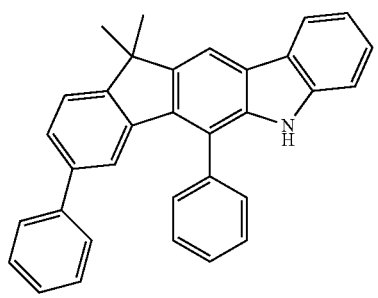
Sub 3-32
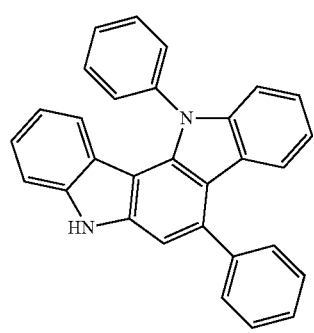
Sub 3-33
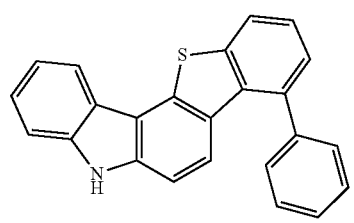
Sub 3-34
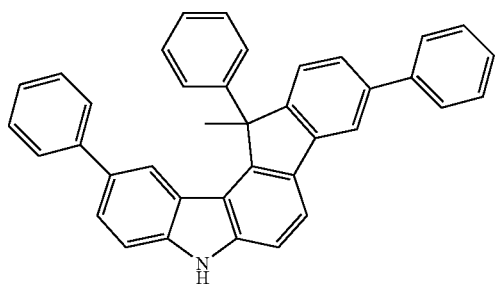
Sub 3-35
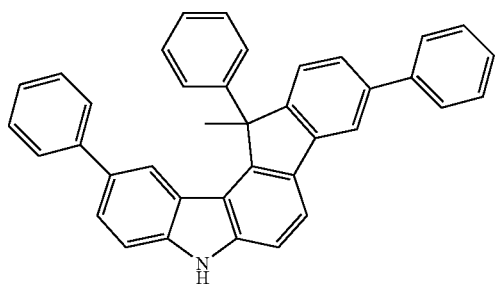
Sub 3-36
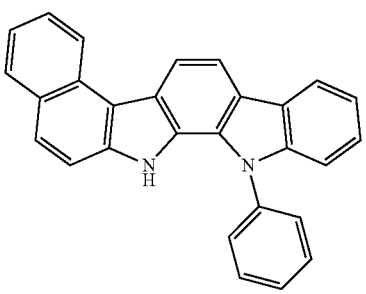
Sub 3-37
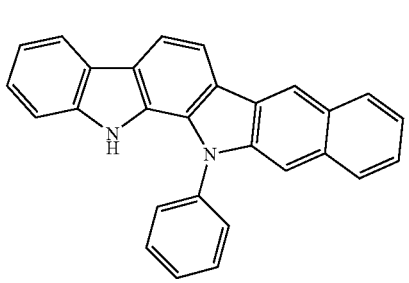
Sub 3-38
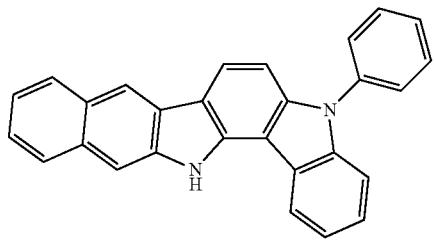
Sub 3-39
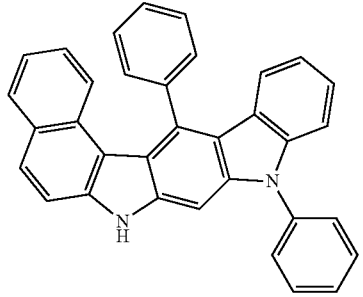
Sub 3-40
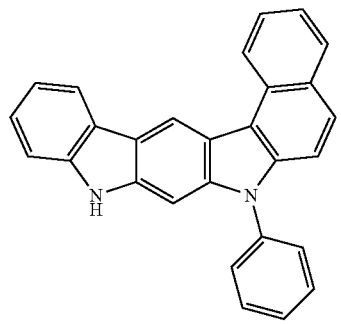

Sub 3-41
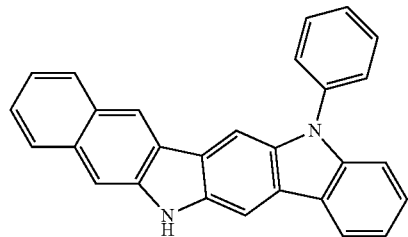
Sub 3-46
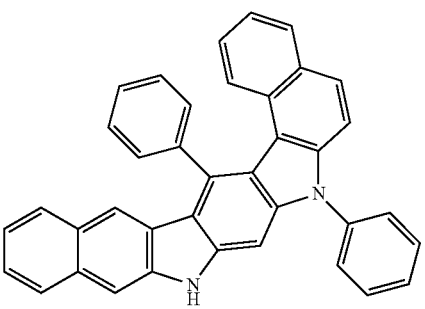
Sub 3-42
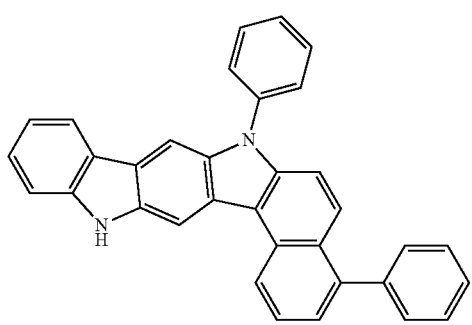
Sub 3-47
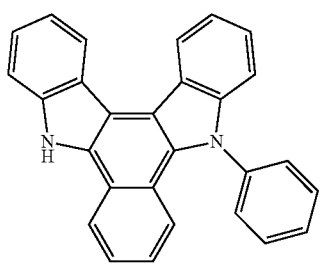
Sub 3-43
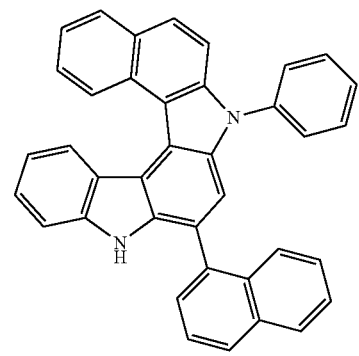
Sub 3-48
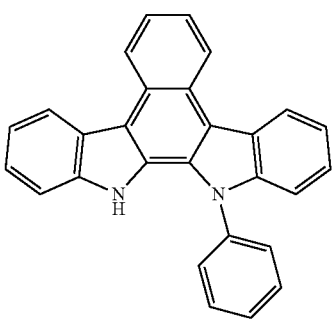
Sub 3-44
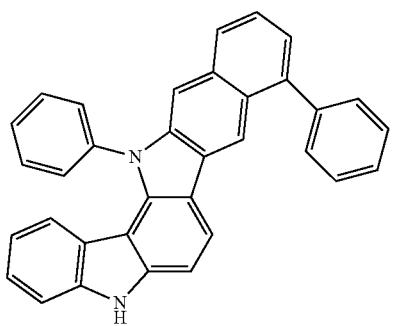
Sub 3-49
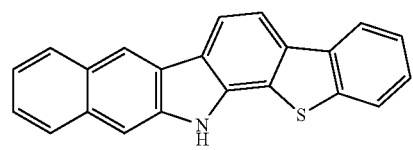
Sub 3-45
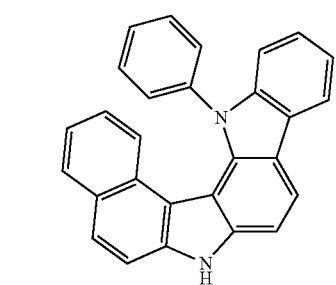
Sub 3-50
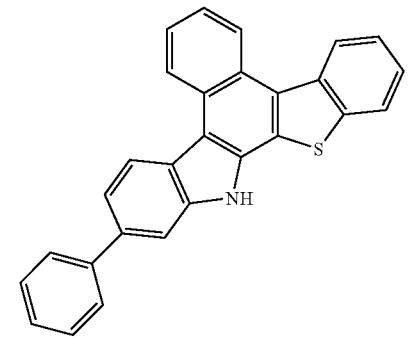

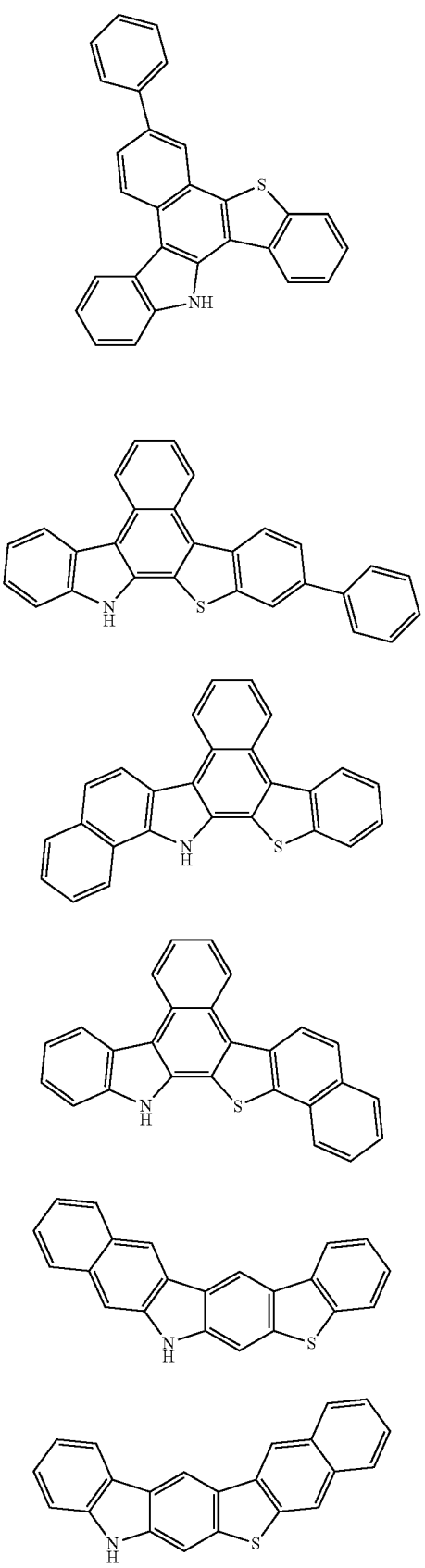
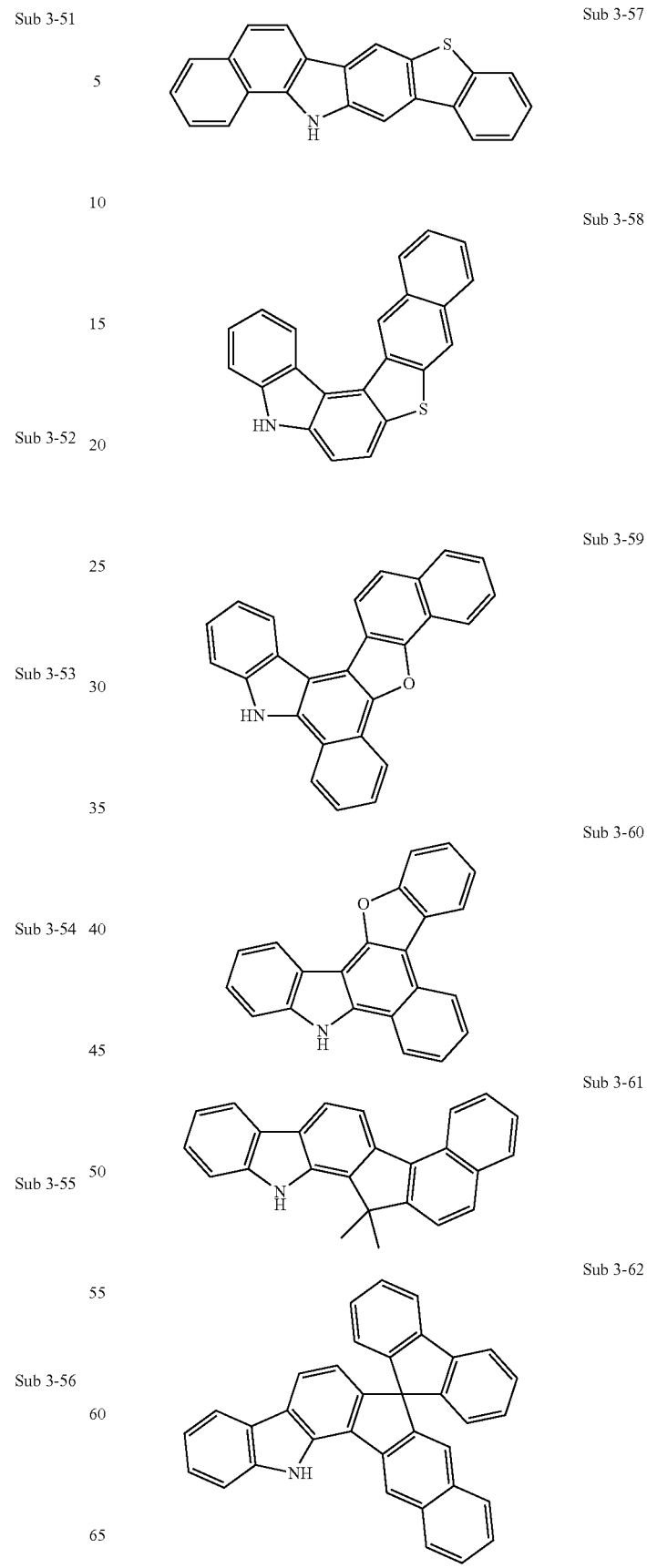
Sub 3-51
Sub 3-52
Sub 3-53
Sub 3-54
Sub 3-55
Sub 3-56
Sub 3-57
Sub 3-58
Sub 3-59
Sub 3-60
Sub 3-61
Sub 3-62

Sub 3-63
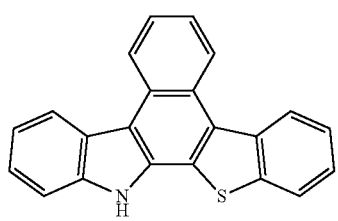
Sub 3-64
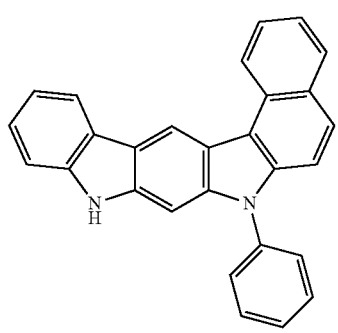
Sub 3-65
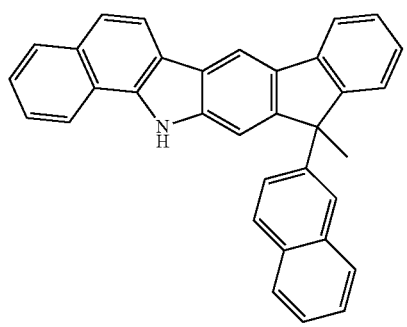
Sub 3-66
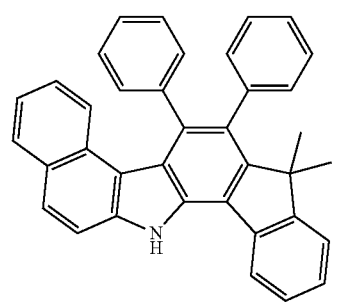
Sub 3-67
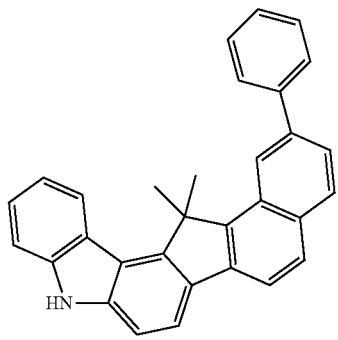
Sub 3-68
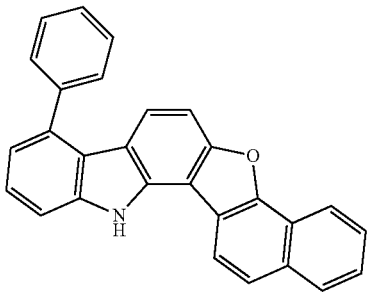
Sub 3-69
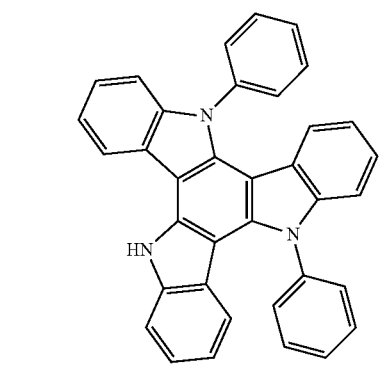
Sub 3-70
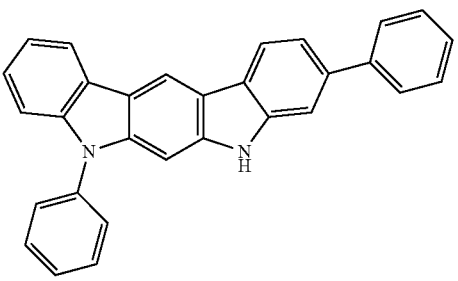
Sub 3-71
The FD-MS values of the compounds belonging to Sub 3 are shown in Table 4 below.

TABLE 4

| Compound | FD-MS | Compound | FD-MS |
|---|---|---|---|
| Sub 3-1 | m/z = 332.13($C_{24}H_{16}N_2$ = 332.41) | Sub 3-2 | m/z = 273.06($C_{18}H_{11}NS$ = 273.35) |
| Sub 3-3 | m/z = 257.08($C_{18}H_{11}NO$ = 257.29) | Sub 3-4 | m/z = 283.14($C_{21}H_{17}N$ = 283.37) |
| Sub 3-5 | m/z = 257.08($C_{18}H_{11}NO$ = 257.29) | Sub 3-6 | m/z = 283.14($C_{21}H_{17}N$ = 283.37) |
| Sub 3-7 | m/z = 332.13($C_{24}H_{16}N_2$ = 332.41) | Sub 3-8 | m/z = 273.06($C_{18}H_{11}NS$ = 273.35) |
| Sub 3-9 | m/z = 257.08($C_{18}H_{11}NO$ = 257.29) | Sub 3-10 | m/z = 283.14($C_{21}H_{17}N$ = 283.37) |
| Sub 3-11 | m/z = 332.13($C_{24}H_{16}N_2$ = 332.41) | Sub 3-12 | m/z = 332.13($C_{24}H_{16}N_2$ = 332.41) |
| Sub 3-13 | m/z = 257.08($C_{18}H_{11}NO$ = 257.29) | Sub 3-14 | m/z = 283.14($C_{21}H_{17}N$ = 283.37) |
| Sub 3-15 | m/z = 358.15($C_{26}H_{18}N_2$ = 358.44) | Sub 3-16 | m/z = 530.15($C_{36}H_{22}N_2OS$ = 530.65) |
| Sub 3-17 | m/z = 333.12($C_{24}H_{15}NO$ = 333.39) | Sub 3-18 | m/z = 408.16($C_{30}H_{20}N_2$ = 408.5) |
| Sub 3-19 | m/z = 407.17($C_{31}H_{21}N$ = 407.52) | Sub 3-20 | m/z = 422.08($C_{24}H_{11}F_5N_2$ = 422.36) |
| Sub 3-21 | m/z = 501.16($C_{36}H_{23}NS$ = 501.65) | Sub 3-22 | m/z = 537.18($C_{38}H_{23}N_3O$ = 537.62) |
| Sub 3-23 | m/z = 313.15($C_{22}H_{19}NO$ = 313.4) | Sub 3-24 | m/z = 408.16($C_{30}H_{20}N_2$ = 408.5) |
| Sub 3-25 | m/z = 333.12($C_{24}H_{15}NO$ = 333.39) | Sub 3-26 | m/z = 359.17($C_{27}H_{21}N$ = 359.47) |
| Sub 3-27 | m/z = 349.09($C_{24}H_{15}NS$ = 349.45) | Sub 3-28 | m/z = 349.09($C_{24}H_{15}N_5$ = 349.45) |
| Sub 3-29 | m/z = 333.12($C_{24}H_{15}NO$ = 333.39) | Sub 3-30 | m/z = 540.22($C_{39}H_{28}N_2$ = 540.67) |
| Sub 3-31 | m/z = 435.2($C_{33}H_{25}N$ = 435.57) | Sub 3-32 | m/z = 408.16($C_{30}H_{20}N_2$ = 408.5) |
| Sub 3-33 | m/z = 349.09($C_{24}H_{15}NS$ = 349.45) | Sub 3-34 | m/z = 333.12($C_{24}H_{15}NO$ = 333.39) |
| Sub 3-35 | m/z = 497.21($C_{38}H_{27}N$ = 497.64) | Sub 3-36 | m/z = 382.15($C_{28}H_{18}N_2$ = 382.47) |
| Sub 3-37 | m/z = 382.15($C_{28}H_{18}N_2$ = 382.47) | Sub 3-38 | m/z = 382.15($C_{28}H_{18}N_2$ = 382.47) |
| Sub 3-39 | m/z = 458.18($C_{34}H_{22}N_2$ = 458.56) | Sub 3-40 | m/z = 382.15($C_{28}H_{18}N_2$ = 382.47) |
| Sub 3-41 | m/z = 382.15($C_{28}H_{18}N_2$ = 382.47) | Sub 3-42 | m/z = 458.18($C_{34}H_{22}N_2$ = 458.56) |
| Sub 3-43 | m/z = 508.19($C_{38}H_{24}N_2$ = 508.62) | Sub 3-44 | m/z = 458.18($C_{34}H_{22}N_2$ = 458.56) |
| Sub 3-45 | m/z = 382.15($C_{28}H_{18}N_2$ = 382.47) | Sub 3-46 | m/z = 508.19($C_{38}H_{24}N_2$ = 508.62) |
| Sub 3-47 | m/z = 382.15($C_{28}H_{18}N_2$ = 382.47) | Sub 3-48 | m/z = 382.15($C_{28}H_{18}N_2$ = 382.47) |
| Sub 3-49 | m/z = 323.08($C_{22}H_{13}NS$ = 323.41) | Sub 3-50 | m/z = 399.11($C_{28}H_{17}NS$ = 399.51) |
| Sub 3-51 | m/z = 399.11($C_{28}H_{17}NS$ = 399.51) | Sub 3-52 | m/z = 399.11($C_{28}H_{17}NS$ = 399.51) |
| Sub 3-53 | m/z = 373.09($C_{26}H_{15}NS$ = 373.47) | Sub 3-54 | m/z = 373.09($C_{26}H_{15}NS$ = 373.47) |
| Sub 3-55 | m/z = 323.08($C_{22}H_{13}NS$ = 323.41) | Sub 3-56 | m/z = 323.08($C_{22}H_{13}NS$ = 323.41) |
| Sub 3-57 | m/z = 323.08($C_{22}H_{13}NS$ = 323.41) | Sub 3-58 | m/z = 323.08($C_{22}H_{13}NS$ = 323.41) |
| Sub 3-59 | m/z = 357.12($C_{26}H_{15}NO$ = 357.41) | Sub 3-60 | m/z = 307.1($C_{22}H_{13}NO$ = 307.35) |
| Sub 3-61 | m/z = 333.15($C_{25}H_{19}N$ = 333.43) | Sub 3-62 | m/z = 455.17($C_{35}H_{21}N$ = 455.56) |
| Sub 3-63 | m/z = 323.08($C_{22}H_{13}NS$ = 323.41) | Sub 3-64 | m/z = 382.15($C_{28}H_{18}N_2$ = 382.47) |
| Sub 3-65 | m/z = 445.18($C_{34}H_{23}N$ = 445.57) | Sub 3-66 | m/z = 485.21($C_{37}H_{27}N$ = 485.63) |
| Sub 3-67 | m/z = 409.18($C_{31}H_{23}N$ = 409.53) | Sub 3-68 | m/z = 383.13($C_{28}H_{17}NO$ = 383.45) |
| Sub 3-69 | m/z = 651.2($C_{48}H_{29}NS$ = 651.83) | Sub 3-70 | m/z = 497.19($C_{36}H_{23}N_3$ = 497.6) |
| Sub 3-71 | m/z = 408.16($C_{30}H_{20}N_2$ = 408.50) | | |

1. Synthesis Example of Sub 3

Sub 3 may be synthesized by the reaction route of the following Reaction Scheme 4-1, but are not limited thereto.

<Reaction Scheme 4-1>

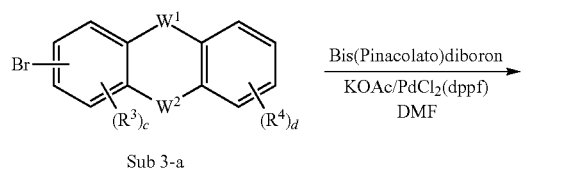

Sub 3-a

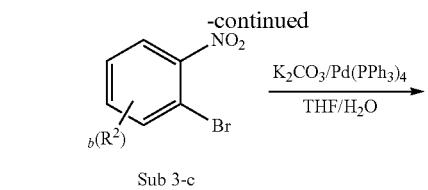

Sub 3-c

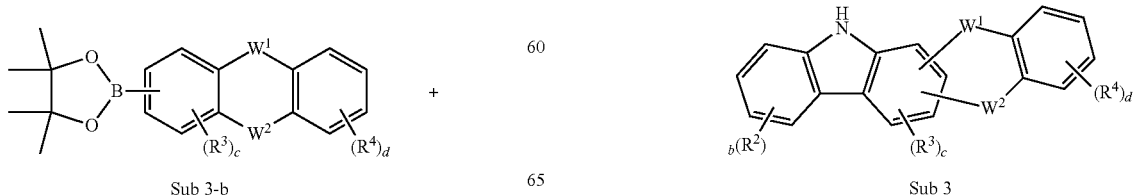

Sub 3-d

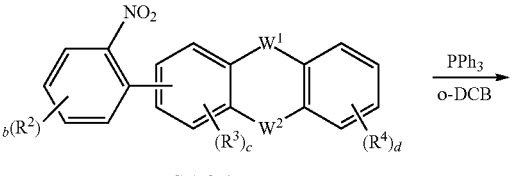

Sub 3

Synthesis Example of Sub 3-7

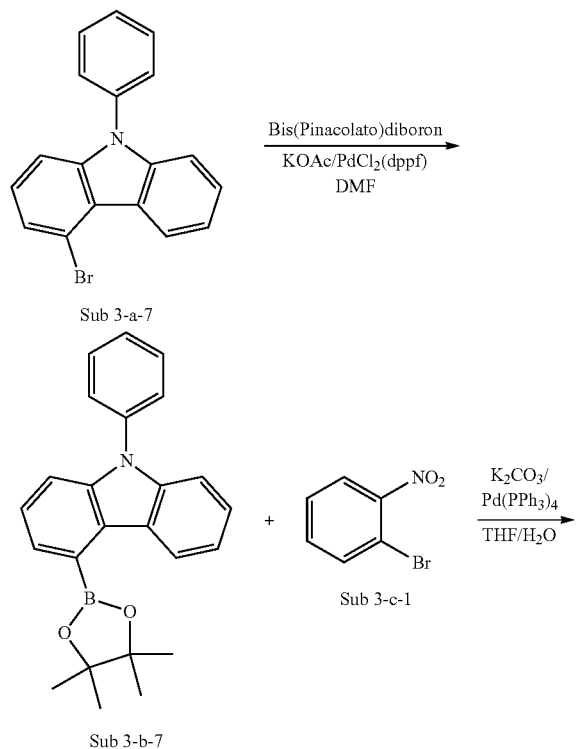

(1) Synthesis of Sub 3-b-7

Sub 3-a-7 (40 g, 124.1 mmol) was dissolved in DMF (600 ml), and bis(pinacolato)diboron (40.9 g, 161.4 mmol), KOAc (36.6 g, 372.4 mmol), PdCl$_2$(dppf) (4.5 g, 6.2 mmol) were added to the solution. Then, the mixture was stirred at 120° C. When the reaction was completed, DMF was removed through distillation and the reaction product was extracted with CH$_2$Cl$_2$ and water. An organic layer was dried over MgSO$_4$ and concentrated. Then, the concentrate was separated by a silica gel column and recrystallized to obtain 35.3 g (yield: 77%) of Sub 3-b-7.

(2) Synthesis of Sub 3-d-7.

Sub 3-b-7 (35 g, 94.8 mmol) was dissolved in THF (600 mL), and Sub 3-c-1 (23 g, 113.7 mmol), K$_2$CO$_3$ (39.3 g, 284.34 mmol), Pd(PPh$_3$)$_4$ (5.5 g, 4.74 mmol) and water (300 mL) were added to the solution. Then, the mixture was stirred at 80° C. When the reaction was completed, the reaction product was extracted with CH$_2$Cl$_2$ and water. An organic layer was dried over MgSO$_4$ and concentrated. Then, the concentrate was separated by a silica gel column and recrystallized to obtain 23.5 g (yield: 68%) of Sub 3-d-7.

(3) Synthesis of Sub 3-7

Sub 3-d-7 (15 g, 41.2 mmol) was dissolved in o-dichlorobenzene (450 mL), and triphenylphosphine (27 g, 102.9 mmol) was added to the solution. Then, the mixture was stirred at 200° C. When the reaction was completed, o-dichlorobenzene was removed through distillation and the reaction product was extracted with CH$_2$Cl$_2$ and water. An organic layer was dried over MgSO$_4$ and concentrated. Then, the concentrate was separated by a silica gel column and recrystallized to obtain Sub 3-7 (8.35 g, yield: 61%).

Synthesis Example of Sub 3-12

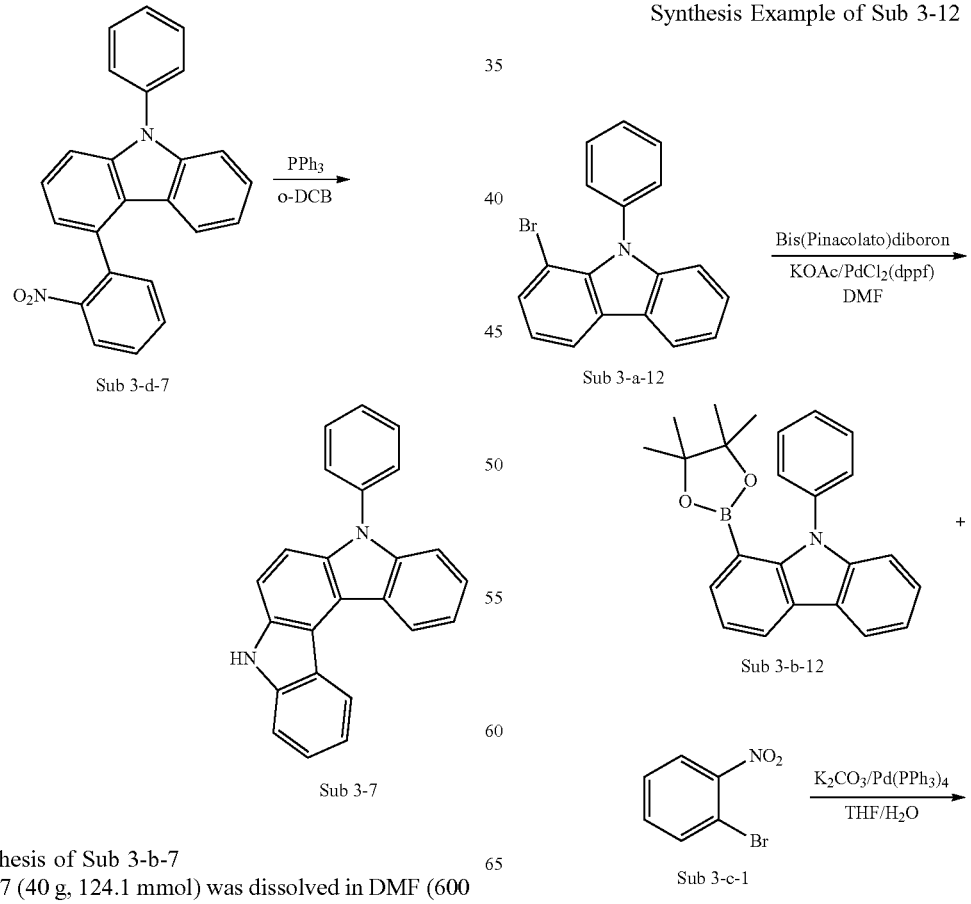

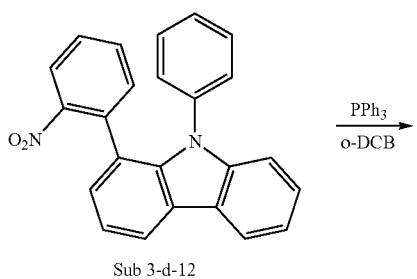

Sub 3-d-12

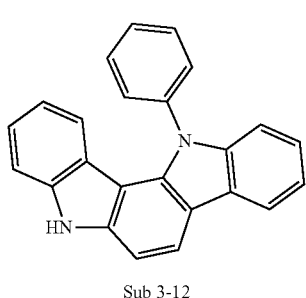

Sub 3-12

(1) Synthesis of Sub 3-b-12

Sub 3-a-12 (35 g, 108.6 mmol) was dissolved in DMF (540 mL)) and bis(pinacolato)diboron (35.9 g, 141.2 mmol), KOAc (32 g, 325.9 mmol), PdCl$_2$(dppf) (4 g, 5.43 mmol) were added to the solution. Then, the reaction was carried out in the same manner as in the synthesis method of Sub 3-b-7 to obtain 29.7 g (yield: 74%) of Sub 3-b-12.

(2) Synthesis of Sub 3-d-12

Sub 3-b-12 (25 g, 67.7 mmol) was dissolved in THF (420 mL) and Sub 3-c-1 (16.4 g, 81.2 mmol), K$_2$CO$_3$ (28.1 g, 203.1 mmol), Pd(PPh$_3$)$_4$ (3.9 g, 3.4 mmol) and water (210 mL) were added to the solution. Then, the reaction was carried out in the same manner as in the synthesis method of Sub 3-d-7 to obtain 17.5 g (yield: 71%) of Sub 3-d-12.

(3) Synthesis of Sub 3-12

Sub 3-d-12 (10 g, 27.44 mmol) was dissolved in o-dichlorobenzene (270 mL) and triphenylphosphine (18 g, 68.6 mmol) was added to the solution. Then, the reaction was carried out in the same manner as in the synthesis method of Sub 3-7 to obtain Sub 3-12 (5.4 g, yield: 59%).

Synthesis Example of Sub 3-36

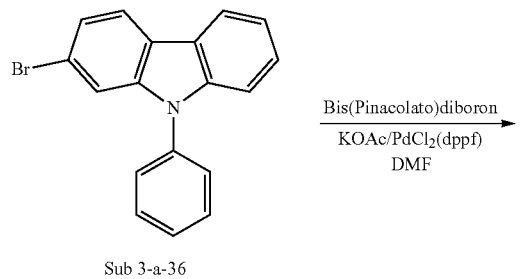

Sub 3-a-36

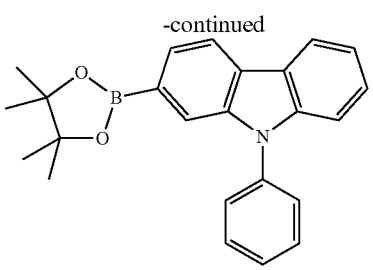

Sub 3-b-36

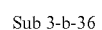

Sub 3-c-2

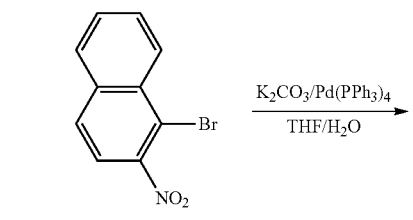

Sub 3-d-36

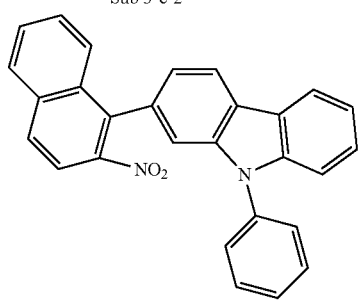

Sub 3-36

(1) Synthesis of Sub 3-b-36

Sub 3-a-36 (28 g, 86.9 mmol) was dissolved in DMF (430 mL) and bis(pinacolato)diboron (28.7 g, 112.9 mmol), KOAc (25.6 g, 260.7 mmol), PdCl$_2$(dppf) (3.2 g, 4.34 mmol) were added to the solution. Then, the reaction was carried out in the same manner as in the synthesis method of Sub 3-b-7 to obtain 26.3 g (yield: 82%) of Sub 3-b-36.

(2) Synthesis of Sub 3-d-36

Sub 3-b-36 (25 g, 67.7 mmol) was dissolved in THF (450 mL) and Sub 3-c-2 (16.4 g, 81.2 mmol), K$_2$CO$_3$ (28.1 g, 203.1 mmol), Pd(PPh$_3$)$_4$ (3.9 g, 3.4 mmol) and water (225 mL) were added to the solution. Then, the reaction was carried out in the same manner as in the synthesis method of Sub 3-d-7 to obtain 20.76 g (yield: 74%) of Sub 3-d-36.

(3) Synthesis of Sub 3-36

Sub 3-d-36 (15 g, 36.19 mmol) was dissolved in o-dichlorobenzene (350 mL) and triphenylphosphine (23.7 g, 90.5 mmol) was added to the solution. Then, the reaction was carried out in the same manner as in the synthesis method of Sub 3-7 to obtain Sub 3-36 (5.8 g, yield: 42%).

Synthesis Example of Sub 3-53

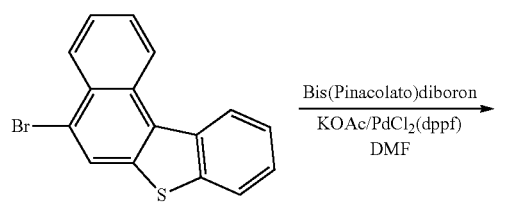
Sub 3-a-53

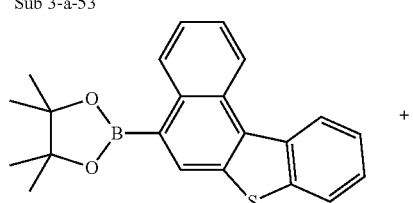
Sub 3-b-53

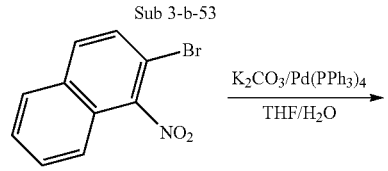
Sub 3-c-3

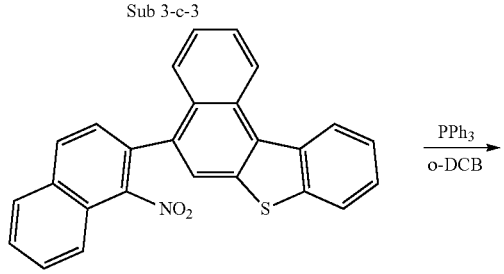
Sub 3-d-53

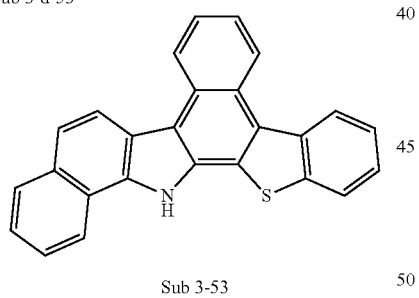
Sub 3-53

(1) Synthesis of Sub 3-b-53

Sub 3-a-53 (40 g, 127.71 mmol) was dissolved in DMF (600 mL) and bis(pinacolato)diboron (42.2 g, 166.02 mol), KOAc (37.6 g, 383.1 mmol), PdCl₂(dppf) (4.7 g, 6.4 mmol) were added to the solution. Then, the reaction was carried out in the same manner as in the synthesis method of Sub 3-b-7 to obtain 38.7 g (yield: 84%) of Sub 3-b-53.

(2) Synthesis of Sub 3-d-53

Sub 3-b-53 (35 g, 97.2 mmol) was dissolved in THF (600 mL) and Sub 3-c-3 (29.4 g, 116.6 mmol), K₂CO₃ (40.3 g, 291.4 mmol), Pd(PPh₃)₄ (5.6 g, 4.9 mmol) and water (300 mL) were added to the solution. Then, the reaction was carried out in the same manner as in the synthesis method of Sub 3-d-7 to obtain 30.7 g (yield: 78%) of Sub 3-d-53.

(3) Synthesis of Sub 3-53

Sub 3-d-53 (15 g, 37 mmol) was dissolved in o-dichlorobenzene (350 mL) and triphenylphosphine (24.3 g, 92.5 mmol) was added to the solution. Then, the reaction was carried out in the same manner as in the synthesis method of Sub 3-7 to obtain Sub 3-53 (8.7 g, yield: 63%).

Synthesis Example of Sub 3-71

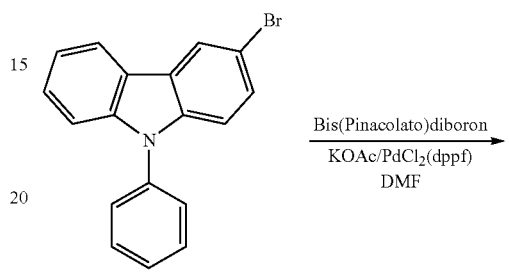
Sub 3-a-71

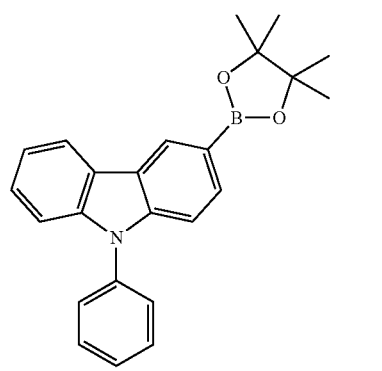
Sub 3-b-71

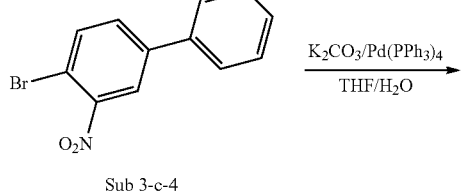
Sub 3-c-4

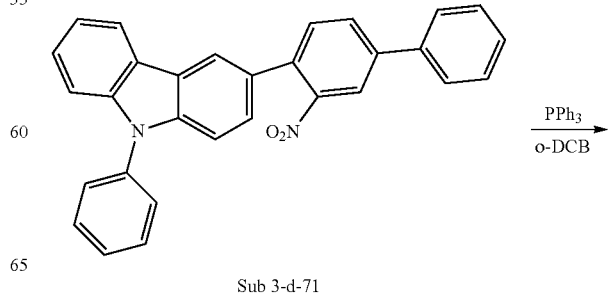
Sub 3-d-71

Sub 3-71

(1) Synthesis of Sub 3-b-71

Sub 3-a-79 (28 g, 86.9 mmol) was dissolved in DMF (430 mL) and bis(pinacolato)diboron (28.7 g, 113 mol), KOAc (25.6 g, 260.7 mmol), PdCl$_2$(dppf) (3.2 g, 4.3 mmol) were added to the solution. Then, the reaction was carried out in the same manner as in the synthesis method of Sub 3-b-7 to obtain 28.2 g (yield: 88%) of Sub 3-b-71.

(2) Synthesis of Sub 3-d-71

Sub 3-b-2 (25 g, 67.7 mmol) was dissolved in THF (450 mL) and Sub 3-c-1 (22.6 g, 81.2 mmol), K$_2$CO$_3$ (28.1 g, 203.1 mmol), Pd(PPh$_3$)$_4$ (3.9 g, 3.4 mmol) and water (220 mL) were added to the solution. Then, the reaction was carried out in the same manner as in the synthesis method of Sub 3-d-7 to obtain 21.8 g (yield: 73%) of Sub 3-d-71.

(3) Synthesis of Sub 3-71

Sub 3-d-79 (20 g, 45.4 mmol) was dissolved in o-dichlorobenzene (420 mL) and triphenylphosphine (29.8 g, 113.5 mmol) was added to the solution. Then, the reaction was carried out in the same manner as in the synthesis method of Sub 3-7 to obtain Sub 3-71 (7.8 g, yield: 42%).

2. Exemplary Compounds of Sub 4

The compounds belonging to Sub 4 of Reaction Scheme 4 are as follows, but are not limited thereto.

Sub 4-1

Sub 4-2

Sub 4-3

Sub 4-4

Sub 4-5

Sub 4-6

Sub 4-7

Sub 4-8

Sub 4-9

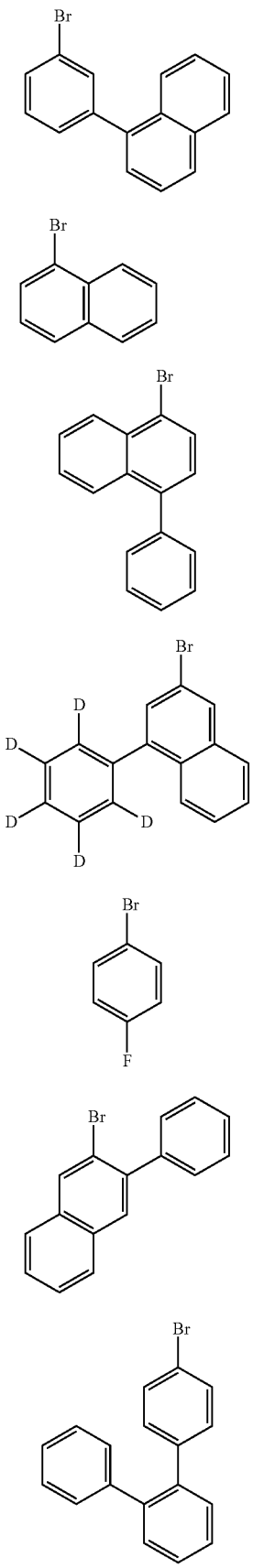
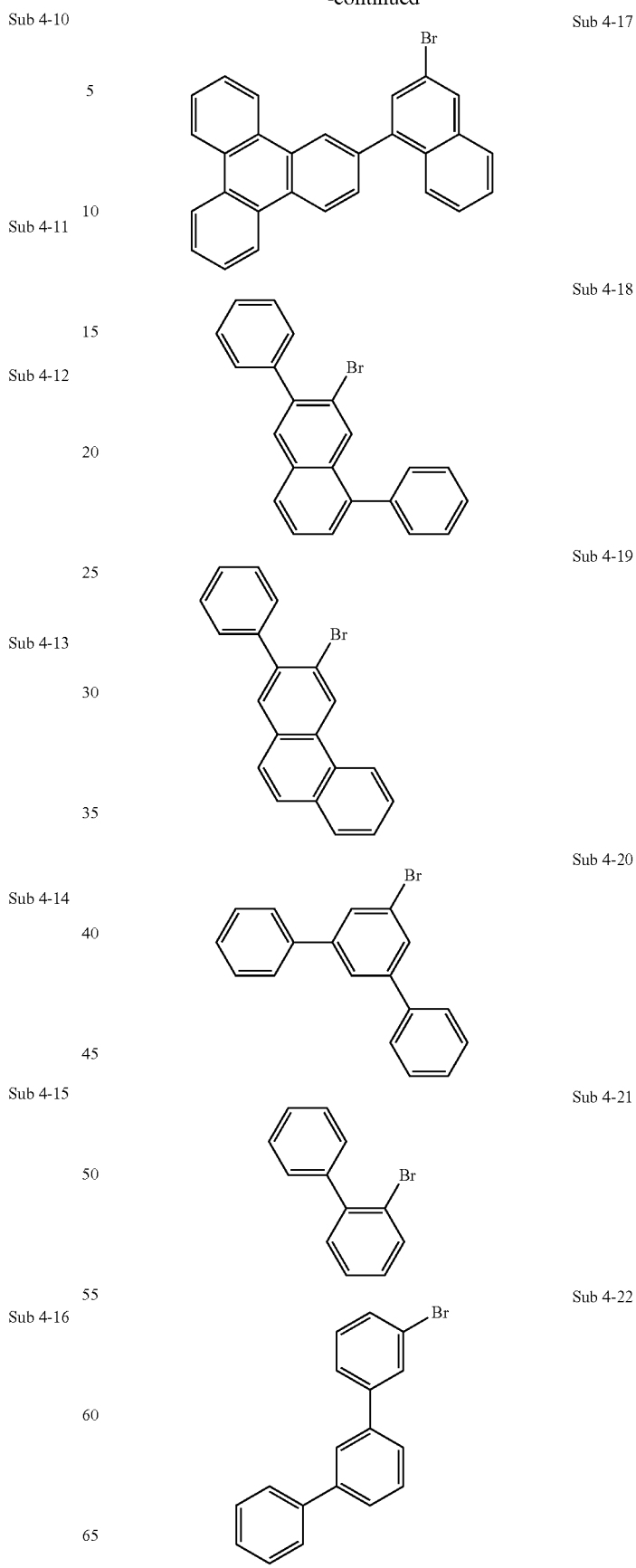
Sub 4-10
Sub 4-11
Sub 4-12
Sub 4-13
Sub 4-14
Sub 4-15
Sub 4-16
Sub 4-17
Sub 4-18
Sub 4-19
Sub 4-20
Sub 4-21
Sub 4-22

-continued
| | |
|---|---|
| Sub 4-23 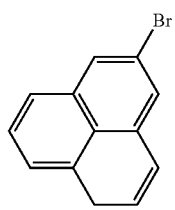 | Sub 4-32 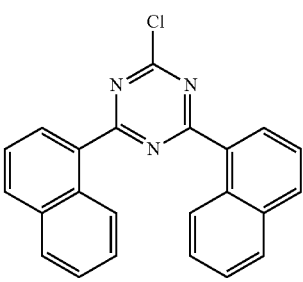 |
| Sub 4-24 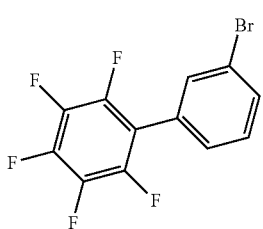 | Sub 4-33 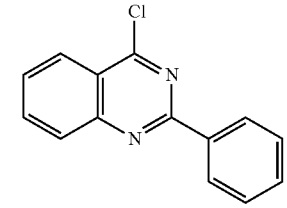 |
| Sub 4-25 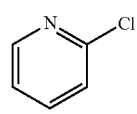 | Sub 4-34 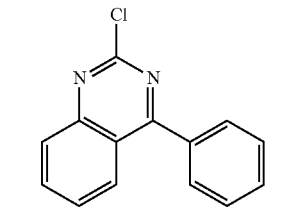 |
| Sub 4-26 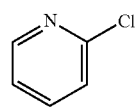 | Sub 4-35 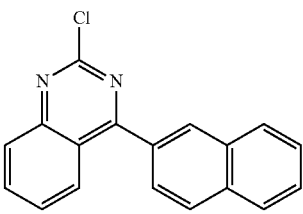 |
| Sub 4-27 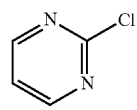 | Sub 4-36 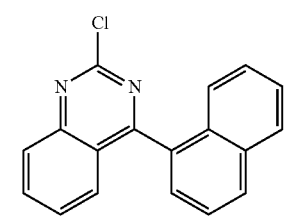 |
| Sub 4-28 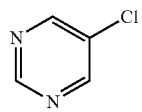 | Sub 4-37 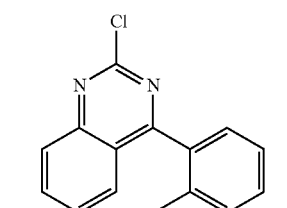 |
| Sub 4-29 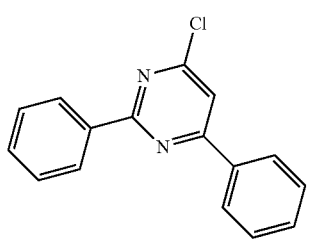 | Sub 4-38 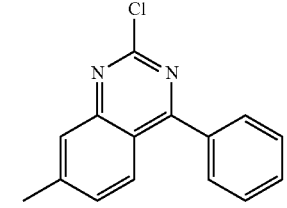 |
| Sub 4-30 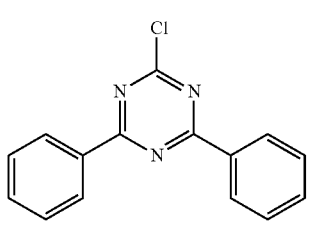 | |
| Sub 4-31 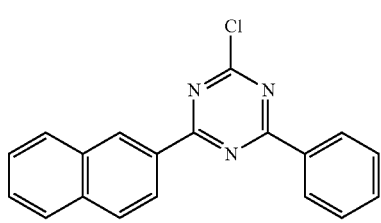 | |

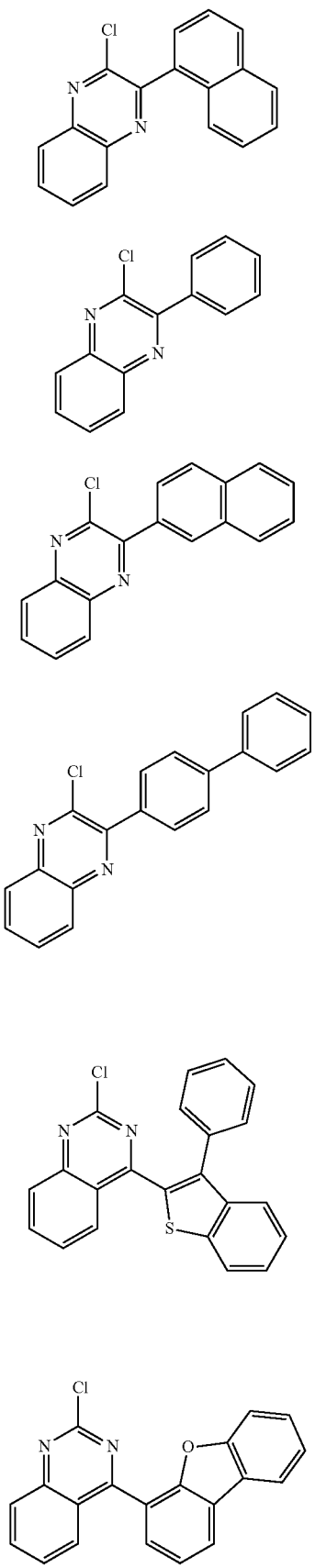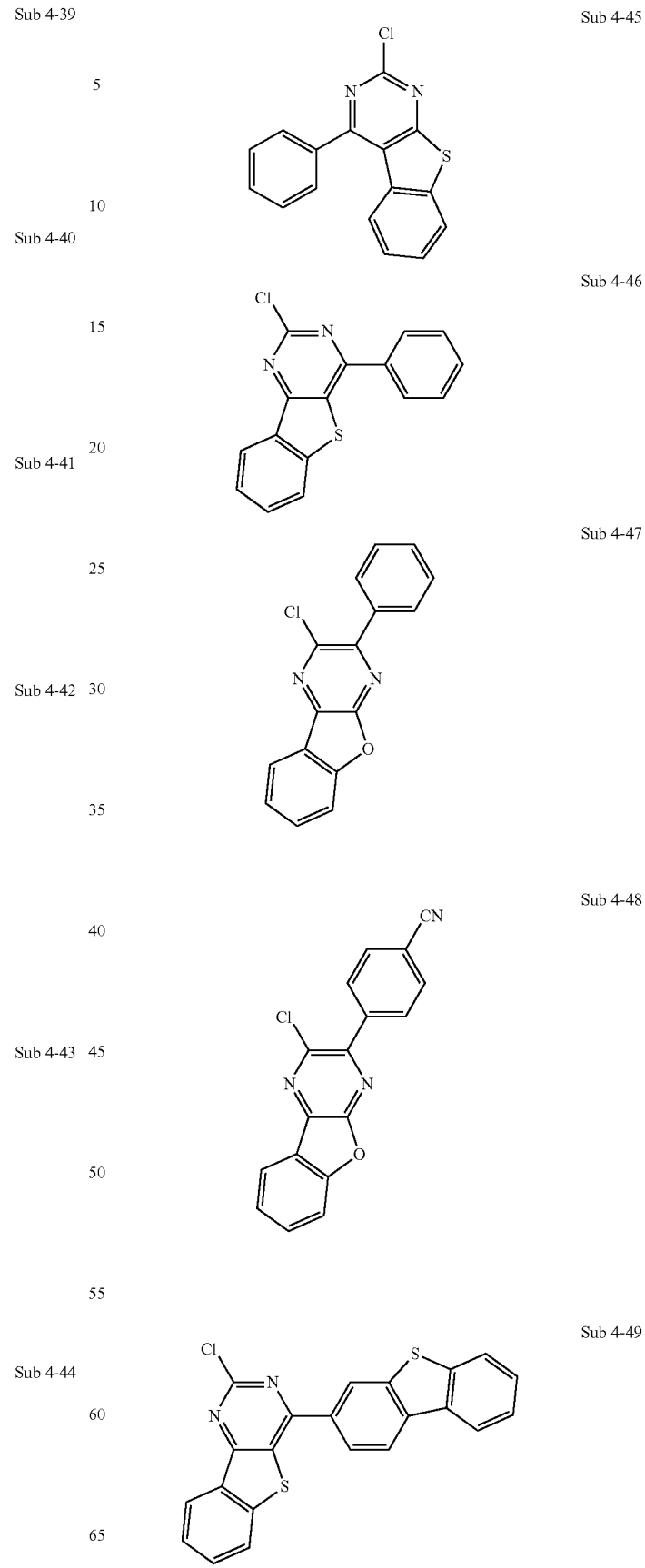
Sub 4-39
Sub 4-40
Sub 4-41
Sub 4-42
Sub 4-43
Sub 4-44
Sub 4-45
Sub 4-46
Sub 4-47
Sub 4-48
Sub 4-49

-continued
Sub 4-50
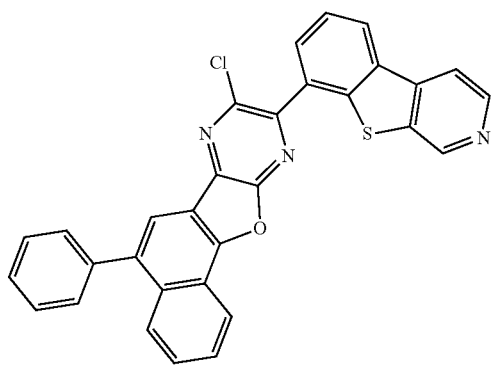
Sub 4-51
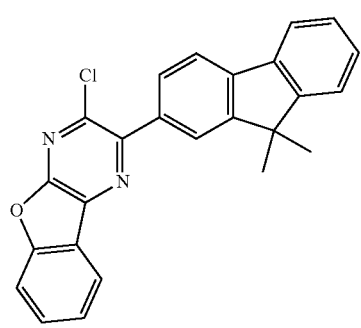
Sub 4-52
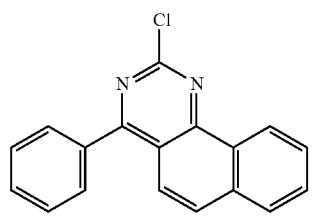
Sub 4-53
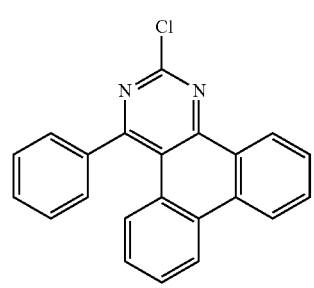
Sub 4-54
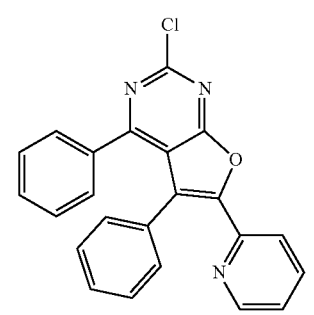
-continued
Sub 4-55
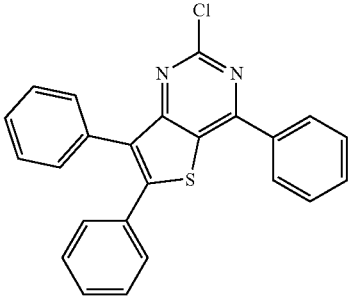
Sub 4-56
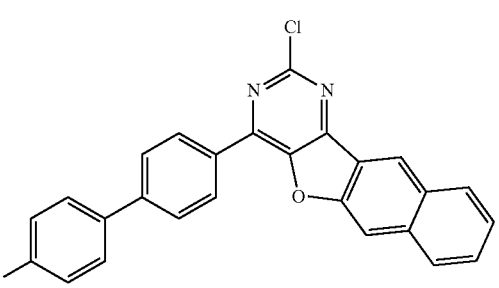
Sub 4-57
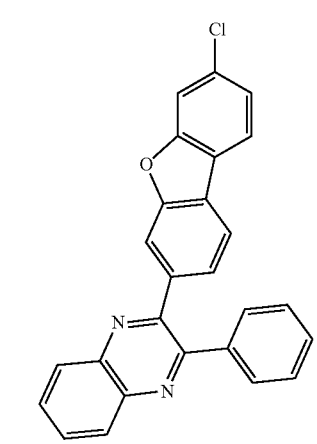
Sub 4-58
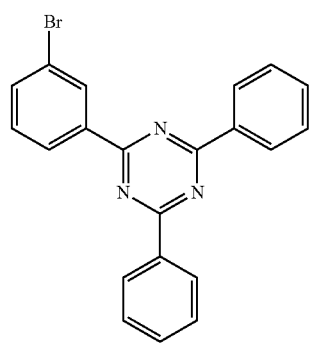

253
-continued
Sub 4-59
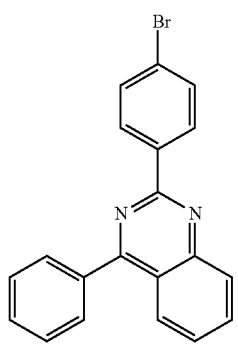
Sub 4-60
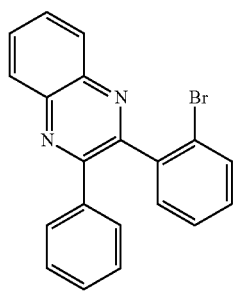
Sub 4-61
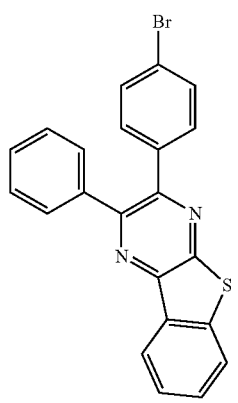
Sub 4-62
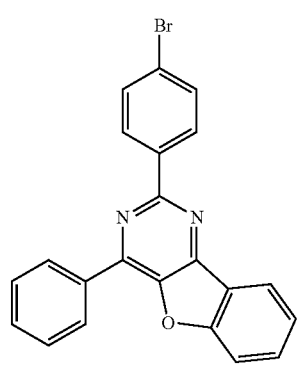
254
-continued
Sub 4-63
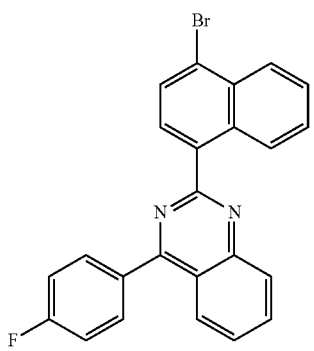
Sub 4-64
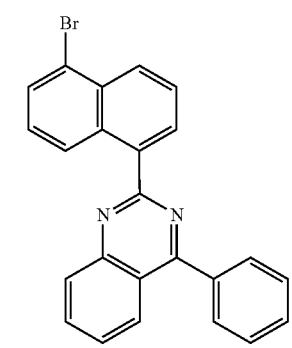
Sub 4-65
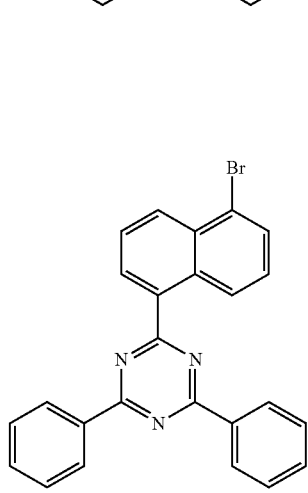
Sub 4-66
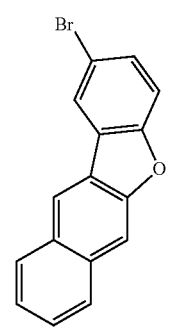

-continued
Sub 4-67
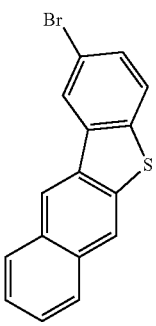
Sub 4-68
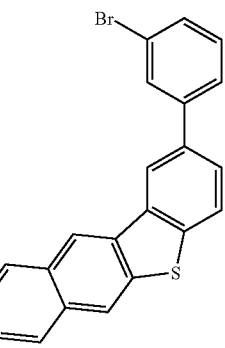
Sub 4-69
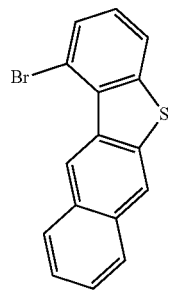
Sub 4-70
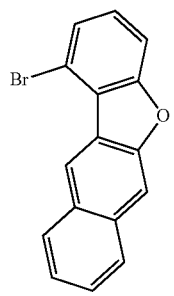
Sub 4-71
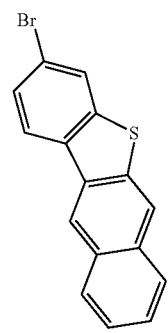
-continued
Sub 4-72
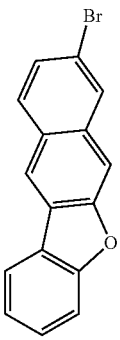
Sub 4-73
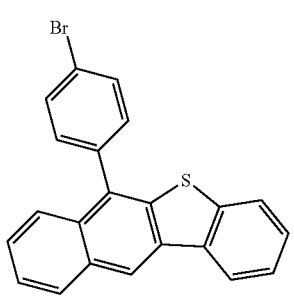
Sub 4-74
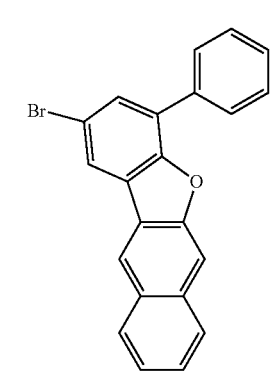
Sub 4-75
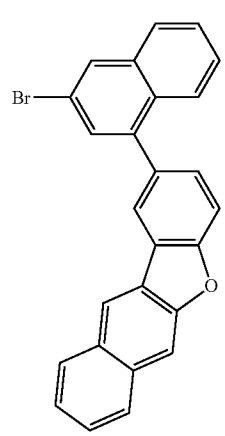

Sub 4-76
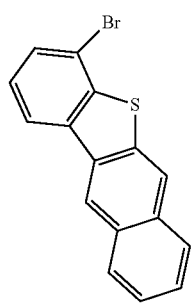
Sub 4-77
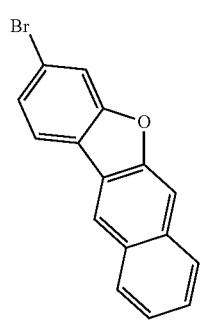
Sub 4-78
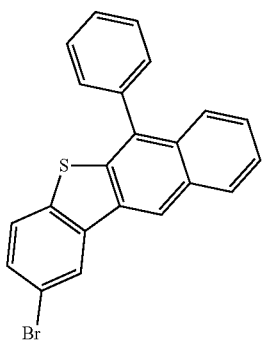
Sub 4-79
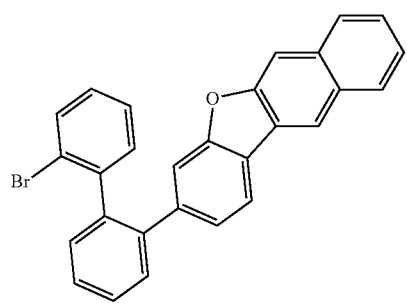
Sub 4-80
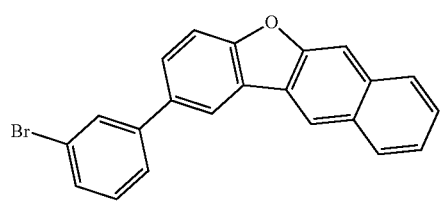
Sub 4-81
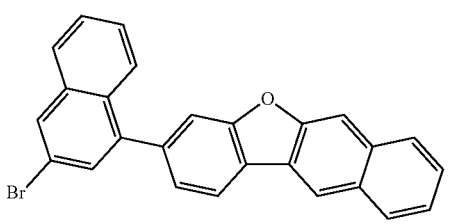
Sub 4-82
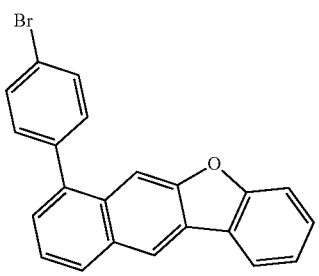
Sub 4-83
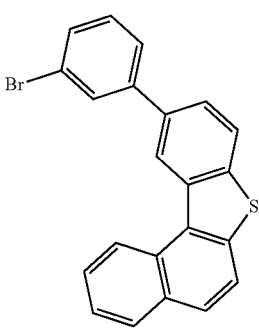

-continued

Sub 4-84

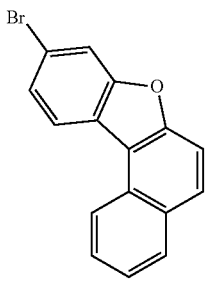

Sub 4-85

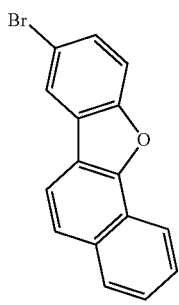

-continued

Sub 4-86

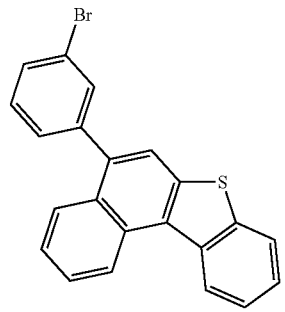

Sub 4-87

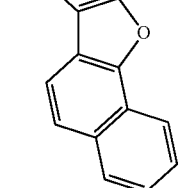

The ED-MS values of the compounds belonging to Sub 4 are shown in Table 5 below.

TABLE 5

| Compound | FD-MS | Compound | FD-MS |
| --- | --- | --- | --- |
| Sub 4-1 | m/z = 155.96($C_6H_5Br$ = 157.01) | Sub 4-2 | m/z = 231.99($C_{12}H_9Br$ = 233.11) |
| Sub 4-3 | m/z = 205.97($C_{10}H_7Br$ = 207.07) | Sub 4-4 | m/z = 231.99($C_{12}H_9Br$ = 233.11) |
| Sub 4-5 | m/z = 282($C_{16}H_{11}Br$ = 283.17) | Sub 4-6 | m/z = 255.99($C_{14}H_9Br$ = 257.13) |
| Sub 4-7 | m/z = 332.02($C_{20}H_{13}Br$ = 333.23) | Sub 4-8 | m/z = 237.02($C_{12}F_{14}D_5Br$ = 238.14) |
| Sub 4-9 | m/z = 308.02($C_{18}H_{13}Br$ = 309.21) | Sub 4-10 | m/z = 282($C_{16}H_{11}Br$ = 283.17) |
| Sub 4-11 | m/z = 205.97($C_{10}H_7Br$ = 207.07) | Sub 4-12 | m/z = 282($C_{16}H_{11}Br$ = 283.17) |
| Sub 4-13 | m/z = 287.04($C_{16}H_6D_5Br$ = 288.2) | Sub 4-14 | m/z = 173.95($C_6H_4BrF$ = 175) |
| Sub 4-15 | m/z = 282($C_{16}H_{11}Br$ = 283.17) | Sub 4-16 | m/z = 308.02($C_{18}H_{13}Br$ = 309.21) |
| Sub 4-17 | m/z = 432.05($C_{28}H_{17}Br$ = 433.35) | Sub 4-18 | m/z = 358.04($C_{22}H_{15}Br$ = 359.27) |
| Sub 4-19 | m/z = 332.02($C_{20}H_{13}Br$ = 333.23) | Sub 4-20 | m/z = 308.02($C_{18}H_{13}Br$ = 309.21) |
| Sub 4-21 | m/z = 231.99($C_{12}H_9Br$ = 233.11) | Sub 4-22 | m/z = 308.02($C_{18}H_{13}Br$ = 309.21) |
| Sub 4-23 | m/z = 243.99($C_{13}H_9Br$ = 245.12) | Sub 4-24 | m/z = 321.94($C_{12}H_4BrF_5$ = 323.06) |
| Sub 4-25 | m/z = 113($C_5H_4ClN$ = 113.54) | Sub 4-26 | m/z = 113($C_5H_4ClN$ = 113.54) |
| Sub 4-27 | m/z = 114($C_4H_3ClN_2$ = 114.53) | Sub 4-28 | m/z = 114($C_4H_3ClN_2$ = 114.53) |
| Sub 4-29 | m/z = 266.06($C_{16}H_{11}ClN_2$ = 266.73) | Sub 4-30 | m/z = 267.06($C_{15}H_{10}ClN_3$ = 267.72) |
| Sub 4-31 | m/z = 317.07($C_{19}H_{12}ClN3$ = 317.78) | Sub 4-32 | m/z = 367.09($C_{23}H_{14}ClN_3$ = 367.84) |
| Sub 4-33 | m/z = 240.05($C_{14}H_9ClN_2$ = 240.69) | Sub 4-34 | m/z = 240.05($C_{14}H_9ClN_2$ = 240.69) |
| Sub 4-35 | m/z = 290.06($C_{18}H_{11}ClN_2$ = 290.75) | Sub 4-36 | m/z = 290.06($C_{18}H_{11}ClN_2$ = 290.75) |
| Sub 4-37 | m/z = 290.06($C_{18}H_{11}ClN_2$ = 290.75) | Sub 4-38 | m/z = 254.06($C_{15}H_{11}ClN_2$ = 254.72) |
| Sub 4-39 | m/z = 290.06($C_{18}H_{11}ClN_2$ = 290.75) | Sub 4-40 | m/z = 240.05($C_{14}H_9ClN_2$ = 240.69) |
| Sub 4-41 | m/z = 290.06($C_{18}H_{11}ClN_2$ = 290.75) | Sub 4-42 | m/z = 316.08($C_{20}H_{13}ClN_2$ = 316.79) |
| Sub 4-43 | m/z = 372.05($C_{22}H_{13}ClN_2S$ = 372.87) | Sub 4-44 | m/z = 330.06($C_{20}H_{11}ClN_2O$ = 330.77) |
| Sub 4-45 | m/z = 296.02($C_{16}H_9ClN_2S$ = 296.77) | Sub 4-46 | m/z = 296.02($C_{16}H_9ClN_2S$ = 296.77) |
| Sub 4-47 | m/z = 280.04($C_{16}H_9ClN_2O$ = 280.71) | Sub 4-48 | m/z = 305.04($C_{17}H_8ClN_3O$ = 305.72) |
| Sub 4-49 | m/z = 402.01($C_{22}H_{11}ClN_2S_2$ = 402.91) | Sub 4-50 | m/z = 513.07($C_{31}H_{16}ClN_3OS$ = 514) |
| Sub 4-51 | m/z = 396.1($C_{25}H_{17}ClN_2O$ = 396.87) | Sub 4-52 | m/z = 290.06($C_{18}H_{11}ClN_2$ = 290.75) |
| Sub 4-53 | m/z = 340.08($C_{22}H_{13}ClN_2$ = 340.81) | Sub 4-54 | m/z = 383.08($C_{23}H_{14}ClN_3O$ = 383.84) |
| Sub 4-55 | m/z = 398.06($C_{24}H_{15}ClN_2S$ = 398.91) | Sub 4-56 | m/z = 431.08($C_{27}H_{14}ClN_3O$ = 431.88) |
| Sub 4-57 | m/z = 406.09($C_{26}H_{15}ClN_2O$ = 406.87) | Sub 4-58 | m/z = 387.04($C_{21}H_{14}BrN_3$ = 388.27) |
| Sub 4-59 | m/z = 360.03($C_{20}H_{13}BrN_2$ = 361.24) | Sub 4-60 | m/z = 360.03($C_{20}H_{13}BrN_2$ = 361.24) |
| Sub 4-61 | m/z = 416($C_{22}H_{13}BrN_2S$ = 417.32) | Sub 4-62 | m/z = 400.02($C_{22}H_{13}BrN_2O$ = 401.26) |
| Sub 4-63 | m/z = 428.03($C_{24}H_{14}BrFN_2$ = 429.29) | Sub 4-64 | m/z = 410.04($C_{24}H_{15}BrN_2$ = 411.3) |
| Sub 4-65 | m/z = 437.05($C_{25}H_{16}BrN_3$ = 438.33) | Sub 4-66 | m/z = 295.98($C_{16}H_9BrO$ = 297.15) |
| Sub 4-67 | m/z = 311.96($C_{16}H_9BrS$ = 313.21) | Sub 4-68 | m/z = 387.99($C_{22}H_{13}BrS$ = 389.31) |
| Sub 4-74 | m/z = 372.01($C_{22}H_{13}BrO$ = 373.25) | Sub 4-75 | m/z = 422.03($C_{26}H_{15}BrO$ = 423.31) |

3. Synthesis Example of Final Compound

Synthesis Example of 2-36

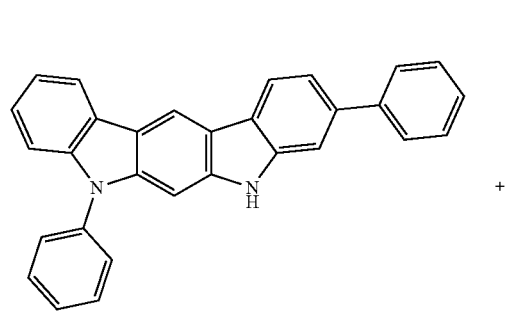

Sub 3-71

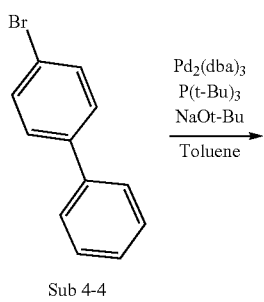

Sub 4-4

$\xrightarrow{\text{Pd}_2(\text{dba})_3 \;\; \text{P(t-Bu)}_3 \;\; \text{NaOt-Bu}}{\text{Toluene}}$

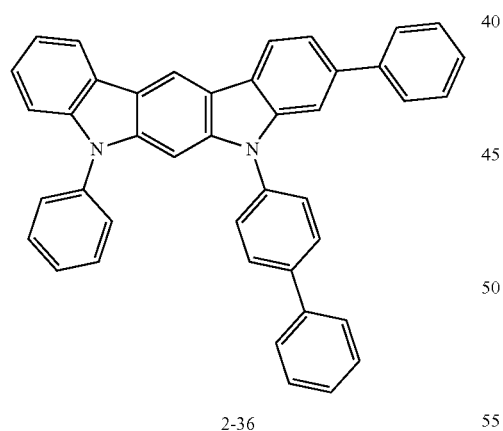

2-36

Sub 3-71 (65 g, 159.12 mmol) was dissolved in toluene (800 mL), and Sub 4-4 (37.09 g, 159.12 mmol), Pd$_2$(dba)$_3$ (4.37 g, 4.77 mmol), P(t-Bu)$_3$ (3.22 g, 15.91 mmol), NaOt-Bu (30.59 g, 318.24 mmol) were added to the solution. Then, the mixture was stirred at 120° C. When the reaction was completed, the reaction product was extracted with CH$_2$Cl$_2$ and water. An organic layer was dried over MgSO$_4$ and concentrated. Then, the concentrate was separated by a silica gel column and recrystallized to obtain 74.94 g (yield: 84%) of the product 2-36.

Synthesis Example of 2-105

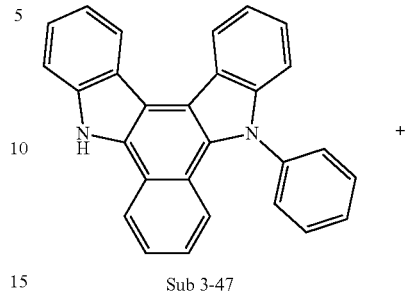

Sub 3-47

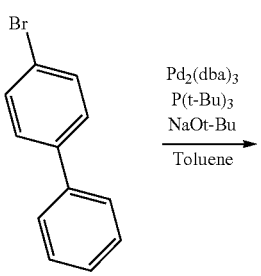

Sub 4-4

$\xrightarrow{\text{Pd}_2(\text{dba})_3 \;\; \text{P(t-Bu)}_3 \;\; \text{NaOt-Bu}}{\text{Toluene}}$

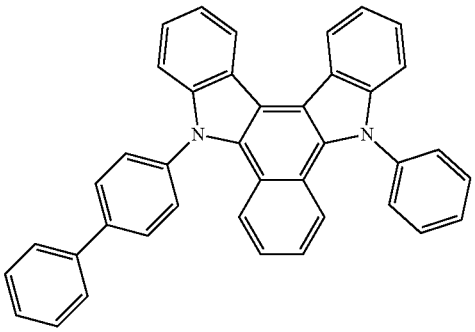

2-105

Sub 3-47 (65 g, 169.95 mmol) was dissolved in toluene (850 mL) and Sub 4-4 (39.62 g, 169.95 mmol), Pd$_2$(dba)$_3$ (4.67 g, 5.10 mmol), P(t-Bu)$_3$ (3.44 g, 16.99 mmol), NaOt-Bu (32.67 g, 339.90 mmol) were added to the solution. Then, the reaction was carried out in the same manner as in the synthesis method of 2-36 to obtain 74.51 g (yield: 82%) of the product 2-105.

Synthesis Example of 2-106

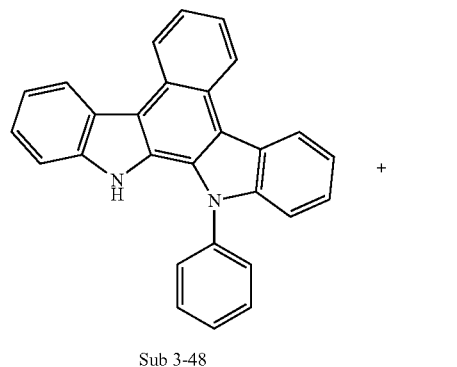

Sub 3-48

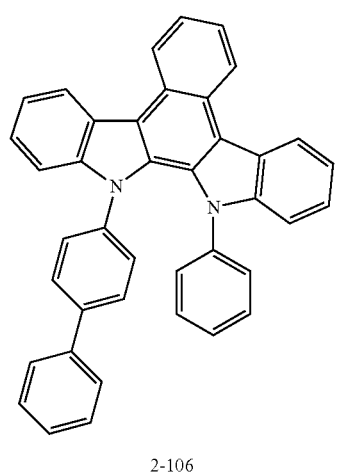

2-106

Sub 3-48 (65 g, 169.95 mmol) was dissolved in toluene (850 mL) and Sub 4-4 (39.62 g, 169.95 mmol), Pd$_2$(dba)$_3$ (4.67 g, 5.10 mmol), P(t-Bu)$_3$ (3.44 g, 16.99 mmol), NaOt-Bu (32.67 g, 339.90 mmol) were added to the solution. Then, the reaction was carried out in the same manner as in the synthesis method of 2-36 to obtain 68.15 g (yield: 75%) of the product 2-106.

Synthesis Example of 2-110

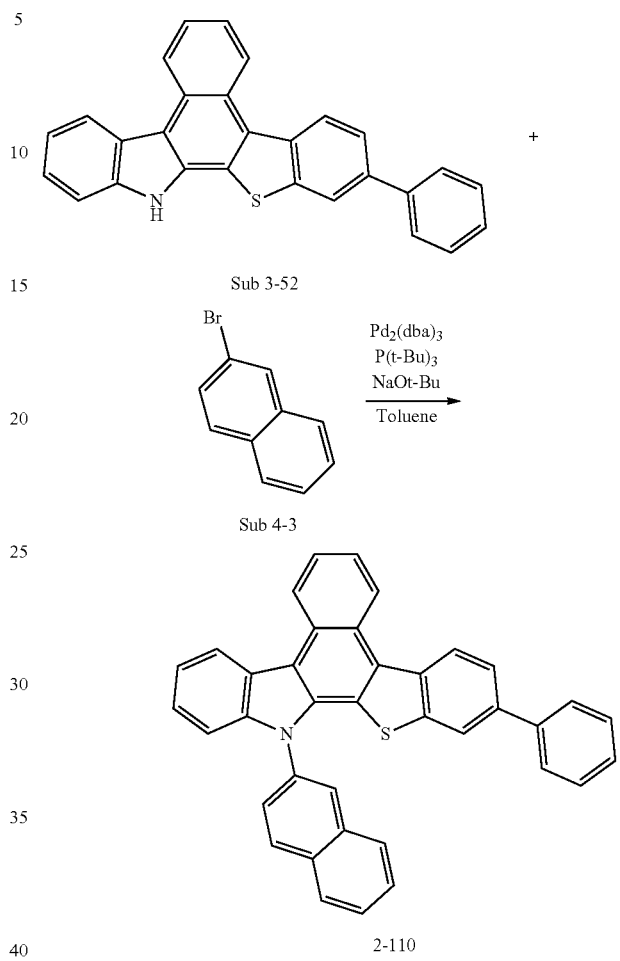

Sub 3-52 (65 g, 162.70 mmol) was dissolved in toluene (800 mL) and Sub 4-3 (33.69 g, 162.70 mmol), Pd$_2$(dba)$_3$ (4.47 g, 4.88 mmol), P(t-Bu)$_3$ (3.29 g, 16.27 mmol), NaOt-Bu (31.27 g, 325.40 mmol) were added to the solution. Then, the reaction was carried out in the same manner as in the synthesis method of 2-36 to obtain 69.28 g (yield: 81%) of the product 2-110.

Synthesis Example of 2-112

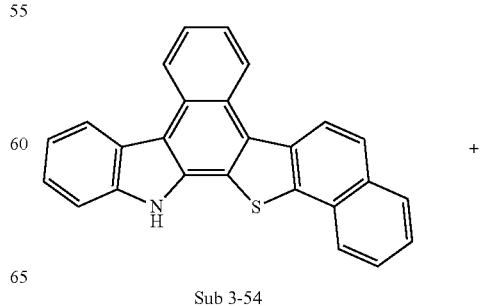

Sub 3-54

265
-continued

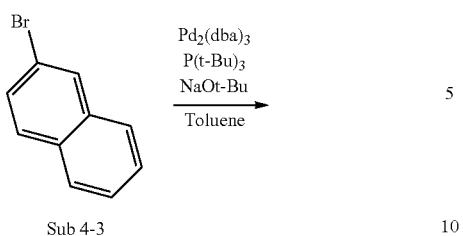

Sub 4-3

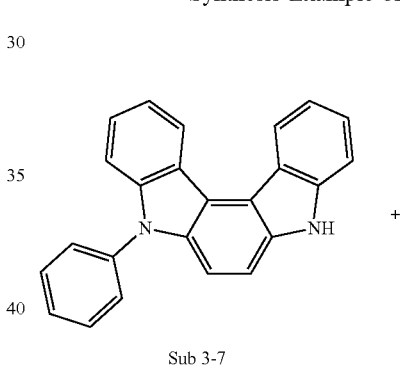

2-112

Sub 3-54 (65 g, 174.04 mmol) was dissolved in toluene (850 mL) and Sub 4-3 (36.04 g, 174.04 mmol), Pd₂(dba)₃ (4.78 g, 5.22 mmol), P(t-Bu)₃ (3.52 g, 17.40 mmol), NaOt-Bu (33.45 g, 348.09 mmol) were added to the solution. Then, the reaction was carried out in the same manner as in the synthesis method of 2-36 to obtain 68.70 g (yield: 79%) of the product 2-112.

Synthesis Example of 2-113

266
-continued

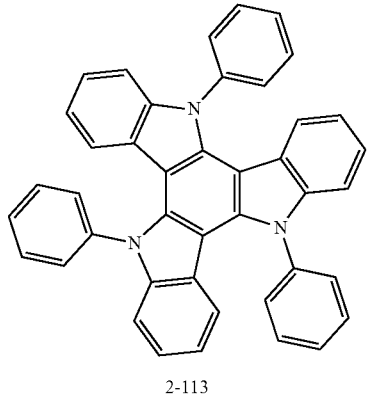

2-113

Sub 3-70 (65 g, 130.63 mmol) was dissolved in toluene (650 mL) and Sub 4-1 (20.51 g, 130.63 mmol), Pd₂(dba)₃ (3.59 g, 3.92 mmol), P(t-Bu)₃ (2.64 g, 13.06 mmol), NaOt-Bu (25.11 g, 261.25 mmol) were added to the solution. Then, the reaction was carried out in the same manner as in the synthesis method of 2-36 to obtain 56.95 g (yield: 76%) of the product 2-113.

Synthesis Example of 2-129

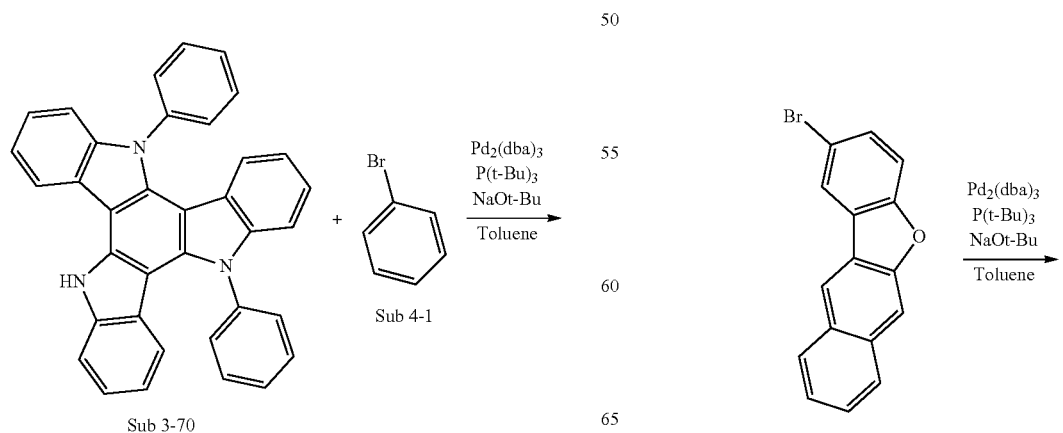

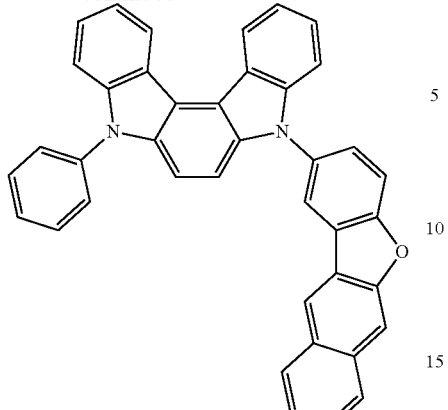

2-129

Sub 3-7 (65 g, 195.54 mmol) was dissolved in toluene (950 mL) and Sub 4-66 (58.11 g, 195.54 mmol), Pd$_2$(dba)$_3$ (5.37 g, 5.87 mmol), P(t-Bu)$_3$ (39.56 g, 195.54 mmol), NaOt-Bu (37.59 g, 391.08 mmol) were added to the solution. Then, the reaction was carried out in the same manner as in the synthesis method of 2-36 to obtain 85.83 g (yield: 80%) of the product 2-129.

The FD-MS values of the compounds 2-1 to 2-166 of the present invention synthesized by the above synthesis method are shown in Table 6 below.

TABLE 6

| Compound | FD-MS | Compound | FD-MS |
|---|---|---|---|
| 2-1 | m/z = 408.16($C_{30}H_{20}N_2$ = 408.5) | 2-2 | m/z = 435.17($C_{31}H_{21}N_3$ = 435.53) |
| 2-3 | m/z = 410.15($C_{28}H_{18}N_4$ = 410.48) | 2-4 | m/z = 536.2($C_{38}H_{24}N_4$ = 536.64) |
| 2-5 | m/z = 586.22($C_{42}H_{26}N_4$ = 586.7) | 2-6 | m/z = 536.2($C_{38}H_{24}N_4$ = 536.64) |
| 2-7 | m/z = 563.21($C_{39}H_{25}N_5$ = 563.66) | 2-8 | m/z = 592.17($C_{40}H_{24}N_4S$ = 592.72) |
| 2-9 | m/z = 491.15($C_{33}H_{21}N_3S$ = 491.61) | 2-10 | m/z = 527.15($C_{36}H_{21}N_3S$ = 527.65) |
| 2-11 | m/z = 533.1($C_{34}H_{19}N_3S_2$ = 533.67) | 2-12 | m/z = 580.17($C_{39}H_{24}N_4S$ = 580.71) |
| 2-13 | m/z = 504.14($C_{33}H_{20}N_4S$ = 504.61) | 2-14 | m/z = 477.13($C_{32}H_{19}N_3S$ = 477.59) |
| 2-15 | m/z = 477.13($C_{32}H_{19}N_3S$ = 477.59) | 2-16 | m/z = 425.12($C_{30}H_{19}NS$ = 425.55) |
| 2-17 | m/z = 734.18($C_{49}H_{26}N_4O_2S$ = 734.83) | 2-18 | m/z = 577.18($C_{40}H_{23}N_3O_2$ = 577.64) |
| 2-19 | m/z = 517.12($C_{34}H_{19}N_3OS$ = 517.61) | 2-20 | m/z = 606.18($C_{42}H_{26}N_2OS$ = 606.74) |
| 2-21 | m/z = 488.16($C_{33}H_{20}N_4O$ = 488.55) | 2-22 | m/z = 459.16($C_{34}H_{21}NO$ = 459.55) |
| 2-23 | m/z = 517.12($C_{34}H_{19}N_3OS$ = 517.61) | 2-24 | m/z = 461.15($C_{32}H_{19}N_3O$ = 461.52) |
| 2-25 | m/z = 552.2($C_{38}H_{24}N_4O$ = 552.64) | 2-26 | m/z = 435.2($C_{33}H_{25}N$ = 435.57) |
| 2-27 | m/z = 527.2($C_{37}H_{25}N_3O$ = 527.63) | 2-28 | m/z = 513.22($C_{37}H_{27}N_3$ = 513.64) |
| 2-29 | m/z = 534.21($C_{40}H_{28}N_2$ = 534.66) | 2-30 | m/z = 485.19($C_{35}H_{23}N_3$ = 485.59) |
| 2-31 | m/z = 586.22($C_{42}H_{26}N_4$ = 586.7) | 2-32 | m/z = 536.2($C_{38}H_{24}N_4$ = 536.64) |
| 2-33 | m/z = 592.17($C_{40}H_{24}N_4S$ = 592.72) | 2-34 | m/z = 586.22($C_{42}H_{26}N_4$ = 586.7) |
| 2-35 | m/z = 563.21($C_{39}H_{25}N_5$ = 563.66) | 2-36 | m/z = 560.23($C_{42}H_{28}N_2$ = 560.7) |
| 2-37 | m/z = 527.15($C_{36}H_{21}N_3S$ = 527.65) | 2-38 | m/z = 577.19($C_{42}H_{27}NS$ = 577.75) |
| 2-39 | m/z = 553.16($C_{38}H_{23}N_3S$ = 553.68) | 2-40 | m/z = 639.09($C_{40}H_{21}N_3S_3$ = 639.81) |
| 2-41 | m/z = 527.15($C_{36}H_{21}N_3S$ = 527.65) | 2-42 | m/z = 527.15($C_{36}H_{21}N_3S$ = 527.65) |
| 2-43 | m/z = 504.14($C_{33}H_{20}N_4S$ = 504.61) | 2-44 | m/z = 351.08($C_{22}H_{13}N_3S$ = 351.43) |
| 2-45 | m/z = 511.17($C_{38}H_{21}N_3O$ = 511.58) | 2-46 | m/z = 613.22($C_{44}H_{27}N_3O$ = 613.72) |
| 2-47 | m/z = 587.2($C_{42}H_{25}N_3O$ = 587.68) | 2-48 | m/z = 538.18($C_{37}H_{22}N_4O$ = 538.61) |
| 2-49 | m/z = 517.12($C_{34}H_{19}N_3OS$ = 517.61) | 2-50 | m/z = 511.17($C_{36}H_{21}N_3O$ = 511.58) |
| 2-51 | m/z = 501.15($C_{34}H_{19}N_3O_2$ = 501.55) | 2-52 | m/z = 461.15($C_{32}H_{19}N_3O$ = 461.52) |
| 2-53 | m/z = 459.2($C_{35}H_{25}N$ = 459.59) | 2-54 | m/z = 649.22($C_{44}H_{31}N_3OS$ = 649.81) |
| 2-55 | m/z = 630.24($C_{44}H_{30}N_4O$ = 630.75) | 2-56 | m/z = 645.22($C_{45}H_{31}N_3S$ = 645.82) |
| 2-57 | m/z = 692.26($C_{49}H_{32}N_4O$ = 692.82) | 2-58 | m/z = 680.24($C_{48}H_{29}FN_4$ = 680.79) |
| 2-59 | m/z = 626.21($C_{44}H_{28}N_4O$ = 626.72) | 2-60 | m/z = 484.19($C_{36}H_{24}N_2$ = 484.6) |
| 2-61 | m/z = 586.22($C_{42}H_{28}N_4$ = 586.7) | 2-62 | m/z = 536.2($C_{36}H_{24}N_4$ = 536.64) |
| 2-63 | m/z = 590.18($C_{42}H_{26}N_2S$ = 590.74) | 2-64 | m/z = 484.19($C_{36}H_{24}N_2$ = 484.6) |
| 2-65 | m/z = 477.13($C_{32}H_{19}N_3S$ = 477.59) | 2-66 | m/z = 525.16($C_{38}H_{23}NS$ = 525.67) |
| 2-67 | m/z = 533.1($C_{34}H_{19}N_3S_2$ = 533.67) | 2-68 | m/z = 517.12($C_{34}H_{19}N_3OS$ = 517.61) |
| 2-69 | m/z = 414.18($C_{30}H_{14}D_5NO$ = 414.52) | 2-70 | m/z = 511.17($C_{36}H_{21}N_3O$ = 511.58) |
| 2-71 | m/z = 537.18($C_{38}H_{23}N_3O$ = 537.62) | 2-72 | m/z = 561.21($C_{42}H_{27}NO$ = 561.68) |
| 2-73 | m/z = 653.25($C_{47}H_{31}N_3O$ = 653.79) | 2-74 | m/z = 485.21($C_{37}H_{27}N$ = 485.63) |
| 2-75 | m/z = 586.22($C_{42}H_{26}N_4$ = 586.7) | 2-76 | m/z = 563.21($C_{39}H_{25}N_5$ = 563.66) |
| 2-77 | m/z = 586.22($C_{42}H_{26}N_4$ = 586.7) | 2-78 | m/z = 663.24($C_{47}H_{29}N_5$ = 663.78) |
| 2-79 | m/z = 551.17($C_{40}H_{25}NS$ = 551.71) | 2-80 | m/z = 464.19($C_{34}H_{16}D_5NO$ = 464.58) |
| 2-81 | m/z = 652.19($C_{45}H_{24}N_4O_2$ = 652.71) | 2-82 | m/z = 593.16($C_{40}H_{23}N_3OS$ = 593.7) |
| 2-83 | m/z = 609.25($C_{47}H_{31}N$ = 609.77) | 2-84 | m/z = 624.16($C_{40}H_{21}F_5N_2$ = 624.61) |
| 2-85 | m/z = 577.19($C_{42}H_{27}NS$ = 577.75) | 2-86 | m/z = 611.22($C_{46}H_{29}NO$ = 611.74) |
| 2-87 | m/z = 634.24($C_{45}H_{31}FN_2O$ = 634.75) | 2-88 | m/z = 635.26($C_{49}H_{33}N$ = 635.81) |
| 2-89 | m/z = 561.25($C_{43}H_{31}N$ = 561.73) | 2-90 | m/z = 560.23($C_{42}H_{28}N_2$ = 560.7) |
| 2-91 | m/z = 601.19($C_{44}H_{27}NS$ = 601.77) | 2-92 | m/z = 575.13($C_{36}H_{18}F_5NO$ = 575.54) |
| 2-93 | m/z = 623.26($C_{48}H_{33}N$ = 623.8) | 2-94 | m/z = 458.18($C_{34}H_{22}N_2$ = 458.56) |
| 2-95 | m/z = 534.21($C_{40}H_{26}N_2$ = 534.66) | 2-96 | m/z = 584.23($C_{44}H_{28}N_2$ = 584.72) |
| 2-97 | m/z = 534.21($C_{40}H_{26}N_2$ = 534.66) | 2-98 | m/z = 610.24($C_{46}H_{30}N_2$ = 610.76) |
| 2-99 | m/z = 534.21($C_{40}H_{26}N_2$ = 534.66) | 2-100 | m/z = 660.26($C_{50}H_{32}N_2$ = 660.82) |
| 2-101 | m/z = 584.23($C_{44}H_{28}N_2$ = 584.72) | 2-102 | m/z = 634.24($C_{48}H_{30}N_2$ = 634.78) |

TABLE 6-continued

| Compound | FD-MS | Compound | FD-MS |
|---|---|---|---|
| 2-103 | m/z = 584.23($C_{44}H_{28}N_2$ = 584.72) | 2-104 | m/z = 660.26($C_{50}H_{32}N_2$ = 660.82) |
| 2-105 | m/z = 534.21($C_{40}H_{26}N_2$ = 534.66) | 2-106 | m/z = 534.21($C_{40}H_{26}N_2$ = 534.66) |
| 2-107 | m/z = 525.16($C_{38}H_{23}NS$ = 525.67) | 2-108 | m/z = 551.17($C_{40}H_{25}NS$ = 551.71) |
| 2-109 | m/z = 601.19($C_{44}H_{27}NS$ = 601.77) | 2-110 | m/z = 525.16($C_{38}H_{23}NS$ = 525.67) |
| 2-111 | m/z = 499.14($C_{36}H_{21}NS$ = 499.63) | 2-112 | m/z = 499.14($C_{36}H_{21}NS$ = 499.63) |
| 2-113 | m/z = 573.22($C_{42}H_{27}N_3$ = 573.7) | 2-114 | m/z = 565.15($C_{40}H_{23}NOS$ = 565.69) |
| 2-115 | m/z = 555.11($C_{38}H_{21}NS_2$ = 555.71) | 2-116 | m/z = 627.18($C_{44}H_{25}N_3S$ = 627.77) |
| 2-117 | m/z = 487.14($C_{35}H_{21}NS$ = 487.62) | 2-118 | m/z = 727.23($C_{54}H_{33}NS$ = 727.93) |
| 2-119 | m/z = 535.19($C_{40}H_{25}NO$ = 535.65) | 2-120 | m/z = 509.18($C_{38}H_{23}NO$ = 509.61) |
| 2-121 | m/z = 535.19($C_{40}H_{25}NO$ = 535.65) | 2-122 | m/z = 485.21($C_{37}H_{27}N$ = 485.63) |
| 2-123 | m/z = 561.25($C_{43}H_{31}N$ = 561.73) | 2-124 | m/z = 603.18($C_{42}H_{25}N_3S$ = 603.74) |
| 2-125 | m/z = 683.26($C_{53}H_{33}N$ = 683.85) | 2-126 | m/z = 521.21($C_{40}H_{27}N$ = 521.66) |
| 2-127 | m/z = 561.25($C_{43}H_{31}N$ = 561.73) | 2-128 | m/z = 739.27($C_{53}H_{33}N_5$ = 739.88) |
| 2-129 | m/z = 548.19($C_{40}H_{24}N_2O$ = 548.65) | 2-130 | m/z = 598.2($C_{44}H_{26}N_2O$ = 598.71) |
| 2-131 | m/z = 564.17($C_{40}H_{24}N_2S$ = 564.71) | 2-132 | m/z = 640.2($C_{46}H_{28}N_2S$ = 640.8) |
| 2-133 | m/z = 489.12($C_{34}H_{19}NOS$ = 489.59) | 2-134 | m/z = 505.1($C_{34}H_{19}NS_2$ = 505.65) |
| 2-135 | m/z = 598.2($C_{44}H_{26}N_2O$ = 598.71) | 2-136 | m/z = 564.17($C_{40}H_{24}N_2S$ = 564.71) |
| 2-137 | m/z = 548.19($C_{40}H_{24}N_2O$ = 548.65) | 2-138 | m/z = 581.13($C_{40}H_{23}NS_2$ = 581.75) |
| 2-139 | m/z = 539.13($C_{38}H_{21}NOS$ = 539.65) | 2-140 | m/z = 615.17($C_{44}H_{25}NOS$ = 615.75) |
| 2-141 | m/z = 489.12($C_{34}H_{19}NOS$ = 489.59) | 2-142 | m/z = 489.12($C_{34}H_{19}NOS$ = 489.59) |
| 2-143 | m/z = 589.15($C_{42}H_{23}NOS$ = 589.71) | 2-144 | m/z = 605.13($C_{42}H_{23}NS_2$ = 605.77) |
| 2-145 | m/z = 664.2($C_{48}H_{28}N_2S$ = 664.83) | 2-146 | m/z = 539.13($C_{38}H_{21}NOS$ = 539.65) |
| 2-147 | m/z = 548.19($C_{40}H_{24}N_2O$ = 548.65) | 2-148 | m/z = 774.27($C_{58}H_{34}N_2O$ = 774.92) |
| 2-149 | m/z = 690.21($C_{50}H_{30}N_2S$ = 690.86) | 2-150 | m/z = 651.26($C_{49}H_{33}NO$ = 651.81) |
| 2-151 | m/z = 548.19($C_{40}H_{24}N_2O$ = 548.65) | 2-152 | m/z = 548.19($C_{40}H_{24}N_2O$ = 548.65) |
| 2-153 | m/z = 640.2($C_{46}H_{28}N_2S$ = 640.8) | 2-154 | m/z = 505.1($C_{34}H_{19}NS_2$ = 505.65) |
| 2-155 | m/z = 549.17($C_{40}H_{23}NO_2$ = 549.63) | 2-156 | m/z = 489.12($C_{34}H_{19}NOS$ = 489.59) |
| 2-157 | m/z = 598.2($C_{44}H_{26}N_2O$ = 598.71) | 2-158 | m/z = 665.18($C_{48}H_{27}NOS$ = 665.81) |
| 2-159 | m/z = 624.22($C_{46}H_{28}N_2O$ = 624.74) | 2-160 | m/z = 724.25($C_{54}H_{32}N_2O$ = 724.86) |
| 2-161 | m/z = 640.2($C_{46}H_{28}N_2S$ = 640.8) | 2-162 | m/z = 598.2($C_{44}H_{26}N_2O$ = 598.71) |
| 2-163 | m/z = 691.2($C_{50}H_{29}NOS$ = 691.85) | 2-164 | m/z = 589.15($C_{42}H_{23}NOS$ = 589.71) |
| 2-165 | m/z = 548.19($C_{40}H_{24}N_2O$ = 548.65) | 2-166 | m/z = 640.2($C_{46}H_{29}N_2S$ = 640.8) |

Manufacturing and Evaluation of Organic Electric Element

[Example 1] to [Example 15] Red OLED (Phosphorescent Host)

On the ITO layer (anode) formed on the glass substrate, 4,4',4"-tris[2-naphthyl(phenyl)amino]triphenylamine (hereinafter, abbreviated as "2-TNATA") was vacuum deposited to a thickness of 60 nm to form a hole injection layer. Then, N,N'-bis(1-naphthalenyl)-N,N'-bis-phenyl-(1,1'-biphenyl)-4,4'-diamine (hereinafter abbreviated as "NPB") was vacuum deposited to a thickness of 55 nm to form a hole transport layer.

Next, a light emitting layer having a thickness of 30 nm was deposited on the hole transport layer by using compound shown in Table 7 below among the compounds represented by Formula 2-K of the present invention as a host material and bis-(1-phenylisoquinolyl)iridium(III) acetylacetonate (hereinafter, abbreviated as "(piq)₂Ir(acac)") as a dopant material, wherein the weight ratio of the host and the dopant was 95:5.

Next, (1,1'-bisphenyl-4-olato)bis(2-methyl-8-quinolinolato)aluminum (hereinafter, "BAlq") was vacuum-deposited to a thickness of 5 nm on the light emitting layer to form a hole blocking layer, and bis(10-hydroxybenzo[h]quinolinato)beryllium (hereinafter, "BeBq₂") was vacuum-deposited to a thickness of 45 nm on the hole blocking layer to form a an electron transport layer. Thereafter, LiF was deposited to a thickness of 0.2 nm to form an electron injection layer on the electron transport layer, and then Al was deposited to a thickness of 150 nm to form a cathode on the electron injection layer. In this way, OLED was manufactured.

[Comparative Example 1] to [Comparative Example 3]

The organic electroluminescent element was manufactured in the same manner as described in Example 1 except that one of the following Comparative Compounds 1 to 3, instead of compound of the present invention, was used as host material of the light emitting layer.

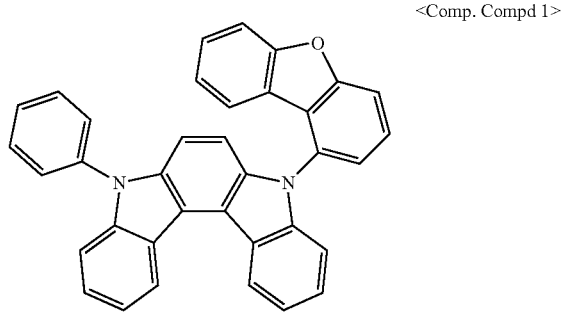

<Comp. Compd 1>

-continued

<Comp. Compd 2>

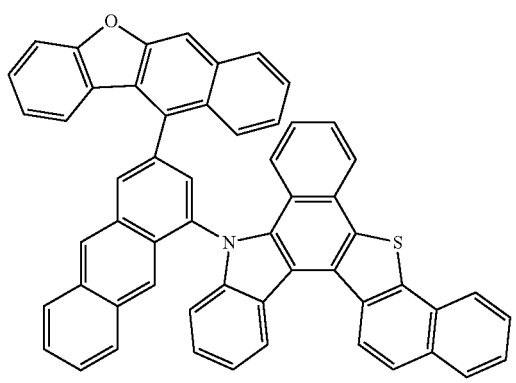

<Comp. Compd 3>

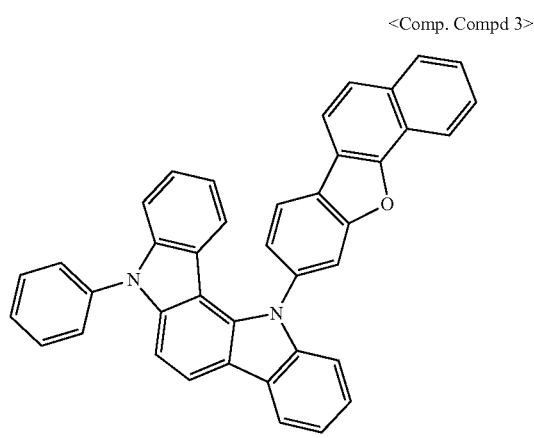

Electroluminescence characteristics were measured with a PR-650 (Photo research) by applying a forward bias DC voltage to the OLEDs prepared in Examples 1 to 15 of the present invention and Comparative Examples 1 to 3. T(95) life time was measured using a life time measuring apparatus manufactured by Mc science Inc. at reference brightness of 2500 cd/in$^2$. The measurement results are shown in the table 7 below.

From Table 7 above, it can be seen that the electric element using the compound represented by Formula 2-K of the present invention as phosphorescent host material of the light emitting layer has a lower driving voltage and significantly improved efficiency and lifespan compared to the case where Comparative Compound is used.

Comparative Compounds 1 to 3 and the compounds used in Examples of the present invention are similar in that they have a heterocyclic group as a basic skeleton as an N-substituent of a polycyclic compound. However, in the compound of the present invention, naphtho[2,3-b]benzofuran is bonded to (substituted for) N of the carbazole moiety of the polycyclic core being 5 or more rings via L (single bond or $C_1$-$C_{12}$ arylen group), whereas Comparative Compound 1 is different from the present invention in that one of the N-substituents of the N—N 5-ring core is dibenzofuran. Comparative Compound 2 differs from the present invention in that naphtho[2,3-b]benzofuran is bonded to the N-substituent group of the N—S 7-ring core via an anthracene ($C_{14}$) linkage, and Comparative Compound 3 is different from the present invention in that one of the N-substituents of the N—N 5-ring core is naphtho[1,2-b]benzofuran.

Comparing Comparative Examples 1 and 3, the element characteristics are better when the Comparative Compound 3 comprising 2,3-naphthobenzofuran is used as host than when Comparative Compound 1 in which dibenzofuran is introduced as an N-substituent to the N—N 5-ring core is used.

Comparing Comparative Examples 2 and 3, they are identical in that a naphthobenzofuran is introduced as an N-substituent to the core of the polycyclic ring. However, there is a difference in that Comparative Compound 2 is an N—S 7-membered ring core, and 2,3-naphthobenzofuran as an N-substituent is introduced via anthracene, whereas Comparative compound 3 is an N—N 5-membered ring core and 1,2-naphthobenzofuran is directly bonded to the core. The driving voltage was lowered and the efficiency was significantly improved, but the lifespan was slightly reduced in the case of Comparative Example 3 using Comparative Compound 3, compared to Comparative Example 2.

In the case of Comparative Compound 2, the physical properties of the compound change due to the hetero element characteristics included in the N—S polycyclic compound core, and thus, it seems that the lifespan of the

TABLE 7

| | Compound | Voltage (V) | Current Density (mA/cm$^2$) | Brightness (cd/m$^2$) | Efficiency (cd/A) | Lifetime T(95) | CIE X | Y |
|---|---|---|---|---|---|---|---|---|
| comp. Ex (1) | Comp. compd 1 | 6.1 | 17.1 | 2500 | 14.6 | 98.4 | 0.66 | 0.33 |
| comp. Ex (2) | Comp. compd 2 | 6.2 | 21.7 | 2500 | 11.5 | 102.6 | 0.66 | 0.33 |
| comp. Ex (3) | Comp. compd 3 | 5.9 | 13.9 | 2500 | 18.0 | 107.9 | 0.66 | 0.34 |
| Ex. (1) | Com. 2-129 | 5.4 | 9.8 | 2500 | 25.5 | 131.8 | 0.66 | 0.34 |
| Ex. (2) | Com. 2-130 | 5.5 | 9.9 | 2500 | 25.3 | 130.3 | 0.66 | 0.34 |
| Ex. (3) | Com. 2-131 | 5.5 | 9.7 | 2500 | 25.8 | 129.9 | 0.67 | 0.33 |
| Ex. (4) | Com. 2-137 | 5.4 | 10.4 | 2500 | 24.1 | 125.2 | 0.67 | 0.33 |
| Ex. (5) | Com. 2-143 | 5.6 | 11.1 | 2500 | 22.5 | 139.1 | 0.66 | 0.33 |
| Ex. (6) | Com. 2-147 | 5.4 | 10.2 | 2500 | 24.4 | 127.6 | 0.66 | 0.34 |
| Ex. (7) | Com. 2-148 | 5.5 | 10.5 | 2500 | 23.8 | 124.4 | 0.66 | 0.34 |
| Ex. (8) | Com. 2-149 | 5.5 | 10.0 | 2500 | 25.0 | 126.2 | 0.66 | 0.33 |
| Ex. (9) | Com. 2-152 | 5.7 | 10.8 | 2500 | 23.2 | 123.2 | 0.66 | 0.34 |
| Ex. (10) | Com. 2-153 | 5.5 | 10.1 | 2500 | 24.8 | 130.6 | 0.66 | 0.34 |
| Ex. (11) | Com. 2-154 | 5.0 | 11.4 | 2500 | 22.0 | 140.7 | 0.66 | 0.34 |
| Ex. (12) | Com. 2-157 | 5.4 | 9.8 | 2500 | 25.4 | 131.4 | 0.67 | 0.33 |
| Ex. (13) | Com. 2-158 | 5.6 | 11.6 | 2500 | 21.5 | 135.8 | 0.67 | 0.33 |
| Ex. (14) | Com. 2-159 | 5.5 | 10.5 | 2500 | 23.7 | 126.5 | 0.66 | 0.33 |
| Ex. (15) | Com. 2-160 | 5.7 | 10.3 | 2500 | 24.2 | 125.6 | 0.66 | 0.34 | element is slightly improved. However, anthracene being a bulky linking group is introduced between the core and the N-substituent, and thus, it seems that the driving voltage and efficiency of the element are lowered.

On the other hand, in the compound represented by Formula 2-K of the present invention, 2,3-naphthobenzofuran or 2,3-naphthobenzothiophene is introduced as an N-substituent of the polycyclic heterocyclic core, and when a linking group is introduced between the polycyclic heterocyclic core and 2,3-naphthobenzofuran or 2,3-naphthobenzothiophene, the linking group is restricted to a $C_6$-$C_{12}$ arylene group (especially, the compound used in Examples is $C_6$). When the compound represented by Formula 2-K of the present invention was used as host (Examples 1 to 15), the element characteristics were significantly improved compared to Comparative Examples 1 to 3.

Referring to Table 8, this will be explained. It can be seen that Comparative Compound 1 has the highest T1 value, Comparative Compound 2 has the smallest T1 value, and Comparative Compound 3 has a slightly smaller T1 value than Comparative Compound 1, and T1 values of compounds 2-147, 2-152 and 2-158 of the present invention are located in the middle range of these comparative compounds (error range of the median value of the minimum and maximum T1 values of the comparative compounds 1 to 3±0.3).

TABLE 8

| | Comp. compd 1 | Comp. compd 2 | Comp. compd 3 | 2-147 | 2-152 | 2-158 |
|---|---|---|---|---|---|---|
| T1 | 2.76 | 1.76 | 2.67 | 2.41 | 2.38 | 2.39 |

The difference in the T1 values in Table 8 suggests that the physical properties of the compound may be remarkably changed depending on the degree of molecular bending and the type of the linking group. It seems that the element characteristics are improved when the compound represented by Formula 2-K of the present invention is used since the compound has an appropriate T1 value for easy red emission compared to the compounds used in Comparative Examples 1 to 3.

The element results of the compound of the present invention and the comparative compounds suggests that the energy level (HOMO, LUMO, T1, etc.) of the compound may vary significantly depending on the type of substituent constituting the compound, the substitution position, and the type of heteroatom and a difference in properties of compound may act as a major factor in improving element performance during the element deposition, resulting in different element results. Furthermore, it can be confirmed that when 2,3-fused DBF/DBT having a linear structure in the direction of condensation of fused DBT/DBF among N-containing polycyclic compounds is introduced as an N-substituent like the compound represented by Formula 2-K of the present invention, this is a structure suitable for improving performance of the element.

[Example 16] Mixed Phosphorescent Host of a Light Emitting Layer

On the ITO layer (anode) formed on the glass substrate, 2-TNATA was vacuum deposited to a thickness of 60 nm to form a hole injection layer. Then, NPB was vacuum deposited to a thickness of 55 nm to form a hole transport layer.

Next, a light emitting layer with a thickness of 30 nm was formed on the hole transport layer, wherein a mixture of a compound 1-61 of the present invention (host 1) and a compound 2-36 of the present invention (host 2) in a weight ratio of 3:7 was used as a host and $(piq)_2Ir(acac)$ was used as a dopant and the host and dopant were used in a weight ratio of 95:5.

Next, a film of a mixture of (8-hydroxyquinoline)aluminum (hereinafter abbreviated as "Alq") and $BeBq_2$ in a weight ratio of 1:1 was deposited on the hole blocking layer to form an electron transport layer having a thickness of 45 nm. Next, LiF on the electron transport layer was deposited to a thickness of 0.2 nm and then Al was deposited to a thickness of 150 nm to form a cathode. In this way, the OLED was manufactured.

[Example 17] to [Example 120]

The organic electroluminescent elements were manufactured in the same manner as described in Example 16, except that a mixture of the first host compound (host 1) and the second host compound (host 2) described in the following Table 9 was used as host material of the light emitting layer.

[Comparative Example 4] to [Comparative Example 7]

The OLEDs were manufactured in the same manner as described in Example 16, except that a single compound 1-92, compound 1-160, compound 2-129 or compound 2-143 as listed in the following Table 9 was used as host of the light emitting layer, respectively.

[Comparative Example 8] to [Comparative Example 10]

The OLEDs were manufactured in the same manner as described in Example 16 except that a mixture of Comparative compounds 4 and 6 or a mixture of Comparative compounds 4 and 7 as listed in the following Table 9 was used as host of a light emitting layer, respectively.

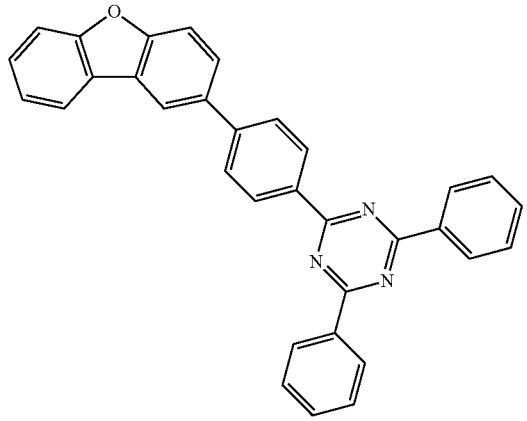

<Comp. Compd 4>

<Comp. Compd 5>

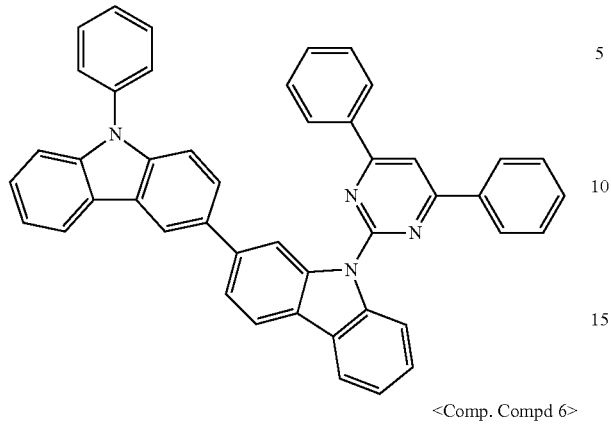

<Comp. Compd 6>

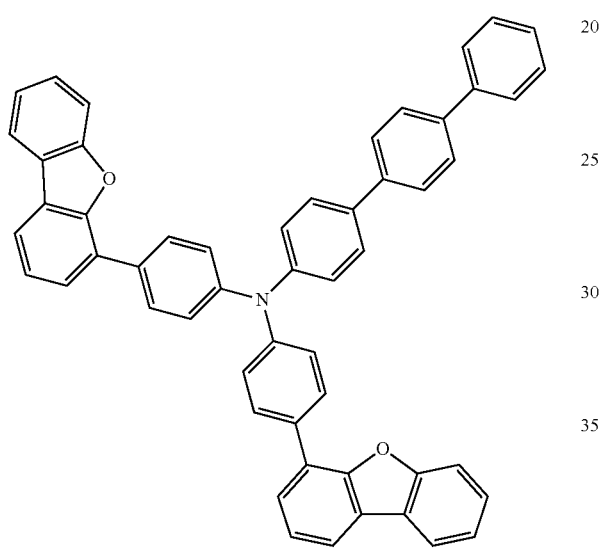

<Comp. Compd 7>

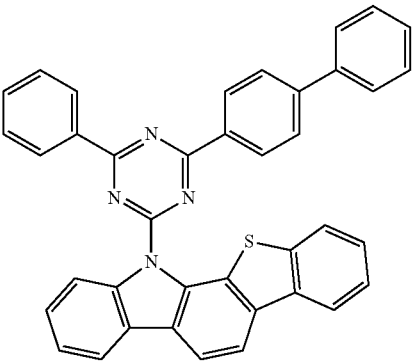

Electroluminescence characteristics were measured with a PR-650 (Photo research) by applying a forward bias DC voltage to the OLEDs prepared in Examples 16 to 120 of the present invention and Comparative Examples 4 to 10. T(95) life time was measured using a life time measuring apparatus manufactured by Mc science Inc. at reference brightness of 2500 cd/m². The measurement results are shown in the table 9 below.

TABLE 9

|  | Host 1 | Host 2 | Voltage (V) | Current Density (mA/cm²) | Brightness (cd/m²) | Efficiency (cd/A) | Lifetime T (95) |
|---|---|---|---|---|---|---|---|
| comp. Ex (4) | Com. 1-92 |  | 5.8 | 13.4 | 2500 | 18.6 | 122 |
| comp. Ex (5) | Com. 1-160 |  | 5.9 | 14.5 | 2500 | 17.3 | 110.7 |
| comp. Ex (6) |  | Com. 2-129 | 5.8 | 13.2 | 2500 | 18.9 | 115.2 |
| comp. Ex (7) |  | Com. 2-143 | 5.9 | 14.2 | 2500 | 17.6 | 117.8 |
| comp. Ex (8) | Comp. compd 4 | Comp. compd 5 | 5.7 | 12.4 | 2500 | 20.1 | 124.1 |
| comp. Ex (9) | Comp. compd 4 | Comp. compd 6 | 5.6 | 12.2 | 2500 | 20.5 | 125.7 |
| comp. Ex (10) | Comp. compd 4 | Comp. compd 7 | 5.5 | 11.7 | 2500 | 21.3 | 130.4 |
| Ex. (16) | Com. 1-61 | Com. 2-36 | 5.0 | 7.8 | 2500 | 32.0 | 145.0 |
| Ex. (17) | Com. 1-91 |  | 4.9 | 7.5 | 2500 | 33.5 | 145.5 |
| Ex. (18) | Com. 1-92 |  | 4.9 | 7.4 | 2500 | 33.7 | 145.7 |
| Ex. (19) | Com. 1-103 |  | 4.9 | 7.5 | 2500 | 33.4 | 145.3 |
| Ex. (20) | Com. 1-121 |  | 5.0 | 7.7 | 2500 | 32.6 | 146.3 |
| Ex. (21) | Com. 1-122 |  | 5.0 | 7.7 | 2500 | 32.3 | 145.8 |
| Ex. (22) | Com. 1-145 |  | 5.0 | 7.8 | 2500 | 32.2 | 145.1 |
| Ex. (23) | Com. 1-148 |  | 5.0 | 7.4 | 2500 | 33.8 | 145.4 |
| Ex. (24) | Com. 1-149 |  | 5.0 | 7.4 | 2500 | 34.0 | 145.5 |
| Ex. (25) | Com. 1-151 |  | 5.0 | 7.5 | 2500 | 33.2 | 145.3 |
| Ex. (26) | Com. 1-158 |  | 5.0 | 7.6 | 2500 | 32.8 | 146.2 |
| Ex. (27) | Com. 1-160 |  | 4.9 | 7.6 | 2500 | 32.9 | 146.5 |
| Ex. (28) | Com. 1-172 |  | 5.0 | 7.7 | 2500 | 32.5 | 146.0 |
| Ex. (29) | Com. 1-173 |  | 4.9 | 7.6 | 2500 | 32.9 | 146.8 |
| Ex. (30) | Com. 1-174 |  | 4.9 | 7.6 | 2500 | 33.1 | 147.0 |
| Ex. (31) | Com. 1-61 | Com. 2-64 | 4.8 | 6.6 | 2500 | 37.6 | 148.8 |
| Ex. (32) | Com. 1-91 |  | 4.9 | 6.4 | 2500 | 39.3 | 149.5 |
| Ex. (33) | Com. 1-92 |  | 4.8 | 6.3 | 2500 | 39.4 | 149.7 |

TABLE 9-continued

| | Host 1 | Host 2 | Voltage (V) | Current Density (mA/cm$^2$) | Brightness (cd/m$^2$) | Efficiency (cd/A) | Lifetime T (95) |
|---|---|---|---|---|---|---|---|
| Ex. (34) | Com. 1-103 | | 4.9 | 6.4 | 2500 | 39.1 | 149.1 |
| Ex. (35) | Com. 1-121 | | 4.8 | 6.6 | 2500 | 38.1 | 150.3 |
| Ex. (36) | Com. 1-122 | | 4.8 | 6.6 | 2500 | 37.9 | 149.8 |
| Ex. (37) | Com. 1-145 | | 4.8 | 6.6 | 2500 | 37.8 | 148.9 |
| Ex. (38) | Com. 1-148 | | 4.9 | 6.3 | 2500 | 39.4 | 149.2 |
| Ex. (39) | Com. 1-149 | | 4.9 | 6.3 | 2500 | 39.6 | 149.4 |
| Ex. (40) | Com. 1-151 | | 4.9 | 6.4 | 2500 | 39.0 | 149.1 |
| Ex. (41) | Com. 1-158 | Com. 2-64 | 4.8 | 6.5 | 2500 | 38.2 | 150.1 |
| Ex. (42) | Com. 1-160 | | 4.8 | 6.5 | 2500 | 38.5 | 150.4 |
| Ex. (43) | Com. 1-172 | | 4.9 | 6.6 | 2500 | 38.0 | 150.0 |
| Ex. (44) | Com. 1-173 | | 4.9 | 6.5 | 2500 | 38.7 | 150.5 |
| Ex. (45) | Com. 1-174 | | 4.9 | 6.4 | 2500 | 38.9 | 150.7 |
| Ex. (46) | Com. 1-61 | Com. 2-105 | 4.9 | 7.0 | 2500 | 35.8 | 147.1 |
| Ex. (47) | Com. 1-91 | | 4.9 | 6.7 | 2500 | 37.2 | 147.9 |
| Ex. (48) | Com. 1-92 | | 4.8 | 6.7 | 2500 | 37.4 | 148.0 |
| Ex. (49) | Com. 1-103 | | 4.9 | 6.7 | 2500 | 37.1 | 147.5 |
| Ex. (50) | Com. 1-121 | | 4.8 | 6.9 | 2500 | 36.0 | 148.6 |
| Ex. (51) | Com. 1-122 | | 4.8 | 7.0 | 2500 | 35.9 | 148.0 |
| Ex. (52) | Com. 1-145 | | 4.9 | 7.0 | 2500 | 35.9 | 147.2 |
| Ex. (53) | Com. 1-148 | | 4.8 | 6.6 | 2500 | 37.6 | 147.5 |
| Ex. (54) | Com. 1-149 | | 4.8 | 6.6 | 2500 | 37.8 | 147.7 |
| Ex. (55) | Com. 1-151 | | 4.8 | 6.8 | 2500 | 36.8 | 147.4 |
| Ex. (56) | Com. 1-158 | | 4.8 | 6.9 | 2500 | 36.2 | 148.3 |
| Ex. (57) | Com. 1-160 | | 4.9 | 6.9 | 2500 | 36.2 | 148.6 |
| Ex. (58) | Com. 1-172 | | 4.8 | 6.9 | 2500 | 36.0 | 148.2 |
| Ex. (59) | Com. 1-173 | | 4.9 | 6.9 | 2500 | 36.4 | 148.9 |
| Ex. (60) | Com. 1-174 | | 4.9 | 6.8 | 2500 | 36.5 | 149.0 |
| Ex. (61) | Com. 1-61 | Com. 2-111 | 5.0 | 7.4 | 2500 | 34.0 | 150.5 |
| Ex. (62) | Com. 1-91 | | 4.9 | 7.1 | 2500 | 35.4 | 151.4 |
| Ex. (63) | Com. 1-92 | | 4.9 | 7.0 | 2500 | 35.6 | 151.6 |
| Ex. (64) | Com. 1-103 | | 4.9 | 7.1 | 2500 | 35.4 | 151.0 |
| Ex. (65) | Com. 1-121 | | 4.9 | 7.3 | 2500 | 34.3 | 152.0 |
| Ex. (66) | Com. 1-122 | | 5.0 | 7.3 | 2500 | 34.1 | 151.7 |
| Ex. (67) | Com. 1-145 | | 5.0 | 7.4 | 2500 | 34.0 | 150.6 |
| Ex. (68) | Com. 1-148 | | 4.8 | 7.0 | 2500 | 35.8 | 151.1 |
| Ex. (69) | Com. 1-149 | | 4.8 | 6.9 | 2500 | 36.0 | 151.3 |
| Ex. (70) | Com. 1-151 | | 5.0 | 7.1 | 2500 | 35.1 | 150.9 |
| Ex. (71) | Com. 1-158 | | 4.9 | 7.3 | 2500 | 34.3 | 152.0 |
| Ex. (72) | Com. 1-160 | | 4.9 | 7.2 | 2500 | 34.5 | 152.1 |
| Ex. (73) | Com. 1-172 | | 4.9 | 7.3 | 2600 | 34.1 | 151.9 |
| Ex. (74) | Com. 1-173 | | 4.8 | 7.2 | 2500 | 34.7 | 152.3 |
| Ex. (75) | Com. 1-174 | | 4.8 | 7.2 | 2600 | 34.8 | 162.4 |
| Ex. (76) | Com. 1-61 | Com. 2-113 | 5.1 | 8.3 | 2600 | 30.0 | 141.5 |
| Ex. (77) | Com. 1-91 | | 5.0 | 7.9 | 2500 | 31.5 | 142.8 |
| Ex. (78) | Com. 1-92 | | 5.0 | 7.9 | 2600 | 31.7 | 143.0 |
| Ex. (79) | Com. 1-103 | | 5.1 | 8.0 | 2600 | 31.3 | 142.2 |
| Ex. (80) | Com. 1-121 | | 5.1 | 8.1 | 2500 | 30.7 | 144.1 |
| Ex. (81) | Com. 1-122 | | 5.1 | 8.2 | 2500 | 30.4 | 143.2 |
| Ex. (82) | Com. 1-145 | | 5.1 | 8.3 | 2600 | 30.3 | 141.8 |
| Ex. (83) | Com. 1-148 | | 5.1 | 7.8 | 2500 | 31.9 | 142.4 |
| Ex. (84) | Com. 1-149 | | 5.1 | 7.8 | 2500 | 32.0 | 142.7 |
| Ex. (85) | Com. 1-151 | | 5.0 | 8.0 | 2600 | 31.3 | 142.0 |
| Ex. (86) | Com. 1-168 | | 5.0 | 8.1 | 2600 | 30.7 | 143.9 |
| Ex. (87) | Com. 1-160 | | 5.0 | 8.1 | 2500 | 30.8 | 144.4 |
| Ex. (88) | Com. 1-172 | | 5.1 | 8.2 | 2600 | 30.6 | 143.5 |
| Ex. (89) | Com. 1-173 | | 5.0 | 8.0 | 2600 | 31.1 | 144.6 |
| Ex. (90) | Com. 1-174 | | 5.0 | 8.0 | 2500 | 31.2 | 144.9 |
| Ex. (91) | Com. 1-61 | Com. 2-129 | 4.8 | 6.1 | 2600 | 41.2 | 152.2 |
| Ex. (92) | Com. 1-91 | | 4.7 | 5.9 | 2600 | 42.6 | 152.9 |
| Ex. (93) | Com. 1-92 | | 4.7 | 5.8 | 2500 | 42.8 | 153.0 |
| Ex. (94) | Com. 1-103 | | 4.8 | 5.9 | 2500 | 42.5 | 152.5 |
| Ex. (95) | Com. 1-121 | | 4.8 | 6.0 | 2600 | 41.7 | 153.5 |
| Ex. (96) | Com. 1-122 | | 4.8 | 6.0 | 2500 | 41.4 | 153.1 |
| Ex. (97) | Com. 1-145 | | 4.7 | 6.1 | 2500 | 41.3 | 152.3 |
| Ex. (98) | Com. 1-148 | | 4.8 | 6.8 | 2600 | 42.9 | 152.5 |
| Ex. (99) | Com. 1-149 | | 4.8 | 5.8 | 2500 | 43.1 | 152.7 |
| Ex. (100) | Com. 1-151 | | 4.8 | 5.9 | 2500 | 42.4 | 152.5 |
| Ex. (101) | Com. 1-158 | | 4.8 | 6.0 | 2600 | 41.8 | 153.3 |
| Ex. (102) | Com. 1-160 | | 4.7 | 6.0 | 2600 | 41.9 | 153.7 |
| Ex. (103) | Com. 1-172 | | 4.8 | 6.0 | 2500 | 41.5 | 153.3 |
| Ex. (104) | Com. 1-173 | | 4.7 | 6.0 | 2500 | 42.0 | 153.8 |
| Ex. (105) | Com. 1-174 | | 4.7 | 5.9 | 2500 | 42.2 | 154.1 |
| Ex. (106) | Com. 1-61 | Com. 2-143 | 4.8 | 6.3 | 2500 | 39.4 | 153.9 |
| Ex. (107) | Com. 1-91 | | 4.7 | 6.1 | 2500 | 40.9 | 154.8 |
| Ex. (108) | Com. 1-92 | | 4.7 | 6.1 | 2500 | 41.1 | 154.9 |
| Ex. (109) | Com. 1-103 | | 4.7 | 6.1 | 2500 | 40.7 | 154.2 |

TABLE 9-continued

|  | Host 1 | Host 2 | Voltage (V) | Current Density (mA/cm$^2$) | Brightness (cd/m$^2$) | Efficiency (cd/A) | Lifetime T (95) |
|---|---|---|---|---|---|---|---|
| Ex. (110) | | Com. 1-121 | 4.8 | 6.3 | 2500 | 40.0 | 155.3 |
| Ex. (111) | | Com. 1-122 | 4.8 | 6.3 | 2500 | 39.7 | 155.0 |
| Ex. (112) | | Com. 1-145 | 4.7 | 6.3 | 2500 | 39.6 | 154.0 |
| Ex. (113) | | Com. 1-148 | 4.8 | 6.1 | 2500 | 41.3 | 154.3 |
| Ex. (114) | | Com. 1-149 | 4.8 | 6.0 | 2500 | 41.4 | 154.5 |
| Ex. (115) | | Com. 1-151 | 4.8 | 6.1 | 2500 | 40.7 | 154.1 |
| Ex. (116) | | Com. 1-158 | 4.8 | 6.2 | 2500 | 40.2 | 155.2 |
| Ex. (117) | | Com. 1-160 | 4.7 | 6.2 | 2500 | 40.3 | 155.3 |
| Ex. (118) | | Com. 1-172 | 4.8 | 6.3 | 2500 | 39.9 | 155.0 |
| Ex. (119) | | Com. 1-173 | 4.7 | 6.2 | 2500 | 40.5 | 155.6 |
| Ex. (120) | | Com. 1-174 | 4.7 | 6.2 | 2500 | 40.6 | 155.8 |

From Table 9, it can be seen that the driving voltage, efficiency and lifetime were remarkably improved when the mixture of the compounds for an organic electroluminescent element of the present invention represented by Formula 1 and Formula 2 was used as a phosphorescent host (Examples 16 to 120), compared to element using a single material (Comparative Examples 4 to 7), the mixture of Comparative Compounds 4 to 7 (Comparative Examples 8 to 10).

Comparing Comparative Examples 4 to 10, Comparative Examples 8 to 10, in which two compounds were mixed and used as a host, exhibited improved element characteristics compared to Comparative Examples 4 and 5 using the compound of the present invention represented by Formula 1 as a single host, or compared to Comparative Examples 6 and 7 in which the compound of the present invention represented by Formula 2 was used as a single host.

In addition, the driving voltage of the element is lowered, and the efficiency and lifespan is significantly improved when the mixture of compounds represented by Formula 1 and Formula 2 of the present invention are used (Example 16 to Example 120) than when the mixture of the comparative compounds are used (Comparative Examples 8 to 10).

From these results, the inventors of the present invention believed that a mixture of compounds of Formulas 1 and 2 has novel characteristics other than those of each compound, and thus the PL lifetime for each of these compounds and mixtures were measured. As a result, it was confirmed that a new PL wavelength for the mixture of compounds of Formula 1 and 2 of the present invention was formed unlike a single compound.

It seems that this is because when a mixture of compounds of the present invention is used, electrons and holes move or energy is transferred through a new region (exciplex) having a new energy level formed by mixing as well as the energy level of each substance, as a result, efficiency and lifetime are increased. This is an important example in which the mixed thin film shows exciplex energy transfer and light emission processes when the mixture of the present invention is used.

In addition, when a mixture of a polycyclic compound of Formula 1 which has a high T1 value with high stability to not only electrons but also holes and compound of Formula 2 which has strong hole properties was used, the charge balance of hoe and electron in the light emitting layer increases, and thus light emission occurs well inside the light-emitting layer, not the interface of the hole transport layer. As a result, the deterioration in the interface of a hole transport layer is also reduced, thereby maximizing the driving voltage, efficiency and lifetime of the element. Therefore, it seems that the overall performance of the element was improved due to electrochemical synergy when the mixture of compounds of Formulas 1 and 2 was used.

[Example 121] to [Example 126]

An OLED was manufactured in the same manner as in Example 16, except that the first host and the second host were mixed in a certain ratio as shown in Table 10 below.

Electroluminescence characteristics were measured with a PR-650 (Photo research) by applying a forward bias DC voltage to the OLEDs prepared in Examples 121 to 126 of the present invention. T(95) life time was measured using a life time measuring apparatus manufactured by Mc science Inc. at reference brightness of 2500 cd/m$^2$. The measurement results are shown in the table 10 below. Examples 33 and 93 show the results of measuring the elements characteristics when host 1 and host 2 were mixed in a ratio of 3:7 and used as a host as in Table 9.

TABLE 10

|  | Host 1 | Host 2 | Mixing ratio (Host 1:Host 2) | Voltage (V) | Current Density (mA/cm$^2$) | Brightness (cd/m$^2$) | Efficiency (cd/A) | Lifetime T (95) |
|---|---|---|---|---|---|---|---|---|
| Ex. (121) | 1-92 | 2-64 | 7:3 | 4.9 | 6.5 | 2500 | 38.2 | 148.2 |
| Ex. (122) | | | 5:5 | 4.9 | 6.4 | 2600 | 39.1 | 149.0 |
| Ex. (33) | | | 3:7 | 4.8 | 6.3 | 2500 | 39.4 | 149.7 |
| Ex. (123) | 1-121 | 2-111 | 7:3 | 5.1 | 7.6 | 2500 | 33.0 | 150.1 |
| Ex. (124) | | | 5:5 | 5.0 | 7.4 | 2600 | 33.9 | 151.4 |
| Ex. (65) | | | 3:7 | 4.9 | 7.3 | 2500 | 34.3 | 152.0 |
| Ex. (125) | 1-92 | 2-129 | 7:3 | 4.9 | 6.0 | 2500 | 41.8 | 152.1 |
| Ex. (126) | | | 5:5 | 4.8 | 5.9 | 2500 | 42.5 | 152.7 |
| Ex. (93) | | | 3:7 | 4.7 | 5.8 | 2500 | 42.6 | 153.0 |

Referring to Table 10, it can be seen that the driving voltage, efficiency and lifespan are the best when the mixing ratio of the first host and the second host was 3:7, and the element characteristics are deteriorated as the amount of the first host was increased. This is because the charge balance in the light emitting layer is maximized as the amount of the compound represented by Formula 2, which has relatively stronger hole characteristics than that of Formula 1, is increased.

Although the exemplary embodiments of the present invention have been described for illustrative purposes, those skilled in the art to which the present invention pertains will be capable of various modifications without departing from the essential characteristics of the present invention. Therefore, the embodiments disclosed in this specification are not intended to limit the present invention, but to illustrate the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

What is claimed is:
1. A compound of Formula 2-K:

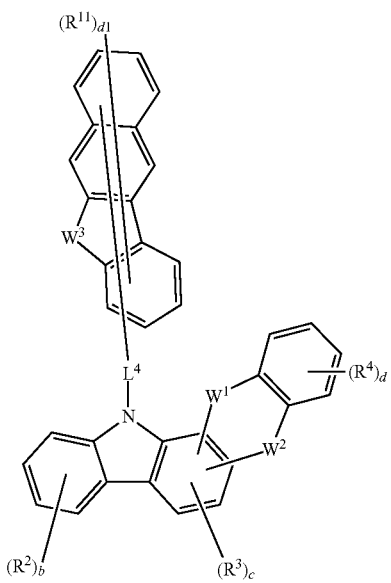

<Formula 2-K> wherein:
$W^1$ and $W^2$ are each independently a single bond, N-L'-(Ar$^4$), O, S or C(R')(R''), with the proviso that both $W^1$ and $W^2$ are not a single bond at the same time,
$W^3$ is O or S,
$L^4$ is a single bond or a $C_6$-$C_{12}$ arylene group,
$R^2$ to $R^4$, $R^{11}$ and R' and R'' are each independently selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N(R$_a$)(R$_b$), and adjacent $R^2$s, adjacent $R^3$s, adjacent $R^4$s or adjacent $R^{11}$s may be bonded to each other to form a ring, and R' and R'' may be bonded to each other to form a ring, b and d are each an integer of 0 to 4, c is an integer of 0 to 2, d1 is an integer of 0 to 9, and where each of b, c, d and d1 is an integer of 2 or more, each of a plurality of $R^2$s, each of a plurality of $R^3$s, each of a plurality of $R^4$s and each of a plurality of $R^{11}$s are the same as or different from each other, Ar$^4$ is selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring, R$_a$ and R$_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring, and $R^2$ to $R^4$, Ar$^4$, $L^4$, L', R$_a$, R$_b$, R', R'', the ring formed by adjacent groups, and the ring formed by R' and R'' may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

2. The compound of claim 1, wherein Formula 2-K is represented by Formula 2-K-1:

<Formula 2-K-1>

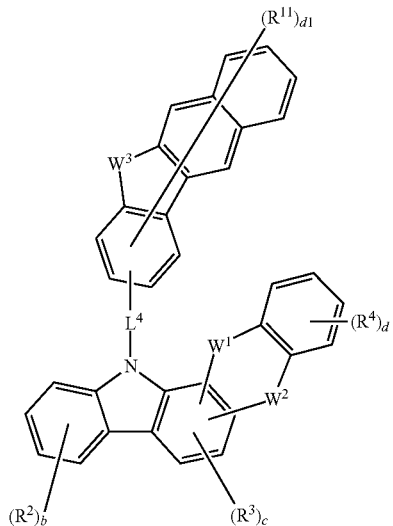

wherein $W^1$ to $W^3$, $R^2$ to $R^4$, $R^{11}$, $L^4$, b to d and d1 are the same as defined in claim 1.

3. The compound of claim 1, wherein Formula 2-K is represented by Formula 2-K-2:

<Formula 2-K-2>

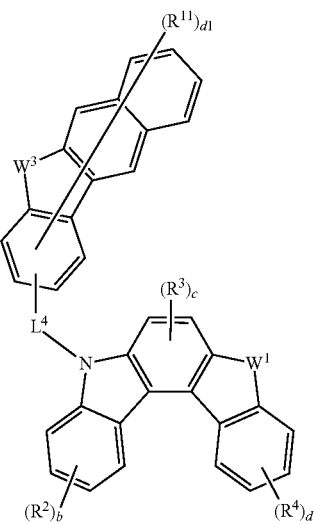

wherein $W^1$, $W^3$, $R^2$ to $R^4$, $R^{11}$, $L^4$, b to d and d1 are the same as defined in claim 1.

4. The compound of claim 1, wherein $W^1$ is N-L'-(Ar$^4$).

5. The compound of claim 1, wherein $W^1$ is N-L'-(Ar$^4$) and $W^2$ is a single bond.

6. The compound of claim 1, wherein at least one of L' and Ar$^4$ is substituted with one or more substituents selected from the group consisting of deuterium, halogen, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, and a $C_3$-$C_{20}$ aliphatic ring group.

7. The compound of claim 1, wherein at least one of L' and Ar$^4$ is substituted with deuterium.

8. The compound of claim 1, wherein Ar$^4$ is a $C_6$-$C_{60}$ aryl group, a fluorenyl group, or a $C_2$-$C_{60}$ heterocyclic group comprising at least one heteroatom selected from the group consisting of O, N, S, Si and P.

9. The compound of claim 8, wherein Ar$^4$ is substituted with deuterium or a $C_6$-$C_{20}$ aryl group substituted with deuterium.

10. The compound of claim 1, wherein the compound of Formula 2-K is one of the following compounds:

2-129

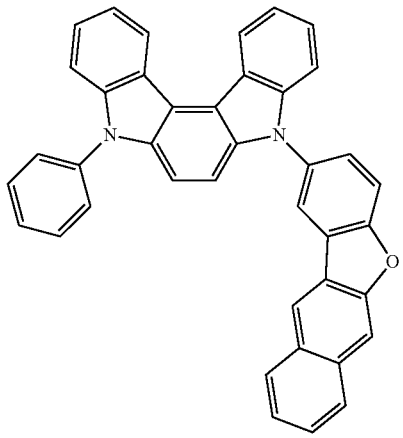

2-130

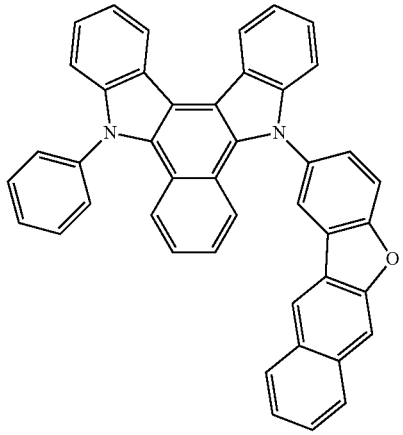

2-131

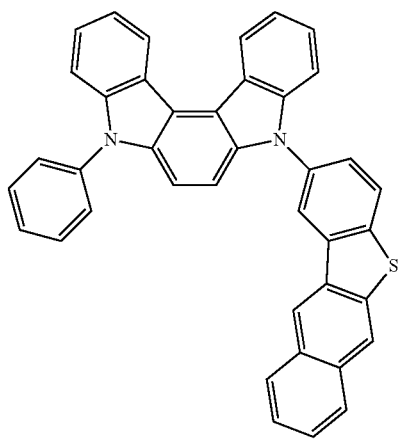

-continued
2-132
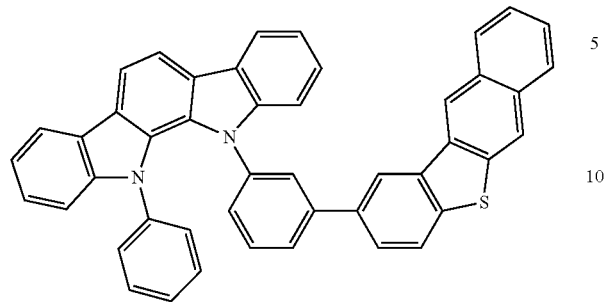
2-133
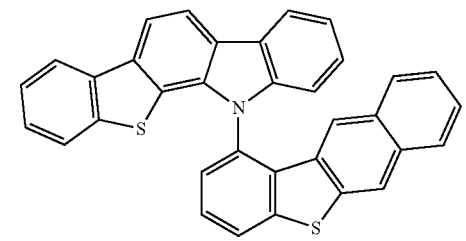
2-134
2-135
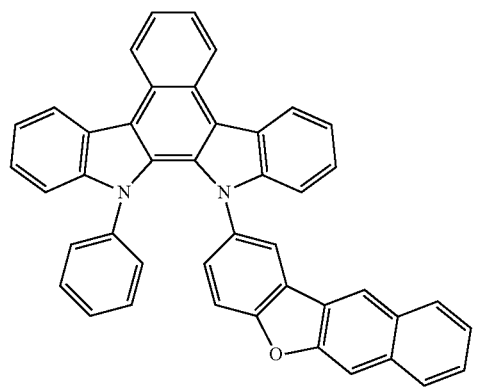
-continued
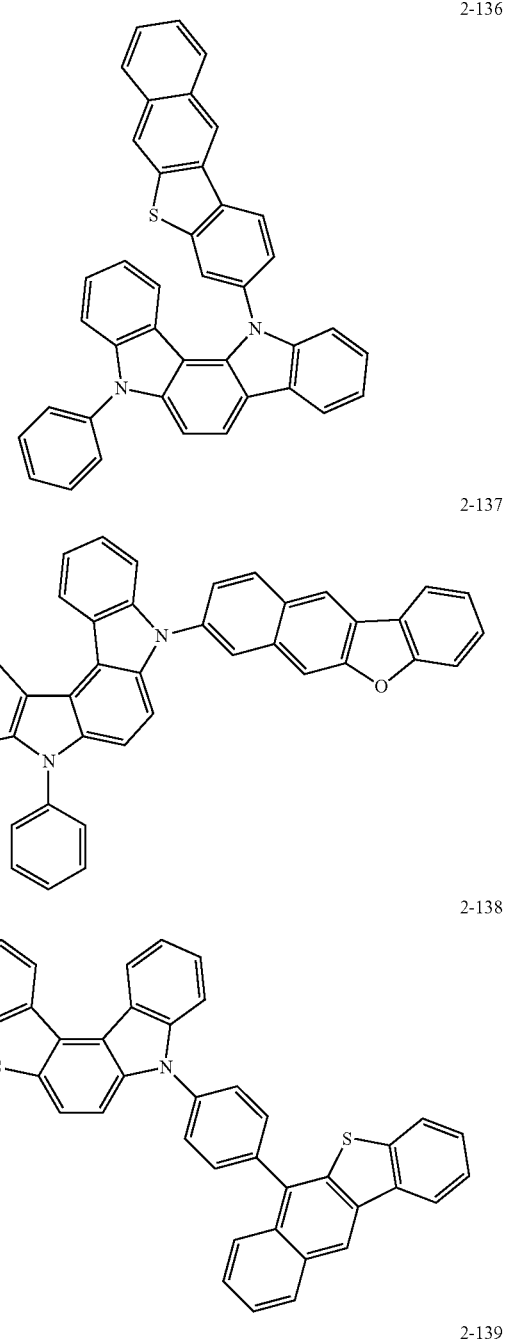
2-136
2-137
2-138
2-139
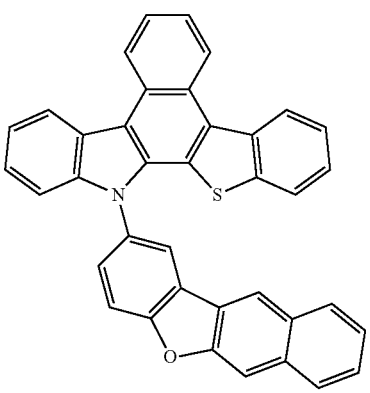

2-140
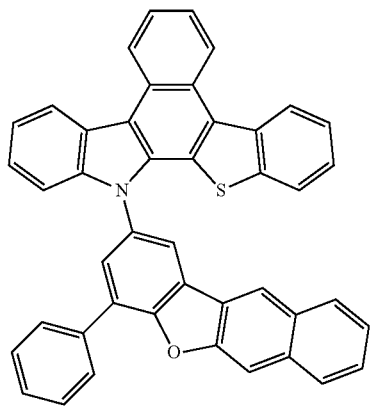
2-141
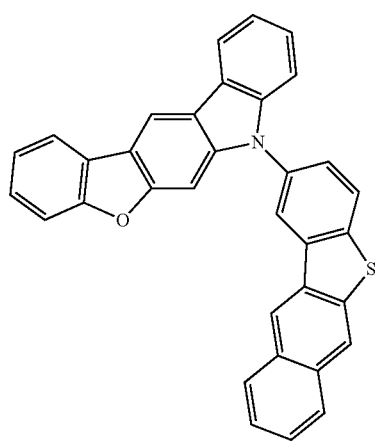
2-142
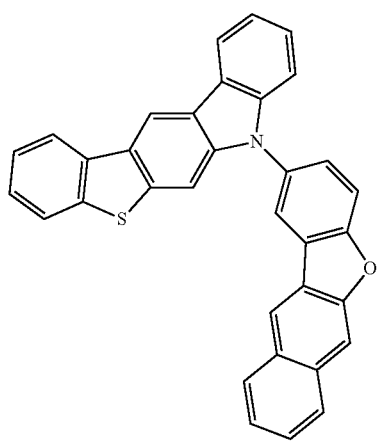
2-143
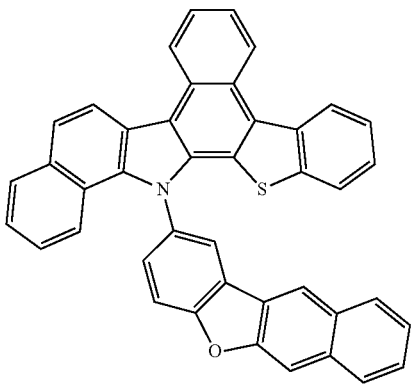
2-144
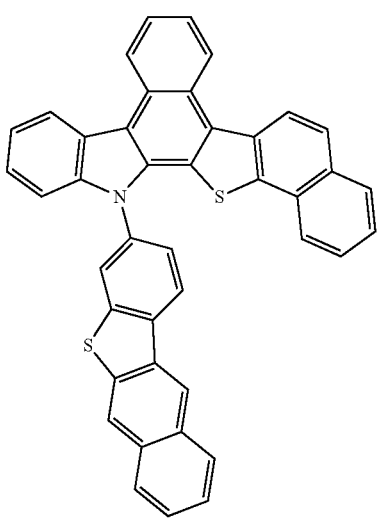
2-145
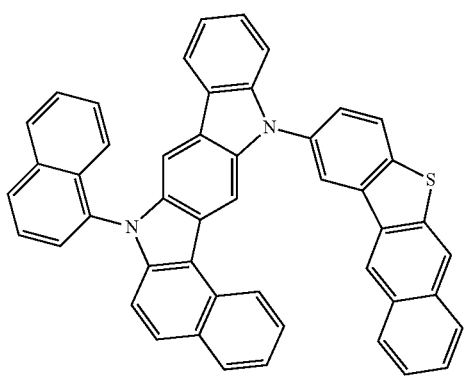

2-146
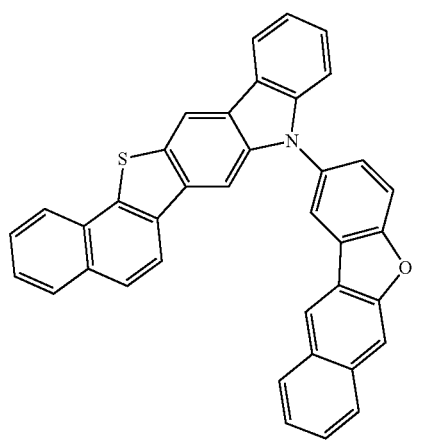
2-147
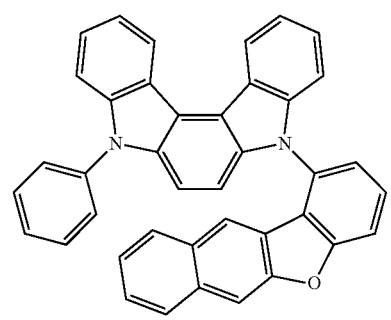
2-148
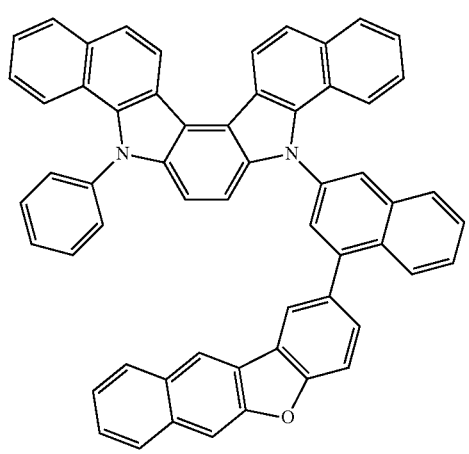
2-149
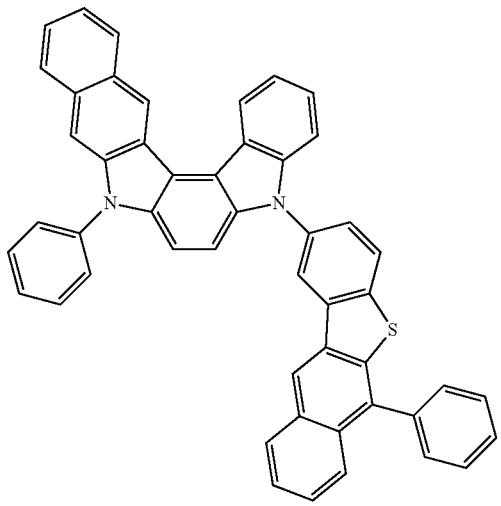
2-150
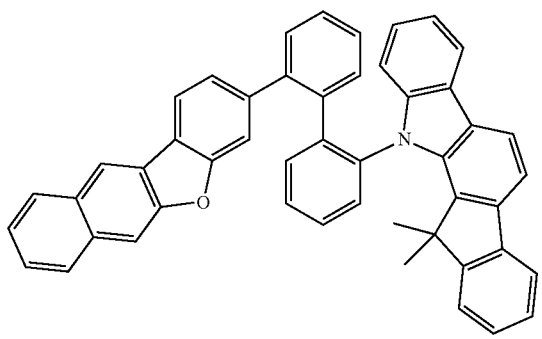
2-151
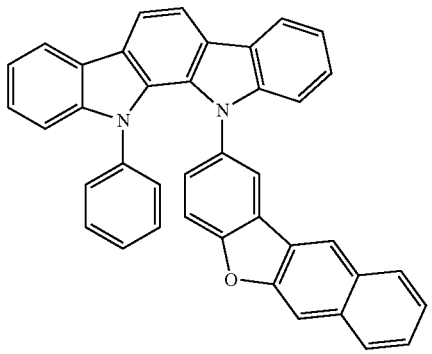
2-152
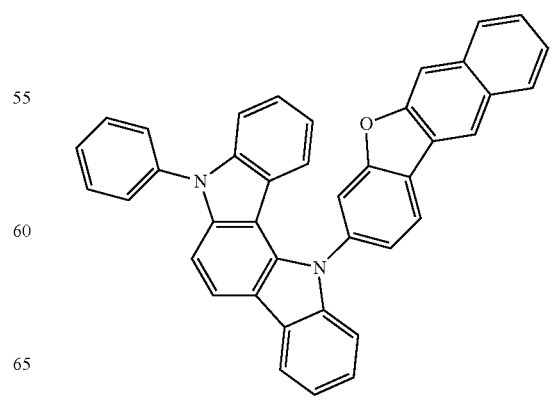

-continued
2-153
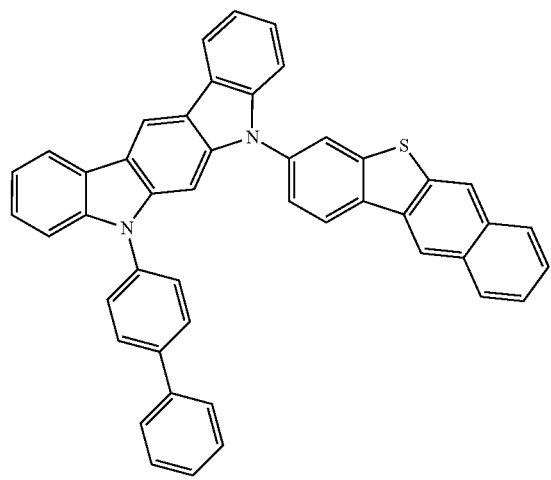
2-154
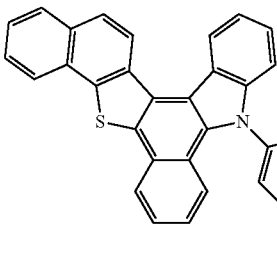
2-155
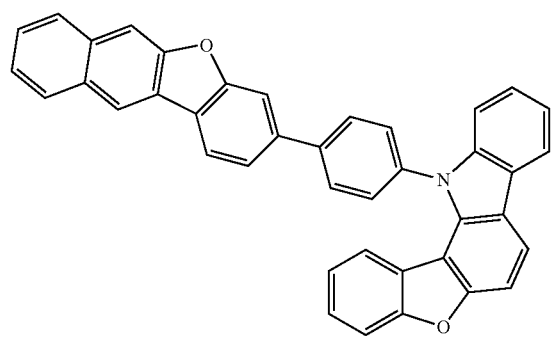
2-156
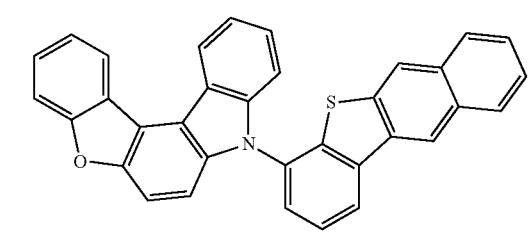
2-157
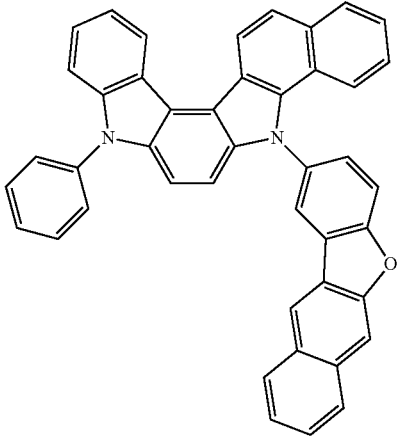
2-158
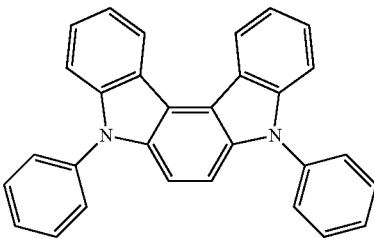
2-159
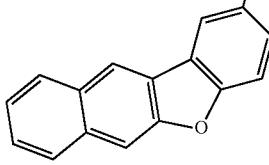
2-160
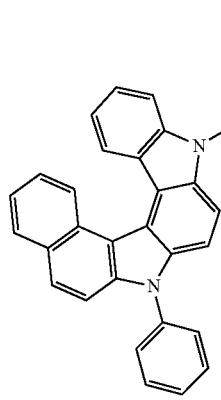

2-163

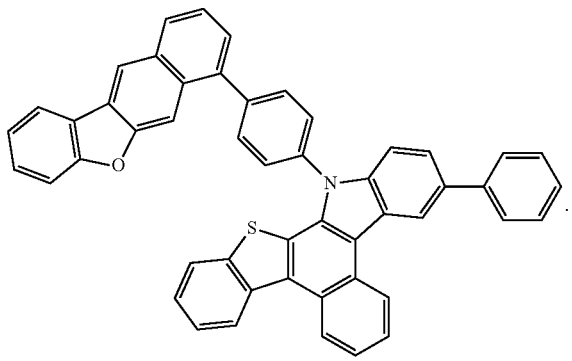

11. An organic electric element comprising a first electrode, a second electrode, and an organic material layer formed between the first electrode and the second electrode, wherein the organic material layer comprises a compound of Formula 2-K of claim 1.

12. The organic electric element of claim 11, wherein the organic material layer comprises a light emitting layer, and the light emitting layer comprises the compound of Formula 2-K.

13. An electronic device comprising a display device and a control unit for driving the display device, wherein the display device comprises the organic electric element of claim 11.

14. The electronic device of claim 13, wherein the organic electric element is selected from the group consisting of an organic light emitting diode, an organic solar cell, an organic photo conductor, an organic transistor, an element for monochromatic illumination and a quantum dot display.

* * * * *